United States Patent
Beigelman et al.

(10) Patent No.: US 11,033,556 B2
(45) Date of Patent: Jun. 15, 2021

(54) BICYCLIC SULFONAMIDES

(71) Applicant: ALIGOS THERAPEUTICS, INC., South San Francisco, CA (US)

(72) Inventors: Leonid Beigelman, San Mateo, CA (US); David Bernard Smith, San Mateo, CA (US)

(73) Assignee: Aligos Therapeutics, Inc., South San Francisco, CA (US)

( * ) Notice: Subject to any disclaimer, the term of this patent is extended or adjusted under 35 U.S.C. 154(b) by 0 days.

(21) Appl. No.: 16/789,298

(22) Filed: Feb. 12, 2020

(65) Prior Publication Data
US 2020/0345749 A1    Nov. 5, 2020

Related U.S. Application Data

(60) Provisional application No. 62/805,725, filed on Feb. 14, 2019.

(51) Int. Cl.
| | | |
|---|---|---|
| *A61K 31/407* | (2006.01) | |
| *A61K 31/554* | (2006.01) | |
| *A61P 31/14* | (2006.01) | |
| *A61P 31/20* | (2006.01) | |
| *C07D 513/04* | (2006.01) | |
| *C07D 515/04* | (2006.01) | |

(52) U.S. Cl.
CPC ............ *A61K 31/554* (2013.01); *A61P 31/20* (2018.01); *C07D 513/04* (2013.01); *C07D 515/04* (2013.01)

(58) Field of Classification Search
CPC ..... A61K 31/407; A61K 31/554; A61P 31/14; A61P 31/20
See application file for complete search history.

(56) References Cited

FOREIGN PATENT DOCUMENTS

| CN | 108264520 | 7/2018 |
|---|---|---|
| WO | WO 2017/001655 | 1/2017 |

OTHER PUBLICATIONS

International Search Report and Written Opinion dated Apr. 29, 2020 for PCT Application No. PCT/US2020/017974, filed Feb. 12, 2020.

*Primary Examiner* — Brenda L Coleman
(74) *Attorney, Agent, or Firm* — Knobbe Martens Olson & Bear LLP

(57) ABSTRACT

Provided herein are compounds of Formulae (I) and (II), or pharmaceutically acceptable salts of the foregoing, pharmaceutical compositions that include a compound described herein (including pharmaceutically acceptable salts of a compound described herein) and methods of synthesizing the same. Also provided herein are methods of treating diseases and/or conditions with a compound of Formulae (I) and/or (II), or a pharmaceutically acceptable salt of any of the foregoing.

27 Claims, 1 Drawing Sheet
Specification includes a Sequence Listing.

The plate map of compound treatment

|   | 1 | 2 | 3 | 4 | 5 | 6 | 7 | 8 | 9 | 10 | 11 | 12 |
|---|---|---|---|---|---|---|---|---|---|---|---|---|
| A |   | High dose | | | 4-fold dilution, 8 dilution points, duplicate | | | | Low dose | | | |
| B | compound 1 | | | | | | | | | ETV(1µM) | 0.5%DMSO control | Blank |
| C | | | | | | | | | | | | |
| D | compound 2 | | | | | | | | | | | |
| E | | | | | | | | | | | | |
| F | compound 3 | | | | | | | | | | | |
| G | | | | | | | | | | | | |
| H |   | High dose | | | 4-fold dilution, 8 dilution points, duplicate | | | | Low dose | | | |

BICYCLIC SULFONAMIDES

INCORPORATION BY REFERENCE TO ANY PRIORITY APPLICATIONS

Any and all applications for which a foreign or domestic priority claim is identified, for example, in the Application Data Sheet or Request as filed with the present application, are hereby incorporated by reference under 37 CFR 1.57, and Rules 4.18 and 20.6, including U.S. Provisional Application No. 62/805,725, filed Feb. 14, 2019.

REFERENCE TO SEQUENCE LISTING

The present application is filed with a Sequence Listing in Electronic format. The Sequence Listing is provided as a file entitled ALIG010.txt, created Jun. 5, 2020, which is approximately 2 kb in size. The information in the electronic format of the sequence listing is incorporated herein by reference in its entirety.

BACKGROUND

Field

The present application relates to the fields of chemistry, biochemistry and medicine. Disclosed herein are compounds of Formulae (I) and (II), or pharmaceutically acceptable salts of the foregoing, pharmaceutical compositions that include a compound described herein (including pharmaceutically acceptable salts of a compound described herein) and methods of synthesizing the same. Also disclosed herein are methods of treating diseases and/or conditions with a compound of Formulae (I) and/or (II), or a pharmaceutically acceptable salt of any of the foregoing.

Description

The hepatitis B virus (HBV) is a DNA virus and a member of the Hepadnaviridae family. HBV infects more than 300 million worldwide and is a causative agent of liver cancer and liver disease such as chronic hepatitis, cirrhosis, and hepatocellular carcinoma. Although there are approved drugs for treating HBV, by either boosting the immune system or slowing down the replication of the HBV virus, HBV continues to be a problem due to the drawbacks associated with each of the approved drugs.

SUMMARY

Some embodiments disclosed herein relate to a compound of Formula (I), or a pharmaceutically acceptable salt thereof. Other embodiments disclosed herein relate to a compound of Formula (II), or a pharmaceutically acceptable salt thereof.

Some embodiments disclosed herein relate to a pharmaceutical composition that can contain an effective amount of a compound of Formula (I), or a pharmaceutically acceptable salt thereof, and/or a compound of Formula (II), or a pharmaceutically acceptable salt thereof.

Some embodiments described herein relate to a method of treating a HBV and/or HDV infection that can include administering to a subject identified as suffering from the HBV and/or HDV infection an effective amount of a compound, or a pharmaceutically acceptable salt thereof, as described herein, or a pharmaceutical composition that includes an effective amount of a compound, or a pharmaceutically acceptable salt thereof, as described herein. Other embodiments described herein relate to a compound, or a pharmaceutically acceptable salt thereof, as described herein, or a pharmaceutical composition that includes an effective amount of a compound, or a pharmaceutically acceptable salt thereof, as described herein for the use of treating a HBV and/or HDV infection.

Some embodiments disclosed herein relate to a method of inhibiting replication of HBV and/or HDV that can include contacting a cell infected with the HBV and/or HDV with an effective amount of a compound, or a pharmaceutically acceptable salt thereof, as described herein, or a pharmaceutical composition that includes an effective amount of a compound, or a pharmaceutically acceptable salt thereof, as described herein. Other embodiments described herein relate to a compound, or a pharmaceutically acceptable salt thereof, as described herein, or a pharmaceutical composition that includes an effective amount of a compound, or a pharmaceutically acceptable salt thereof, as described herein for the use of inhibiting the replication HBV and/or HDV.

These are other embodiments are described in greater detail below

BRIEF DESCRIPTION OF THE DRAWINGS

The FIGURE shows the plate map of compound treatment for the HBV-DNA Antiviral Assay described herein.

DETAILED DESCRIPTION

HBV is a partially double-stranded circular DNA of about 3.2 kilobase (kb) pairs, and is classified into eight genotypes, A to H. The HBV replication pathway has been studied in great detail. T. J. Liang, Heptaology (2009) 49(5 Suppl): S13-S21. On part of replication includes the formation of the covalently closed circular (cccDNA) form. The presence of the cccDNA gives rise to the risk of viral reemergence throughout the life of the host organism. HBV carriers can transmit the disease for many years. An estimated 300 million people are living with hepatitis B virus infection, and it is estimated that over 750,000 people worldwide die of hepatitis B each year. In addition, immunosuppressed individuals or individuals undergoing chemotherapy are especially at risk for reactivation of a HBV infection. HBV can be acute and/or chronic. Acute HBV infection can be either asymptomatic or present with symptomatic acute hepatitis.

HBV can be transmitted by blood, semen, and/or another body fluid. This can occur through direct blood-to-blood contact, unprotected sex, sharing of needles, and from an infected mother to her baby during the delivery process. The HBV surface antigen (HBsAg) is most frequently used to screen for the presence of this infection. Currently available medications do not cure a HBV and/or HDV infection. Rather, the medications suppress replication of the virus.

The hepatitis D virus (HDV) is a DNA virus, also in the Hepadnaviridae family of viruses. HDV can propagate only in the presence of HBV. The routes of transmission of HDV are similar to those for HBV. Transmission of HDV can occur either via simultaneous infection with HBV (coinfection) or in addition to chronic hepatitis B or hepatitis B carrier state (superinfection). Both superinfection and coinfection with HDV results in more severe complications compared to infection with HBV alone. These complications include a greater likelihood of experiencing liver failure in acute infections and a rapid progression to liver cirrhosis, with an increased risk of developing liver cancer in chronic infections. In combination with hepatitis B, hepatitis D has the highest fatality rate of all the hepatitis infections, at 20%. There is currently no cure or vaccine for hepatitis D.

Definitions

Unless defined otherwise, all technical and scientific terms used herein have the same meaning as is commonly understood by one of ordinary skill in the art. All patents, applications, published applications and other publications referenced herein are incorporated by reference in their entirety unless stated otherwise. In the event that there are a plurality of definitions for a term herein, those in this section prevail unless stated otherwise.

Whenever a group is described as being "optionally substituted" that group may be unsubstituted or substituted with one or more of the indicated substituents. Likewise, when a group is described as being "unsubstituted or substituted" if substituted, the substituent(s) may be selected from one or more of the indicated substituents. If no substituents are indicated, it is meant that the indicated "optionally substituted" or "substituted" group may be substituted with one or more group(s) individually and independently selected from deuterium, alkyl, alkenyl, alkynyl, cycloalkyl, cycloalkenyl, aryl, heteroaryl, heterocyclyl, aryl (alkyl), heteroaryl(alkyl), (heterocyclyl)alkyl, hydroxy, alkoxy, acyl, cyano, halogen, thiocarbonyl, O-carbamyl, N-carbamyl, O-thiocarbamyl, N-thiocarbamyl, C-amido, N-amido, S-sulfonamido, N-sulfonamido, C-carboxy, O-carboxy, isocyanato, thiocyanato, nitro, azido, silyl, sulfenyl, sulfinyl, sulfonyl, haloalkyl, haloalkoxy, trihalomethanesulfonyl, trihalomethanesulfonamido, an amino, a mono-substituted amino group and a di-substituted amino group.

As used herein, "$C_a$ to $C_b$" in which "a" and "b" are integers refer to the number of carbon atoms in an alkyl, alkenyl or alkynyl group, or the number of carbon atoms in the ring of a cycloalkyl, cycloalkenyl, aryl, heteroaryl or heterocyclyl group. That is, the alkyl, alkenyl, alkynyl, ring of the cycloalkyl, ring of the cycloalkenyl, ring of the aryl, ring of the heteroaryl or ring of the heterocyclyl can contain from "a" to "b", inclusive, carbon atoms. Thus, for example, a "$C_1$ to $C_4$ alkyl" group refers to all alkyl groups having from 1 to 4 carbons, that is, $CH_3$—, $CH_3CH_2$—, $CH_3CH_2CH_2$—, $(CH_3)_2CH$—, $CH_3CH_2CH_2CH_2$—, $CH_3CH_2CH(CH_3)$— and $(CH_3)_3C$—. If no "a" and "b" are designated with regard to an alkyl, alkenyl, alkynyl, cycloalkyl cycloalkenyl, aryl, heteroaryl or heterocyclyl group, the broadest range described in these definitions is to be assumed.

As used herein, "alkyl" refers to a straight or branched hydrocarbon chain that comprises a fully saturated (no double or triple bonds) hydrocarbon group. The alkyl group may have 1 to 20 carbon atoms (whenever it appears herein, a numerical range such as "1 to 20" refers to each integer in the given range; e.g., "1 to 20 carbon atoms" means that the alkyl group may consist of 1 carbon atom, 2 carbon atoms, 3 carbon atoms, etc., up to and including 20 carbon atoms, although the present definition also covers the occurrence of the term "alkyl" where no numerical range is designated). The alkyl group may also be a medium size alkyl having 1 to 10 carbon atoms. The alkyl group could also be a lower alkyl having 1 to 6 carbon atoms. The alkyl group of the compounds may be designated as "$C_1$-$C_4$ alkyl" or similar designations. By way of example only, "$C_1$-$C_4$ alkyl" indicates that there are one to four carbon atoms in the alkyl chain, i.e., the alkyl chain is selected from methyl, ethyl, propyl, iso-propyl, n-butyl, iso-butyl, sec-butyl and t-butyl. Typical alkyl groups include, but are in no way limited to, methyl, ethyl, propyl, isopropyl, butyl, isobutyl, tertiary butyl, pentyl and hexyl. The alkyl group may be substituted or unsubstituted.

As used herein, "alkenyl" refers to an alkyl group that contains in the straight or branched hydrocarbon chain one or more double bonds. The length of an alkenyl can vary. For example, the alkenyl can be a $C_{2-4}$ alkenyl, $C_{2-6}$ alkenyl or $C_{2-8}$ alkenyl. Examples of alkenyl groups include allenyl, vinylmethyl and ethenyl. An alkenyl group may be unsubstituted or substituted.

As used herein, "alkynyl" refers to an alkyl group that contains in the straight or branched hydrocarbon chain one or more triple bonds. The length of an alkynyl can vary. For example, the alkynyl can be a $C_{2-4}$ alkynyl, $C_{2-6}$ alkynyl or $C_{2-8}$ alkynyl. Examples of alkynyls include ethynyl and propynyl. An alkynyl group may be unsubstituted or substituted.

As used herein, "cycloalkyl" refers to a completely saturated (no double or triple bonds) mono- or multi-cyclic hydrocarbon ring system. When composed of two or more rings, the rings may be joined together in a fused fashion. Cycloalkyl groups can contain 3 to 10 atoms in the ring(s). 3 to 8 atoms in the ring(s) or 3 to 6 atoms in the ring(s). A cycloalkyl group may be unsubstituted or substituted. Typical cycloalkyl groups include, but are in no way limited to, cyclopropyl, cyclobutyl, cyclopentyl, cyclohexyl, cycloheptyl and cyclooctyl.

As used herein, "cycloalkenyl" refers to a mono- or multi-cyclic hydrocarbon ring system that contains one or more double bonds in at least one ring; although, if there is more than one, the double bonds cannot form a fully delocalized pi-electron system throughout all the rings (otherwise the group would be "aryl," as defined herein). When composed of two or more rings, the rings may be connected together in a fused fashion. A cycloalkenyl can contain 3 to 10 atoms in the ring(s) or 3 to 8 atoms in the ring(s). A cycloalkenyl group may be unsubstituted or substituted.

As used herein, "aryl" refers to a carbocyclic (all carbon) monocyclic or multicyclic aromatic ring system (including fused ring systems where two carbocyclic rings share a chemical bond) that has a fully delocalized pi-electron system throughout all the rings. The number of carbon atoms in an aryl group can vary. For example, the aryl group can be a $C_6$-$C_{14}$ aryl group, a $C_6$-$C_{10}$ aryl group, or a $C_6$ aryl group. Examples of aryl groups include, but are not limited to, benzene, naphthalene and azulene. An aryl group may be substituted or unsubstituted.

As used herein, "heteroaryl" refers to a monocyclic, bicyclic and tricyclic aromatic ring system (a ring system with fully delocalized pi-electron system) that contain(s) one or more heteroatoms (for example, 1 to 5 heteroatoms), that is, an element other than carbon, including but not limited to, nitrogen, oxygen and sulfur. The number of atoms in the ring(s) of a heteroaryl group can vary. For example, the heteroaryl group can contain 4 to 14 atoms in the ring(s), 5 to 10 atoms in the ring(s) or 5 to 6 atoms in the ring(s). Furthermore, the term "heteroaryl" includes fused ring systems where two rings, such as at least one aryl ring and at least one heteroaryl ring, or at least two heteroaryl rings, share at least one chemical bond. Examples of heteroaryl rings include, but are not limited to, furan, furazan, thiophene, benzothiophene, phthalazine, pyrrole, oxazole, benzoxazole, 1,2,3-oxadiazole, 1,2,4-oxadiazole, thiazole, 1,2,3-thiadiazole, 1,2,4-thiadiazole, benzothiazole, imidazole, benzimidazole, indole, indazole, pyrazole, benzopyrazole, isoxazole, benzoisoxazole, isothiazole, triazole, benzotriazole, thiadiazole, tetrazole, pyridine, pyridazine, pyrimidine, pyrazine, purine, pteridine, quinoline, isoquinoline, quinazoline, quinoxaline, cinnoline and triazine. A heteroaryl group may be substituted or unsubstituted.

As used herein, "heterocyclyl" refers to a monocyclic, bicyclic and tricyclic ring system wherein carbon atoms together with from 1 to 5 heteroatoms constitute said ring system. A heterocycle may optionally contain one or more unsaturated bonds situated in such a way, however, that a fully delocalized pi-electron system does not occur throughout all the rings. The number of atoms in the ring(s) of a heterocyclyl group can vary. For example, the heterocyclyl group can contain 4 to 14 atoms in the ring(s), 5 to 10 atoms in the ring(s) or 5 to 6 atoms in the ring(s). The heteroatom(s) is an element other than carbon including, but not limited to, oxygen, sulfur and nitrogen. A heterocycle may further contain one or more carbonyl or thiocarbonyl functionalities, so as to make the definition include oxo-systems and thio-systems such as lactams, lactones, cyclic imides, cyclic thioimides and cyclic carbamates. When composed of two or more rings, the rings may be joined together in a fused fashion. Additionally, any nitrogens in a heterocyclyl may be quaternized. Heterocyclyl groups may be unsubstituted or substituted. Examples of such "heterocyclyl groups include but are not limited to, 1,3-dioxin, 1,3-dioxane, 1,4-dioxane, 1,2-dioxolane, 1,3-dioxolane, 1,4-dioxolane, 1,3-oxathiane, 1,4-oxathiin, 1,3-oxathiolane, 1,3-dithiole, 1,3-dithiolane, 1,4-oxathiane, tetrahydro-1,4-thiazine, 2H-1,2-oxazine, maleimide, succinimide, barbituric acid, thiobarbituric acid, dioxopiperazine, hydantoin, dihydrouracil, trioxane, hexahydro-1,3,5-triazine, imidazoline, imidazolidine, isoxazoline, isoxazolidine, oxazoline, oxazolidine, oxazolidinone, thiazoline, thiazolidine, morpholine, oxirane, piperidine N-Oxide, piperidine, piperazine, pyrrolidine, pyrrolidone, pyrroldione, 4-piperidone, pyrazoline, pyrazolidine, 2-oxopyrrolidine, tetrahydropyran, 4H-pyran, tetrahydrothiopyran, thiomorpholine, thiomorpholine sulfoxide, thiomorpholine sulfone and their benzo-fused analogs (e.g., benzimidazolidinone, tetrahydroquinoline and 3,4-methylenedioxyphenyl).

As used herein, "aryl(alkyl)" refer to an aryl group connected, as a substituent, via a lower alkylene group. The lower alkylene and aryl group of an aryl(alkyl) may be substituted or unsubstituted. Examples include but are not limited to benzyl, 2-phenyl(alkyl), 3-phenyl(alkyl), and naphthyl(alkyl).

As used herein, "heteroaryl(alkyl)" refer to a heteroaryl group connected, as a substituent, via a lower alkylene group. The lower alkylene and heteroaryl group of heteroaryl(alkyl) may be substituted or unsubstituted. Examples include but are not limited to 2-thienyl(alkyl), 3-thienyl(alkyl), furyl(alkyl), thienyl(alkyl), pyrrolyl(alkyl), pyridyl(alkyl), isoxazolyl(alkyl), imidazolyl(alkyl), and their benzo-fused analogs.

A "(heterocyclyl)alkyl" refer to a heterocyclic group connected, as a substituent, via a lower alkylene group. The lower alkylene and heterocyclyl of a heterocyclyl(alkyl) may be substituted or unsubstituted. Examples include but are not limited tetrahydro-2H-pyran-4-yl(methyl), piperidin-4-yl(ethyl), piperidin-4-yl(propyl), tetrahydro-2H-thiopyran-4-yl(methyl) and 1,3-thiazinan-4-yl(methyl).

"Lower alkylene groups" are straight-chained —$CH_2$— tethering groups, forming bonds to connect molecular fragments via their terminal carbon atoms. Examples include but are not limited to methylene (—$CH_2$—), ethylene (—$CH_2CH_2$—), propylene (—$CH_2CH_2CH_2$—) and butylene (—$CH_2CH_2CH_2CH_2$—). A lower alkylene group can be substituted by replacing one or more hydrogen of the lower alkylene group with a substituent(s) listed under the definition of "substituted."

As used herein, "alkoxy" refers to the formula —OR wherein R is an alkyl, an alkenyl, an alkynyl, a cycloalkyl, a cycloalkenyl, aryl, heteroaryl, heterocyclyl, aryl(alkyl), heteroaryl(alkyl) or heterocyclyl(alkyl) is defined herein. A non-limiting list of alkoxys are methoxy, ethoxy, n-propoxy, 1-methylethoxy (isopropoxy), n-butoxy, iso-butoxy, sec-butoxy, tert-butoxy, phenoxy and benzoxy. An alkoxy may be substituted or unsubstituted.

As used herein, "acyl" refers to a hydrogen an alkyl, an alkenyl, an alkynyl, a cycloalkyl, a cycloalkenyl, aryl, heteroaryl, heterocyclyl, aryl(alkyl), heteroaryl(alkyl) or heterocyclyl(alkyl) connected, as substituents, via a carbonyl group. Examples include formyl, acetyl, propanoyl, benzoyl, and acryl. An acyl may be substituted or unsubstituted.

As used herein, "hydroxyalkyl" refers to an alkyl group in which one or more of the hydrogen atoms are replaced by a hydroxy group. Exemplary hydroxyalkyl groups include but are not limited to, 2-hydroxyethyl, 3-hydroxypropyl, 2-hydroxypropyl and 2,2-dihydroxyethyl. A hydroxyalkyl may be substituted or unsubstituted.

As used herein, "haloalkyl" refers to an alkyl group in which one or more of the hydrogen atoms are replaced by a halogen (e.g., mono-haloalkyl, di-haloalkyl and tri-haloalkyl). Such groups include but are not limited to, chloromethyl, fluoromethyl, difluoromethyl, trifluoromethyl, 1-chloro-2-fluoromethyl and 2-fluoroisobutyl. A haloalkyl may be substituted or unsubstituted.

As used herein, "haloalkoxy" refers to a O-alkyl group in which one or more of the hydrogen atoms are replaced by a halogen (e.g., mono-haloalkoxy, di-haloalkoxy and tri-haloalkoxy). Such groups include but are not limited to, chloromethoxy, fluoromethoxy, difluoromethoxy, trifluoromethoxy, 1-chloro-2-fluoromethoxy and 2-fluoroisobutoxy. A haloalkoxy may be substituted or unsubstituted.

A "sulfenyl" group refers to an "—SR" group in which R can be hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl). A sulfenyl may be substituted or unsubstituted.

A "sulfinyl" group refers to an "—S(=O)—R" group in which R can be the same as defined with respect to sulfenyl. A sulfinyl may be substituted or unsubstituted.

A "sulfonyl" group refers to an "$SO_2R$" group in which R can be the same as defined with respect to sulfenyl. A sulfonyl may be substituted or unsubstituted.

An "O-carboxy" group refers to a "RC(=O)O—" group in which R can be hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl), as defined herein. An O-carboxy may be substituted or unsubstituted.

The terms "ester" and "C-carboxy" refer to a "—C(=O)OR" group in which R can be the same as defined with respect to O-carboxy. An ester and C-carboxy may be substituted or unsubstituted.

A "thiocarbonyl" group refers to a "—C(=S)R" group in which R can be the same as defined with respect to O-carboxy. A thiocarbonyl may be substituted or unsubstituted.

A "trihalomethanesulfonyl" group refers to an "$X_3CSO_2$—" group wherein each X is a halogen.

A "trihalomethanesulfonamido" group refers to an "$X_3CS(O)_2N(R)$—" group wherein each X is a halogen, and $R_A$ is hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl).

The term "amino" as used herein refers to a —NH$_2$ group.

As used herein, the term "hydroxy" refers to a —OH group.

A "cyano" group refers to a "—CN" group.

The term "azido" as used herein refers to a —N$_3$ group.

An "isocyanato" group refers to a "—NCO" group.

A "thiocyanato" group refers to a "—CNS" group.

An "isothiocyanato" group refers to an "—NCS" group.

A "mercapto" group refers to an "—SH" group.

A "carbonyl" group refers to a C=O group.

An "S-sulfonamido" group refers to a "—SO$_2$N(R$_A$R$_B$)" group in which R$_A$ and R$_B$ can be independently hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl). An S-sulfonamido may be substituted or unsubstituted.

An "N-sulfonamido" group refers to a "RSO$_2$N(R$_A$)—" group in which R and R$_A$ can be independently hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl). An N-sulfonamido may be substituted or unsubstituted.

An "O-carbamyl" group refers to a "—OC(=O)N(R$_A$R$_B$)" group in which R$_A$ and R$_B$ can be independently hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl). An O-carbamyl may be substituted or unsubstituted.

An "N-carbamyl" group refers to an "ROC(=O)N(R$_A$)—" group in which R and R$_A$ can be independently hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl). An N-carbamyl may be substituted or unsubstituted.

An "O-thiocarbamyl" group refers to a "—OC(=S)—N(R$_A$R$_B$)" group in which R$_A$ and R$_B$ can be independently hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl). An O-thiocarbamyl may be substituted or unsubstituted.

An "N-thiocarbamyl" group refers to an "ROC(=S)N(R$_A$)—" group in which R and R$_A$ can be independently hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl). An N-thiocarbamyl may be substituted or unsubstituted.

A "C-amido" group refers to a "—C(=O)N(R$_A$R$_B$)" group in which R$_A$ and R$_B$ can be independently hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl). A C-amido may be substituted or unsubstituted.

An "N-amido" group refers to a "RC(=O)N(R$_A$)—" group in which R and R$_A$ can be independently hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl). An N-amido may be substituted or unsubstituted.

The term "halogen atom" or "halogen" as used herein, means any one of the radio-stable atoms of column 7 of the Periodic Table of the Elements, such as, fluorine, chlorine, bromine and iodine.

The term "α-amino acid" is used as understood by those skilled in the art. Examples of α-amino acids include, but are not limited to, alanine, asparagine, aspartate, cysteine, glutamate, glutamine, glycine, proline, serine, tyrosine, arginine, histidine, isoleucine, leucine, lysine, methionine, phenylalanine, threonine, tryptophan and valine.

The term "—O-linked α-amino acid" refers to an α-amino acid that is attached via the hydroxy from its main-chain carboxylic acid group. When the α-amino acid is attached in an —O-linked α-amino acid, the hydrogen that is part of the hydroxy from its main-chain carboxylic acid group is not present and the α-amino acid is attached via the oxygen. An —O-linked α-amino acid can be substituted or unsubstituted.

Where the numbers of substituents is not specified (e.g. haloalkyl), there may be one or more substituents present. For example, "haloalkyl" may include one or more of the same or different halogens. As another example, "C$_1$-C$_3$ alkoxyphenyl" may include one or more of the same or different alkoxy groups containing one, two or three atoms.

As used herein, the abbreviations for any protective groups, amino acids and other compounds, are, unless indicated otherwise, in accord with their common usage, recognized abbreviations, or the IUPAC-IUB Commission on Biochemical Nomenclature (See, Biochem. 11:942-944 (1972)).

The term "pharmaceutically acceptable salt" refers to a salt of a compound that does not cause significant irritation to an organism to which it is administered and does not abrogate the biological activity and properties of the compound. In some embodiments, the salt is an acid addition salt of the compound. Pharmaceutical salts can be obtained by reacting a compound with inorganic acids such as hydrohalic acid (e.g., hydrochloric acid or hydrobromic acid), sulfuric acid, nitric acid and phosphoric acid. Pharmaceutical salts can also be obtained by reacting a compound with an organic acid such as aliphatic or aromatic carboxylic or sulfonic acids, for example formic, acetic, succinic, lactic, malic, tartaric, citric, ascorbic, nicotinic, methanesulfonic, ethanesulfonic, p-toluenesulfonic, salicylic or naphthalenesulfonic acid. Pharmaceutical salts can also be obtained by reacting a compound with a base to form a salt such as an ammonium salt, an alkali metal salt, such as a sodium or a potassium salt, an alkaline earth metal salt, such as a calcium or a magnesium salt, a salt of organic bases such as dicyclohexylamine, N-methyl-D-glucamine, tris(hydroxymethyl)methylamine, C$_1$-C$_7$ alkylamine, cyclohexylamine, triethanolamine, ethylenediamine, and salts with amino acids such as arginine and lysine.

Terms and phrases used in this application, and variations thereof, especially in the appended claims, unless otherwise expressly stated, should be construed as open ended as opposed to limiting. As examples of the foregoing, the term 'including' should be read to mean 'including, without limitation,' 'including but not limited to,' or the like; the term 'comprising' as used herein is synonymous with 'including,' 'containing,' or 'characterized by,' and is inclusive or open-ended and does not exclude additional, unrecited elements or method steps; the term 'having' should be interpreted as 'having at least;' the term 'includes' should be interpreted as 'includes but is not limited to;' the term 'example' is used to provide exemplary instances of the item in discussion, not an exhaustive or limiting list thereof. In addition, the term "comprising" is to be interpreted synonymously with the phrases "having at least" or "including at least". When used in the context of a compound or composition, the term "comprising" means that the compound or composition includes at least the recited features or components but may also include additional features or components.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. The indefinite article "a" or "an" does not exclude a plurality.

It is understood that, in any compound described herein having one or more chiral centers, if an absolute stereochemistry is not expressly indicated, then each center may independently be of (R)-configuration or (S)-configuration or a mixture thereof. Thus, the compounds provided herein may be enantiomerically pure, enantiomerically enriched, racemic mixture, diastereomerically pure, diastereomerically enriched, or a stereoisomeric mixture. In addition, it is understood that, in any compound described herein having one or more double bond(s) generating geometrical isomers that can be defined as E or Z, each double bond may independently be E or Z a mixture thereof. Likewise, it is understood that, in any compound described, all tautomeric forms are also intended to be included.

It is to be understood that where compounds disclosed herein have unfilled valencies, then the valencies are to be filled with hydrogens or isotopes thereof, e.g., hydrogen-1 (protium) and hydrogen-2 (deuterium).

It is understood that the compounds described herein can be labeled isotopically. Substitution with isotopes such as deuterium may afford certain therapeutic advantages resulting from greater metabolic stability, such as, for example, increased in vivo half-life or reduced dosage requirements. Each chemical element as represented in a compound structure may include any isotope of said element. For example, in a compound structure a hydrogen atom may be explicitly disclosed or understood to be present in the compound. At any position of the compound that a hydrogen atom may be present, the hydrogen atom can be any isotope of hydrogen, including but not limited to hydrogen-1 (protium) and hydrogen-2 (deuterium). Thus, reference herein to a compound encompasses all potential isotopic forms unless the context clearly dictates otherwise.

Where a range of values is provided, it is understood that the upper and lower limit, and each intervening value between the upper and lower limit of the range is encompassed within the embodiments.

Compounds

Some embodiments disclosed herein relate to a compound of Formula (I), or a pharmaceutically acceptable salt thereof:

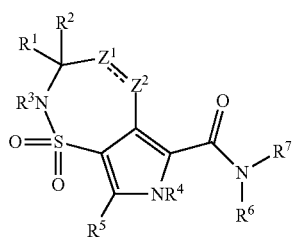

(I)

wherein: ----- indicates a single or a double bond, wherein when ----- is a single bond, then $Z^1$ can be $CR^{8A}R^{9A}$ and $Z^2$ can be $CR^{8B}R^{9B}$; and wherein when ----- is a double bond, then $Z^1$ and $Z^2$ can be each independently $CR^{10}$; $R^1$ can be a substituted or an unsubstituted $C_{2-8}$ alkenyl or a substituted or an unsubstituted $C_{2-8}$ alkynyl, wherein the substituted $C_{2-8}$ alkenyl and the substituted $C_{2-8}$ alkynyl is substituted with one or more substituents independently selected from halogen, hydroxy, an optionally substituted monocyclic $C_{3-6}$ cycloalkyl, an optionally substituted bicyclic $C_{3-8}$ cycloalkyl, an optionally substituted monocyclic heterocyclyl and $R^{11A}$; $R^2$ can be hydrogen, deuterium or a substituted or an unsubstituted $C_{1-4}$ alkyl, wherein the substituted $C_{1-4}$ alkyl is substituted with one or more substituents selected from halogen, hydroxy and $R^{11B}$; $R^3$ can be hydrogen, deuterium or an unsubstituted $C_{1-4}$ alkyl; $R^4$ can be hydrogen, deuterium or an unsubstituted $C_{1-4}$ alkyl; $R^5$ can be hydrogen, deuterium, halogen, an unsubstituted $C_{1-4}$ alkyl, cyano, an unsubstituted $C_{1-4}$ haloalkyl or an unsubstituted $C_{3-8}$ monocyclic cycloalkyl; $R^6$ can be a substituted phenyl or a substituted pyridyl, wherein the substituted phenyl and the substituted pyridyl can be substituted with one or more substituents independently selected from halogen, cyano, an unsubstituted $C_{1-4}$ haloalkyl and an unsubstituted $C_{1-4}$ alkyl; $R^7$ can be hydrogen, deuterium or an unsubstituted $C_{1-4}$ alkyl; $R^{8A}$, $R^{8B}$, $R^{9A}$ and $R^{9B}$ can be independently hydrogen, deuterium, halogen, an unsubstituted $C_{1-4}$ alkyl or hydroxy; each $R^{10}$ can be independently hydrogen, deuterium, halogen or an unsubstituted $C_{1-4}$ alkyl; and $R^{11A}$ and $R^{11B}$ can be independently an optionally substituted —O-acyl, an unsubstituted O-linked α-amino acid, —O—P(=O)(OH)$_2$ or —CH$_2$—P(=O)(OH)$_2$.

Compounds of Formula (I), or a pharmaceutically salt thereof, can include one or more chiral centers. As provided herein, if an absolute stereochemistry is not expressly indicated, then each center may independently be of (R)-configuration or (S)-configuration or a mixture thereof. Those skilled in the art recognize that the carbon to which $R^1$ and $R^2$ are attached can be a chiral center. In some embodiments, the stereochemistry of the carbon to which $R^1$ and $R^2$ are attached is (R). In other embodiments, the stereochemistry of the carbon to which $R^1$ and $R^2$ are attached is (S). A compound of Formula (I), or a pharmaceutically acceptable salt, can have a structure selected from:

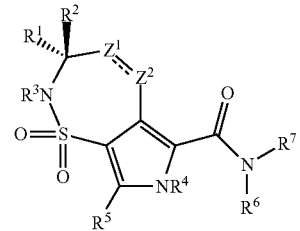

(Ia)

and

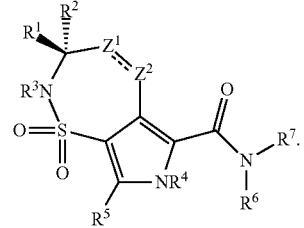

(Ib)

As shown in Formula (I) ----- can be a single or a double bond. When ----- is a single bond, Z can be $CR^{8A}R^{9A}$ and $Z^2$ can be $CR^{8B}R^{9B}$, such that Formula (I) has the structure:

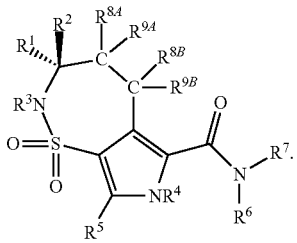

In some embodiments, $Z^1$ can be $CH_2$. In some embodiments, $Z^2$ can be $CH_2$. In some embodiments, $R^{8A}$ and/or $R^{8B}$ can be a deuterium. In some embodiments, $R^{8A}$ and/or $R^{8B}$ can be a halogen (such as F or Cl). In some embodiments, $R^{8A}$ and/or $R^{8B}$ can be an unsubstituted $C_{1-4}$ alkyl. In some embodiments, $R^{8A}$ and/or $R^{8B}$ can be hydroxy. In some embodiments, $R^{9A}$ and/or $R^{9B}$ can be a deuterium. In some embodiments, $R^{9A}$ and/or $R^{9B}$ can be a halogen (such as F or Cl). In some embodiments, $R^{9A}$ and/or $R^{9B}$ can be an unsubstituted $C_{1-4}$ alkyl. In some embodiments, $R^{9A}$ and/or $R^{9B}$ can be hydroxy. When, $R^{8A}$, $R^{8B}$, $R^{9A}$, and/or $R^{9B}$ is an unsubstituted $C_{1-4}$ alkyl, the $C_{1-4}$ alkyl can be methyl, ethyl, n-propyl, iso-propyl, n-butyl, iso-butyl or tert-butyl.

When ----- is a double bond, $Z^1$ and $Z^2$ can be each independently $CR^{10}$, and the compound of Formula (I), or a pharmaceutically acceptable salt, can be

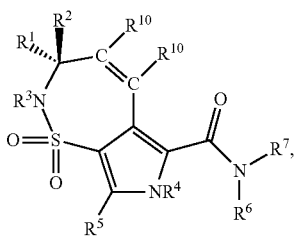

wherein each $R^{10}$ can be independently hydrogen, deuterium, halogen and an unsubstituted $C_{1-4}$ alkyl. In some embodiments, $Z^1$ can be CH. In other embodiments, $Z^1$ can be CD. In some embodiments, $Z^2$ can be CH. In other embodiments, $Z^2$ can be CD. The substituent attached to $Z^1$ and/or $Z^2$ can also be a halogen, such as F or Cl. In some embodiments, $Z^1$ can have an unsubstituted $C_{1-4}$ alkyl attached. In some embodiments, $Z^2$ can have an unsubstituted $C_{1-4}$ alkyl attached. Examples of unsubstituted $C_{1-4}$ alkyls are described herein, including the previous paragraph. When two $R^{10}$ groups are present, in some embodiments, the $R^{10}$ groups can be the same. In other embodiments, when two $R^{10}$ groups are present, the $R^{10}$ groups can be different.

Various alkenyls and alkynyls can be attached to the seven-membered ring of Formula (I) are provided herein. The alkenyl can have 2 to 8 carbons, 2 to 5 carbons or 3 to 4 carbons. In some embodiments, $R^1$ can be an unsubstituted $C_{2-8}$ alkenyl. In other embodiments, $R^1$ can be an unsubstituted $C_{2-8}$ alkenyl. In still other embodiments, $R^1$ can be a substituted $C_{2-8}$ alkenyl, wherein the substituted $C_{2-8}$ alkenyl can be substituted with one or more substituents independently selected from halogen, hydroxy, an optionally substituted monocyclic $C_{3-6}$ cycloalkyl, an optionally substituted bicyclic $C_{3-8}$ cycloalkyl, an optionally substituted monocyclic heterocyclyl and $R^{11A}$. In yet still other embodiments, $R^1$ can be a substituted $C_{3-4}$ alkenyl, wherein the substituted $C_{3-4}$ alkenyl can be substituted with one or more substituents independently selected from halogen, hydroxy, an optionally substituted monocyclic $C_{3-6}$ cycloalkyl, an optionally substituted bicyclic $C_{3-8}$ cycloalkyl, an optionally substituted monocyclic heterocyclyl and $R^{11A}$.

Examples of substituted alkenyls include a substituted alkenyl substituted with one or more halogens (such as F and/or Cl), a substituted alkenyl substituted with one or more hydroxys, a substituted alkenyl substituted with an unsubstituted monocyclic $C_{3-6}$ cycloalkyl, a substituted alkenyl substituted with a substituted monocyclic $C_{3-6}$ cycloalkyl, a substituted alkenyl substituted with an unsubstituted bicyclic $C_{3-8}$ cycloalkyl selected from an unsubstituted fused bicyclic $C_{3-8}$ cycloalkyl, an unsubstituted bridged bicyclic $C_{3-8}$ cycloalkyl and an unsubstituted spiro bicyclic $C_{3-8}$ cycloalkyl, a substituted alkenyl substituted with a substituted bicyclic $C_{3-8}$ cycloalkyl selected from a substituted fused bicyclic $C_{3-8}$ cycloalkyl, a substituted bridged bicyclic $C_{3-8}$ cycloalkyl and a substituted spiro bicyclic $C_{3-8}$ cycloalkyl, a substituted alkenyl substituted with an unsubstituted monocyclic heterocyclyl, a substituted alkenyl substituted with a substituted monocyclic heterocyclyl and a substituted alkenyl substituted with $R^{11A}$.

When $R^1$ is an alkenyl, the alkenyl can include a single double bond. The position of the double bond can vary. In some embodiments, the double bond can be located between the terminal carbon and a carbon adjacent to the terminal carbon. In some embodiments, the double bond can be located between the carbon adjacent to the seven-membered ring of Formula (I) and the next carbon away from the seven-membered ring of Formula (I).

The alkynyl can have 2 to 8 carbons. In some embodiments, the alkynyl for $R^1$ can be a $C_{2-8}$ alkynyl. In other embodiments, the alkynyl for $R^1$ can be a $C_{2-5}$ alkynyl. In still embodiments, the alkynyl for $R^1$ can be a $C_{3-5}$ alkynyl. In some embodiments, $R^1$ can be a substituted $C_{2-8}$ alkynyl, wherein the substituted $C_{2-8}$ alkynyl can be substituted with one or more substituents independently selected from halogen, hydroxy, an optionally substituted monocyclic $C_{3-6}$ cycloalkyl, an optionally substituted bicyclic $C_{3-8}$ cycloalkyl, an optionally substituted monocyclic heterocyclyl and $R^{11A}$. In some embodiments, $R^1$ can be a substituted $C_{3-5}$ alkynyl, wherein the substituted $C_{3-5}$ alkynyl can be substituted with one or more substituents independently selected from halogen, hydroxy, an optionally substituted monocyclic $C_{3-6}$ cycloalkyl, an optionally substituted bicyclic $C_{3-8}$ cycloalkyl, an optionally substituted monocyclic heterocyclyl and $R^{11A}$.

The alkynyl described herein for $R^1$ can be a substituted alkynyl substituted with one or more halogens (for example, F or Cl), a substituted alkynyl substituted with one or more hydroxys, a substituted alkynyl substituted with an unsubstituted monocyclic $C_{3-6}$ cycloalkyl, a substituted alkynyl substituted with a substituted monocyclic $C_{3-6}$ cycloalkyl, a substituted alkynyl substituted with an unsubstituted bicyclic $C_{3-8}$ cycloalkyl selected from an unsubstituted fused bicyclic $C_{3-8}$ cycloalkyl, an unsubstituted bridged bicyclic $C_{3-8}$ cycloalkyl and an unsubstituted spiro bicyclic $C_{3-8}$ cycloalkyl, a substituted alkynyl substituted with a substituted bicyclic $C_{3-8}$ cycloalkyl selected from a substituted fused bicyclic $C_{3-8}$ cycloalkyl, a substituted bridged bicyclic $C_{3-8}$ cycloalkyl and a substituted spiro bicyclic $C_{3-8}$ cycloalkyl, a substituted alkynyl substituted with an unsubstituted monocyclic heterocyclyl, a substituted alkynyl substituted with a substituted monocyclic heterocyclyl and a substituted alkynyl substituted with $R^{11A}$. Those skilled in the art will appreciate that when $R^1$ is substituted with an optionally substituted monocyclic $C_{3-6}$ cycloalkyl, an optionally substituted bicyclic $C_{3-8}$ cycloalkyl or an optionally substituted monocyclic heterocyclyl, the optionally substituted monocyclic $C_{3-6}$ cycloalkyl, the optionally substituted bicyclic $C_{3-8}$ cycloalkyl and the optionally substituted monocyclic heterocyclyl may substitute $R^1$ by replacing two hydrogens of $R^1$. For example, when $R^1$ is a $C_3$-alkenyl substituted with a tetrahydropyran (a monocyclic heterocyclyl) by replacing two hydrogens of $R^1$, $R^1$ may have the structure

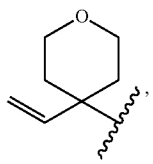

wherein the tetrahydropyran moiety is connected in a spiro-fashion. In some embodiments, $R^1$ is substituted with an optionally substituted monocyclic $C_{3-6}$ cycloalkyl, an optionally substituted bicyclic $C_{3-8}$ cycloalkyl or an optionally substituted monocyclic heterocyclyl, wherein the optionally substituted monocyclic $C_{3-6}$ cycloalkyl, the optionally substituted bicyclic $C_{3-8}$ cycloalkyl or the optionally substituted monocyclic heterocyclyl replaces one hydrogen. In other embodiments, $R^1$ is substituted with an optionally substituted monocyclic $C_{3-6}$ cycloalkyl, an optionally substituted bicyclic $C_{3-8}$ cycloalkyl or an optionally substituted monocyclic heterocyclyl, wherein the optionally substituted monocyclic $C_{3-6}$ cycloalkyl, the optionally substituted bicyclic $C_{3-8}$ cycloalkyl or the optionally substituted monocyclic heterocyclyl replaces two hydrogen such that the aforementioned moieties are connected in a spiro-fashion.

The alkynyl of $R^1$ can include a single triple bond. The position of the triple bond can vary. In some embodiments, the triple bond can be located between the terminal carbon and a carbon adjacent to the terminal carbon. In some embodiments, the triple bond can be located between the carbon adjacent to the seven-membered ring of Formula (I) and the next carbon away from the seven-membered ring of Formula (I).

When $R^1$ is a substituted alkenyl or a substituted alkynyl as described herein and substituted with $R^{11A}$, $R^{11A}$ can be an optionally substituted —O-acyl prodrug or an unsubstituted —O-linked α-amino acid prodrug. An example of an optionally substituted —O-acyl is —O—C(=O)$R^{11A1}$, wherein $R^{11A1}$ can be an optionally substituted $C_{1-6}$ alkyl or an optionally substituted $C_6$ or $C_{14}$ aryl. In some embodiments, $R^{11A}$ can be —O—C(=O)$R^{11A1}$, wherein $R^{11A1}$ can be an unsubstituted $C_{1-6}$ alkyl.

Alpha-amino acids are known to those skilled in the art, and include those described herein. In some embodiments, $R^{11A}$ can be —O-linked glycine, —O-linked valine, —O-linked leucine or —O-linked isoleucine. As provided herein, $R^{11A}$ can be a phosphate or a phosphonate. In some embodiments, $R^{11A}$ can be —O—P(=O)(OH)$_2$. In other embodiments, $R^{11A}$ can be —CH$_2$—P(=O)(OH)$_2$.

For $R^2$, in some embodiments, $R^2$ can be hydrogen. In other embodiments, $R^2$ can be deuterium. In still other embodiments, $R^2$ can be an unsubstituted $C_{1-4}$ alkyl, for example, methyl, ethyl, n-propyl, iso-propyl, n-butyl, iso-butyl and tert-butyl. In some embodiments, $R^2$ can be a substituted $C_{1-4}$ alkyl, wherein the substituted $C_{1-4}$ alkyl can be substituted with one or more substituents selected from halogen (for example F or Cl), hydroxy and $R^{11B}$. Examples of $R^{13}$ begin a substituted $C_{1-4}$ alkyl include —CF$_3$, —CHF$_2$, —CH$_2$OH and —CH(OH)CH$_3$.

As with $R^{11A}$, $R^{11B}$ can be an optionally substituted —O-acyl prodrug or an unsubstituted —O-linked α-amino acid prodrug. The optionally substituted —O-acyl of $R^{11B}$ can be —O—C(=O)$R^{1B}$, wherein $R^{11B1}$ can be an optionally substituted $C_{1-6}$ alkyl or an optionally substituted $C_6$ or $C_{14}$ aryl. In some embodiments, $R^{11B}$ can be —O—C(=O)$R^{11B1}$ wherein $R^{11B1}$ can be an unsubstituted $C_{1-6}$ alkyl. In some embodiments, $R^{11B}$ can be —O-linked glycine, —O-linked valine, —O-linked leucine or —O-linked isoleucine. Exemplary —O-linked α-amino acid for $R^{11A}$ and/or $R^{11B}$ include, but are not limited to,

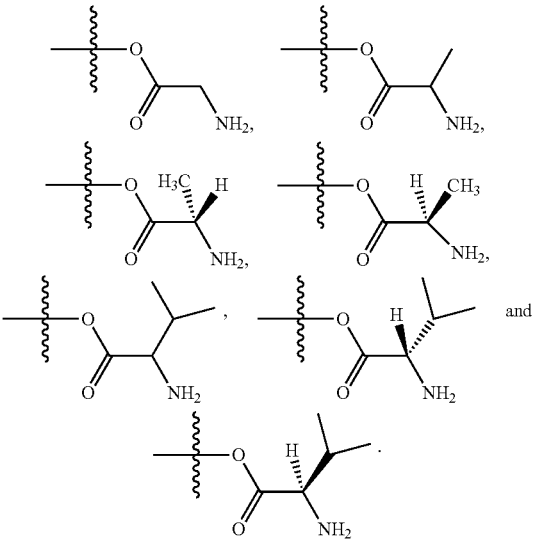

A phosphate or a phosphonate can be present at $R^{11B}$. In some embodiments, $R^{11B}$ can be —O—P(=O)(OH)$_2$. In other embodiments, $R^{11B}$ can be —CH$_2$—P(=O)(OH)$_2$.

In some embodiments, $R^3$ can be hydrogen. In other embodiments, $R^3$ can be deuterium. In still other embodiments, $R^3$ can be an unsubstituted $C_{1-4}$ alkyl, such as those described herein. In some embodiments, $R^3$ can be methyl.

The 5-membered ring of Formula (I) can be unsubstituted or substituted with an unsubstituted $C_{1-4}$ alkyl, cyano and/or an unsubstituted $C_{1-4}$ haloalkyl. In some embodiments, $R^4$ can be hydrogen. In other embodiments, $R^4$ can be deuterium. In still other embodiments, $R^4$ can be an unsubstituted $C_{1-4}$ alkyl. In some embodiments, $R^5$ can be hydrogen. In other embodiments, $R^5$ can be deuterium. In still other embodiments, $R^5$ can be halogen (for example, F or Cl). In yet still other embodiments, $R^5$ can be an unsubstituted $C_{1-4}$ alkyl such as those described herein. In some embodiments, $R^5$ can be cyano. In other embodiments, $R^5$ can be an unsubstituted $C_{1-4}$ haloalkyl. An example of a suitable $C_{1-4}$ haloalkyl is CF$_3$. In still other embodiments, $R^5$ can be an unsubstituted $C_{3-8}$ monocyclic cycloalkyl. In some embodiments, $R^4$ can be methyl; and $R^5$ can be hydrogen.

The C-amide of Formula (I) can include a substituted phenyl or a substituted pyridyl as described herein. In some embodiments, $R^6$ can be a substituted phenyl, wherein the phenyl can be substituted with one or more substituents independently selected from halogen, cyano, an unsubstituted $C_{1-4}$ haloalkyl and an unsubstituted $C_{1-4}$ alkyl. In other embodiments, $R^6$ can be a substituted pyridyl, wherein the pyridyl can be substituted with one or more substituents independently selected from halogen, cyano, an unsubstituted $C_{1-4}$ haloalkyl and an unsubstituted $C_{1-4}$ alkyl. The phenyl and pyridyl of $R^6$ can be substituted with one or more substituents as described herein. In some embodiments, $R^6$ can be a mono-substituted phenyl. In other embodiments, $R^6$ can be a di-substituted phenyl. In some embodiments, the phenyl of $R^6$ can be substituted at the para-position and/or meta-position. In some embodiments, the phenyl of $R^6$ can be a 3,4-disubstituted phenyl. In still other embodiments, $R^6$ can be a mono-substituted pyridyl. In yet still other embodiments, $R^6$ can be a di-substituted pyridyl. In some embodiments, the pyridyl can be substituted on a carbon adjacent to the nitrogen of the pyridyl. The unsubstituted $C_{1-4}$ alkyl(s) that can be substituted on $R^6$ can be methyl, ethyl, n-propyl, iso-propyl, n-butyl, iso-butyl or tert-butyl. Examples of unsubstituted $C_{1-4}$ haloalkyls are $CF_3$, $CHF_2$ and $CH_2F$. In some embodiments, $R^6$ can be substituted with F and/or Cl. In some embodiments, $R^6$ can be substituted with F, Cl and/or Br. In some embodiments, $R^6$ can be substituted with $CF_3$. In some embodiments, $R^6$ can be substituted with $CH_3$. When $R^6$ is di-substituted, the two groups can be the same or different.

The other group of the C-amide of Formula (I), $R^7$, can be hydrogen, deuterium or an unsubstituted $C_{1-4}$ alkyl. In some embodiments, $R^7$ can be hydrogen. In other embodiments, $R^7$ can be deuterium. In still other embodiments, $R^7$ can be an unsubstituted $C_{1-4}$ alkyl.

Examples of compounds of Formula (I), including pharmaceutically acceptable salts thereof, include the following:

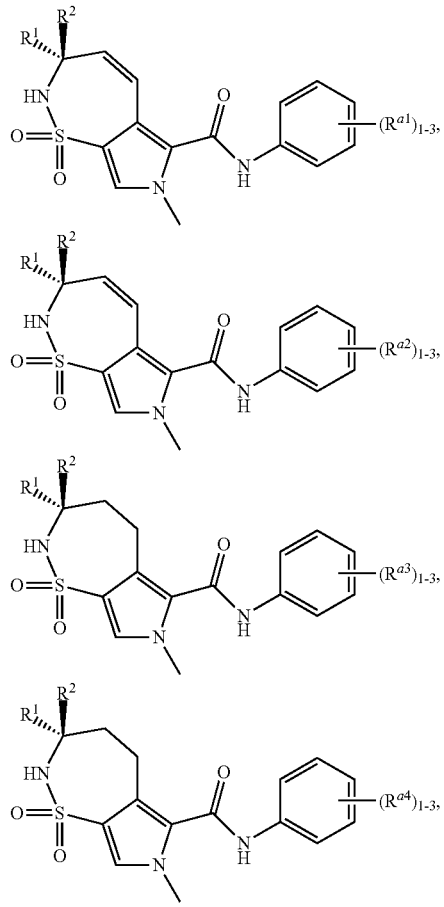

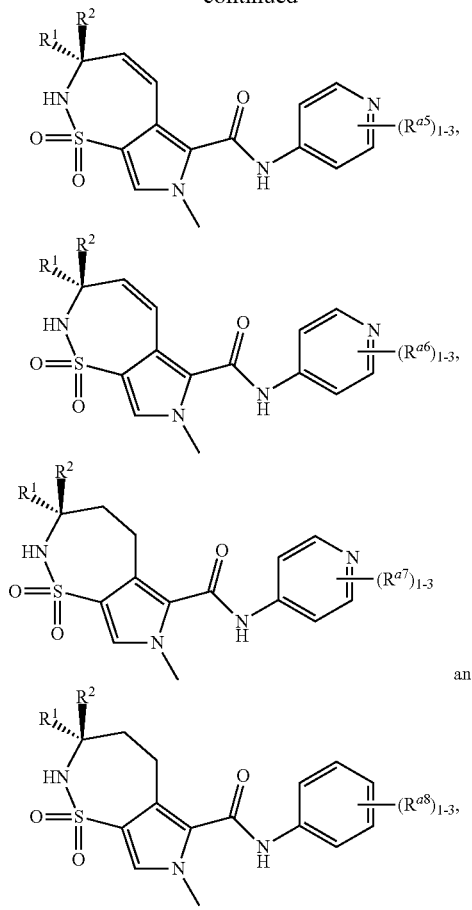

wherein each $R^{a1}$, each $R^{a2}$, each $R^{a3}$, each $R^{a4}$, each $R^{a5}$, each $R^{a6}$, each $R^{a7}$ and each $R^{a8}$ are independently selected from methyl, ethyl, n-propyl, iso-propyl, n-butyl, iso-butyl, tert-butyl, cyano, $CF_3$, $CHF_2$, $CH_2F$, F, Cl and Br.

Some embodiments disclosed herein relate to a compound of Formula (II), or a pharmaceutically acceptable salt thereof:

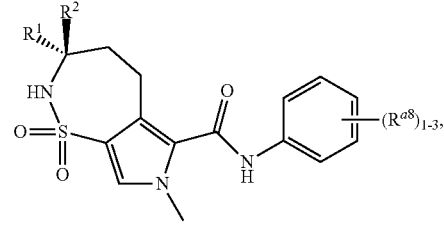

wherein: $R^{12}$ can be a substituted or an unsubstituted $C_{2-8}$ alkenyl or a substituted or an unsubstituted $C_{2-8}$ alkynyl, wherein the substituted $C_{2-8}$ alkenyl and the substituted $C_{2-8}$ alkynyl can be substituted with one or more substituents independently selected from halogen, hydroxy, an optionally substituted monocyclic $C_{3-6}$ cycloalkyl, an optionally substituted bicyclic $C_{3-8}$ cycloalkyl, an optionally substituted monocyclic heterocyclyl and $R^{19A}$; $R^{13}$ can be hydrogen, deuterium or a substituted or an unsubstituted $C_{1-4}$ alkyl, wherein the substituted $C_{1-4}$ alkyl can be substituted with one or more substituents selected from halogen, hydroxy and $R^{19B}$; $R^{14}$ can be hydrogen, deuterium or an unsubstituted $C_{1-4}$ alkyl; $R^{15}$ can be hydrogen, deuterium or an unsubstituted $C_{1-4}$ alkyl; $R^{16}$ can be hydrogen, deuterium, halogen, an unsubstituted $C_{1-4}$ alkyl, cyano, an unsubstituted $C_{1-4}$ haloalkyl or an unsubstituted $C_{3-8}$ monocyclic cycloalkyl; $R^{17}$ can be a substituted phenyl or a substituted pyridyl, wherein the substituted phenyl and the substituted pyridyl can be substituted with one or more substituents independently selected from halogen, cyano, an unsubstituted $C_{1-4}$ haloalkyl and an unsubstituted $C_{1-4}$ alkyl; $R^{18}$ can be hydrogen, deuterium or an unsubstituted $C_{1-4}$ alkyl; and $R^{19A}$ and $R^{19B}$ can be independently an optionally substituted —O-acyl, an unsubstituted O-linked α-amino acid, —O—P(=O)(OH)$_2$ or —CH$_2$—P(=O)(OH)$_2$.

A compound of Formula (II), or a pharmaceutically acceptable salt thereof, can have the following structures:

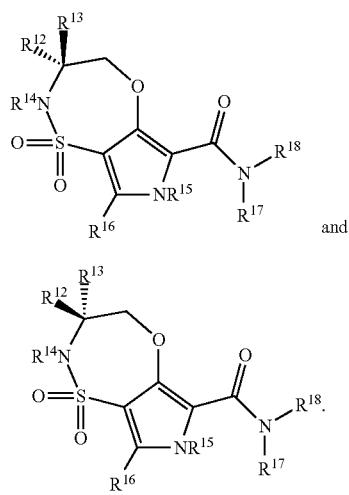

The groups present on $R^{12}$ can be a $C_{2-8}$ alkenyl or a $C_{2-8}$ alkynyl. In some embodiments, $R^{12}$ can be a $C_{2-8}$ alkenyl. In other embodiments, $R^{12}$ can be a $C_{2-5}$ alkenyl. In still other embodiments, $R^{12}$ can be a $C_{3-4}$ alkenyl. In some embodiments, $R^{12}$ can be an unsubstituted $C_{2-8}$ alkenyl. As provided herein, in some embodiments, $R^{12}$ can be a substituted $C_{2-8}$ alkenyl, wherein the substituted $C_{2-8}$ alkenyl can be substituted with one or more substituents independently selected from halogen, hydroxy, an optionally substituted monocyclic $C_{3-6}$ cycloalkyl, an optionally substituted bicyclic $C_{3-8}$ cycloalkyl, an optionally substituted monocyclic heterocyclyl and $R^{19A}$. In some embodiments, $R^{12}$ can be a substituted $C_{3-4}$ alkenyl, wherein the substituted $C_{3-4}$ alkenyl can be substituted with one or more substituents independently selected from halogen, hydroxy, an optionally substituted monocyclic $C_{3-6}$ cycloalkyl, an optionally substituted bicyclic $C_{3-8}$ cycloalkyl, an optionally substituted monocyclic heterocyclyl and $R^{19A}$.

Examples of substituted alkenyls for $R^{12}$ include a substituted alkenyl substituted with one or more halogens (for example, F and/or Cl), a substituted alkenyl substituted with one or more hydroxys, a substituted alkenyl substituted with an unsubstituted monocyclic $C_{3-6}$ cycloalkyl, a substituted alkenyl substituted with a substituted monocyclic $C_{3-6}$ cycloalkyl, a substituted alkenyl substituted with an unsubstituted bicyclic $C_{3-8}$ cycloalkyl selected from an unsubstituted fused bicyclic $C_{3-8}$ cycloalkyl, an unsubstituted bridged bicyclic $C_{3-8}$ cycloalkyl and an unsubstituted spiro bicyclic $C_{3-8}$ cycloalkyl, a substituted alkenyl substituted with a substituted bicyclic $C_{3-8}$ cycloalkyl selected from a substituted fused bicyclic $C_{3-8}$ cycloalkyl, a substituted bridged bicyclic $C_{3-8}$ cycloalkyl and a substituted spiro bicyclic $C_{3-8}$ cycloalkyl, a substituted alkenyl substituted with an unsubstituted monocyclic heterocyclyl, a substituted alkenyl substituted with a substituted monocyclic heterocyclyl and a substituted alkenyl substituted with $R^{19A}$.

When $R^{12}$ is an alkenyl, the alkenyl can include a single double bond. The position of the double bond can vary. In some embodiments, the double bond can be located between the terminal carbon and a carbon adjacent to the terminal carbon. In some embodiments, the double bond can be located between the carbon adjacent to the seven-membered ring of Formula (I) and the next carbon away from the seven-membered ring of Formula (I).

In some embodiments $R^{12}$ can be an unsubstituted $C_{2-8}$ alkynyl. In other embodiments, $R^{12}$ can be a substituted $C_{2-8}$ alkynyl, wherein the substituted $C_{2-8}$ alkynyl can be substituted with one or more substituents independently selected from halogen, hydroxy, an optionally substituted monocyclic $C_{3-6}$ cycloalkyl, an optionally substituted bicyclic $C_{3-8}$ cycloalkyl, an optionally substituted monocyclic heterocyclyl and $R^{19A}$. The alkynyl can have 2 to 8 carbons, 3 to 6 carbons or 3 to 5 carbons. In some embodiments, $R^{12}$ is a substituted $C_{3-8}$ alkynyl, wherein the substituted $C_{3-5}$ alkynyl can be substituted with one or more substituents independently selected from halogen, hydroxy, an optionally substituted monocyclic $C_{3-6}$ cycloalkyl, an optionally substituted bicyclic $C_{3-8}$ cycloalkyl, an optionally substituted monocyclic heterocyclyl and $R^{19A}$.

Examples of substituted $C_{2-8}$ alkynyl for $R^{12}$ include a substituted alkynyl substituted with one or more halogens (for example, F or Cl), a substituted alkynyl substituted with one or more hydroxys, a substituted alkynyl substituted with an unsubstituted monocyclic $C_{3-6}$ cycloalkyl, a substituted alkynyl substituted with a substituted monocyclic $C_{3-6}$ cycloalkyl, a substituted alkynyl substituted with an unsubstituted bicyclic $C_{3-8}$ cycloalkyl selected from an unsubstituted fused bicyclic $C_{3-8}$ cycloalkyl, an unsubstituted bridged bicyclic $C_{3-8}$ cycloalkyl and an unsubstituted spiro bicyclic $C_{3-8}$ cycloalkyl, a substituted alkynyl substituted with a substituted bicyclic $C_{3-8}$ cycloalkyl selected from a substituted fused bicyclic $C_{3-8}$ cycloalkyl, a substituted bridged bicyclic $C_{3-8}$ cycloalkyl and a substituted spiro bicyclic $C_{3-8}$ cycloalkyl, a substituted alkynyl substituted with an unsubstituted monocyclic heterocyclyl, a substituted alkynyl substituted with a substituted monocyclic heterocyclyl and a substituted alkynyl substituted with $R^{19A}$. When $R^{12}$ is substituted with an optionally substituted monocyclic $C_{3-6}$ cycloalkyl, an optionally substituted bicyclic $C_{3-8}$ cycloalkyl or an optionally substituted monocyclic heterocyclyl, the optionally substituted monocyclic $C_{3-6}$ cycloalkyl, the optionally substituted bicyclic $C_{3-8}$ cycloalkyl and the optionally substituted monocyclic heterocyclyl may substitute $R^{12}$ by replacing two hydrogens of $R^{12}$. For example, when $R^{12}$ is a $C_3$-alkenyl substituted with an oxetane (a monocyclic heterocyclyl) by replacing two hydrogens of $R^{12}$, $R^{12}$ may have the structure

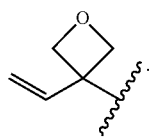 [SMILES: *C1(C=C)COC1]

In some embodiments, $R^{12}$ is substituted with an optionally substituted monocyclic $C_{3-6}$ cycloalkyl, an optionally substituted bicyclic $C_{3-8}$ cycloalkyl or an optionally substituted monocyclic heterocyclyl, wherein the optionally substituted monocyclic $C_{3-6}$ cycloalkyl, the optionally substituted bicyclic $C_{3-8}$ cycloalkyl or the optionally substituted monocyclic heterocyclyl replaces one hydrogen. In other embodiments, $R^{12}$ is substituted with an optionally substituted monocyclic $C_{3-6}$ cycloalkyl, an optionally substituted bicyclic $C_{3-8}$ cycloalkyl or an optionally substituted monocyclic heterocyclyl, wherein the optionally substituted monocyclic $C_{3-6}$ cycloalkyl, the optionally substituted bicyclic $C_{3-8}$ cycloalkyl or the optionally substituted monocyclic heterocyclyl replaces two hydrogen such that the aforementioned moieties are connected in a spiro-fashion.

The alkynyl of $R^{12}$ can include a single triple bond. The position of the triple bond can vary. In some embodiments, the triple bond can be located between the terminal carbon and a carbon adjacent to the terminal carbon. In some embodiments, the triple bond can be located between the carbon adjacent to the seven-membered ring of Formula (I) and the next carbon away from the seven-membered ring of Formula (I).

When $R^{12}$ is an alkenyl substituted with $R^{19A}$ or an alkynyl substituted with $R^{19A}$, $R^{9A}$ can be an optionally substituted —O-acyl prodrug or an unsubstituted —O-linked α-amino acid prodrug. When $R^{12}$ is a substituted alkenyl or a substituted alkynyl substituted with an optionally substituted —O-acyl, the optionally substituted —O-acyl can have the structure —O—C(=O)$R^{19A1}$, wherein $R^{19A1}$ can be an optionally substituted $C_{1-6}$ alkyl or an optionally substituted $C_6$ or $C_{14}$ aryl. In some embodiments, $R^{9A}$ can be —O—C(=O)$R^{19A1}$, wherein $R^{19A1}$ can be an unsubstituted $C_{1-6}$ alkyl.

When the alkenyl and/or alkynyl of $R^{12}$ is substituted, each of the aforementioned can be substituted with an unsubstituted —O-linked α-amino acid, such as those known in the art and described herein. In some embodiments, $R^{19A}$ can be —O-linked glycine, —O-linked valine, —O-linked leucine or —O-linked isoleucine. A phosphate or a phosphonate can be present at $R^{19A}$. In some embodiments, $R^{19A}$ can be —O—P(=O)(OH)$_2$. In other embodiments, $R^{19A}$ can be —CH$_2$—P(=O)(OH)$_2$.

As provided herein, $R^{13}$ can be hydrogen, deuterium or a substituted or an unsubstituted $C_{1-4}$ alkyl, wherein the substituted $C_{1-4}$ alkyl can be substituted with one or more substituents selected from halogen, hydroxy and $R^{19B}$. In some embodiments, $R^{13}$ can be hydrogen. In other embodiments, $R^{13}$ can be deuterium. In still other embodiments, $R^{13}$ can be an unsubstituted $C_{1-4}$ alkyl. In yet still other embodiments, $R^{13}$ can be a substituted $C_{1-4}$ alkyl, substituted with one or more substituents selected from halogen (for example F or Cl), hydroxy and $R^{19B}$. Examples of $R^{13}$ begin a substituted $C_{1-4}$ alkyl include —CF$_3$, —CHF$_2$, —CH$_2$OH and —CH(OH)CH$_3$. In some embodiments, $R^{19B}$ can be —O—P(=O)(OH)$_2$. In other embodiments, $R^{19B}$ can be —CH$_2$—P(=O)(OH)$_2$.

Suitable $C_{1-4}$ alkyls for $R^{12}$ and $R^{13}$ are described herein, and include methyl, ethyl, n-propyl, iso-propyl, n-butyl, iso-butyl or tert-butyl. When, $R^{13}$ is a substituted $C_{1-4}$ alkyl, substituted with $R^{19B}$, $R^{19B}$ can be an optionally substituted —O-acyl prodrug or an unsubstituted —O-linked α-amino acid prodrug. The optionally substituted —O-acyl of $R^{19B}$ can be —O—C(=O)$R^{19B1}$, wherein $R^{19B1}$ can be an optionally substituted $C_{1-6}$ alkyl or an optionally substituted $C_6$ or $C_{14}$ aryl. In some embodiments, $R^{19B}$ can be —O—C(=O)$R^{19B1}$ wherein $R^{19B1}$ can be an unsubstituted $C_{1-6}$ alkyl.

As described herein, $R^{12}$ and $R^{13}$ can include an —O-linked α-amino acid, such as —O-linked glycine, —O-linked valine, —O-linked leucine or —O-linked isoleucine. When $R^{19A}$ and/or $R^{19B}$ is an —O-linked α-amino acid, in some embodiments, $R^{19A}$ and/or $R^{19B}$ can be selected from:

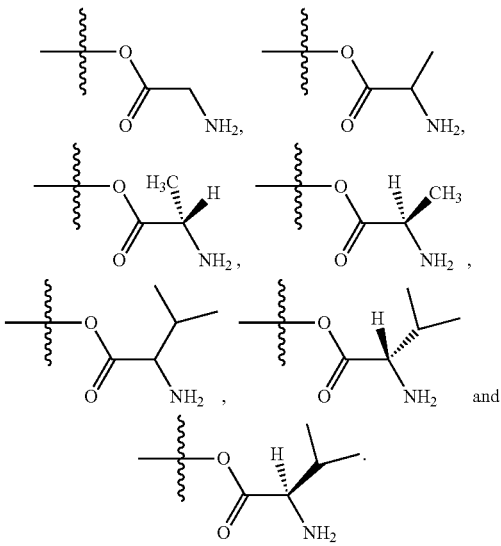

In some embodiments, $R^{14}$ can be hydrogen. In other embodiments, $R^{14}$ can be deuterium. In still other embodiments, $R^{14}$ can be an unsubstituted $C_{1-4}$ alkyl such as those described herein. In some embodiments, $R^{14}$ can be methyl.

Formula (II) includes a 5-membered ring that can be unsubstituted or substituted with an unsubstituted $C_{1-4}$ alkyl, cyano and/or an unsubstituted $C_{1-4}$ haloalkyl. In some embodiments, $R^{15}$ can be hydrogen. In other embodiments, $R^{15}$ can be deuterium. In still other embodiments, $R^{15}$ can be an unsubstituted $C_{1-4}$ alkyl (for example, methyl, ethyl, n-propyl, iso-propyl, n-butyl, iso-butyl or tert-butyl). In some embodiments, $R^{16}$ can be hydrogen. In other embodiments, $R^{16}$ can be deuterium. In still other embodiments, $R^{16}$ can be halogen (for example, F or Cl). In yet still other embodiments, $R^{16}$ can be an unsubstituted $C_{1-4}$ alkyl such as those described herein. In some embodiments, $R^{16}$ can be cyano. In other embodiments, $R^{16}$ can be an unsubstituted $C_{1-4}$ haloalkyl, such as CF$_3$. In still other embodiments, $R^{16}$ can be an unsubstituted $C_{3-8}$ monocyclic cycloalkyl. In some embodiments, $R^{15}$ can be methyl; and $R^{16}$ can be hydrogen.

The —C(=O)NR$^{17}$R$^{18}$ moiety of Formula (II) can include a substituted phenyl or a substituted pyridyl as described herein. In some embodiments, $R^{17}$ can be a substituted phenyl, wherein the phenyl can be substituted with one or more substituents independently selected from halogen, cyano, an unsubstituted $C_{1-4}$ haloalkyl and an unsubstituted $C_{1-4}$ alkyl. In other embodiments, $R^{17}$ can be a substituted pyridyl, wherein the pyridyl can be substituted with one or more substituents independently selected from halogen, cyano, an unsubstituted $C_{1-4}$ haloalkyl and an unsubstituted $C_{1-4}$ alkyl. The phenyl and pyridyl of $R^{17}$ can be substituted with one or more substituents as described herein. In some embodiments, $R^{17}$ can be a mono-substituted phenyl. In other embodiments, $R^{17}$ can be a di-substituted phenyl. In some embodiments, the phenyl of $R^{17}$ can be substituted at the para-position and/or meta-position. In some embodiments, the phenyl of $R^{17}$ can be a 3,4-disubstituted phenyl. In still other embodiments, $R^{17}$ can be a mono-substituted pyridyl. In yet still other embodiments, $R^{17}$ can be a di-substituted pyridyl. In some embodiments, the pyridyl can be substituted on a carbon adjacent to the nitrogen of the pyridyl. The unsubstituted $C_{1-4}$ alkyl(s) that can be substituted on $R^{17}$ can be methyl, ethyl, n-propyl, iso-propyl, n-butyl, iso-butyl or tert-butyl. Examples of unsubstituted $C_{1-4}$ haloalkyls are $CF_3$, $CHF_2$ and $CH_2F$. In some embodiments, $R^{17}$ can be substituted with F and/or Cl. In some embodiments, $R^{17}$ can be substituted with F, $C_1$ and/or Br. In some embodiments, $R^{17}$ can be substituted with $CF_3$. In some embodiments, $R^{17}$ can be substituted with $CH_3$. When $R^{17}$ is di-substituted, the two groups can be the same or different. In some embodiments, $R^{17}$ cannot be substituted with 2 fluoros. For example, in some embodiments, $R^{17}$ cannot be 3,4-difluorophenyl.

As described herein, $R^{18}$ group of —C(=O)NR$^{17}$R$^{18}$ can be hydrogen, deuterium or an unsubstituted $C_{1-4}$ alkyl. In some embodiments, $R^{18}$ can be hydrogen. In other embodiments, $R^{18}$ can be deuterium. In still other embodiments, $R^{18}$ can be an unsubstituted $C_{1-4}$ alkyl.

Some examples of compounds of Formula (II), including pharmaceutically acceptable salts thereof, include the following:

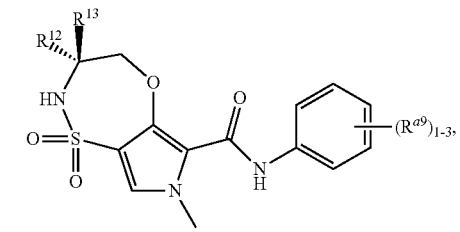

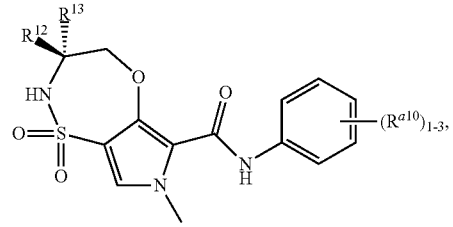

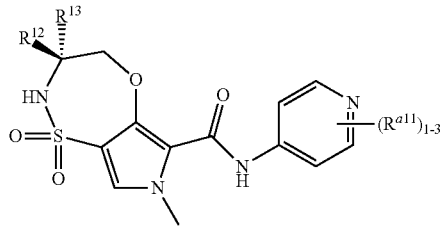

and

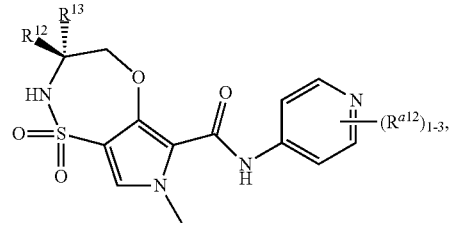

wherein each $R^{a9}$, each $R^{a10}$, each $R^{a11}$ and each $R^{a12}$ are independently selected from methyl, ethyl, n-propyl, iso-propyl, n-butyl, iso-butyl, tert-butyl, cyano, $CF_3$, $CHF_2$, $CH_2F$, F, Cl and Br.

In some embodiments, when $R^{12}$ is an unsubstituted 2-butynyl, $R^{13}$ is hydrogen, $R^{14}$ and $R^{18}$ are each hydrogen, $R^{15}$ is methyl and $R^{16}$ is hydrogen, then $R^{17}$ cannot be 3,4-difluorophenyl. In some embodiments, a compound of Formula (II) cannot be

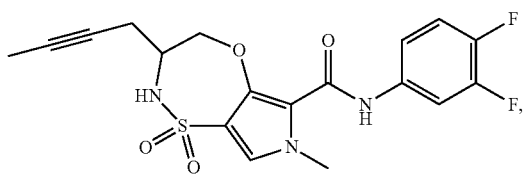 [SMILES: CC#CCC1COc2c(cn(C)c2C(=O)Nc2ccc(F)c(F)c2)S(=O)(=O)N1]

or a pharmaceutically acceptable salt thereof. In some embodiments, a compound of Formula (II) cannot be

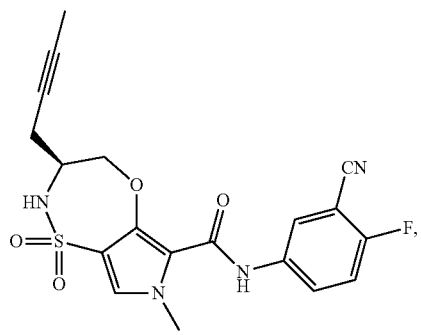 [SMILES: CC#CC[C@H]1COc2c(cn(C)c2C(=O)Nc2ccc(F)c(C#N)c2)S(=O)(=O)N1]

or a pharmaceutically acceptable salt thereof.

For Formula (I) and (II), exemplary $R^1$, $R^2$, $R^{12}$, $R^{13}$, $R^6$ and $R^{17}$ moieties include, but are not limited to, the following:

| $R^1/R^{12}$ |
| --- |

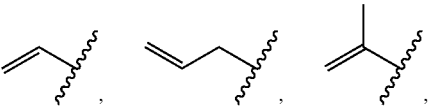

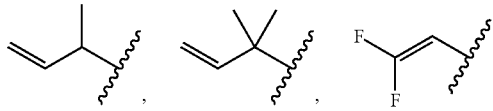

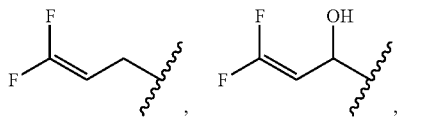 [SMILES: *CC=C(F)F ; *C(O)C=C(F)F]

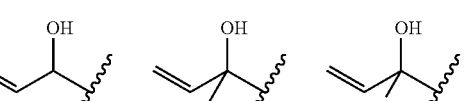

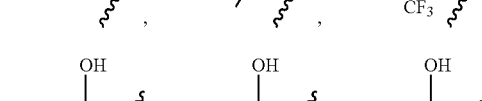

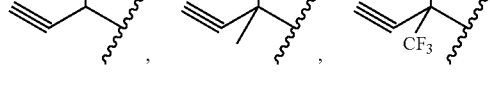

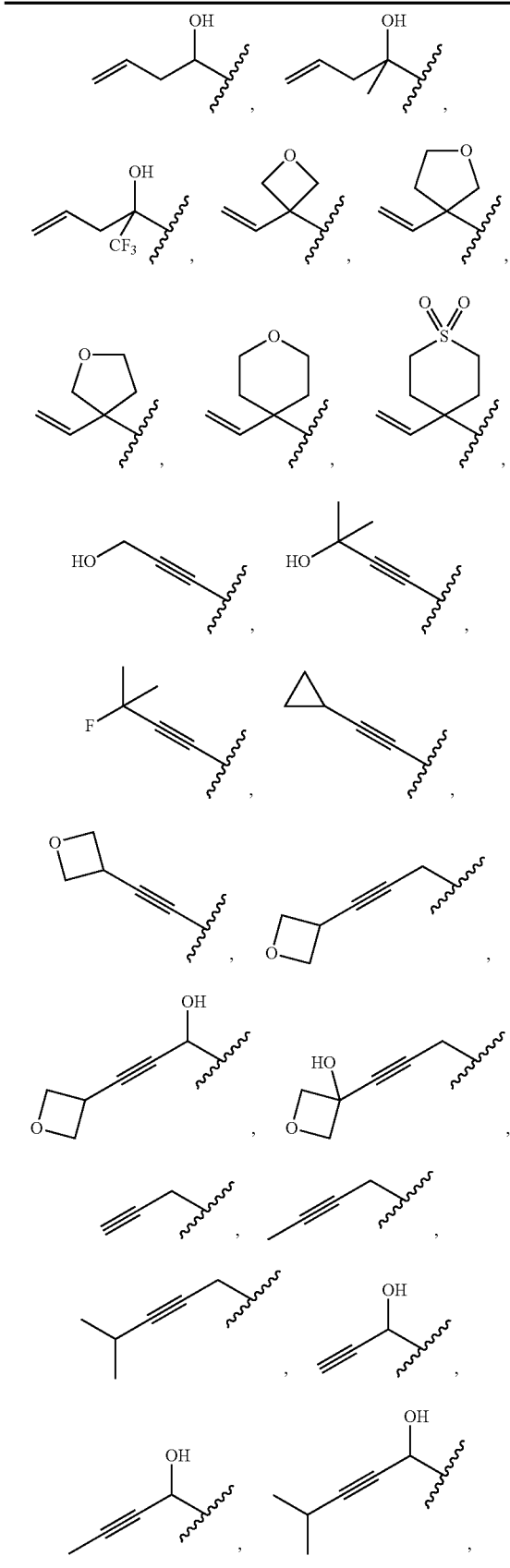
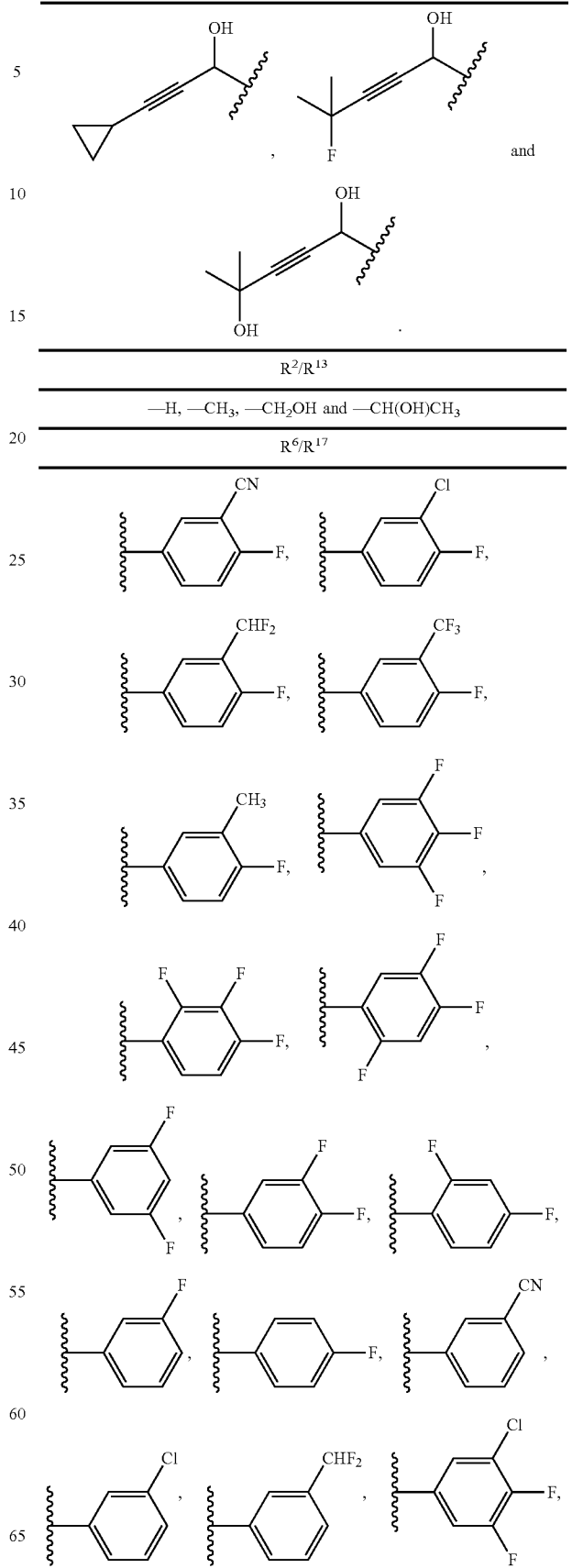
| $R^2/R^{13}$ |
|---|
| —H, —CH$_3$, —CH$_2$OH and —CH(OH)CH$_3$ |
| $R^6/R^{17}$ |

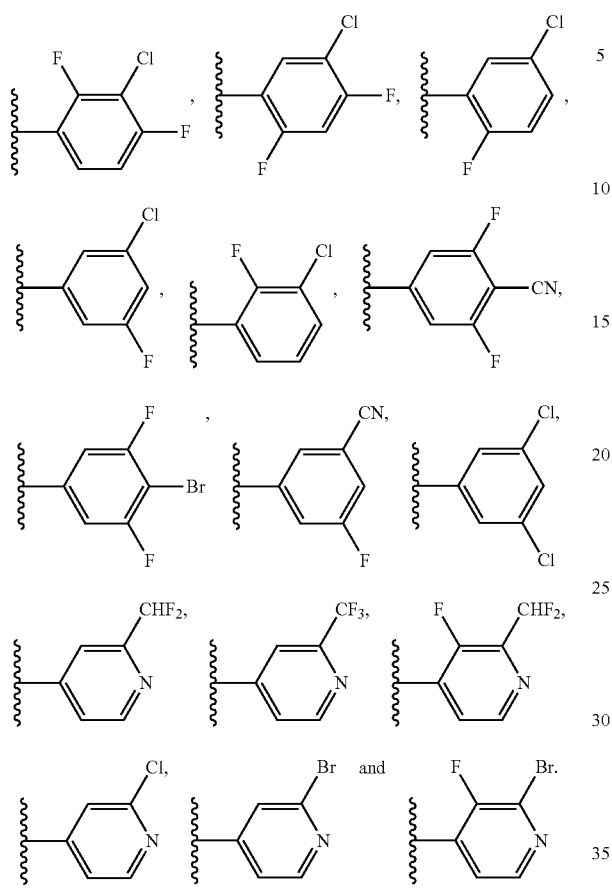
Examples of compounds of Formulae (I) and (II), or a pharmaceutically acceptable salt of any of the foregoing, include the following:
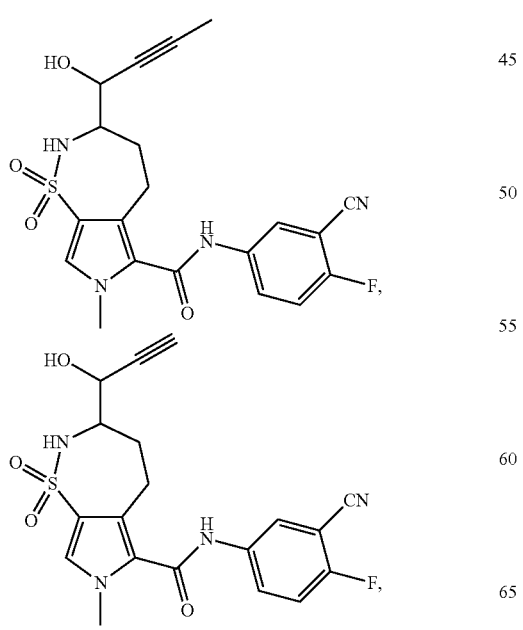
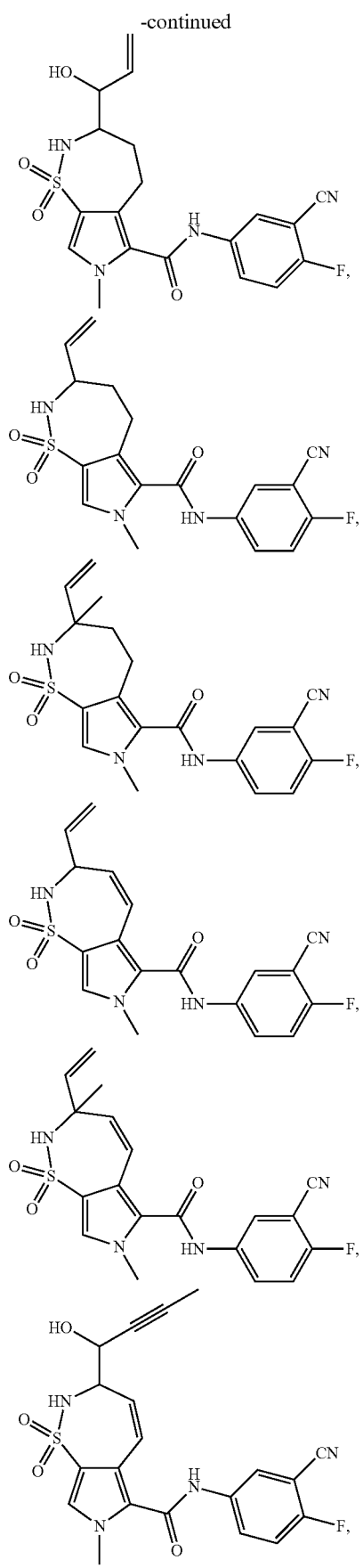

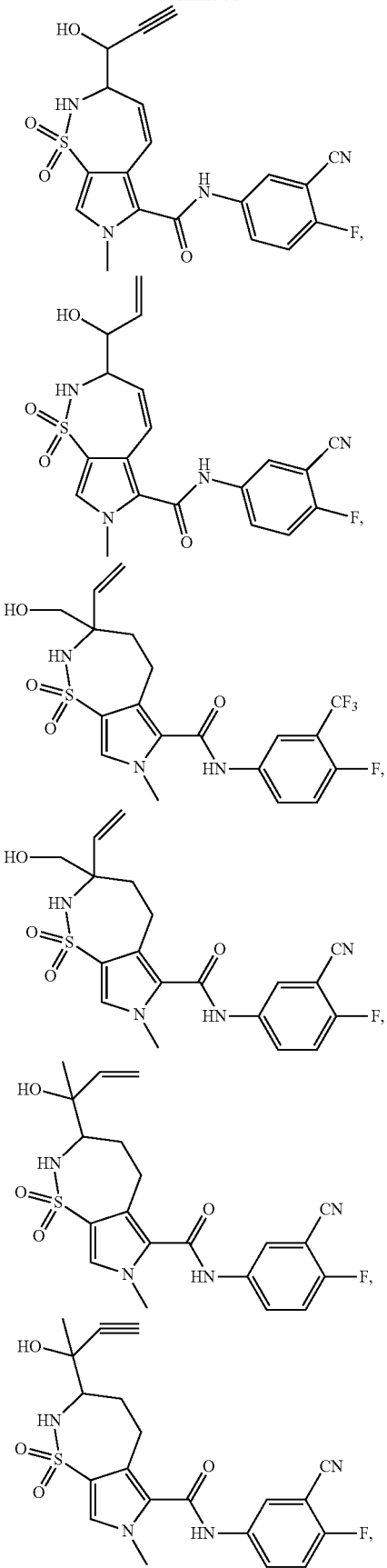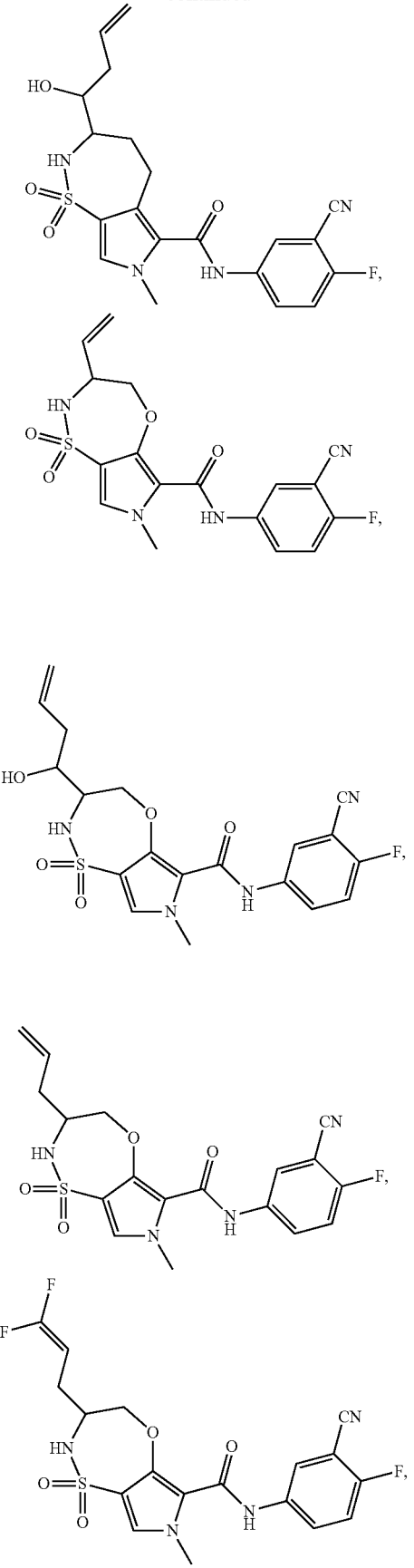

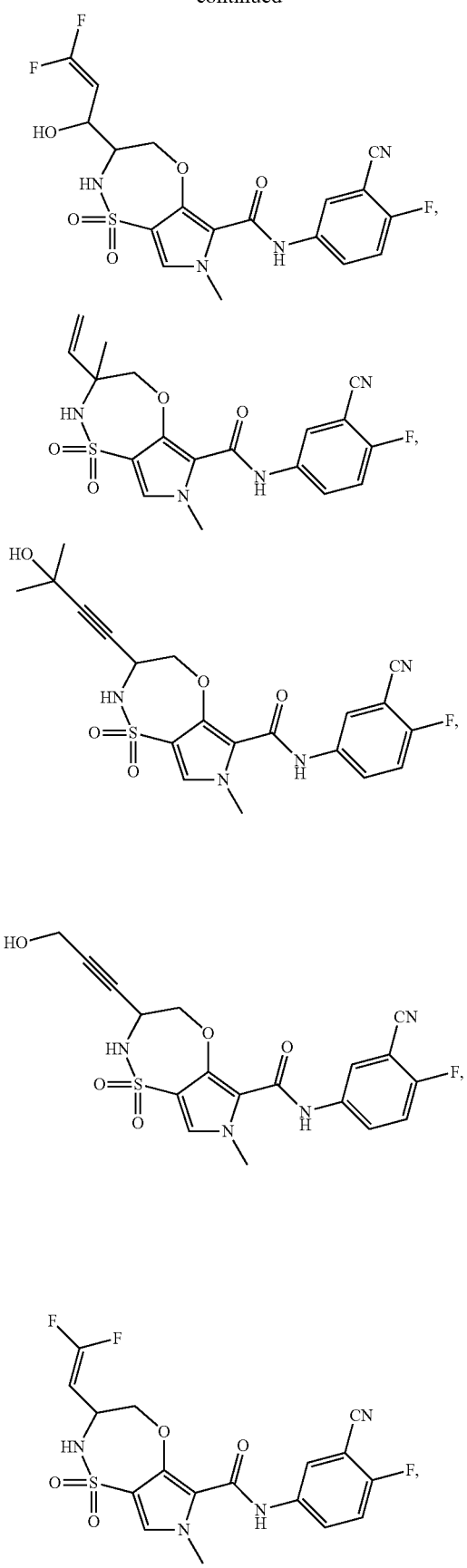
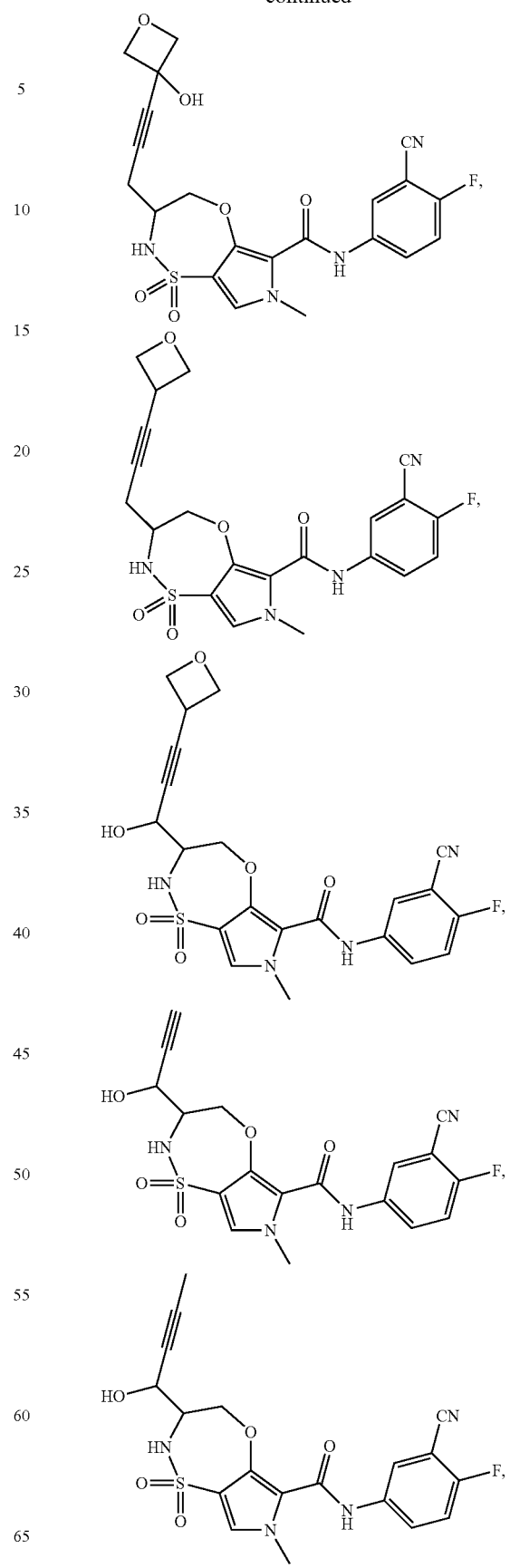

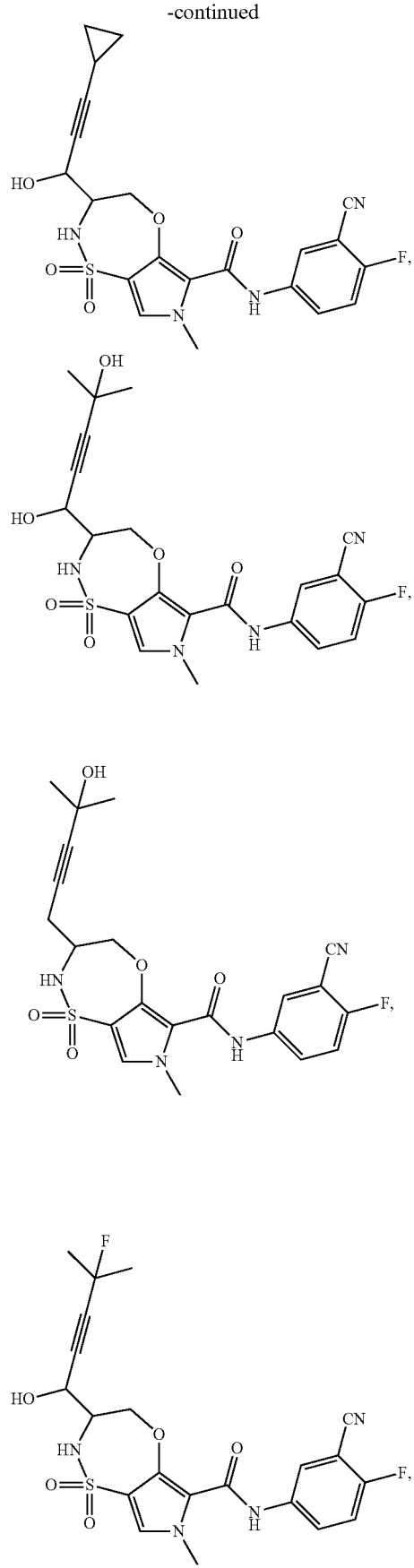
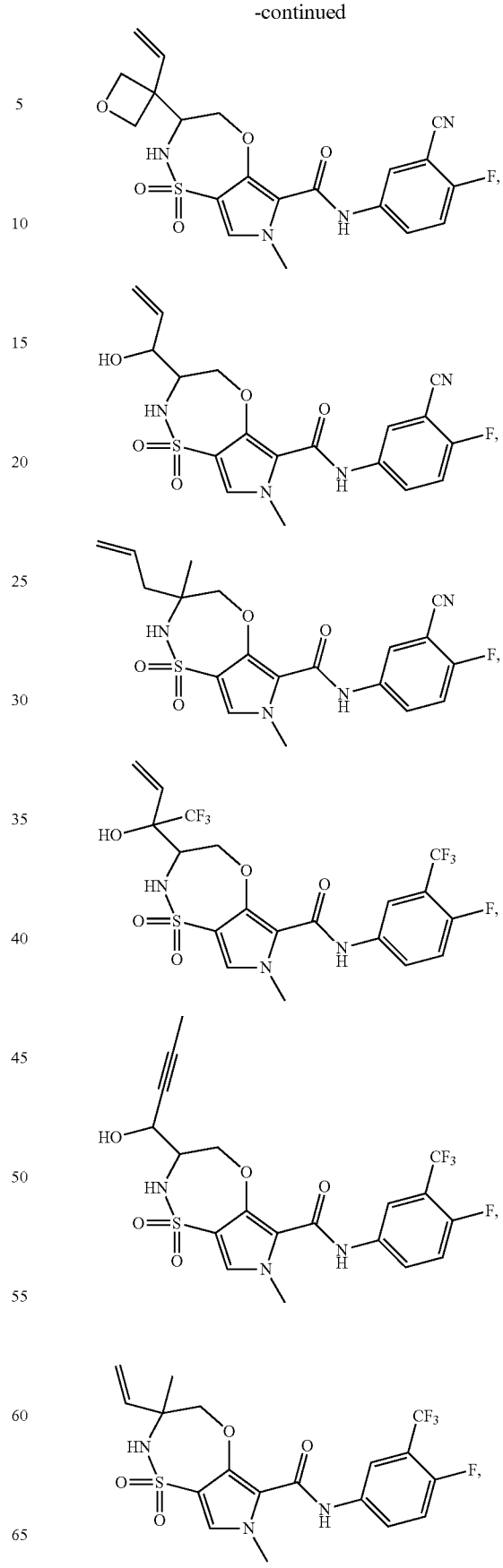

33
-continued
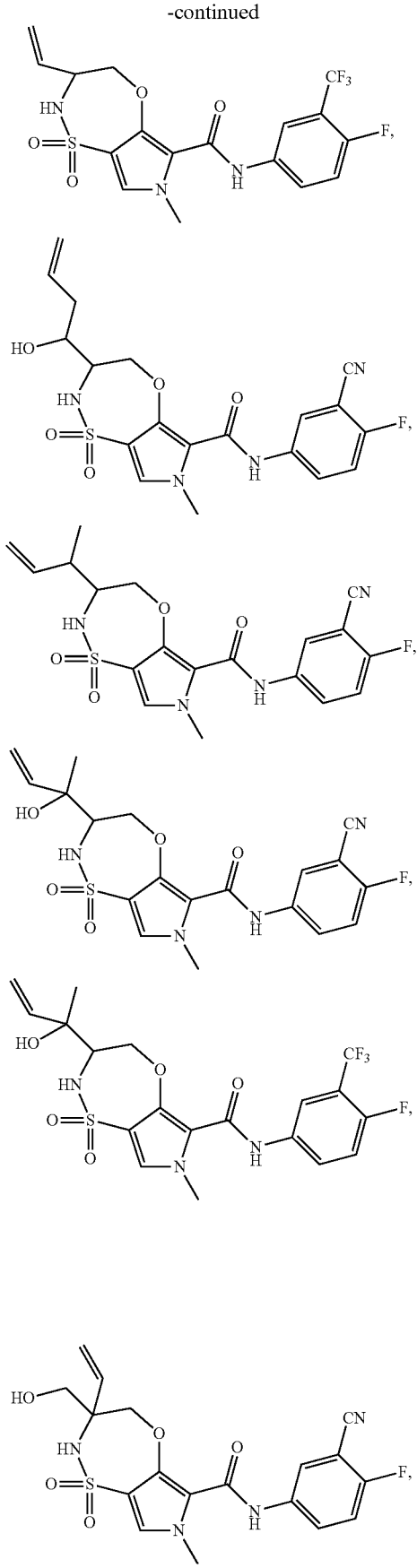
34
-continued
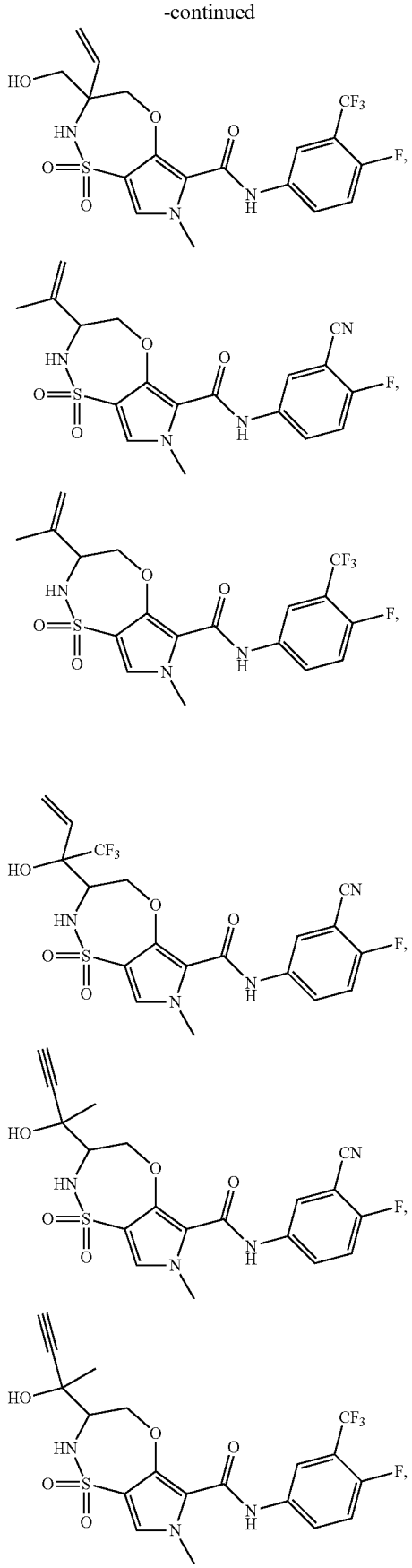

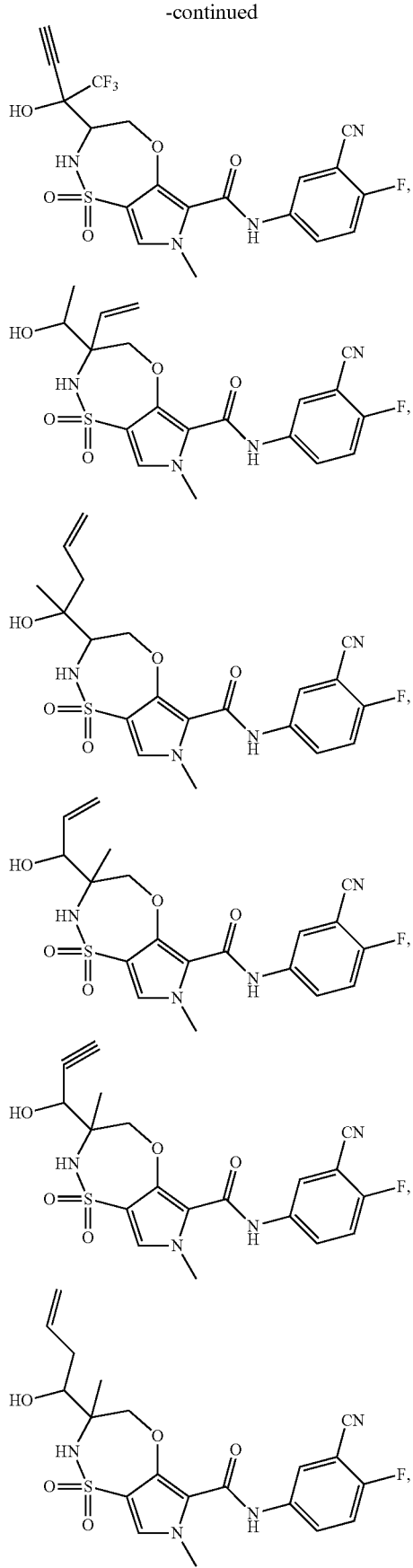
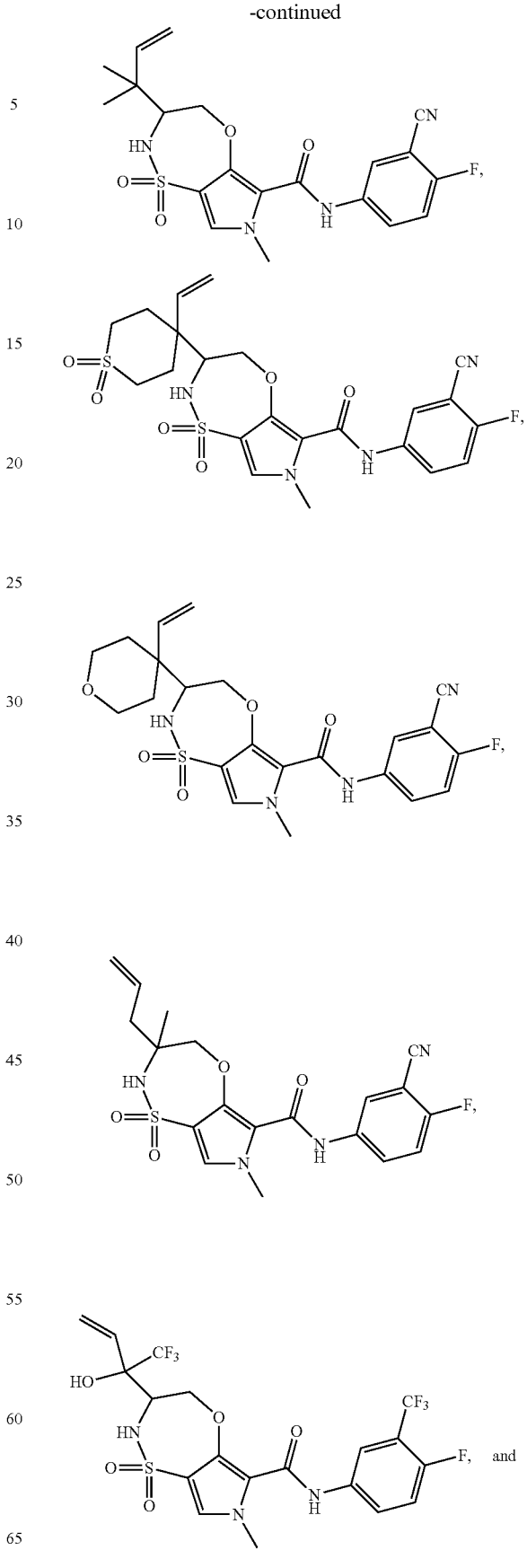

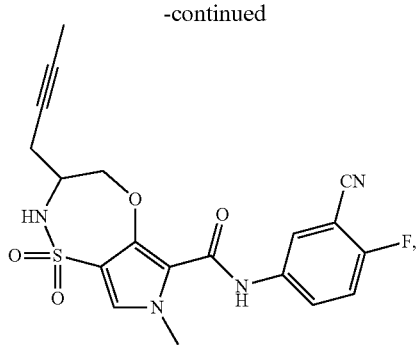
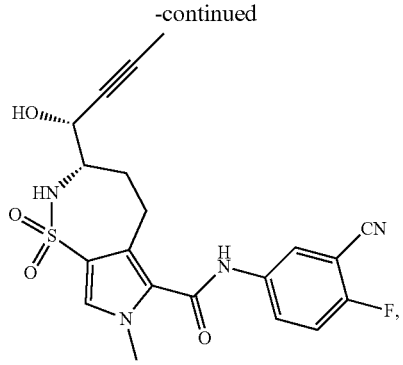
or a pharmaceutically acceptable salt of any of the foregoing.
As provided herein, Compounds of Formulae (I) and (II) may include one or more chiral centers; and therefore, the compounds may exist as enantiomers and/or diastereomers.
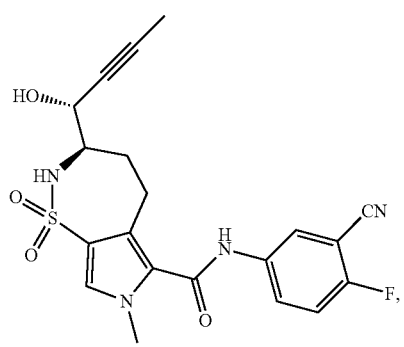
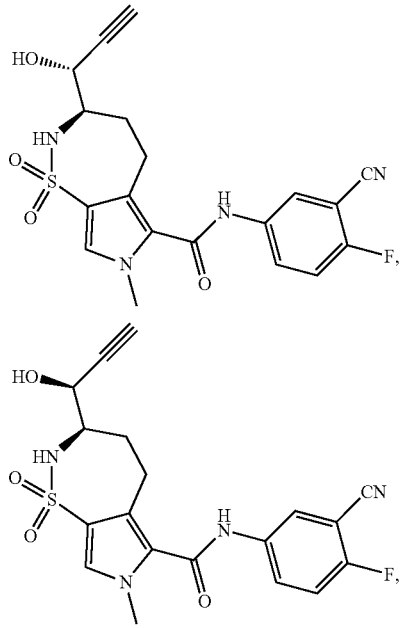
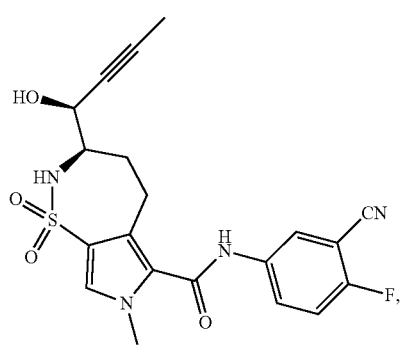
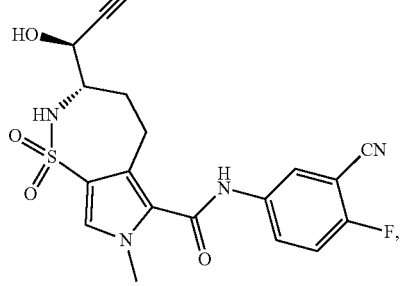
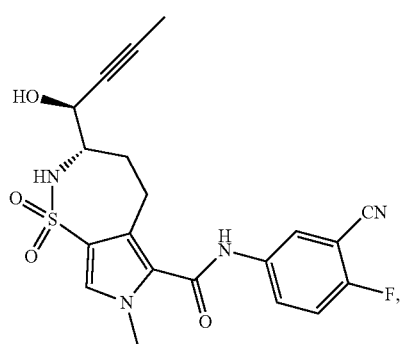
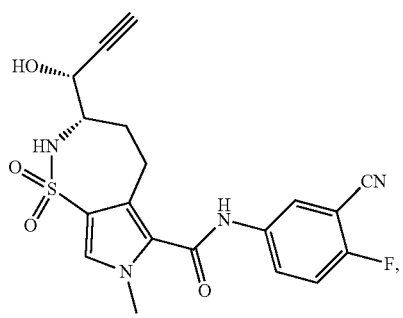

-continued

41
-continued
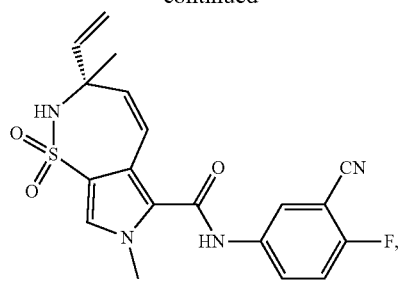
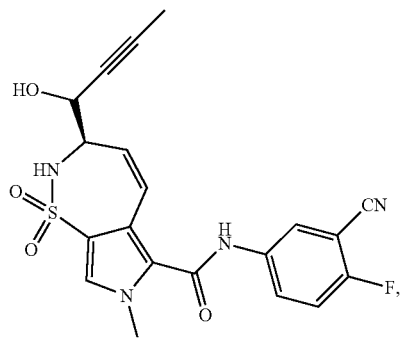
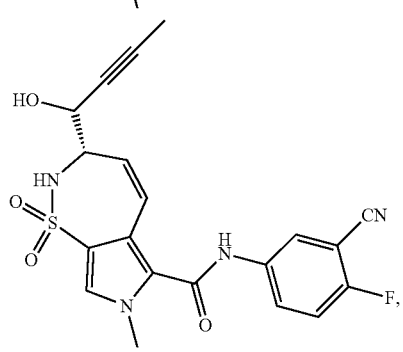
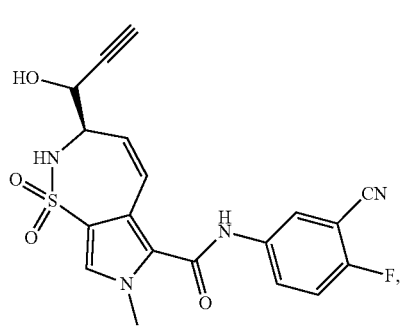
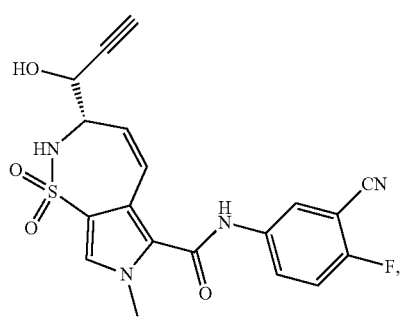
42
-continued
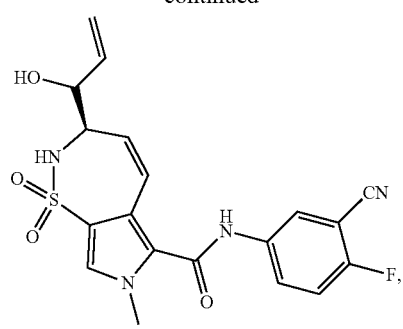
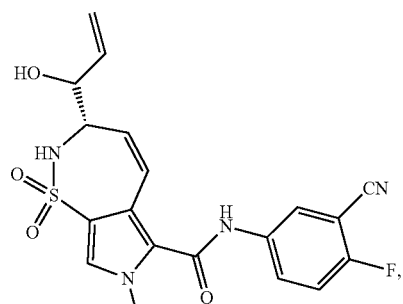
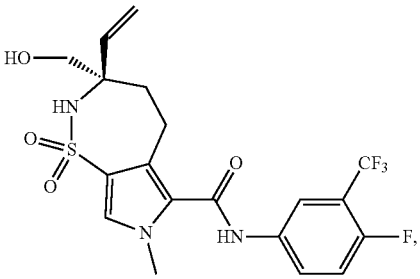
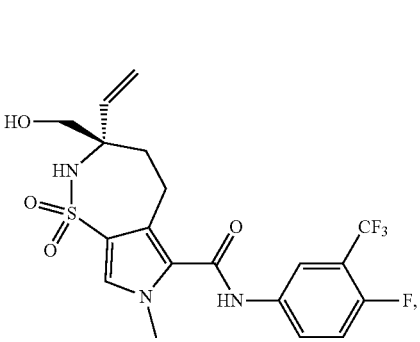
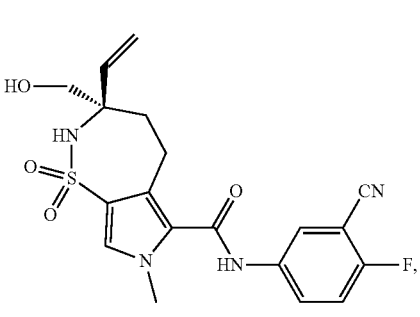

-continued
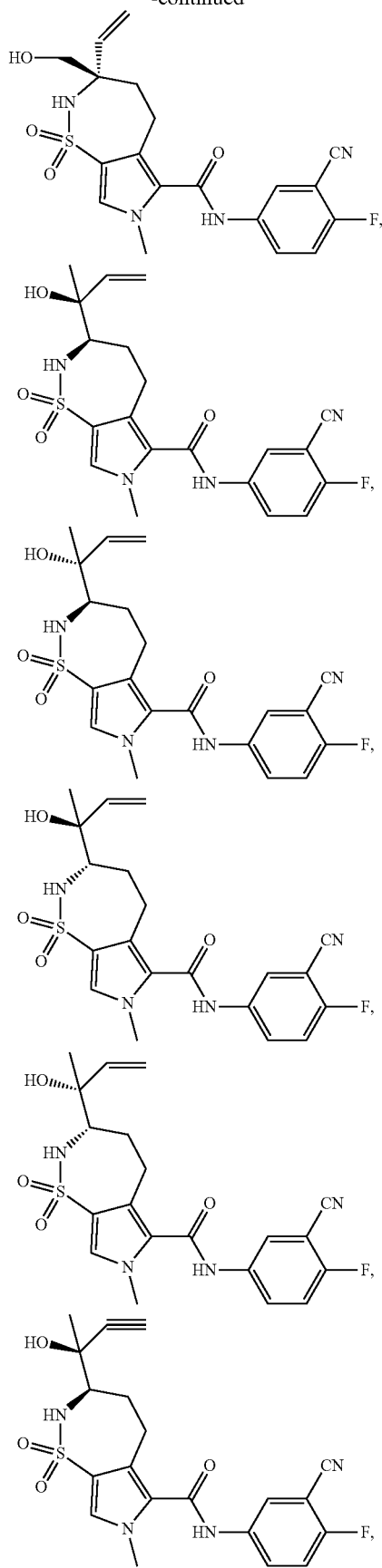
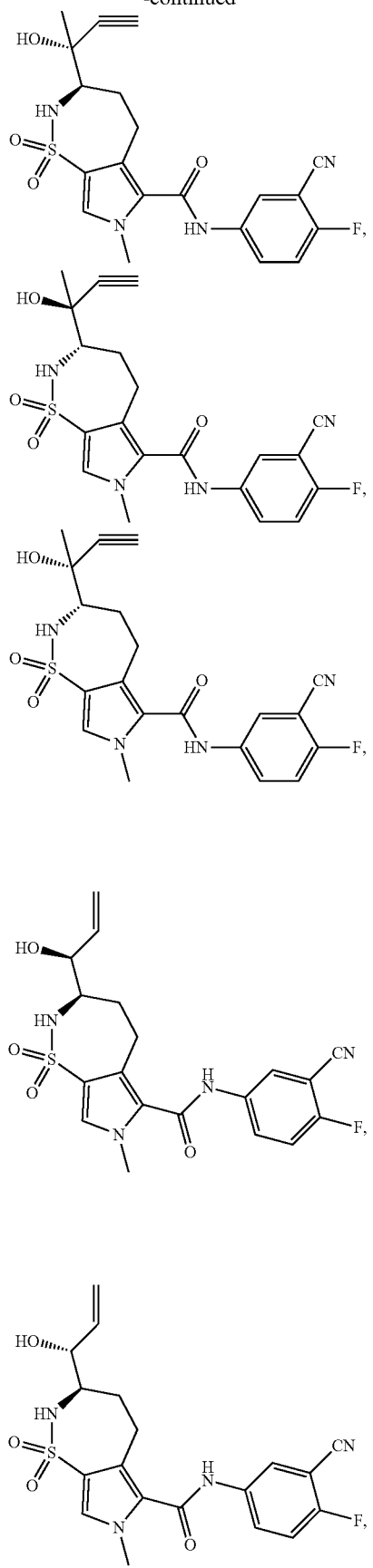

-continued
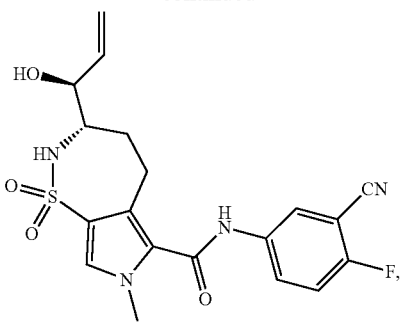
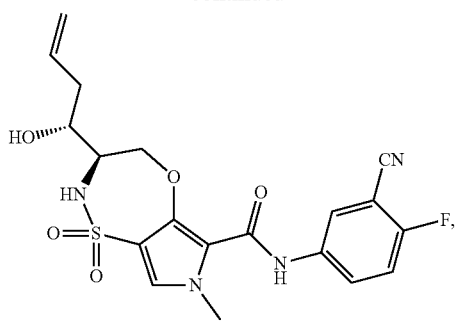
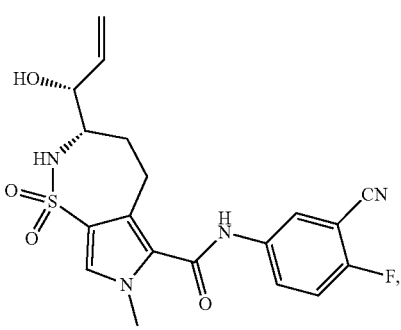
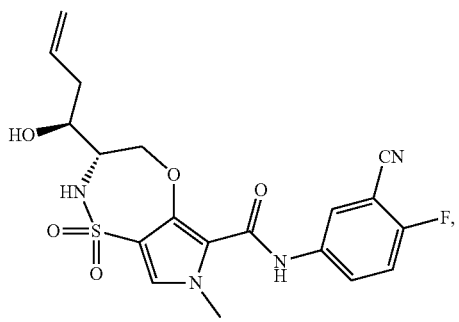
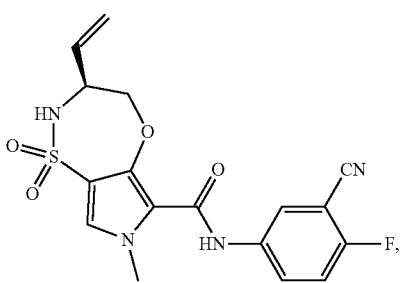
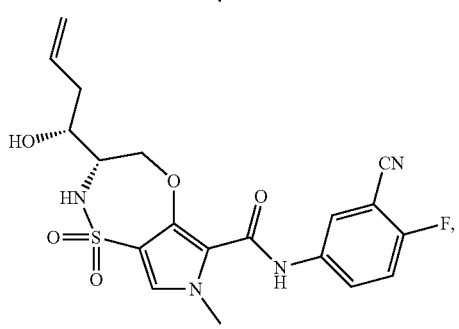
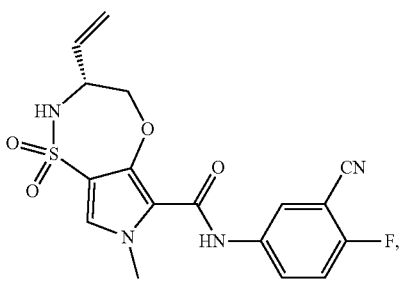
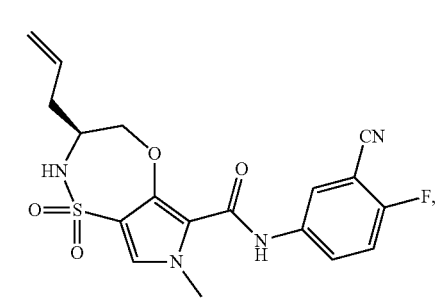
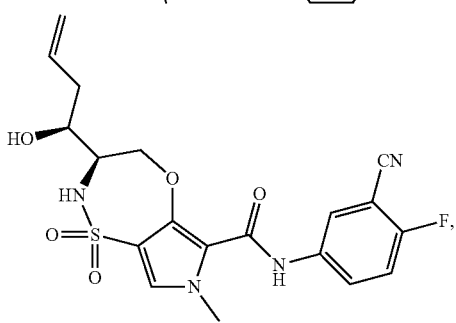
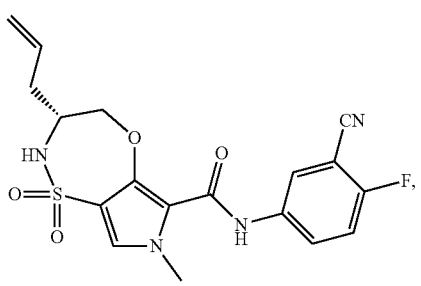

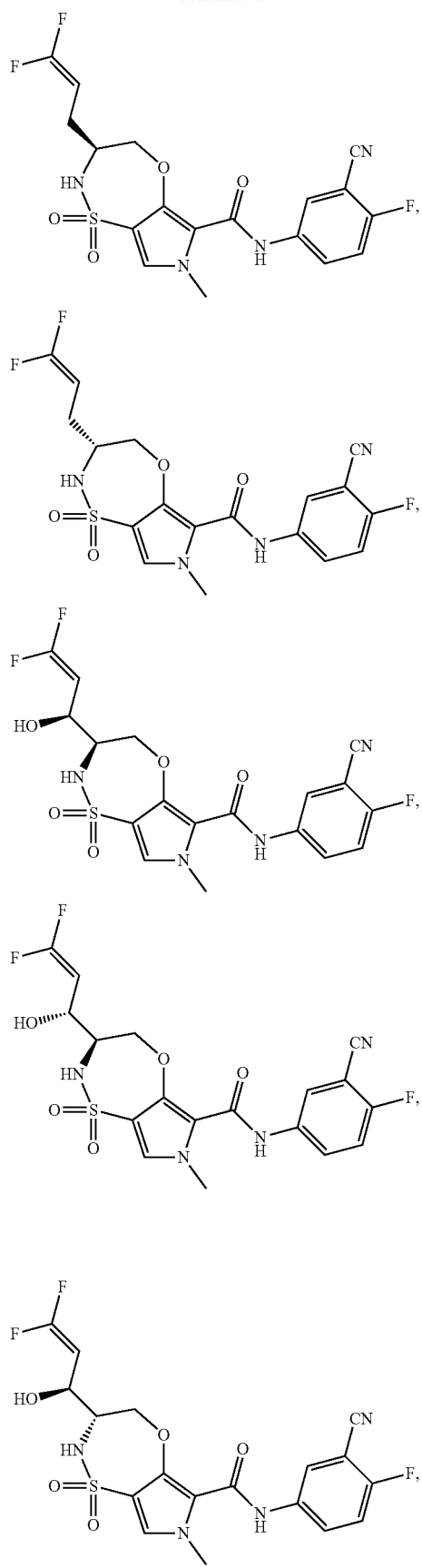
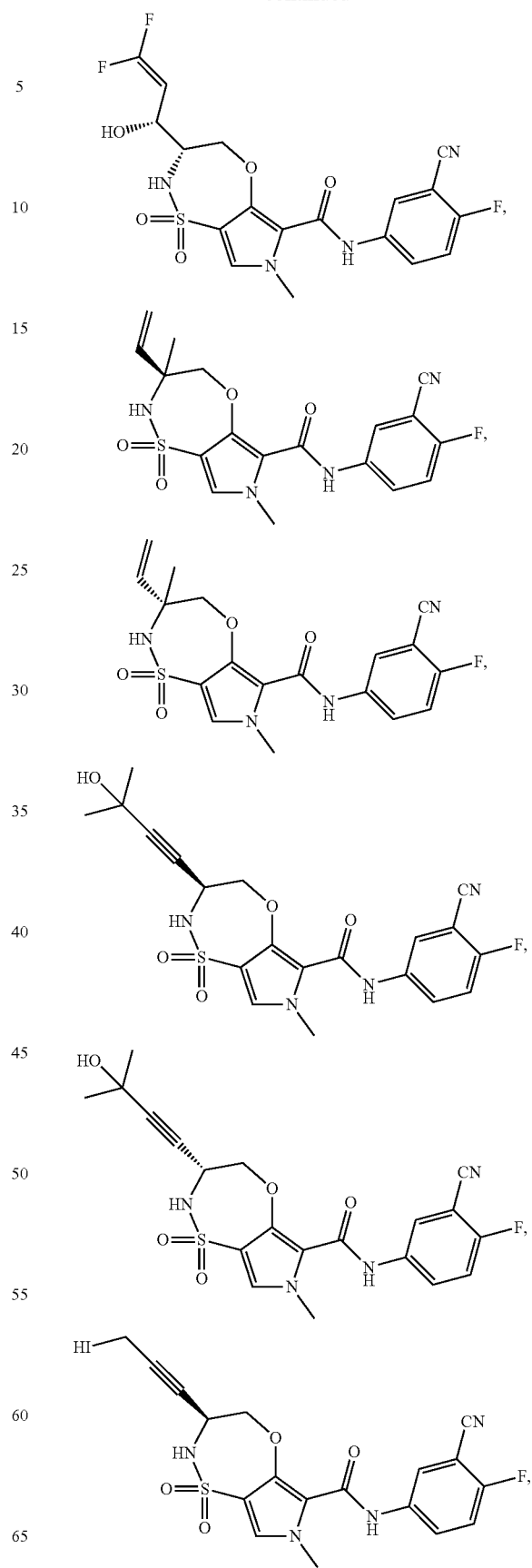

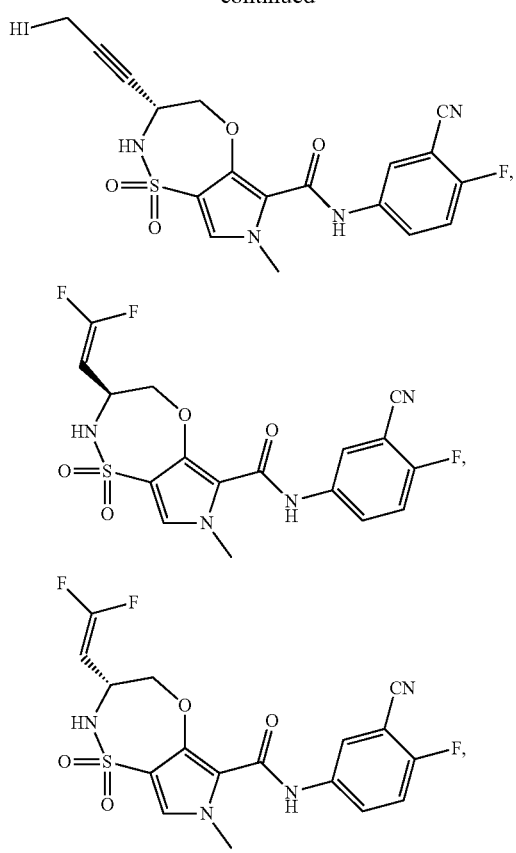
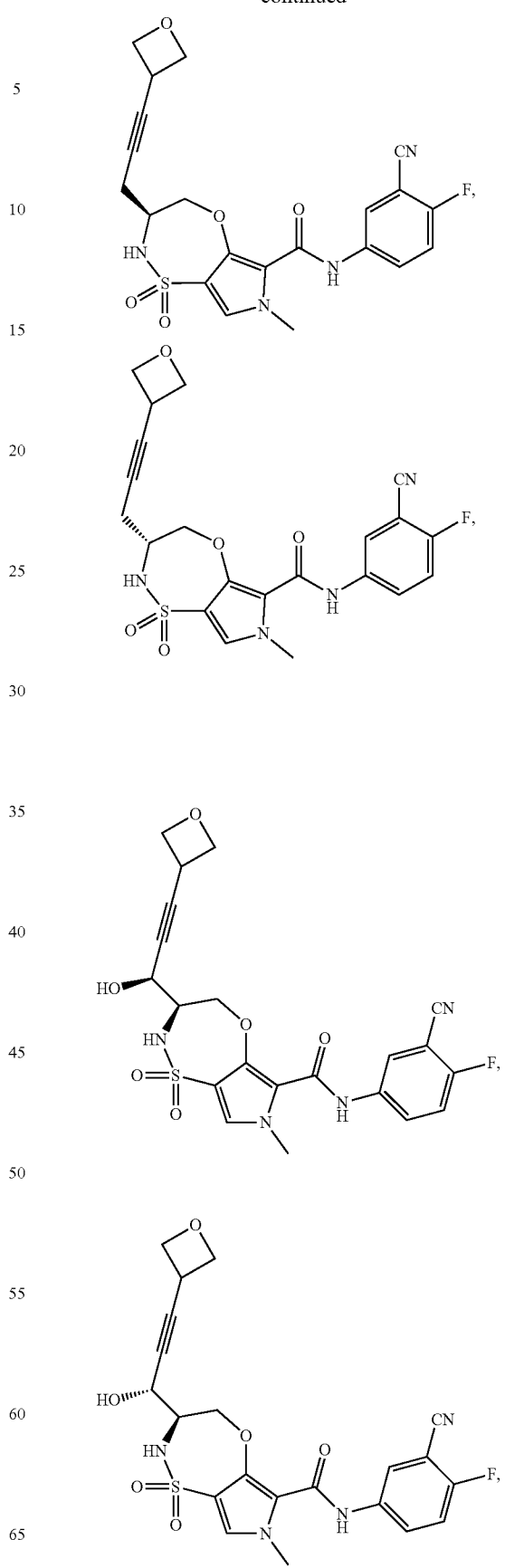

51
-continued
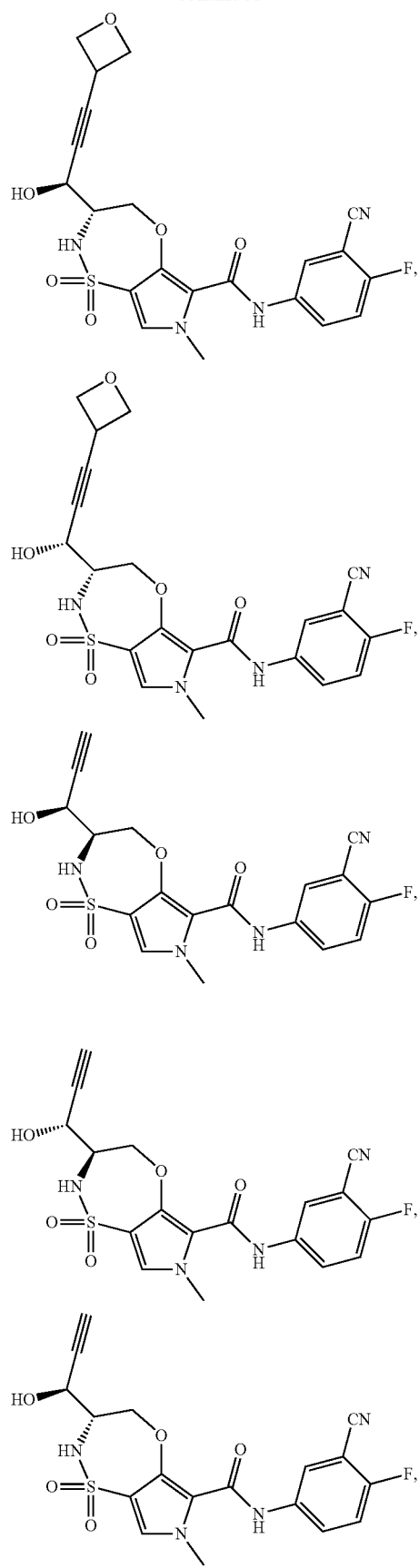
52
-continued
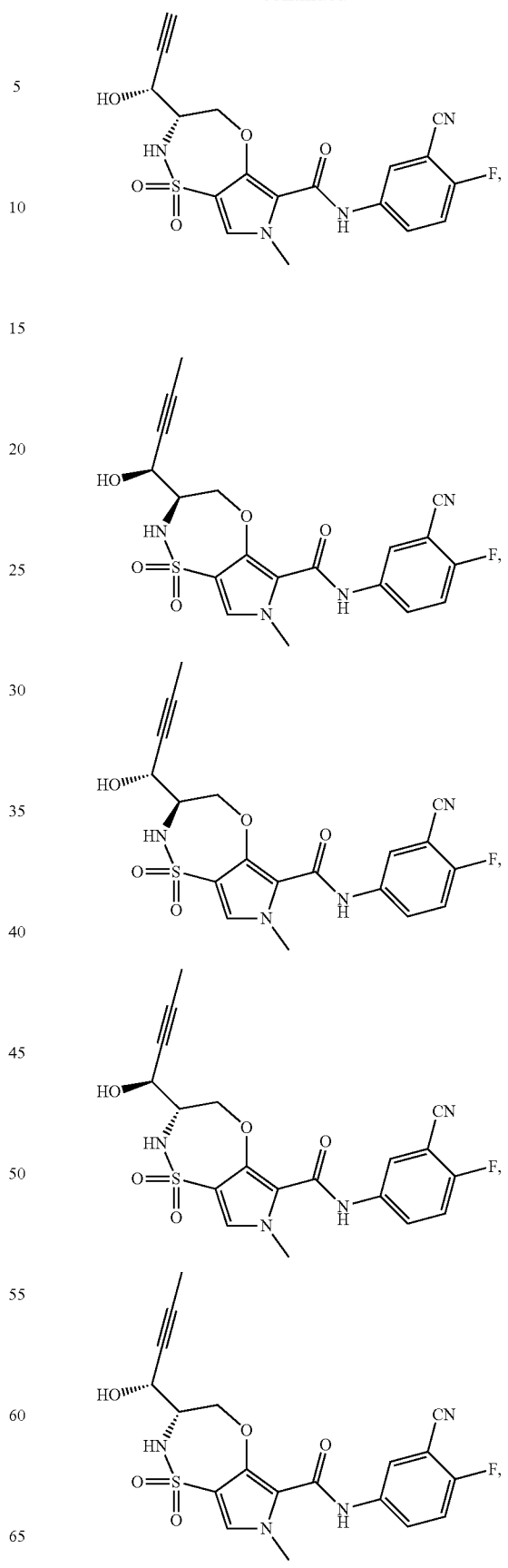

53
-continued
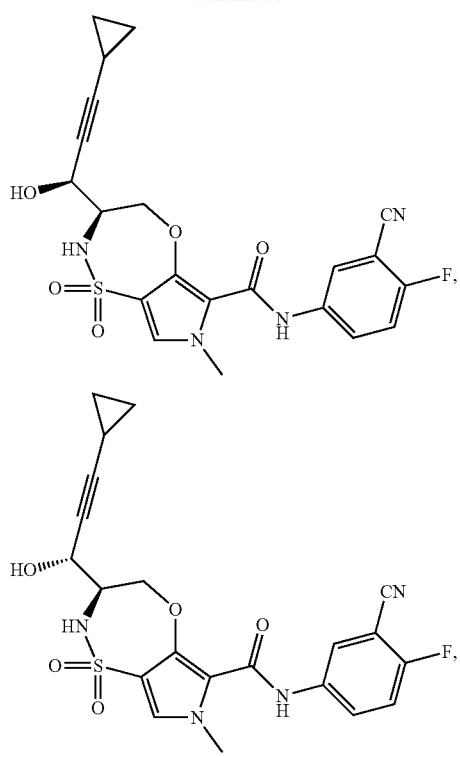
54
-continued
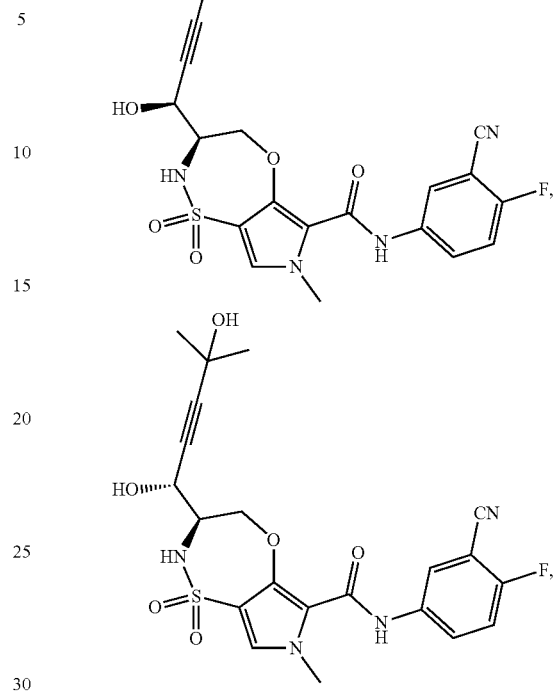
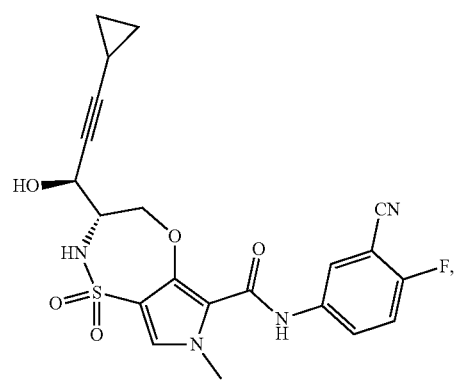
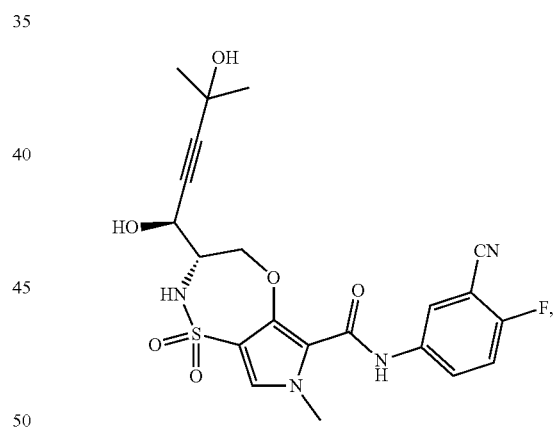
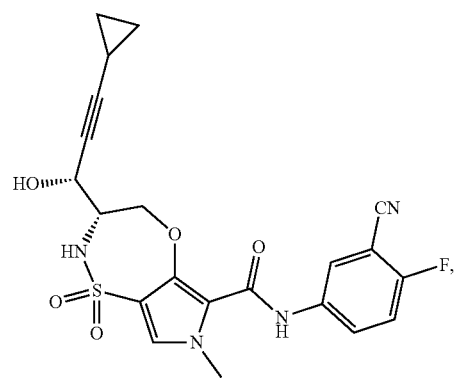
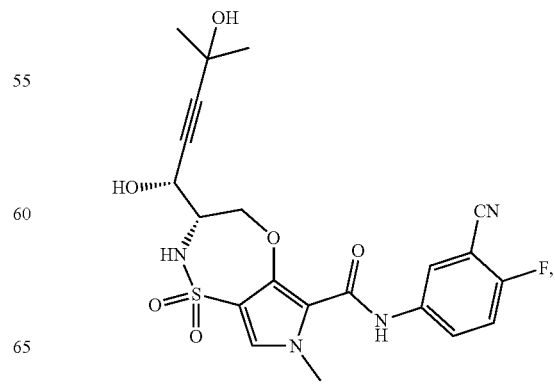

55
-continued
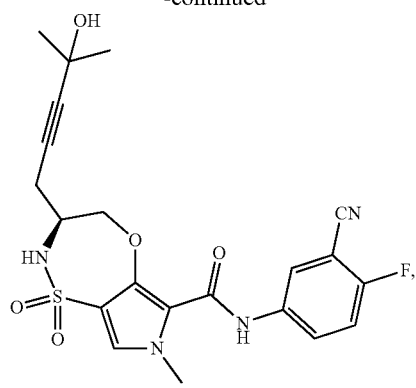
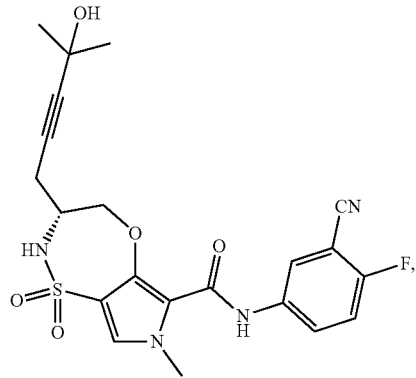
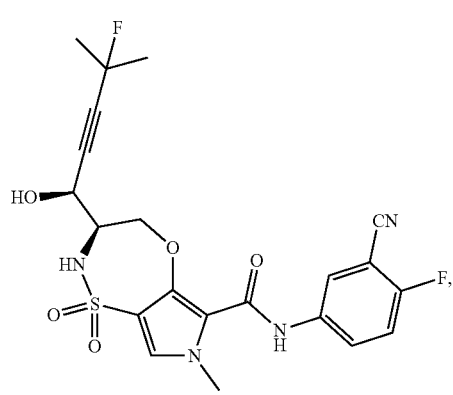
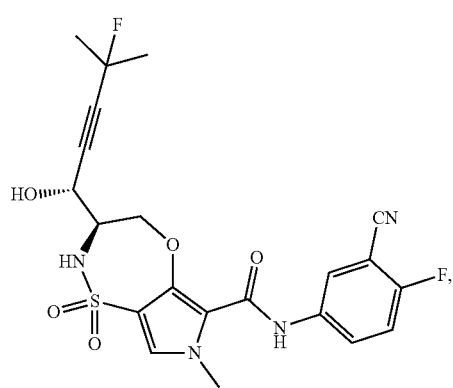
56
-continued
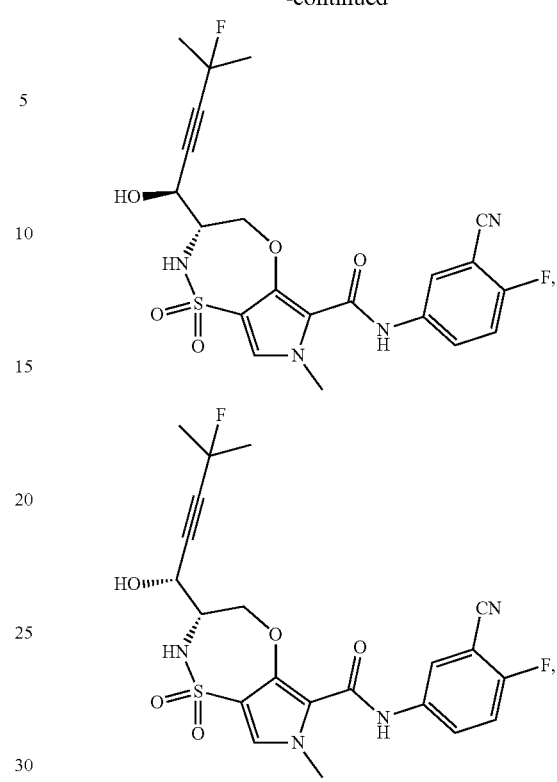
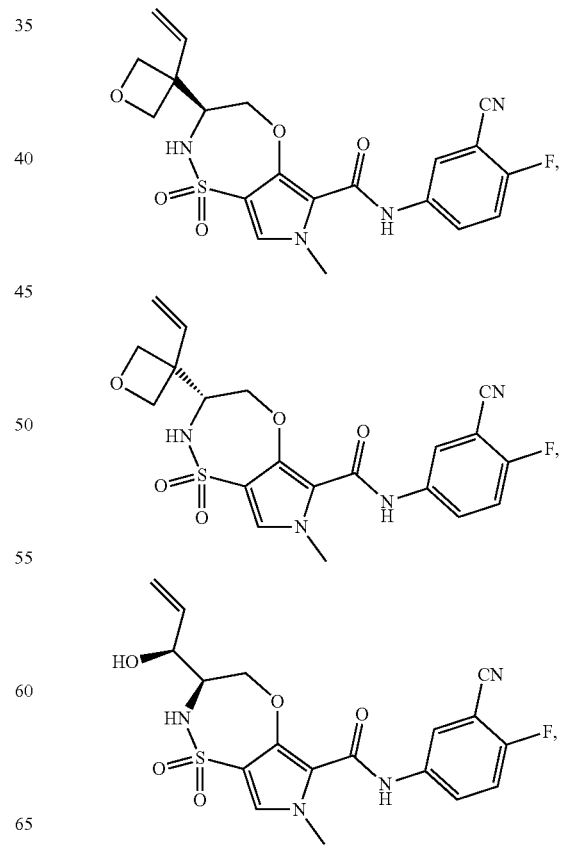

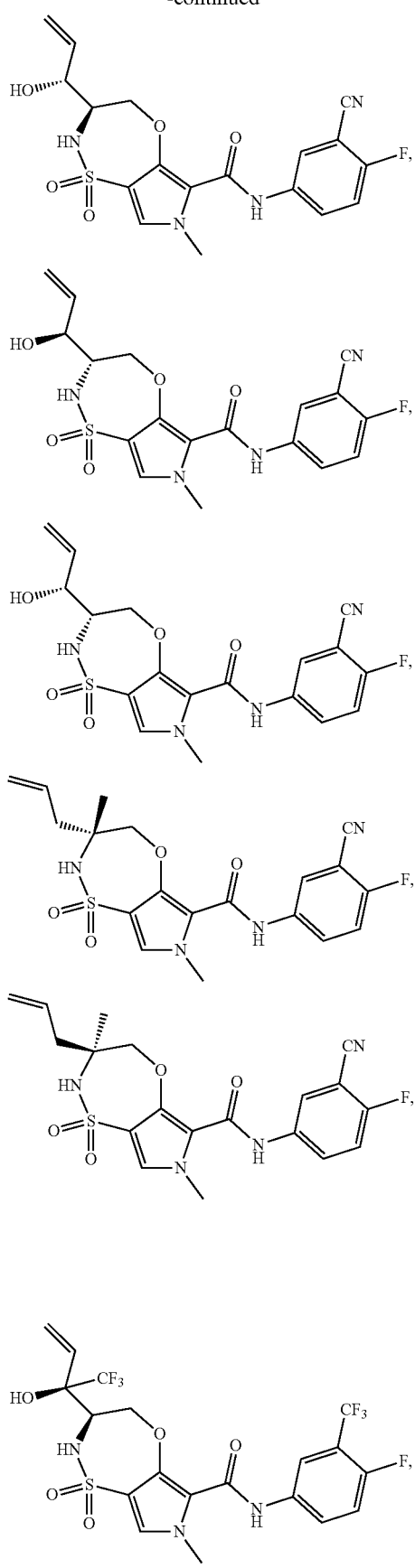
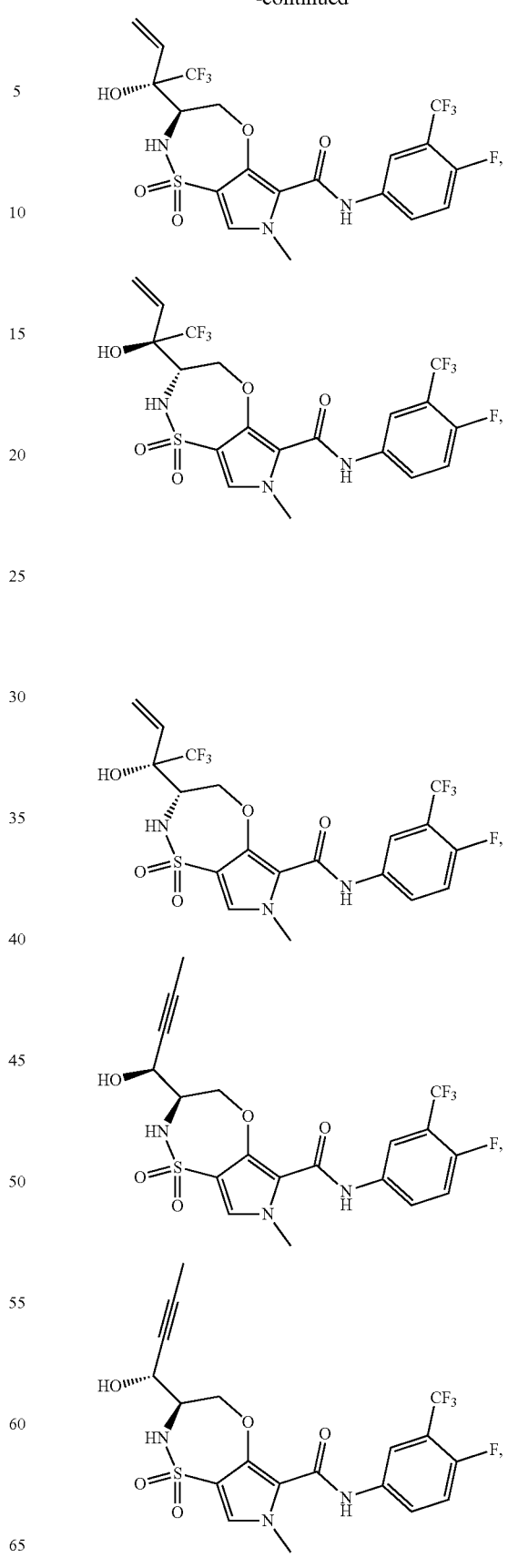

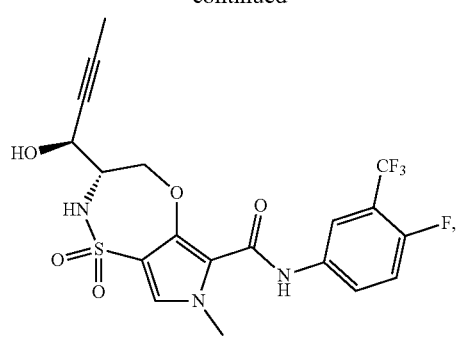
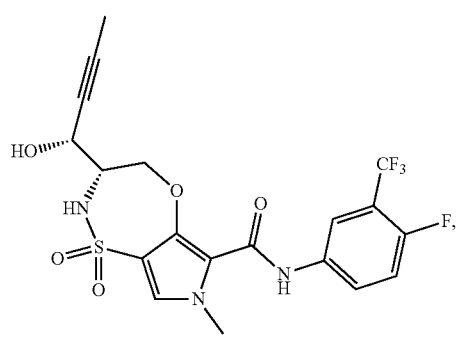
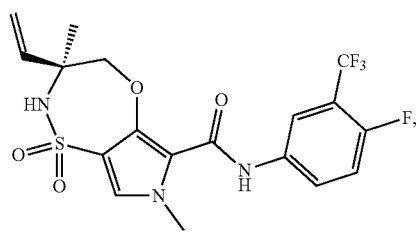
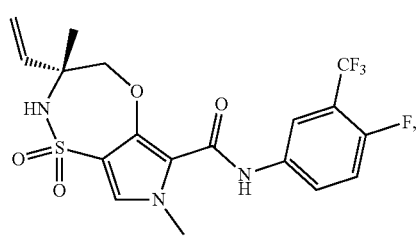
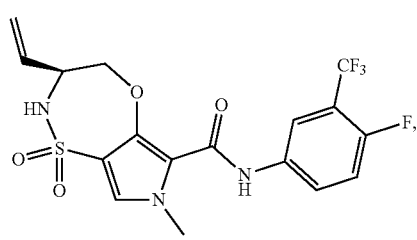
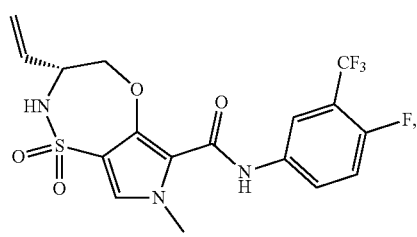
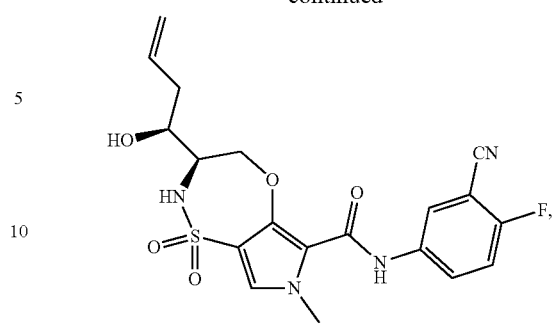
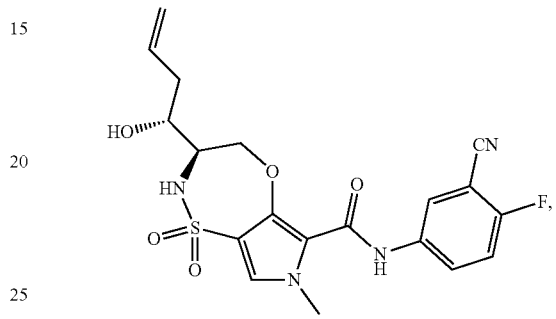
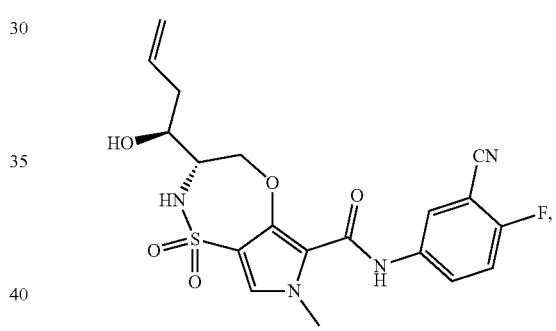
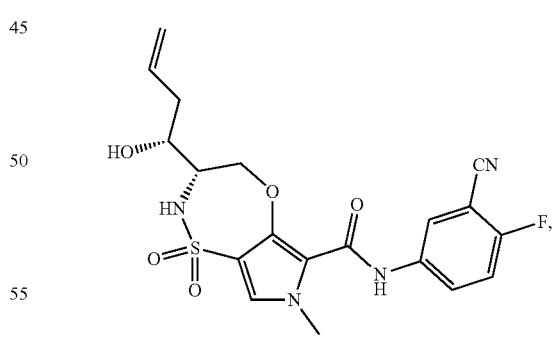
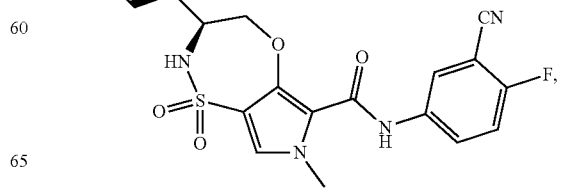

61
-continued
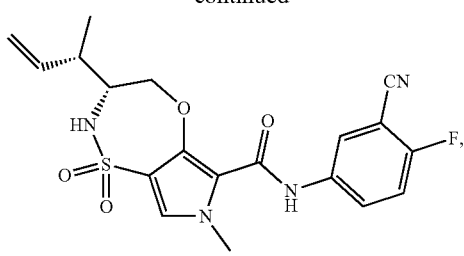
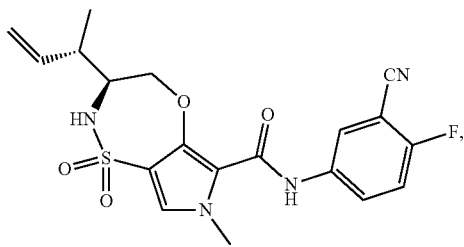
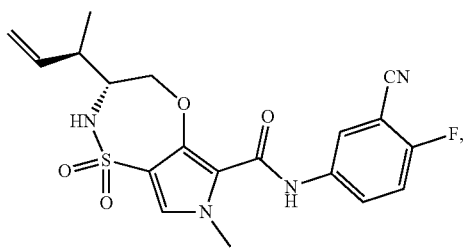
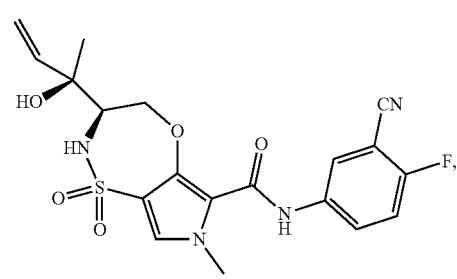
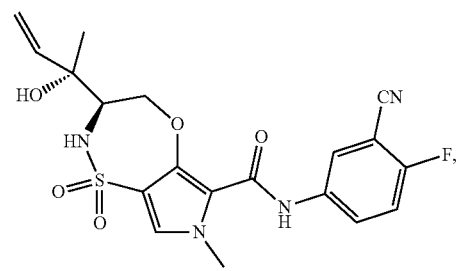
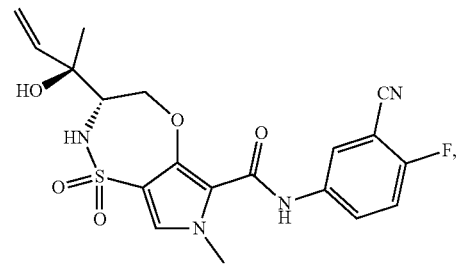
62
-continued
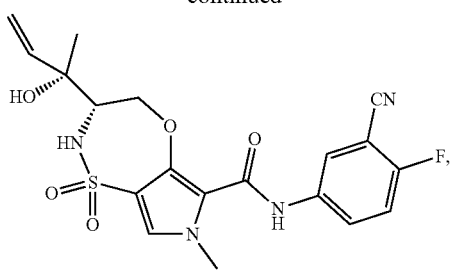
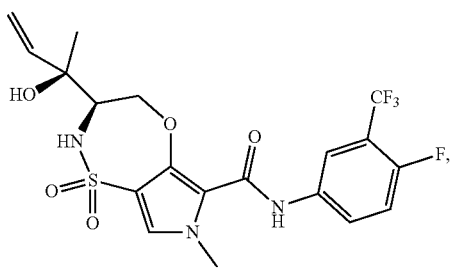
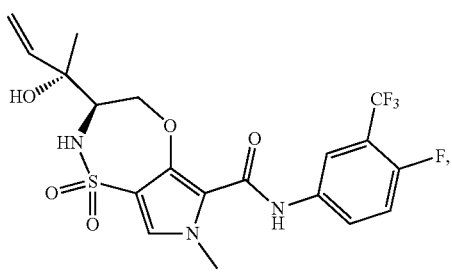
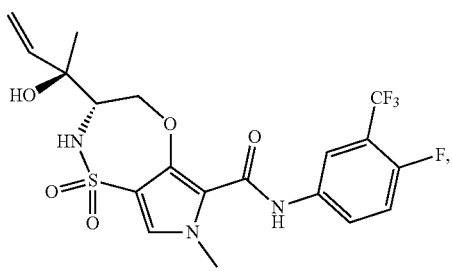
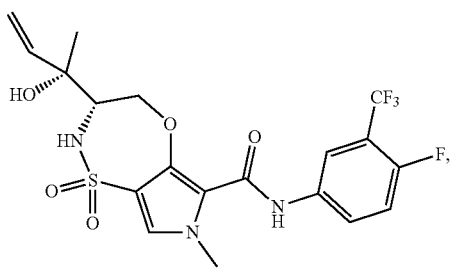
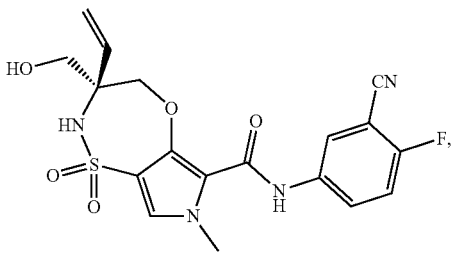

-continued
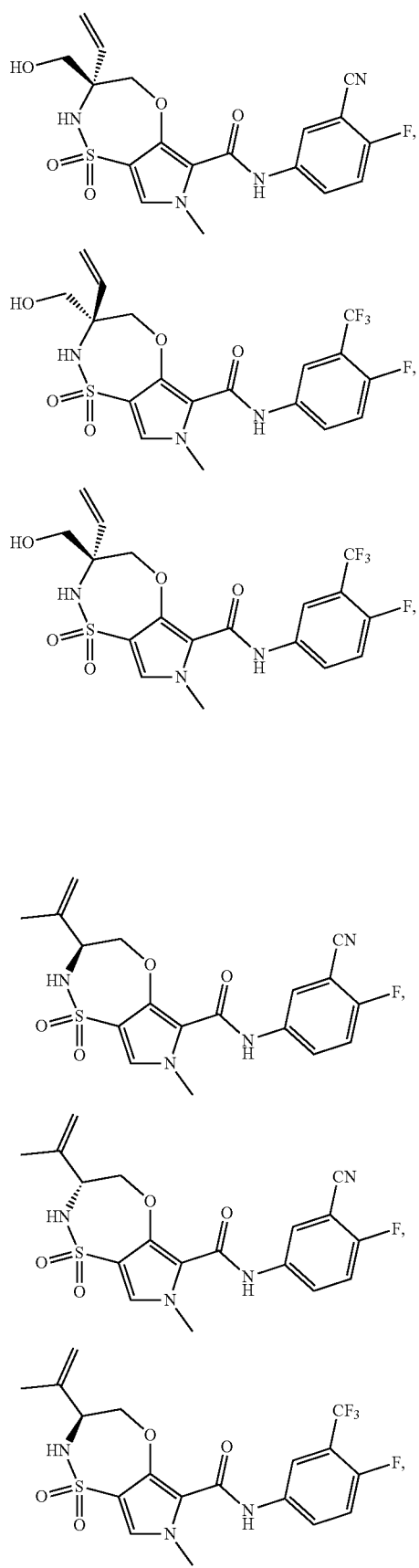
-continued
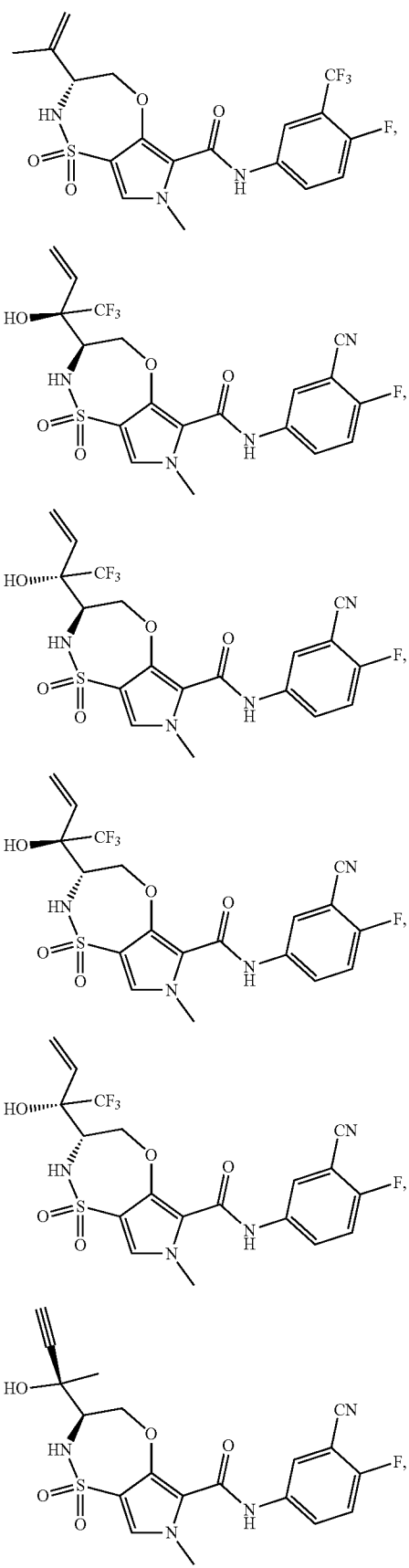

-continued
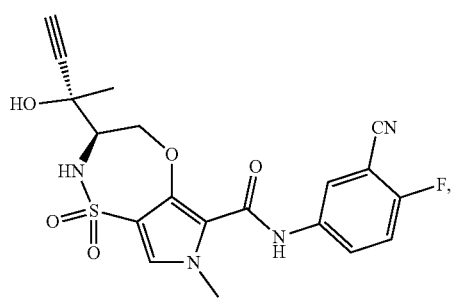
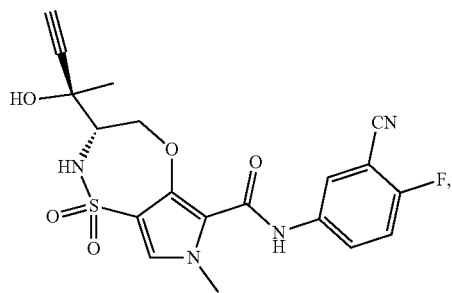
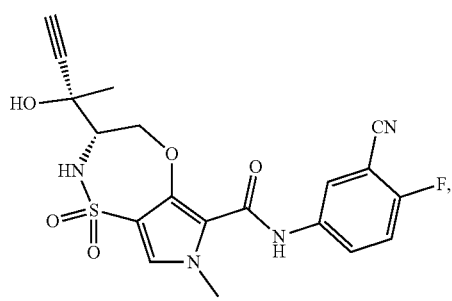
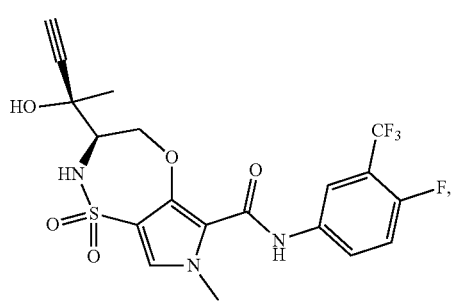
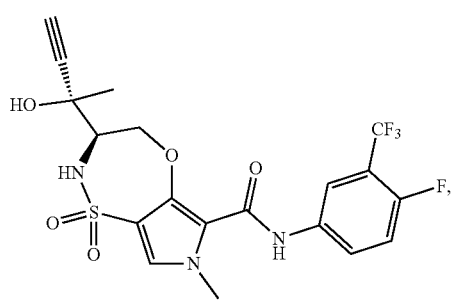
-continued
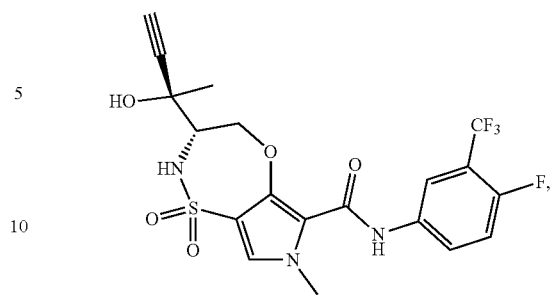
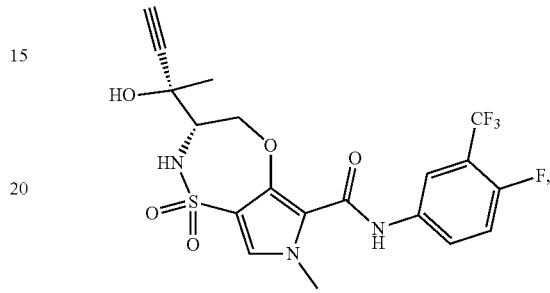
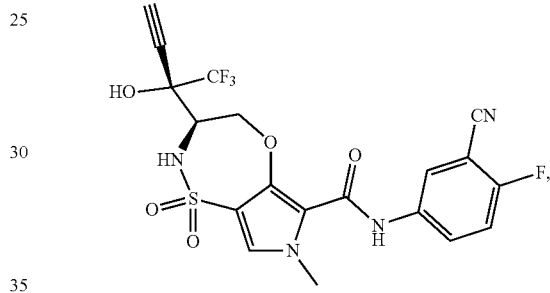
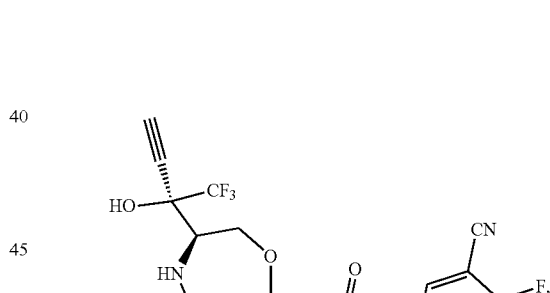
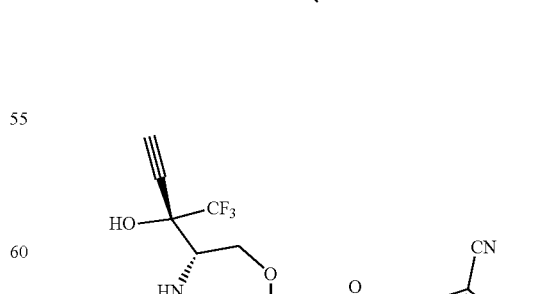

67
-continued
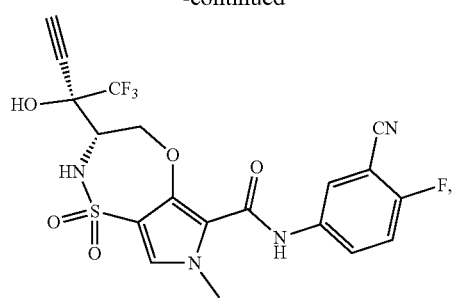
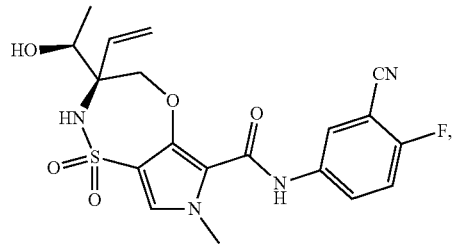
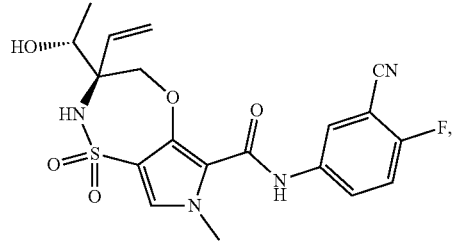
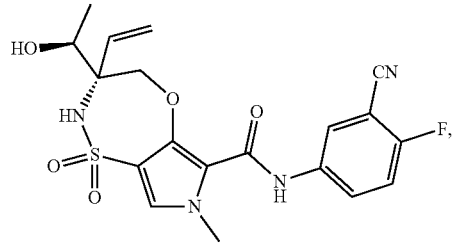
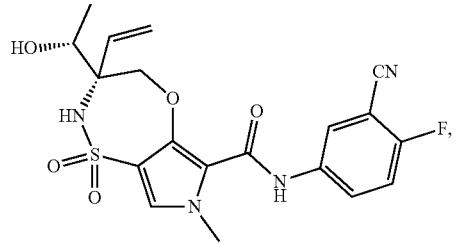
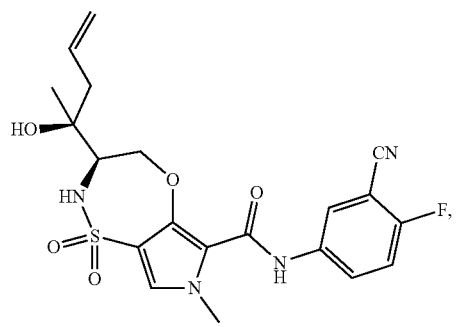
68
-continued
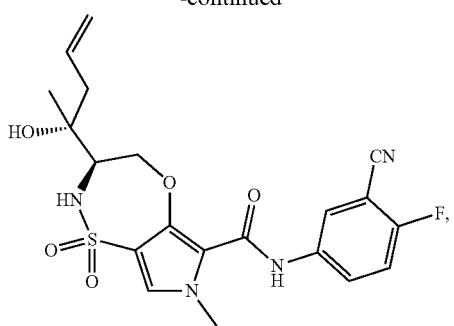
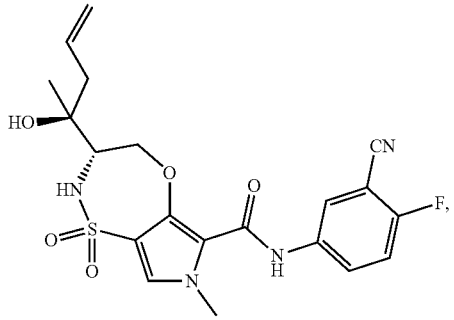
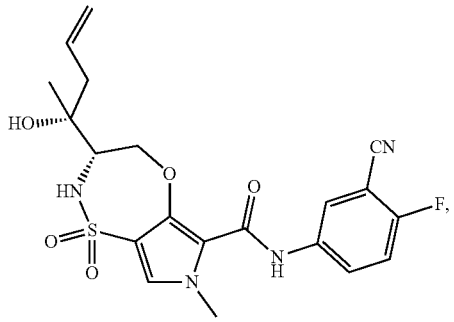
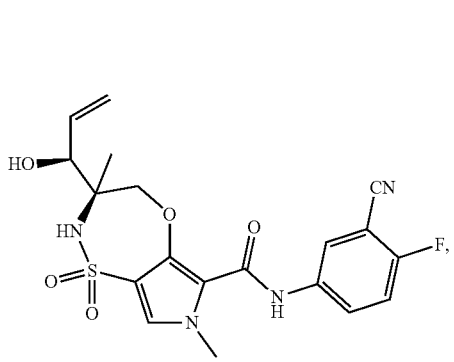
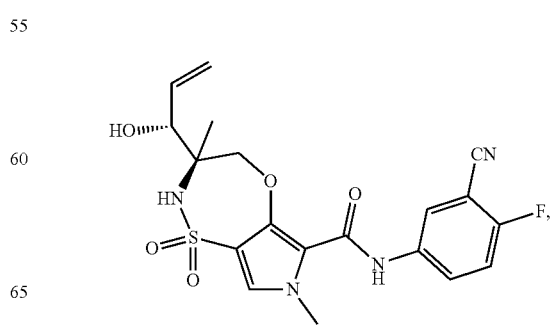

69
-continued
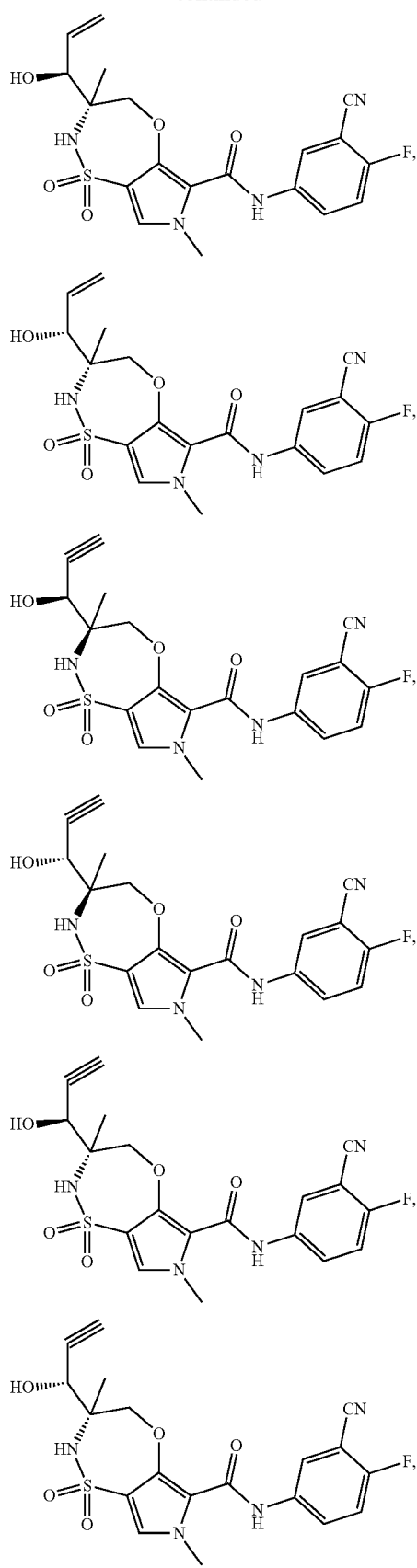
70
-continued
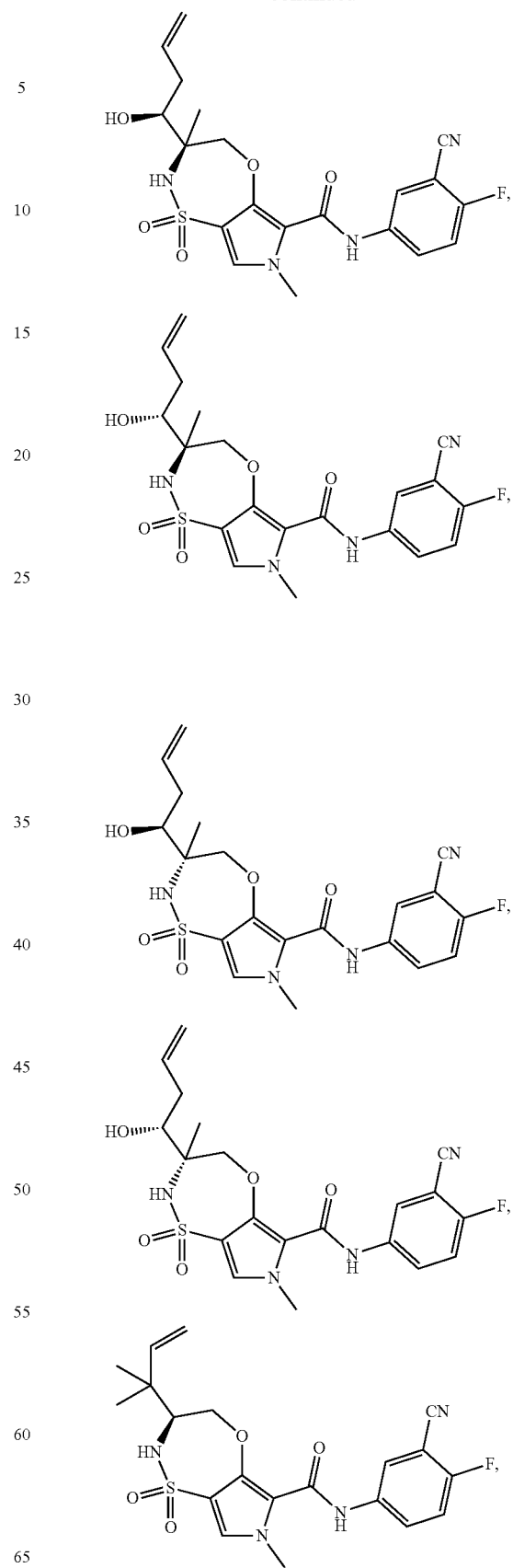

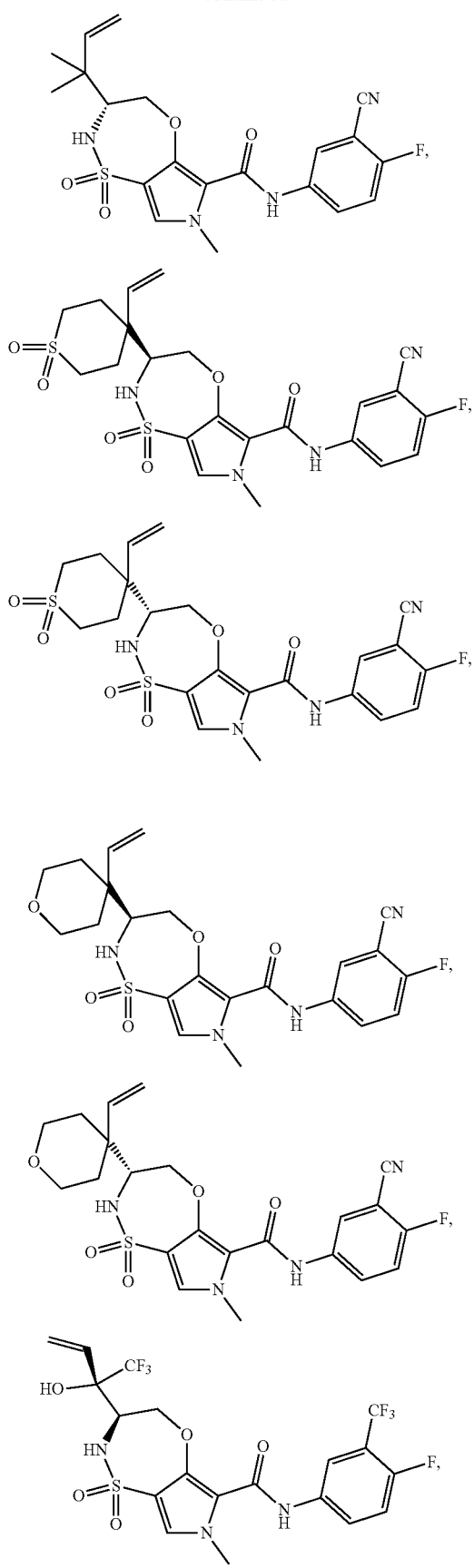
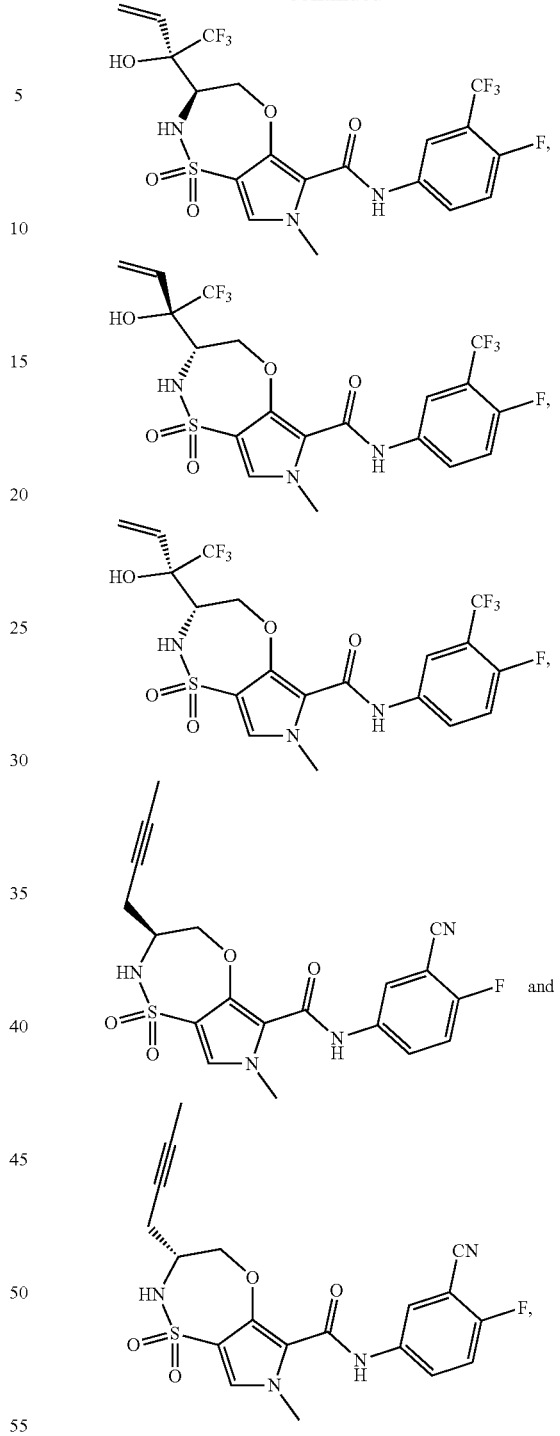

or a pharmaceutically acceptable salt of any of the foregoing.

Synthesis

Compounds of Formulae (I) and (II) along with those described herein may be prepared in various ways. General synthetic routes for preparing compounds of Formulae (I) and (II) are shown and described herein along with some examples of starting materials used to synthesize compounds described herein. The routes shown and described herein are illustrative only and are not intended, nor are they to be construed, to limit the scope of the claims in any manner whatsoever. Those skilled in the art will be able to recognize modifications of the disclosed syntheses and to devise alternate routes based on the disclosures herein; all such modifications and alternate routes are within the scope of the claims.

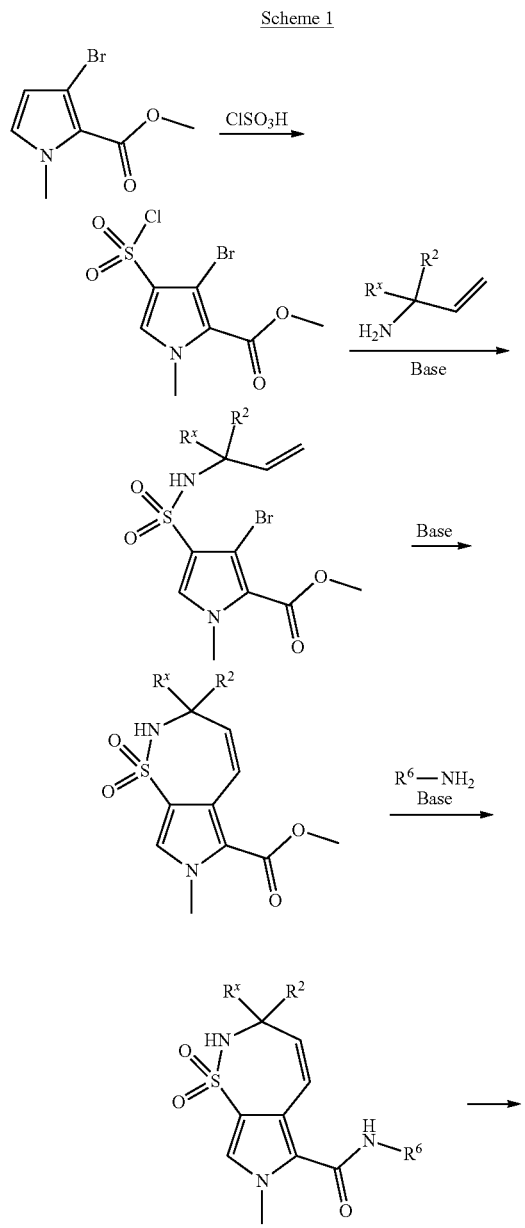

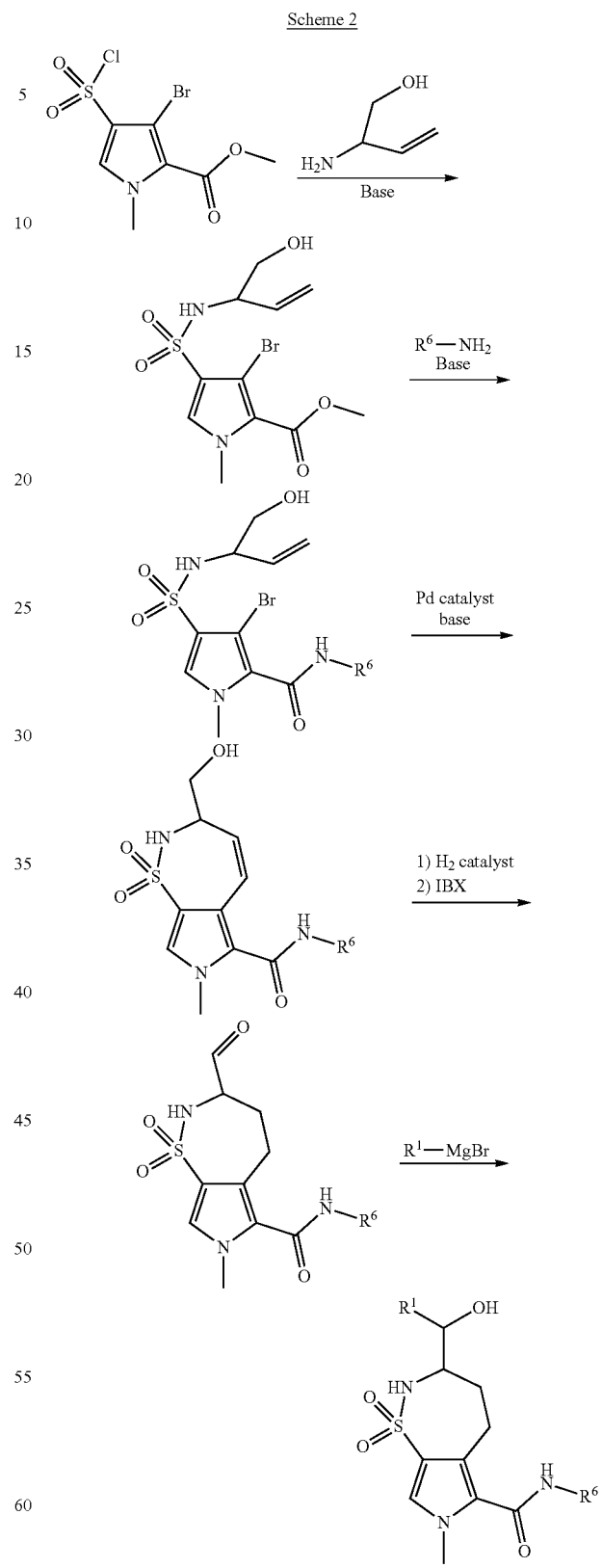

As shown in Scheme 1, sulfonyl chloride can be added to the pyrrolyl ring. The sulfonyl chloride can be then transformed to a sulfonamide utilizing an amine. Using a suitable base, the 7-membered ring can be formed, and the C-carboxy can be transformed to a C-amido using conditions known to those skilled in the art, such as a base and $R^6$—$NH_2$. In Scheme 1, $R^x$ can be $R^1$, or $R^X$ can be transformed to $R^1$ during an appropriate step in the synthesis using methods known to those skilled in the art.

Bicyclic sulfonamides described herein can be also prepared as shown in Scheme 2. After the addition of the sulfonyl chloride as shown in Scheme 1, a sulfonamide can be prepared by reacting the sulfonyl chloride attached to the pyrrolyl with an amine. The C-amido can be formed via an amidation reaction using a suitable base and $R^6$—$NH_2$. Using a catalyst and base, for example a palladium catalyst, the saturated 7-membered ring can be formed. The hydroxyalkyl group attached to the saturated 7-membered ring can then be oxidized to an aldehyde using methods known to those skilled in the art (such as IBX). The $R^1$ group can then be added to the aldehyde to form the secondary alcohol using suitable conditions, such as a Grignard reaction. Using Wittig reaction conditions known to those skilled in the art, the aldehyde can be transformed to an alkenyl derivative.

Scheme 3

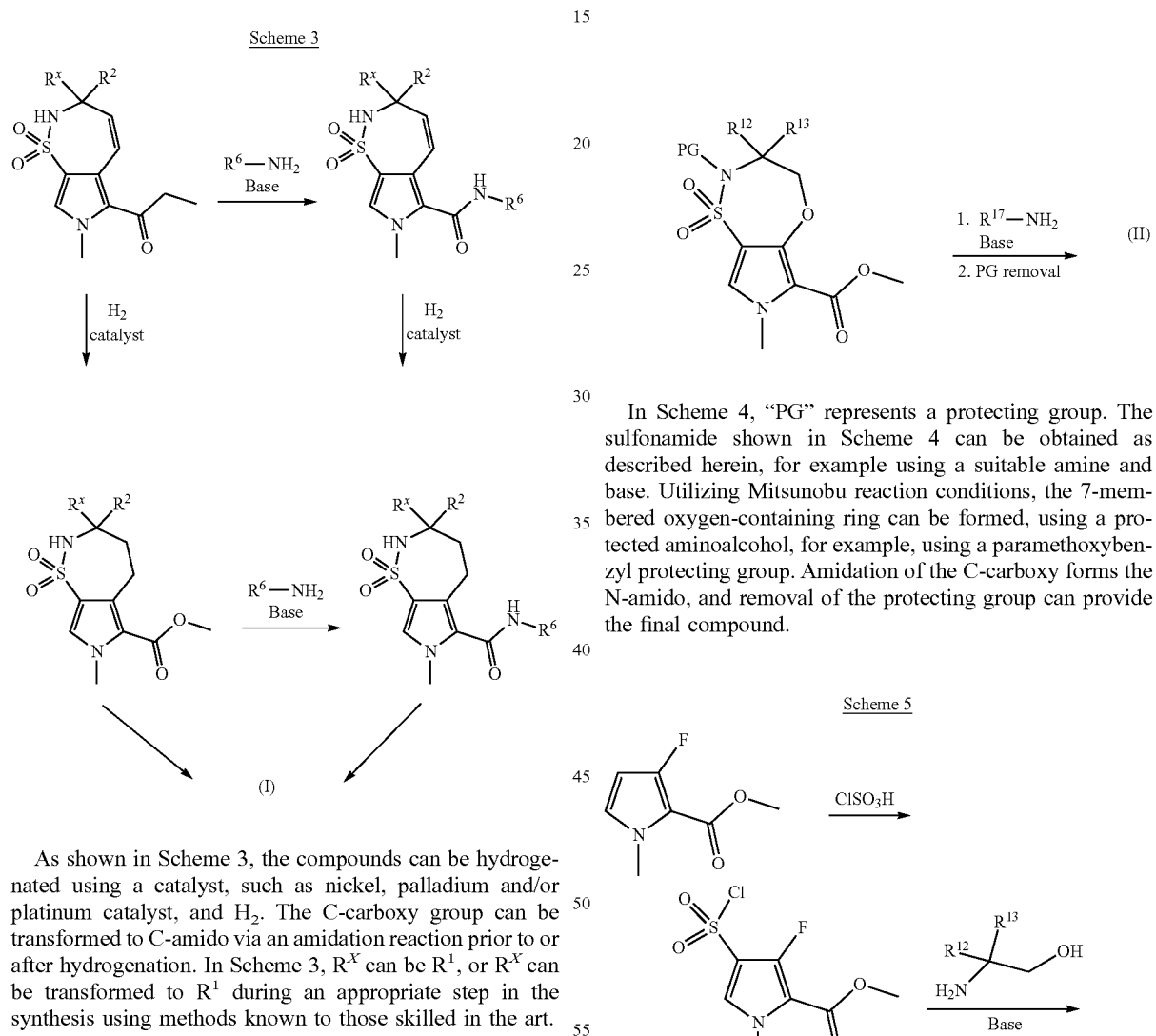

As shown in Scheme 3, the compounds can be hydrogenated using a catalyst, such as nickel, palladium and/or platinum catalyst, and $H_2$. The C-carboxy group can be transformed to C-amido via an amidation reaction prior to or after hydrogenation. In Scheme 3, $R^x$ can be $R^1$, or $R^x$ can be transformed to $R^1$ during an appropriate step in the synthesis using methods known to those skilled in the art.

Scheme 4

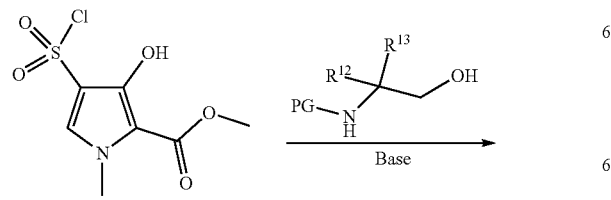

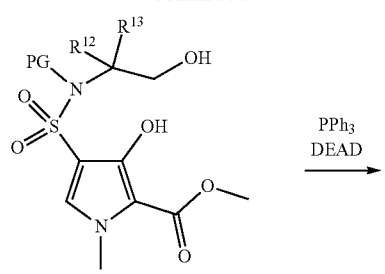

In Scheme 4, "PG" represents a protecting group. The sulfonamide shown in Scheme 4 can be obtained as described herein, for example using a suitable amine and base. Utilizing Mitsunobu reaction conditions, the 7-membered oxygen-containing ring can be formed, using a protected aminoalcohol, for example, using a paramethoxybenzyl protecting group. Amidation of the C-carboxy forms the N-amido, and removal of the protecting group can provide the final compound.

Scheme 5

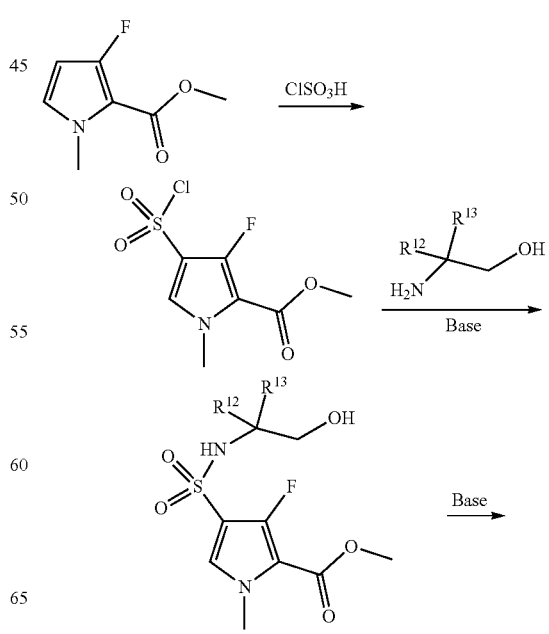

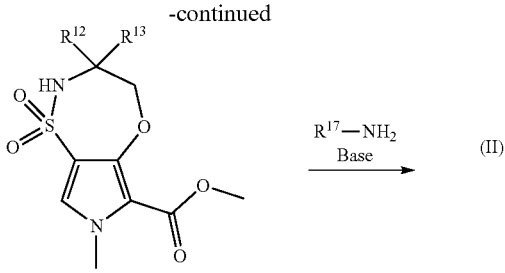

The shown bicyclic sulfonamides can be prepared in a similar manner as described for Scheme 1. The sulfonyl chloride can be added to the pyrrolyl. Formation of the sulfonamide can be accomplished using a suitable amine and base. Using a suitable base, the 7-membered ring can be formed. The C-carboxy can be converted utilizing a base and $R^{17}$—$NH_2$.

Pharmaceutical Compositions

Some embodiments described herein relate to a pharmaceutical composition, that can include an effective amount of a compound described herein (e.g., a compound, or a pharmaceutically acceptable salt thereof, as described herein) and a pharmaceutically acceptable carrier, excipient or combination thereof. A pharmaceutical composition described herein is suitable for human and/or veterinary applications.

As used herein, a "carrier" refers to a compound that facilitates the incorporation of a compound into cells or tissues. For example, without limitation, dimethyl sulfoxide (DMSO) is a commonly utilized carrier that facilitates the uptake of many organic compounds into cells or tissues of a subject.

As used herein, a "diluent" refers to an ingredient in a pharmaceutical composition that lacks pharmacological activity but may be pharmaceutically necessary or desirable. For example, a diluent may be used to increase the bulk of a potent drug whose mass is too small for manufacture and/or administration. It may also be a liquid for the dissolution of a drug to be administered by injection, ingestion or inhalation. A common form of diluent in the art is a buffered aqueous solution such as, without limitation, phosphate buffered saline that mimics the composition of human blood.

As used herein, an "excipient" refers to an inert substance that is added to a pharmaceutical composition to provide, without limitation, bulk, consistency, stability, binding ability, lubrication, disintegrating ability etc., to the composition. A "diluent" is a type of excipient.

Pharmaceutical compositions may be formulated in a variety forms, such as tablets, capsules or solutions for oral administration; suppositories for rectal or vaginal administration; sterile solutions or suspensions for injectable administration. Injectables can be prepared in conventional forms, either as liquid solutions or suspensions, solid forms suitable for solution or suspension in liquid prior to injection, or as emulsions.

Proper formulation is dependent upon the route of administration chosen. Techniques for formulation and administration of the compounds described herein are known to those skilled in the art. Multiple techniques of administering a compound exist in the art including, but not limited to, oral, rectal, topical, aerosol, injection and parenteral delivery, including intramuscular, subcutaneous, intravenous, intramedullary injections, intrathecal, direct intraventricular, intraperitoneal, intranasal and intraocular injections. Pharmaceutical compositions will generally be tailored to the specific intended route of administration.

One may also administer the compound in a local rather than systemic manner, for example, via injection of the compound directly into the infected area, often in a depot or sustained release formulation. Furthermore, one may administer the compound in a targeted drug delivery system, for example, in a liposome coated with a tissue-specific antibody. The liposomes may be targeted to and taken up selectively by the organ.

The pharmaceutical compositions disclosed herein may be manufactured in a manner that is itself known, e.g., by means of conventional mixing, dissolving, granulating, dragee-making, levigating, emulsifying, encapsulating, entrapping or tableting processes. As described herein, compounds used in a pharmaceutical composition may be provided as salts with pharmaceutically compatible counterions.

Methods of Use

Some embodiments described herein relate to a method of treating a HBV and/or HDV infection that can include administering to a subject identified as suffering from the HBV and/or HDV infection an effective amount of a compound, or a pharmaceutically acceptable salt thereof, as described herein, or a pharmaceutical composition that includes an effective amount of a compound, or a pharmaceutically acceptable salt thereof, as described herein. Other embodiments described herein relate to using a compound, or a pharmaceutically acceptable salt thereof, as described herein in the manufacture of a medicament for treating a HBV and/or HDV infection. Still other embodiments described herein relate to the use of a compound, or a pharmaceutically acceptable salt thereof, as described herein or a pharmaceutical composition that includes a compound, or a pharmaceutically acceptable salt thereof, as described herein for treating a HBV and/or HDV infection.

Some embodiments disclosed herein relate to a method of treating a HBV and/or HDV infection that can include contacting a cell infected with the HBV and/or HDV with an effective amount of a compound, or a pharmaceutically acceptable salt thereof, as described herein, or a pharmaceutical composition that includes an effective amount of a compound, or a pharmaceutically acceptable salt thereof, as described herein. Other embodiments described herein relate to using a compound, or a pharmaceutically acceptable salt thereof, as described herein in the manufacture of a medicament for treating a HBV and/or HDV infection. Still other embodiments described herein relate to the use of a compound, or a pharmaceutically acceptable salt thereof, as described herein described herein, or a pharmaceutical composition that includes an effective amount of a compound, or a pharmaceutically acceptable salt thereof, as described herein for treating a HBV and/or HDV infection.

Some embodiments disclosed herein relate to a method of inhibiting replication of HBV and/or HDV that can include contacting a cell infected with the HBV and/or HDV with an effective amount of a compound, or a pharmaceutically acceptable salt thereof, as described herein, or a pharmaceutical composition that includes an effective amount of a compound, or a pharmaceutically acceptable salt thereof, as described herein. Other embodiments described herein relate to using a compound, or a pharmaceutically acceptable salt thereof, as described herein in the manufacture of a medicament for inhibiting replication of HBV and/or HDV. Still other embodiments described herein relate to the use of a compound, or a pharmaceutically acceptable salt thereof, as described herein, or a pharmaceutical composition that includes an effective amount of a compound, or a pharmaceutically acceptable salt thereof, as described herein, for inhibiting replication of HBV and/or HDV.

In some embodiments, the HBV infection can be an acute HBV infection. In some embodiments, the HBV infection can be a chronic HBV infection.

Some embodiments disclosed herein relate to a method of treating liver cirrhosis that is developed because of a HBV and/or HDV infection that can include administering to a subject suffering from liver cirrhosis and/or contacting a cell infected with the HBV and/or HDV in a subject suffering from liver cirrhosis with an effective amount of a compound, or a pharmaceutically acceptable salt thereof, as described herein, or a pharmaceutical composition that includes an effective amount of a compound, or a pharmaceutically acceptable salt thereof, as described herein. Other embodiments described herein relate to using a compound, or a pharmaceutically acceptable salt thereof, as described herein in the manufacture of a medicament for treating liver cirrhosis with an effective amount of the compound, or a pharmaceutically acceptable salt thereof. Still other embodiments described herein relate to the use of a compound, or a pharmaceutically acceptable salt thereof, as described herein, or a pharmaceutical composition that includes an effective amount of a compound, or a pharmaceutically acceptable salt thereof, as described herein for treating liver cirrhosis.

Some embodiments disclosed herein relate to a method of treating liver cancer (such as hepatocellular carcinoma) that is developed because of a HBV and/or HDV infection that can include administering to a subject suffering from the liver cancer and/or contacting a cell infected with the HBV and/or HDV in a subject suffering from the liver cancer with an effective amount of a compound, or a pharmaceutically acceptable salt thereof, as described herein, or a pharmaceutical composition that includes an effective amount of a compound, or a pharmaceutically acceptable salt thereof, as described herein. Other embodiments described herein relate to using a compound, or a pharmaceutically acceptable salt thereof, as described herein in the manufacture of a medicament for treating liver cancer (such as hepatocellular carcinoma). Still other embodiments described herein relate to the use of a compound, or a pharmaceutically acceptable salt thereof, as described herein, or a pharmaceutical composition that includes an effective amount of a compound, or a pharmaceutically acceptable salt thereof, as described herein for treating liver cancer (such as hepatocellular carcinoma).

Some embodiments disclosed herein relate to a method of treating liver failure that is developed because of a HBV and/or HDV infection that can include administering to a subject suffering from liver failure and/or contacting a cell infected with the HBV and/or HDV in a subject suffering from liver failure with an effective amount of a compound, or a pharmaceutically acceptable salt thereof, as described herein, or a pharmaceutical composition that includes an effective amount of a compound, or a pharmaceutically acceptable salt thereof, as described herein. Other embodiments described herein relate to using a compound, or a pharmaceutically acceptable salt thereof, as described herein in the manufacture of a medicament for treating liver failure. Still other embodiments described herein relate to the use of a compound, or a pharmaceutically acceptable salt thereof, as described herein, or a pharmaceutical composition that includes an effective amount of a compound, or a pharmaceutically acceptable salt thereof, as described herein for treating liver failure.

Various indicators for determining the effectiveness of a method for treating an HBV and/or HDV infection are also known to those skilled in the art. Examples of suitable indicators include, but are not limited to, a reduction in viral load indicated by reduction in HBV DNA (or load) (e.g., reduction $<10^5$ copies/mL in serum), HBV surface antigen (HBsAg) and HBV e-antigen (HBeAg), a reduction in plasma viral load, a reduction in viral replication, a reduction in time to seroconversion (virus undetectable in patient serum), an increase in the rate of sustained viral response to therapy, an improvement in hepatic function, and/or a reduction of morbidity or mortality in clinical outcomes.

As used herein, the terms "treat," "treating," "treatment," "therapeutic," and "therapy" do not necessarily mean total cure or abolition of the disease or condition. Any alleviation of any undesired signs or symptoms of a disease or condition, to any extent can be considered treatment and/or therapy. Furthermore, treatment may include acts that may worsen the subject's overall feeling of well-being or appearance.

As used herein, a "subject" refers to an animal that is the object of treatment, observation or experiment. "Animal" includes cold- and warm-blooded vertebrates and invertebrates such as fish, shellfish, reptiles and, in particular, mammals. "Mammal" includes, without limitation, mice, rats, rabbits, guinea pigs, dogs, cats, sheep, goats, cows, horses, primates, such as monkeys, chimpanzees, and apes, and, in particular, humans. In some embodiments, the subject is human.

The term "effective amount" is used to indicate an amount of an active compound, or pharmaceutical agent, that elicits the biological or medicinal response indicated. For example, an effective amount of compound can be the amount needed to alleviate or ameliorate symptoms of disease or prolong the survival of the subject being treated This response may occur in a tissue, system, animal or human and includes alleviation of the signs or symptoms of the disease being treated. Determination of an effective amount is well within the capability of those skilled in the art, in view of the disclosure provided herein. The effective amount of the compounds disclosed herein required as a dose will depend on the route of administration, the type of animal, including human, being treated, and the physical characteristics of the specific animal under consideration. The dose can be tailored to achieve a desired effect, but will depend on such factors as weight, diet, concurrent medication and other factors which those skilled in the medical arts will recognize.

In some embodiments, an effective amount of a compound, or a pharmaceutically acceptable salt thereof, as described herein is an amount that is effective to achieve a sustained virologic response, for example, a sustained viral response 12 month after completion of treatment.

Subjects who are clinically diagnosed with a HBV and/or HDV infection include "naïve" subjects (e.g., subjects not previously treated for HBV and/or HDV) and subjects who have failed prior treatment for HBV and/or HDV ("treatment failure" subjects). Treatment failure subjects include "non-responders" (subjects who did not achieve sufficient reduction in ALT (alanine aminotransferase) levels, for example, subject who failed to achieve more than 1 log 10 decrease from base-line within 6 months of starting an anti-HBV and/or anti-HDV therapy) and "relapsers" (subjects who were previously treated for HBV and/or HDV whose ALT levels have increased, for example, ALT >twice the upper normal limit and detectable serum HBV DNA by hybridization assays). Further examples of subjects include subjects with a HBV and/or HDV infection who are asymptomatic.

In some embodiments, a compound, or a pharmaceutically acceptable salt thereof, as described herein can be provided to a treatment failure subject suffering from HBV and/or HDV. In some embodiments, a compound, or a pharmaceutically acceptable salt thereof, as described herein can be provided to a non-responder subject suffering from HBV and/or HDV. In some embodiments, a compound, or a pharmaceutically acceptable salt thereof, as described herein can be provided to a relapser subject suffering from HBV and/or HDV. In some embodiments, the subject can have HBeAg positive chronic hepatitis B. In some embodiments, the subject can have HBeAg negative chronic hepatitis B. In some embodiments, the subject can have liver cirrhosis. In some embodiments, the subject can be asymptomatic, for example, the subject can be infected with HBV and/or HDV but does not exhibit any symptoms of the viral infection. In some embodiments, the subject can be immunocompromised. In some embodiments, the subject can be undergoing chemotherapy.

Examples of agents that have been used to treat HBV and/or HDV include immunomodulating agents, and nucleosides/nucleotides. Examples of immunomodulating agents include interferons (such as IFN-α and pegylated interferons that include PEG-IFN-α-2a); and examples of nucleosides/nucleotides include lamivudine, telbivudine, adefovir dipivoxil, clevudine, entecavir, tenofovir alafenamide and tenofovir disoproxil. However, some of the drawbacks associated with interferon treatment are the adverse side effects, the need for subcutaneous administration and high cost. Potential advantages of a compound of Formula (I) and/or (II), or a pharmaceutically acceptable salt of any of the foregoing, can be less adverse side effects, delay in the onset of an adverse side effect and/or reduction in the severity of an adverse side effect. A drawback with nucleoside/nucleotide treatment can be the development of resistance, including cross-resistance.

Resistance can be a cause for treatment failure. The term "resistance" as used herein refers to a viral strain displaying a delayed, lessened and/or null response to an anti-viral agent. In some embodiments, a compound, or a pharmaceutically acceptable salt thereof, as described herein can be provided to a subject infected with an HBV and/or HDV strain that is resistant to one or more anti-HBV and/or anti-HDV agents. Examples of anti-viral agents wherein resistance can develop include lamivudine, telbivudine, adefovir dipivoxil, clevudine, entecavir, tenofovir alafenanide and tenofovir disoproxil. In some embodiments, development of resistant HBV and/or HDV strains is delayed when a subject is treated with a compound, or a pharmaceutically acceptable salt thereof, as described herein compared to the development of HBV and/or HDV strains resistant to other HBV and/or HDV anti-viral agents, such as those described.

The dosage may range broadly, depending upon the desired effects and the therapeutic indication. Alternatively, dosages may be based and calculated upon the surface area of the patient, as understood by those of skill in the art. Although the exact dosage will be determined on a drug-by-drug basis, in most cases, some generalizations regarding the dosage can be made. The daily dosage regimen for an adult human patient may be, for example, an oral dose of between 0.01 mg and 3000 mg of each active ingredient, preferably between 1 mg and 700 mg, e.g. 5 to 200 mg. The dosage may be a single one or a series of two or more given in the course of one or more days, as is needed by the subject.

In instances where human dosages for compounds have been established for at least some condition, those same dosages may be used, or dosages that are between about 0.1% and 500%, more preferably between about 25% and 250% of the established human dosage. Where no human dosage is established, as will be the case for newly-discovered pharmaceutical compositions, a suitable human dosage can be inferred from $ED_{50}$ or $ID_{50}$ values, or other appropriate values derived from in vitro or in vivo studies, as qualified by toxicity studies and efficacy studies in animals.

In cases of administration of a pharmaceutically acceptable salt, dosages may be calculated as the free base. As will be understood by those of skill in the art, in certain situations it may be necessary to administer the compounds disclosed herein in amounts that exceed, or even far exceed, the above-stated, preferred dosage range in order to effectively and aggressively treat particularly aggressive diseases or infections.

Dosage amount and interval may be adjusted individually to provide plasma levels of the active moiety which are sufficient to maintain the modulating effects, or minimal effective concentration (MEC). The MEC will vary for each compound but can be estimated from in vitro data. Dosages necessary to achieve the MEC will depend on individual characteristics and route of administration. However, HPLC assays or bioassays can be used to determine plasma concentrations. Dosage intervals can also be determined using MEC value. Compositions should be administered using a regimen which maintains plasma levels above the MEC for 10-90% of the time, preferably between 30-90% and most preferably between 50-90%. In cases of local administration or selective uptake, the effective local concentration of the drug may not be related to plasma concentration.

It should be noted that the attending physician would know how to and when to terminate, interrupt, or adjust administration due to toxicity or organ dysfunctions. Conversely, the attending physician would also know to adjust treatment to higher levels if the clinical response were not adequate (precluding toxicity). The magnitude of an administrated dose in the management of the disorder of interest will vary with the severity of the condition to be treated and to the route of administration. The severity of the condition may, for example, be evaluated, in part, by standard prognostic evaluation methods. Further, the dose and perhaps dose frequency, will also vary according to the age, body weight, and response of the individual patient. A program comparable to that discussed above may be used in veterinary medicine.

Compounds disclosed herein can be evaluated for efficacy and toxicity using known methods. For example, the toxicology of a particular compound, or of a subset of the compounds, sharing certain chemical moieties, may be established by determining in vitro toxicity towards a cell line, such as a mammalian, including a human cell line. The results of such studies are often predictive of toxicity in animals, such as mammals, or more specifically, humans. Alternatively, the toxicity of particular compounds in an animal model, such as mice, rats, rabbits, or monkeys, may be determined using known methods. The efficacy of a particular compound may be established using several recognized methods, such as in vitro methods, animal models, or human clinical trials. When selecting a model to determine efficacy, the skilled artisan can be guided by the state of the art to choose an appropriate model, dose, route of administration and/or regime.

Combination Therapies

In some embodiments, a compound, or a pharmaceutically acceptable salt thereof, as described herein can be used in combination with one or more additional agent(s) for treating and/or inhibiting replication HBV and/or HDV. Additional agents include, but are not limited to, an interferon, nucleoside/nucleotide analogs, a capsid assembly modulator, a sequence specific oligonucleotide (such as anti-sense oligonucleotide and siRNA), nucleic acid polymers (NAPs) (such as STOPS™ compounds and other nucleic acid polymers that reduce HBsAg levels) an entry inhibitor and/or a small molecule immunomodulator. Examples of additional agents include recombinant interferon alpha 2b, IFN-α, PEG-IFN-α-2a, lamivudine, telbivudine, adefovir dipivoxil, clevudine, entecavir, tenofovir alafenamide, tenofovir disoproxil, JNJ-6379, GLS4, ABI-H0731, JNJ-440, NZ-4, RG7907, AB-423, AB-506 and ABI-H2158. Examples of NAPs include, but are not limited to, REP 2139, REP 2165 and those STOPS™ compounds described in U.S. application Ser. No. 16/676,929, filed Nov. 7, 2019, which is hereby incorporated by reference for the purpose of its disclosure of the STOPS™ compounds described in the aforementioned U.S. application.

In some embodiments, a compound, or a pharmaceutically acceptable salt thereof, as described herein can be administered with one or more additional agent(s) together in a single pharmaceutical composition. In some embodiments, a compound, or a pharmaceutically acceptable salt thereof, can be administered with one or more additional agent(s) as two or more separate pharmaceutical compositions. Further, the order of administration of a compound, or a pharmaceutically acceptable salt thereof, as described herein with one or more additional agent(s) can vary.

EXAMPLES

Additional embodiments are disclosed in further detail in the following examples, which are not in any way intended to limit the scope of the claims.

Example 1

(3S)—N-(3-cyano-4-fluorophenyl)-3-ethenyl-7-methyl-1,1-dioxo-2H,3H,4H-11λ6-pyrrolo[3,4-b][1,4,5]oxathiazepine-6-carboxamide (Compound 1)

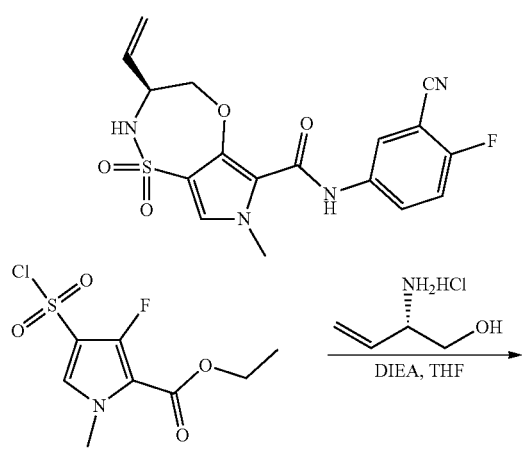

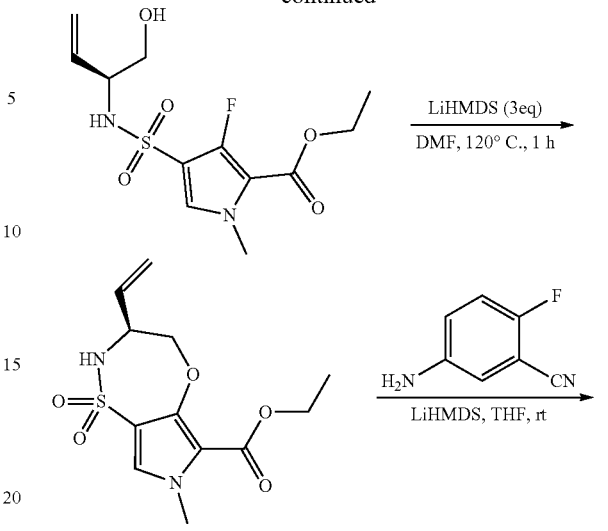

Compound 1

To a stirred solution/mixture of ethyl 4-(chlorosulfonyl)-3-fluoro-1-methylpyrrole-2-carboxylate (1000 mg, 3.7 mmol, 1.00 eq.) and (2S)-1-hydroxybut-3-en-2-aminium chloride (687.4 mg, 5.6 mmol, 1.50 eq.) in THF (20 mL) were added DIEA (2.39 g, 18.5 mmol, 5.00 eq.) dropwise at room temperature (rt) under $N_2$ atmosphere. The resulting was stirred overnight at rt under $N_2$ atmosphere. The mixture was diluted with $H_2O$ (30 mL) and extracted with EtOAc (3×20 mL). The combined organic layers were washed with brine (1×30 mL), dried over anhydrous $Na_2SO_4$, and filtered. The filtrate was concentrated under reduced pressure, and the product was obtained (ethyl 3-fluoro-4-[[(2S)-1-hydroxybut-3-en-2-yl]sulfamoyl]-1-methylpyrrole-2-carboxylate (1.2914 g, 88%)) as an off-white solid. LC-MS (Column: HALO C18, 3.0*30 mm, 2.0 um; Column Oven: 40 C; Mobile Phase A: Water/0.1% FA, Mobile Phase B: ACN/0.1% FA; Flow rate: 1.5 mL/min; Gradient: 5% B to 100% B in 1.2 min, hold 0.5 min; 254 nm): Rt=0.569 min). (ES, m/z): 321 [M+H]$^+$, exact mass=320.

To a stirred solution of ethyl 3-fluoro-4-[[(2S)-1-hydroxybut-3-en-2-yl]sulfamoyl]-1-methylpyrrole-2-carboxylate (250.70 mg, 0.783 mmol, 1.00 eq.) in DMF (10 mL) was added LiHMDS (1.0 mo/L in THF, 2.40 mL, 2.400 mmol, 3.00 eq.) dropwise at rt. The mixture was stirred at 120° C. for 1 h. The mixture was cooled to rt and diluted with $H_2O$ (10 mL), then extracted with EtOAc (3×10 mL). The combined organic layers were washed with brine (20 mL), dried over anhydrous $Na_2SO_4$, and filtered. The filtrate was concentrated under reduced pressure. The residue was purified by silica gel column chromatography, eluted with PE/EtOAc (3:1) to afford ethyl (3S)-3-ethenyl-7-methyl-1,1-dioxo-2H,3H,4H-11λ6-pyrrolo[3,4-b][1,4,5]oxathiazepine-6-carboxylate (31.6 mg) as an off-white solid. LC-MS (Column: Ascentis Express C18, 3.0*50 mm, 2.7 um; Column Oven: 40 C; Mobile Phase A: Water/0.1% FA, Mobile Phase B: ACN/0.1% FA; Flow rate: 1.2 mL/min; Gradient: 10% B to 100% B in 2.0 min, hold 0.6 min; 254 nm): Rt=1.004 min). (ES, m/z): 301 [M+H]$^+$, exact mass=300.

To a stirred solution of ethyl (3S)-3-ethenyl-7-methyl-1,1-dioxo-2H,3H,4H-11λ6-pyrrolo[3,4-b][1,4,5]oxathiazepine-6-carboxylate (31.60 mg, 0.105 mmol, 1.00 eq.) and 5-amino-2-fluorobenzonitrile (17.19 mg, 0.126 mmol, 1.20 eq.) in THF (3 mL) were added LiHMDS (1.0 mol/L in THF, 0.65 mL, 6.00 eq.) dropwise at rt under N₂ atmosphere. The mixture was stirred at rt for 12 h, diluted with H₂O (10 mL) and extracted with EtOAc (3×10 mL). The combined organic layers were washed with brine (20 mL), dried over anhydrous Na₂SO₄. After filtration, the filtrate was concentrated under reduced pressure. The residue was purified by silica gel column chromatography, eluted with PE/EtOAc (1:1) to afford Compound 1 (20.2 mg) as an off-white solid. LC-MS (Column: ACE Excel 3 SuperC18, 3.0*50 mm, 3.0 um; Column Oven: 40 C; Mobile Phase A: Water/5 mM NH₄HCO₃, Mobile Phase B: ACN; Flow rate: 1.2 mL/min; Gradient: 10% B to 95% B in 2.1 min, hold 0.6 min; 254 nm): Rt=3.064 min). (ES, m/z): 391 [M+H]⁺, exact mass=390. ¹H-NMR: (DMSO-d6, 300 MHz, ppm): δ 9.56 (s, 1H), 8.20 (dd, J=5.7, 2.6 Hz, 1H), 8.12-8.01 (m, 1H), 7.92 (d, J=9.6 Hz, 1H), 7.59-7.49 (m, 2H), 5.93-5.78 (m, 1H), 5.42 (d, J=17.4 Hz, 1H), 5.29 (d, J=10.7 Hz, 1H), 4.69 (d, J=12.7 Hz, 1H), 4.41-4.29 (m, 1H), 3.93 (dd, J=12.7, 9.3 Hz, 1H), 3.85 (s, 3H).

Example 2

(3R)—N-(3-cyano-4-fluorophenyl)-3-formyl-7-methyl-1,1-dioxo-2H,3H,4H,5H-1λ6-pyrrolo[3,4-f][1,2]thiazepine-6-carboxamide (Compound A)

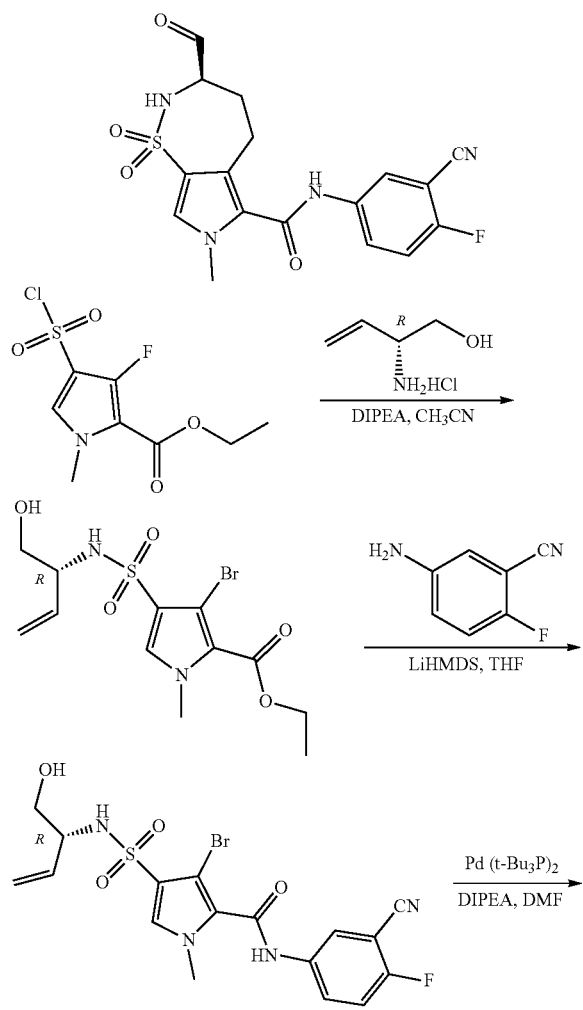

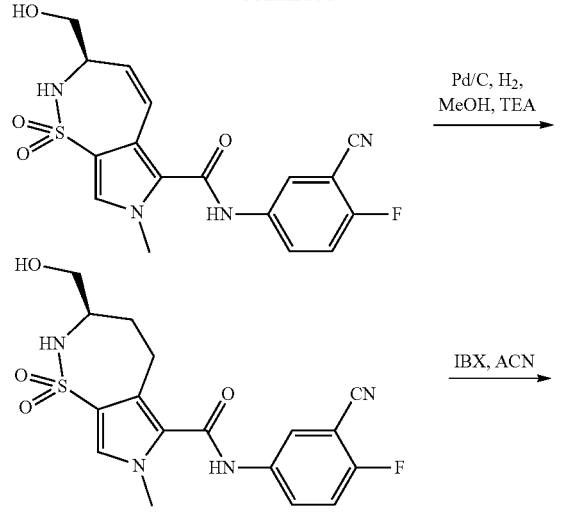

Compound A

To a solution of (2R)-2-aminobut-3-en-1-ol hydrochloride (1.46 g, 11.814 mmol, 1.30 eq.) in CH₃CN (30 mL) was added DIPEA (3.52 g, 27.235 mmol, 3.00 eq.), ethyl 3-bromo-4-(chlorosulfonyl)-1-methylpyrrole-2-carboxylate (3.00 g, 9.075 mmol, 1.00 eq.). The solution was stirred for 1 h at 80° C. The mixture was concentrated. The residue was applied onto a silica gel column with EA/PE (40:60). Ethyl 3-bromo-4-[[(2R)-1-hydroxybut-3-en-2-yl]sulfamoyl]-1-methylpyrrole-2-carboxylate (3.1 g, 89.60%) was obtained as a white solid. LC-MS (Column: Ascentis Express C18, 3.0*50 mm, 2.7 um; Column Oven: 40 C; Mobile Phase A: Water/0.1% FA, Mobile Phase B: ACN/0.1% FA; Flow rate: 1.2 mL/min; Gradient: 10% B to 100% B in 2.0 min, hold 0.6 min; 254 nm; Rt=1.295 min). (ES, m/z):381 [M+H]⁺, exact mass=380.0.

To a solution of ethyl 3-bromo-4-[[(2R)-1-hydroxybut-3-en-2-yl]sulfamoyl]-1-methylpyrrole-2-carboxylate (100 mg, 0.262 mmol, 1.00 eq.) in THF (3.00 mL) was added 5-amino-2-fluorobenzonitrile (53.56 mg, 0.393 mmol, 1.50 eq.) and LiHMDS (1 mol/L in THF, 12.59 mL, 12.590 mmol, 48.00 eq.). The solution was stirred for overnight at 25° C. The reaction was then quenched with water (10 mL). The solution was extracted with EA (2×10 mL). The mixture was washed with brine (1×10 mL). The mixture was dried over anhydrous sodium sulfate and concentrated. The residue was applied onto a silica gel column with EA/PE (40:60). 3-bromo-N-(3-cyano-4-fluorophenyl)-4-[[(2R)-1-hydroxybut-3-en-2-yl]sulfamoyl]-1-methylpyrrole-2-carboxamide (66.8 mg, 52.95%) was obtained as a red solid. LC-MS (Column: HALO C18, 3.0*30 mm, 2.0 um; Mobile Phase A: Water/0.05% TFA, Mobile Phase B: ACN/0.05% TFA; Flow rate: 0.5 mL/min; Gradient: 5% B to 100% B in 1.2 min, hold 0.5 min; 254 nm; Rt=1.408 min). (ES, m/z): 471 [M+H]⁺, exact mass=470.0.

To a solution of 3-bromo-N-(3-cyano-4-fluorophenyl)-4-[[(2R)-1-hydroxybut-3-en-2-yl]sulfamoyl]-1-methylpyrrole-2-carboxamide (0.20 g, 0.424 mmol, 1.00 eq.) in DMF (3.00 mL) was added DIEA (71.30 mg, 0.552 mmol, 1.30 eq.) and Pd(t-Bu₃P)₂ (43.37 mg, 0.085 mmol, 0.20 eq.). The mixture was irradiated with microwave radiation for 1 h at 130° C. The solution was diluted with water (15 mL). The solution was extracted with EA (2×15 mL). The mixture was washed with brine (1×15 mL). The mixture was dried over anhydrous sodium sulfate and concentrated. The residue was applied onto a silica gel column with CH$_2$Cl$_2$/CH$_3$OH (120:1). (3R)—N-(3-cyano-4-fluorophenyl)-3-(hydroxymethyl)-7-methyl-1,1-dioxo-2H,3H-1λ6-pyrrolo[3,4-f][1,2]thiazepine-6-carboxamide (63.1 mg, 36.18%) was obtained as a red solid. LC-MS (Column: Shim-pack XR-ODS, 3.0*50 mm, 2.2 um; Mobile Phase A: Water/0.05% TFA, Mobile Phase B: ACN/0.05% TFA; Flow rate: 1.2 mL/min; Gradient: 5% B to 100% B in 2.0 min, hold 0.7 min; 254 nm; Rt=1.356 min). (ES, m/z):391 [M+H]$^+$, exact mass=390.1.

To a solution of (3R)—N-(3-cyano-4-fluorophenyl)-3-(hydroxymethyl)-7-methyl-1,1-dioxo-2H,3H-11λ6-pyrrolo[3,4-f][1,2]thiazepine-6-carboxamide (200.00 mg, 0.512 mmol, 1.00 eq.) in MeOH (6 mL) was added TEA (103.68 mg, 1.025 mmol, 2.00 eq.), Pd/C (100.00 mg, 10%). The solution was stirred for 2 h at 25° C. under H$_2$ (1 atm) atmosphere. The filtrate was collected by filtration and concentrated. The crude product was slurry with ACN. The solid was collected by filtration. (3R)—N-(3-cyano-4-fluorophenyl)-3-(hydroxymethyl)-7-methyl-1,1-dioxo-2H,3H,4H,5H-1λ6-pyrrolo[3,4-f][1,2]thiazepine-6-carboxamide (76.2 mg, 37.90%) of as an off-white solid. LC-MS (Column: Shim-pack XR-ODS, 3.0*50 mm, 2.2 um; Mobile Phase A: Water/0.05% TFA, Mobile Phase B: ACN/0.05% TFA; Flow rate: 1.2 mL/min; Gradient: 5% B to 100% B in 1.1 min, hold 0.7 min; 254 nm; Rt=1.445 min). (ES, m/z):393 [M+H]$^+$, exact mass=392.1.

To a solution of (3R)—N-(3-cyano-4-fluorophenyl)-3-(hydroxymethyl)-7-methyl-1,1-dioxo-2H,3H,4H,5H-1λ6-pyrrolo[3,4-f][1,2]thiazepine-6-carboxamide (400 mg, 1.019 mmol, 1.00 eq.) in ACN (40.00 mL) was followed by the addition of IBX (570.87 mg, 2.039 mmol, 2.00 eq.) at 80° C. The solution was stirred for 40 min at 80° C. The solids were filtered out, and the mixture was concentrated. The residue was applied onto a silica gel column with CH$_2$Cl$_2$/CH$_3$OH (110:1). Compound A (300 mg, 75.39%) was obtained as a yellow solid. LC-MS (Column: YMC-Triart C18, 3.0 um; 50*3.0 mm; Column Oven: 40 C; Mobile Phase A: 0.04% NH$_4$OH, Mobile Phase B: ACN; Flow rate: 1.2 mL/min; Gradient: 10% B to 95% B in 2.1 min, hold 0.6 min; 254 nm; Rt=0.826 min). (ES, m/z):391 [M+H]$^+$, exact mass=390.1 $^1$H-NMR: $^1$H NMR (400 MHz, DMSO-d$_6$) δ 10.60 (m, 1H), 9.54 (s, 1H), 8.20 (m, 1H), 7.98-7.94 (m, 1H), 7.57-7.54 (m, 2H), 5.82 (m, 1H), 4.74-4.22 (m, 1H), 3.69 (s, 3H), 3.11-3.01 (m, 1H), 2.87-2.67 (m, 1H), 2.09 (s, 1H), 1.56-1.32 (m, 1H).

Example 3

Compounds 2A, 2B, 2C and 2D

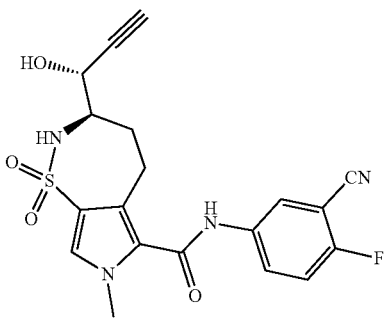
2A

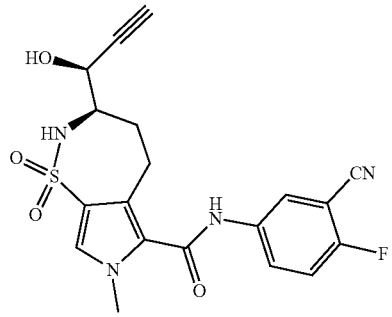
2B

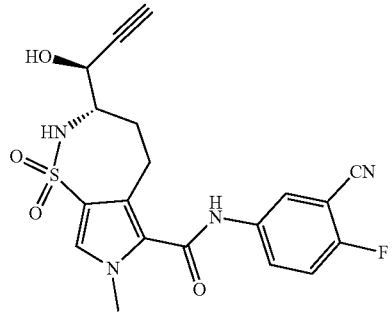
2C

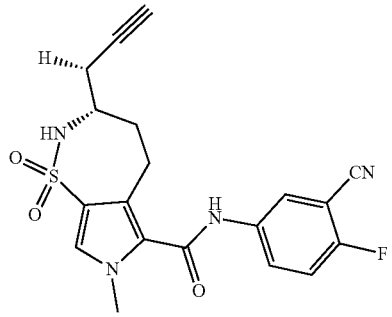
2D

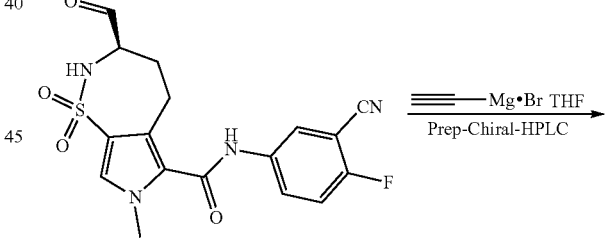
Compounds 2A, 2B, 2C and 2D

To a solution of (3R)—N-(3-cyano-4-fluorophenyl)-3-formyl-7-methyl-1,1-dioxo-2H,3H,4H,5H-1λ6-pyrrolo[3,4-f][1,2]thiazepine-6-carboxamide (250 mg, 0.640 mmol, 1.00 eq.) in THF (6 mL) bromo(ethynyl)magnesium (0.5 mol/L in THF, 6.40 mL, 3.200 mmol, 5.00 eq.) added dropwise with stirring at 0° C. The solution was stirred for 2 h at 0° C. The reaction was then quenched with water (8 mL). The solution was extracted with EA (2×15 mL), washed with brine (1×15 mL), dried over anhydrous sodium sulfate and concentrated. The residue was applied onto a silica gel column with CH$_2$C$_2$/CH$_3$OH (120:1). The crude product was purified by Prep-HPLC (conditions: 2 #SHIMADZU (HPLC-01)): Column, XBridge Prep C18 OBD Column, 30*50 mm, 5 um, 13 nm; mobile phase, Water (10M MOL/L NH$_4$HCO$_3$) and ACN (30% Phase B up to 38% in 9 min)). This resulted in the racemic product which was purified by chiral-Prep-HPLC (conditions: Column: CHIRALPAK IG, 3*25 cm, 5um; Mobile Phase A: Hex (8 mmol/L NH$_3$.MeOH)-HPLC, Mobile Phase B: EtOH-HPLC; Flow rate: 40 mL/min; Gradient: 40 B to 40 B in 20 min; 254/220 nm; RT1:11.42; RT2:11.706. (3R)—N-(3-cyano-4-fluorophenyl)-3-[(1R)-1-hydroxyprop-2-yn-1-yl]-7-methyl-1,1-dioxo-2H,3H,4H,5H-1λ6-pyrrolo[3,4-f][1,2]thiazepine-6-carboxamide (1 mg, 0.36%, Compound 2A) was obtained as a white solid; (3S)—N-(3-cyano-4-fluorophenyl)-3-[(1R)-1-hydroxyprop-2-yn-1-yl]-7-methyl-1,1-dioxo-2H,3H,4H,5H-1λ6-pyrrolo[3,4-f][1,2]thiazepine-6-carboxamide (7.8 mg, 2.90%, Compound 2D) was obtained as a white solid. A mixture of two other product (9.6 mg) was also obtained.

The mixture of products (9.6 mg) was purified by Chiral-Prep-HPLC (conditions: Column: CHIRALPAK IA, 2*25 cm, 5um; Mobile Phase A: MTBE (10 mM NH$_3$.MeOH)-HPLC, Mobile Phase B: EtOH-HPLC; Flow rate: 20 mL/min; Gradient: 10 B to 10 B in 11 min; 220/254 nm; RT1:7.657; RT2:9.222. (3R)—N-(3-cyano-4-fluorophenyl)-3-[(1S)-1-hydroxyprop-2-yn-1-yl]-7-methyl-1,1-dioxo-2H,3H,4H,5H-1λ6-pyrrolo[3,4-f][1,2]thiazepine-6-carboxamide (3.3 mg, 1.23%, Compound 2B) was obtained as a white solid and (3S)—N-(3-cyano-4-fluorophenyl)-3-[(1S)-1-hydroxyprop-2-yn-1-yl]-7-methyl-1,1-dioxo-2H,3H,4H,5H-1λ6-pyrrolo[3,4-f][1,2]thiazepine-6-carboxamide (1 mg, 0.37%, Compound 2C) was obtained as a white solid. The skilled in the art understand that Compounds 2A, 2B, 2C and 2D are diastereomers. The stereochemistry shown for each of Compounds 2A, 2B, 2C and 2D is relative and not absolute.

Compound 2A: LC-MS (Column: HALO C18, 3.0*30 mm, 2.0 um; Column Oven: 40° C.; Mobile Phase A: Water/0.05% TFA, Mobile Phase B: ACN/0.05% TFA; Flow rate: 1.5 mL/min; Gradient: 5% B to 100% B in 1.2 min, hold 0.5 min; 254 nm; Rt=1.110 min). (ES, m/z):417 [M+H]$^+$, exact mass=416.1. $^1$H-NMR: (400 MHz, DMSO-d$_6$) δ 10.61 (s, 1H), 8.20 (dd, J=5.8, 2.7 Hz, 1H), 7.97 (ddd, J=9.2, 4.9, 2.7 Hz, 1H), 7.55 (t, J=9.1 Hz, 1H), 7.45 (s, 1H), 6.92 (d, J=10.2 Hz, 1H), 5.61 (d, J=5.9 Hz, 1H), 4.25 (td, J=5.6, 2.2 Hz, 1H), 3.70 (s, 3H), 3.54 (td, J=10.0, 4.9 Hz, 1H), 3.34 (d, J=2.2 Hz, 1H), 3.13-3.03 (m, 1H), 2.86-2.75 (m, 1H), 2.08 (q, J=7.8, 6.5 Hz, 1H), 1.52 (q, J=12.4 Hz, 1H).

Compound 2B: LC-MS (Column: ACE Excel 3 SuperC18, 3.0*50 mm, 3.0 um; Column Oven: 40 C; Mobile Phase A: Water/5 mM N NH$_4$HCO$_3$, Mobile Phase B: ACN; Flow rate: 1.2 mL/min; Gradient: 10% B to 95% B in 2.1 min, hold 0.6 min; 254 nm; Rt=1.458 min). (ES, m/z):417 [M+H]$^+$, exact mass=416.1. $^1$H-NMR: (400 MHz, DMSO-d$_6$) δ 10.61 (s, 1H), 8.20 (dd, J=5.8, 2.7 Hz, 1H), 7.97 (ddd, J=9.2, 4.9, 2.7 Hz, 1H), 7.55 (t, J=9.1 Hz, 1H), 7.46 (s, 1H), 7.06 (d, J=10.2 Hz, 1H), 5.72 (d, J=6.5 Hz, 1H), 4.13 (td, J=6.7, 2.2 Hz, 1H), 3.70 (s, 3H), 3.49 (q, J=9.9 Hz, 1H), 3.35 (d, J=2.1 Hz, 1H), 3.09 (dd, J=15.3, 6.6 Hz, 1H), 2.83-2.72 (m, 1H), 2.21 (dd, J=14.3, 6.7 Hz, 1H), 1.39 (q, J=12.3 Hz, 1H).

Compound 2C: LC-MS (Column: ACE Excel 3 SuperC18, 3.0*50 mm, 3.0 um; Column Oven: 40 C; Mobile Phase A: water/5 mM NH$_4$HCO$_3$, Mobile Phase B: Acetonitrile; Flow rate: 1.2 mL/min; Gradient: 10% B to 95% B in 2.1 min, hold 0.6 min; 254 nm; Rt=1.460 min). (ES, m/z):417 [M+H]$^+$, exact mass=416.1. $^1$H-NMR: (400 MHz, DMSO-d$_6$) δ 10.61 (s, 1H), 8.20 (dd, J=5.8, 2.7 Hz, 1H), 7.97 (ddd, J=9.3, 4.9, 2.7 Hz, 1H), 7.55 (t, J=9.1 Hz, 1H), 7.46 (s, 1H), 7.06 (d, J=10.2 Hz, 1H), 5.72 (d, J=6.5 Hz, 1H), 4.13 (td, J=6.7, 2.2 Hz, 1H), 3.70 (s, 3H), 3.49 (q, J=9.6 Hz, 1H), 3.36 (d, J=2.1 Hz, 1H), 3.09 (dd, J=15.1, 6.6 Hz, 1H), 2.78 (dd, J=15.2, 12.3 Hz, 1H), 2.21 (dd, J=14.3, 6.6 Hz, 1H), 1.39 (q, J=12.4 Hz, 1H).

Compound 2D: LC-MS (Column: ACE Excel 3 SuperC18, 3.0*50 mm, 3.0 um; Column Oven: 40 C; Mobile Phase A: water/5 mM NH$_4$HCO$_3$, Mobile Phase B: Acetonitrile; Flow rate: 1.2 mL/min; Gradient: 10% B to 95% B in 2.1 min, hold 0.6 min; 254 nm; Rt=1.453 min). (ES, m/z):417 [M+H]$^+$, exact mass=416.1. $^1$H-NMR: (400 MHz, DMSO-d$_6$) δ 10.61 (s, 1H), 8.20 (dd, J=5.9, 2.7 Hz, 1H), 7.97 (ddd, J=9.3, 4.9, 2.7 Hz, 1H), 7.55 (t, J=9.1 Hz, 1H), 7.45 (s, 1H), 6.92 (d, J=10.2 Hz, 1H), 5.62 (d, J=6.0 Hz, 1H), 4.25 (td, J=5.6, 2.2 Hz, 1H), 3.70 (s, 3H), 3.54 (td, J=10.2, 5.3 Hz, 1H), 3.34 (d, J=2.1 Hz, 1H), 3.13-3.03 (m, 1H), 2.86-2.75 (m, 1H), 2.07 (d, J=5.0 Hz, 1H), 1.52 (q, J=12.4 Hz, 1H).

Example 4

Compounds 3A, 3B, 3C and 3D

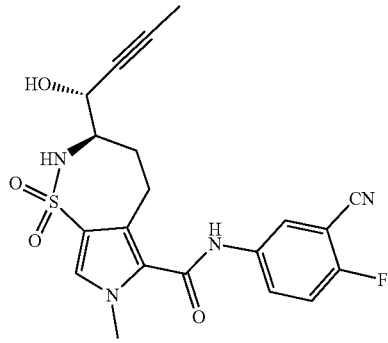

3A

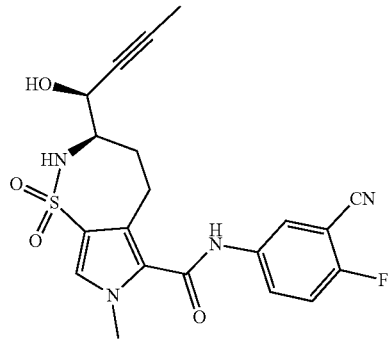

3B

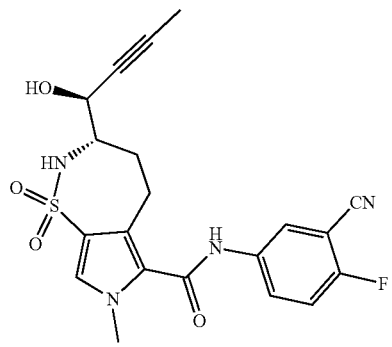

3C

-continued

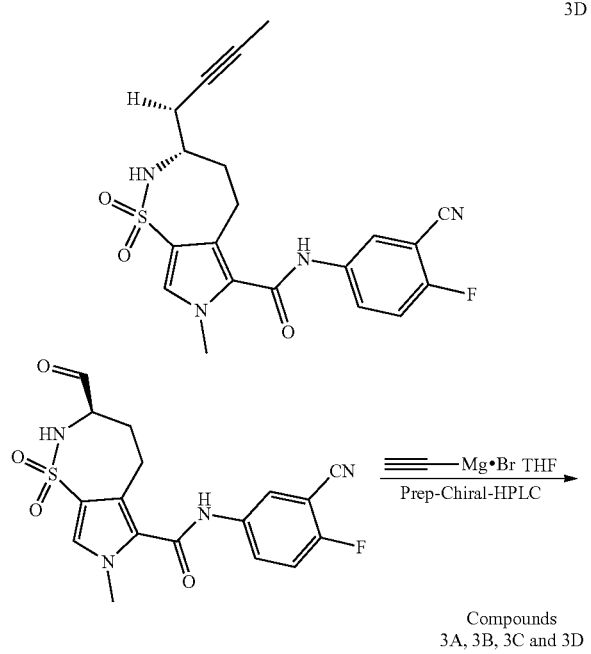

Compounds 3A, 3B, 3C and 3D

To a solution of (3R)—N-(3-cyano-4-fluorophenyl)-3-formyl-7-methyl-1,1-dioxo-2H,3H,4H,5H-1λ6-pyrrolo[3,4-f][1,2]thiazepine-6-carboxamide (350 mg, 0.897 mmol, 1.00 eq.) in THF (7.00 mL) was added of bromo(prop-1-yn-1-yl)magnesium (8.97 mL, 4.485 mmol, 5.00 eq., 0.5 mol/L in THF) dropwise with stirring at 0° C. The solution was stirred for 2 h at 0° C. The reaction was quenched with water (10 mL). The solution was extracted with ethyl acetate (2×15 mL). The mixture was washed with brine (1×15 mL). The mixture was concentrated. The residue was applied onto a silica gel column with $CH_2Cl_2/CH_3OH$ (120:1). The crude product was purified by Prep-HPLC (conditions: 2 #SHI-MADZU (HPLC-01)): Column, XBridge Prep OBD C18 Column, 30*150 mm 5um; mobile phase, Water (10M MOL/L $NH_4HCO_3$) and ACN (30% Phase B up to 52% in 9 min)). This resulted in racemic product was purified by Chiral-Prep-HPLC (conditions: (Prep-HPLC-009): Column, CHIRALPAK IE, 2*25 cm, 5um; mobile phase, Hex (8 mmol/L $NH_3$.MeOH) and EtOH— (hold 50% EtOH- in 19 min)). (3R)—N-(3-cyano-4-fluorophenyl)-3-[(1R)-1-hydroxybut-2-yn-1-yl]-7-methyl-1,1-dioxo-2H,3H,4H,5H-1λ6-pyrrolo[3,4-f][1,2]thiazepine-6-carboxamide (2 mg, 0.51%, Compound 3A) was obtained as a solid, and (3S)—N-(3-cyano-4-fluorophenyl)-3-[(1R)-1-hydroxybut-2-yn-1-yl]-7-methyl-1,1-dioxo-2H,3H,4H,5H-1λ6-pyrrolo[3,4-f][1,2]thiazepine-6-carboxamide (2 mg, 0.51%, Compound 3D) as a white solid. A mixture of two other product (27.3 mg) was also obtained.

The mixture of products (27.3 mg) was purified by Chiral-Prep-HPLC (conditions: Column: CHIRAL ART Cellulose-SB, 2*25 cm, 5 um; Mobile Phase A: Hex (8 mmol/L $NH_3$.MeOH) HPLC, Mobile Phase B: EtOH-HPLC; Flow rate: 20 mL/min; Gradient: 35 B to 35 B in 16 min; 220/254 nm; RT1:10.984; RT2:12.642). This resulted in (3R)—N-(3-cyano-4-fluorophenyl)-3-[(1R)-1-hydroxybut-2-yn-1-yl]-7-methyl-1,1-dioxo-2H,3H,4H,5H-1λ6-pyrrolo[3,4-f][1,2]thiazepine-6-carboxamide (5.6 mg, 1.45%, Compound 3B) as a white solid and (3S)—N-(3-cyano-4-fluorophenyl)-3-[(1S)-1-hydroxybut-2-yn-1-yl]-7-methyl-1,1-dioxo-2H,3H,4H,5H-1λ6-pyrrolo[3,4-f][1,2]thiazepine-6-carboxamide (10.7 mg, 2.74%, Compound 3C) as a white solid. The skilled in the art understand that Compounds 3A, 3B, 3C and 3D are diastereomers. The stereochemistry shown for each of Compounds 3A, 3B, 3C and 3D is relative and not absolute.

Compound 3A: LC-MS (Column: Shim-pack XR-ODS, 3.0*50 mm, 2.2 um; Mobile Phase A: Water/0.05% TFA, Mobile Phase B: ACN/0.05% TFA; Flow rate: 1.2 mL/min; Gradient: 5% B to 100% B in 2.0 min, hold 0.7 min; 254 nm; Rt=1.337 min, (ES, m/z):431 [M+H]$^+$, exact mass=430.1. $^1$H-NMR: (400 MHz, DMSO-d$_6$) δ 10.61 (s, 1H), 8.20 (dd, J=5.8, 2.7 Hz, 1H), 7.97 (ddd, J=9.2, 4.9, 2.7 Hz, 1H), 7.55 (t, J=9.1 Hz, 1H), 7.46 (s, 1H), 6.83 (d, J=10.3 Hz, 1H), 5.44 (d, J=5.6 Hz, 1H), 4.22 (dq, J=5.6, 2.4 Hz, 1H), 3.70 (s, 3H), 3.50 (td, J=10.8, 5.4 Hz, 1H), 3.08 (dd, J=15.7, 6.3 Hz, 1H), 2.78 (dd, J=15.3, 12.3 Hz, 1H), 2.15-2.05 (m, 1H), 1.79 (d, J=2.1 Hz, 3H), 1.48 (m, 1H).

Compound 3B: LC-MS (Column: Kinetex C18 100A 50*3.0 mm, 2.6 um; Column Oven: 40 C; Mobile Phase A: Water/0.05% TFA, Mobile Phase B: ACN/0.05% TFA; Flow rate: 1.2 mL/min; Gradient: 5% B to 100% B in 2.1 min, hold 0.6 min; 254 nm; Rt=1.295 min, (ES, m/z):431 [M+H]$^+$, exact mass=430.1. $^1$H-NMR: (400 MHz, DMSO-d$_6$) δ 10.60 (s, 1H), 8.20 (dd, J=5.8, 2.7 Hz, 1H), 7.97 (ddd, J=9.3, 4.9, 2.7 Hz, 1H), 7.55 (t, J=9.1 Hz, 1H), 7.45 (s, 1H), 6.94 (d, J=10.2 Hz, 1H), 5.48 (d, J=6.3 Hz, 1H), 4.14 (ddt, J=6.2, 4.1, 2.3 Hz, 1H), 3.70 (s, 3H), 3.51-3.40 (m, 1H), 3.08 (dd, J=15.2, 6.6 Hz, 1H), 2.82-2.72 (m, 1H), 2.17 (dd, J=14.4, 6.7 Hz, 1H), 1.82 (d, J=2.1 Hz, 3H), 1.41 (m, 1H).

Compound 3C: LC-MS (Column: Kinetex C18 100A 50*3.0 mm, 2.6 um; Column Oven: 40 C; Mobile Phase A: Water/0.05% TFA, Mobile Phase B: ACN/0.05% TFA; Flow rate: 1.2 mL/min; Gradient: 5% B to 100% B in 2.1 min, hold 0.6 min; 254 nm; Rt=1.283 min, (ES, m/z):431 [M+H]$^+$, exact mass=430.1. $^1$H-NMR: (400 MHz, DMSO-d$_6$) δ 10.60 (s, 1H), 8.20 (dd, J=5.8, 2.7 Hz, 1H), 7.97 (ddd, J=9.2, 4.9, 2.7 Hz, 1H), 7.55 (t, J=9.1 Hz, 1H), 7.45 (s, 1H), 6.94 (d, J=9.7 Hz, 1H), 5.48 (d, J=6.2 Hz, 1H), 4.14 (ddq, J=6.1, 4.1, 2.1 Hz, 1H), 3.70 (s, 3H), 3.46 (td, J=10.3, 5.5 Hz, 1H), 3.13-3.03 (m, 1H), 2.78 (dd, J=15.1, 12.4 Hz, 1H), 2.17 (dd, J=14.3, 6.7 Hz, 1H), 1.82 (d, J=2.1 Hz, 3H), 1.44-1.32 (m, 1H).

Compound 3D: LC-MS (Column: Kinetex C18 100A 50*3.0 mm, 2.6 um; Column Oven: 40 C; Mobile Phase A: Water/0.05% TFA, Mobile Phase B: ACN/0.05% TFA; Flow rate: 1.2 mL/min; Gradient: 5% B to 100% B in 2.1 min, hold 0.6 min; 254 nm; Rt=1.293 min, (ES, m/z):431 [M+H]$^+$, exact mass=430.1. $^1$H-NMR: (400 MHz, DMSO-d$_6$) δ 10.60 (s, 1H), 8.20 (dd, J=5.8, 2.7 Hz, 1H), 7.97 (ddd, J=9.2, 4.9, 2.7 Hz, 1H), 7.55 (t, J=9.1 Hz, 1H), 7.45 (s, 1H), 6.94 (d, J=9.7 Hz, 1H), 5.48 (d, J=6.2 Hz, 1H), 4.14 (ddq, J=6.1, 4.1, 2.1 Hz, 1H), 3.70 (s, 3H), 3.46 (td, J=10.3, 5.5 Hz, 1H), 3.13-3.03 (m, 1H), 2.78 (dd, J=15.1, 12.4 Hz, 1H), 2.17 (dd, J=14.3, 6.7 Hz, 1H), 1.82 (d, J=2.1 Hz, 3H), 1.44-1.32 (m, 1H).

Example 5

Compounds 4A, 4B, 4C and 4D

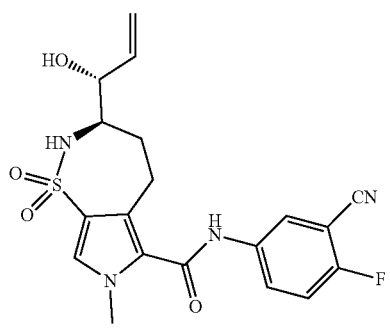
4A

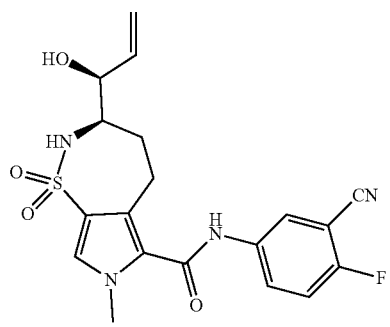
4B

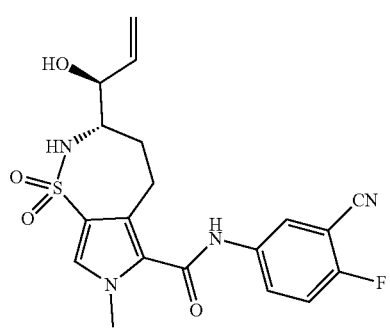
4C

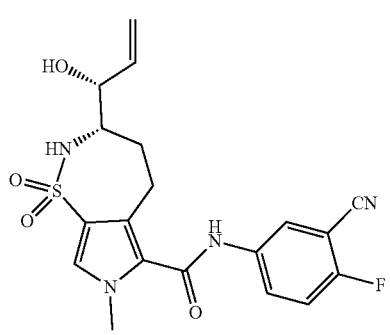
4D

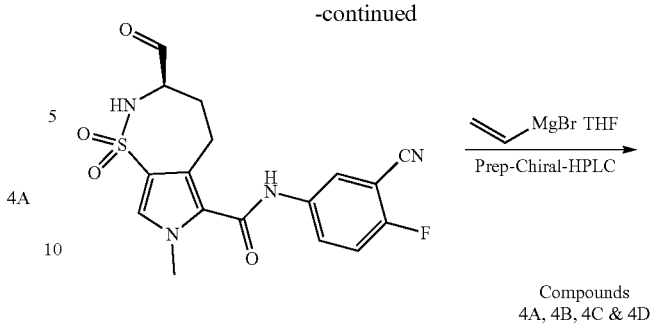

Compounds 4A, 4B, 4C & 4D

To a solution of (3R)—N-(3-cyano-4-fluorophenyl)-3-formyl-7-methyl-1,1-dioxo-2H,3H,4H,5H-1λ6-pyrrolo[3,4-f][1,2]thiazepine-6-carboxamide (430 mg, 1.101 mmol, 1.00 eq.) in THF (8.00 mL) was added bromo(ethenyl)magnesium (1 mol/L in THF, 5.51 mL, 5.5 mmol, 5.00 eq.) dropwise with stirring at 0° C. The solution was stirred for 2 h at 0° C. The reaction was then quenched with water (8 mL). The solution was extracted with ethyl acetate (2×15 mL). The mixture was washed with brine (1×15 mL). The mixture was dried over anhydrous sodium sulfate. The residue was applied onto a silica gel column with $CH_2Cl_2$/$CH_3OH$ (120:1). The crude product was purified by Prep-HPLC (conditions: 2 #SHIMADZU (HPLC-01)): Column, XBridge Prep OBD C18 Column, 30*150 mm 5 um; mobile phase, Water (10M MOL/L $NH_4HCO_3$) and ACN (25% Phase B up to 50% in 9 min)). This resulted in racemic product was purified by Chiral-Prep-HPLC (conditions: (Prep-HPLC-009): Column: CHIRALPAK IC, 2*25 cm, 5 um; Mobile Phase A: Hex (8 mmol/L $NH_3$.MeOH)-HPLC, Mobile Phase B: EtOH-HPLC; Flow rate: 20 mL/min; Gradient: 30 B to 30 B in 18 min; 220/254 nm; RT1:4.178; RT2:11.194). (3R)—N-(3-cyano-4-fluorophenyl)-3-[(1R)-1-hydroxyprop-2-en-1-yl]-7-methyl-1,1-dioxo-2H,3H,4H,5H-1λ6-pyrrolo[3,4-f][1,2]thiazepine-6-carboxamide (1.8 mg, 0.38%, Compound 4A) was obtained as a white solid; (3S)—N-(3-cyano-4-fluorophenyl)-3-[(1R)-1-hydroxyprop-2-en-1-yl]-7-methyl-1,1-dioxo-2H,3H,4H,5H-1λ6-pyrrolo[3,4-f][1,2]thiazepine-6-carboxamide (8.6 mg, 1.83%, Compound 4D) was obtained as a white solid. A mixture of two other product (13 mg) was also obtained.

The mixture of products (13 mg) was purified by Chiral-Prep-HPLC (conditions: Column: CHIRALPAK IE, 2*25 cm, 5 um; Mobile Phase A: Hex(8 mmol/L $NH_3$.MeOH)-HPLC, Mobile Phase B: EtOH-HPLC; Flow rate: 18 mL/min; Gradient: 50 B to 50 B in 17 min; 220/254 nm; RT1:10.973; RT2:14.752). (3R)—N-(3-cyano-4-fluorophenyl)-3-[(1S)-1-hydroxyprop-2-en-1-yl]-7-methyl-1,1-dioxo-2H,3H,4H,5H-1λ6-pyrrolo[3,4-f][1,2]thiazepine-6-carboxamide (1 mg, 0.21%, Compound 4B) was obtained as a white solid; (3S)—N-(3-cyano-4-fluorophenyl)-3-[(1S)-1-hydroxyprop-2-en-1-yl]-7-methyl-1,1-dioxo-2H,3H,4H,5H-1λ6-pyrrolo[3,4-f][1,2]thiazepine-6-carboxamide (1 mg, 0.21%, Compound 4D) was obtained as a white solid. The skilled in the art understand that Compounds 4A, 4B, 4C and 4D are diastereomers. The stereochemistry shown for each of Compounds 4A, 4B, 4C and 4D is relative and not absolute.

Compound 4A: LC-MS (Column: ACE Excel 3 Super C18, 3.0*50 mm, 3.0 um; Column Oven: 40 C; Mobile Phase A: Water/5 mM $NH_4HCO_3$, Mobile Phase B: ACN; Flow rate: 1.2 mL/min; Gradient: 10% B to 95% B in 2.1 min, hold 0.6 min; 254 nm; Rt=2.457 min). (ES, m/z):419

[M+H]+, exact mass=418.1. 1H NMR (400 MHz, DMSO-d6) δ 10.60 (s, 1H), 8.19 (dd, J=5.8, 2.7 Hz, 1H), 7.96 (ddd, J=9.1, 4.8, 2.7 Hz, 1H), 7.55 (t, J=9.2 Hz, 1H), 7.45 (s, 1H), 6.95 (d, J=10.3 Hz, 1H), 5.96 (ddd, J=17.2, 10.5, 5.2 Hz, 1H), 5.24 (dt, J=17.3, 1.8 Hz, 1H), 5.12 (dd, J=10.4, 1.9 Hz, 1H), 5.04 (d, J=5.7 Hz, 1H), 3.93-3.86 (m, 1H), 3.70 (s, 3H), 3.38 (t, J=8.8 Hz, 1H), 3.06 (dd, J=15.2, 6.5 Hz, 1H), 2.82-2.70 (m, 1H), 2.11 (dd, J=14.2, 6.6 Hz, 1H), 1.38 (m, 1H).

Compound 4B: LC-MS (Column: ACE Excel 3 Super C18, 3.0*50 mm, 3.0 um; Column Oven: 40 C; Mobile Phase A: Water/5 mM NH4HCO3, Mobile Phase B: ACN; Flow rate: 1.2 mL/min; Gradient: 10% B to 95% B in 2.1 min, hold 0.6 min; 254 nm; Rt=1.307 min). (ES, m/z):419 [M+H]+, exact mass=418.1. 1H NMR (400 MHz, DMSO-d6) δ 10.60 (s, 1H), 8.19 (dd, J=5.8, 2.7 Hz, 1H), 7.96 (ddd, J=9.2, 4.8, 2.6 Hz, 1H), 7.55 (t, J=9.1 Hz, 1H), 7.45 (s, 1H), 6.95 (d, J=10.3 Hz, 1H), 5.96 (ddd, J=17.3, 10.5, 5.2 Hz, 1H), 5.24 (dt, J=17.2, 1.9 Hz, 1H), 5.12 (dt, J=10.5, 1.8 Hz, 1H), 5.04 (d, J=5.6 Hz, 1H), 3.90 (q, J=5.9 Hz, 1H), 3.70 (s, 3H), 3.43-3.33 (m, 1H), 3.06 (dd, J=15.0, 6.7 Hz, 1H), 2.82-2.70 (m, 1H), 2.11 (dd, J=15.1, 7.2 Hz, 1H), 1.35 (d, J=12.8 Hz, 1H).

Compound 4C: LC-MS (Column: ACE Excel 3 Super C18, 3.0*50 mm, 3.0 um; Column Oven: 40 C; Mobile Phase A: Water/5 mM NH4HCO3, Mobile Phase B: ACN; Flow rate: 1.2 mL/min; Gradient: 10% B to 95% B in 2.1 min, hold 0.6 min; 254 nm; Rt=2.450 min). (ES, m/z):419 [M+H]+, exact mass=418.1. 1H NMR (400 MHz, DMSO-d6) δ 10.60 (s, 1H), 8.19 (dd, J=5.7, 2.7 Hz, 1H), 7.96 (ddd, J=9.2, 4.9, 2.7 Hz, 1H), 7.55 (t, J=9.1 Hz, 1H), 7.45 (s, 1H), 6.78 (d, J=10.4 Hz, 1H), 5.92 (ddd, J=17.1, 10.5, 5.0 Hz, 1H), 5.24 (dt, J=17.2, 1.9 Hz, 1H), 5.10 (dt, J=10.4, 1.9 Hz, 1H), 5.01 (d, J=5.2 Hz, 1H), 4.04 (d, J=4.9 Hz, 1H), 3.69 (s, 3H), 3.55 (t, J=11.8 Hz, 1H), 3.05 (dd, J=15.1, 6.4 Hz, 1H), 2.84-2.72 (m, 1H), 1.90 (dd, J=14.2, 6.6 Hz, 1H), 1.43 (d, J=12.4 Hz, 1H).

Compound 4D: LC-MS (Column: ACE Excel 3 Super C18, 3.0*50 mm, 3.0 um; Column Oven: 40 C; Mobile Phase A: Water/5 mM NH4HCO3, Mobile Phase B: ACN; Flow rate: 1.2 mL/min; Gradient: 10% B to 95% B in 2.1 min, hold 0.6 min; 254 nm; Rt=1.307 min). (ES, m/z):419 [M+H]+, exact mass=418.1. 1H NMR (400 MHz, DMSO-d6) δ 10.60 (s, 1H), 8.19 (dd, J=5.8, 2.7 Hz, 1H), 7.96 (ddd, J=9.2, 4.8, 2.7 Hz, 1H), 7.55 (t, J=9.2 Hz, 1H), 7.45 (s, 1H), 6.79 (d, J=10.4 Hz, 1H), 5.92 (ddd, J=17.2, 10.5, 5.0 Hz, 1H), 5.24 (dt, J=17.2, 1.9 Hz, 1H), 5.10 (dt, J=10.6, 1.8 Hz, 1H), 5.01 (d, J=5.2 Hz, 1H), 4.04 (q, J=4.9 Hz, 1H), 3.69 (s, 3H), 3.55 (ddd, J=14.1, 10.2, 3.9 Hz, 1H), 3.10-3.00 (m, 1H), 2.78 (t, J=13.7 Hz, 1H), 1.90 (dd, J=14.2, 6.4 Hz, 1H), 1.40 (d, J=12.8 Hz, 1H).

Example 6

Compounds 5A and 5B

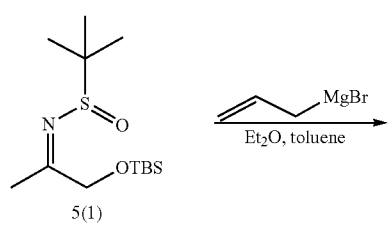

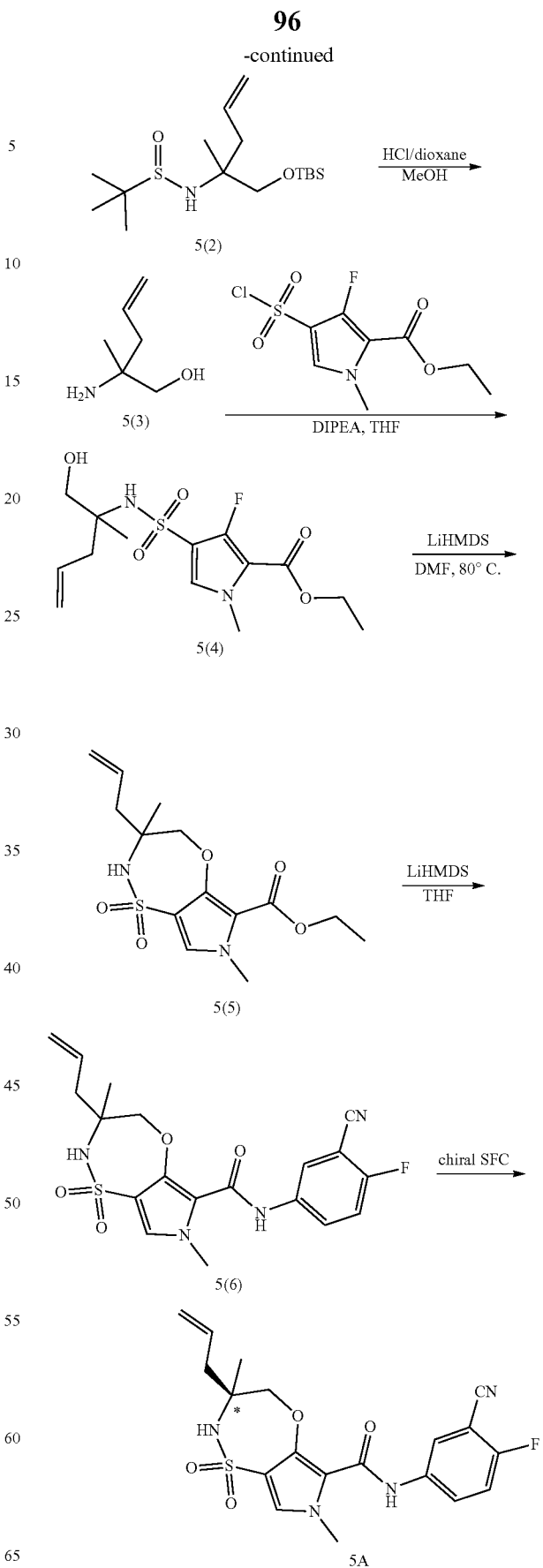

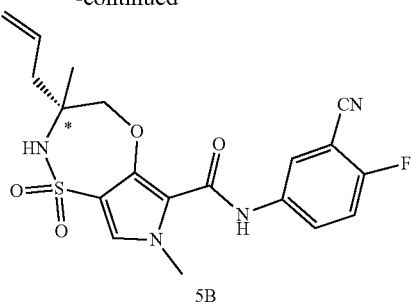

5B

To a solution of 5(1) (4 g, 13.72 mmol, 1 eq.) in toluene (40 mL) was added dropwise allyl(bromo)magnesium (1 M in Et$_2$O, 34.30 mL, 2.5 eq.) at −78° C. under N$_2$. The mixture was stirred at −78° C. for 2 h. The reaction was quenched with sat. NH$_4$Cl (40 mL), then was allowed to warm to 15° C. slowly and extracted with EtOAc (30 mL×3). The combined organic layers were concentrated under reduced pressure to give a residue. The residue was purified by flash silica gel chromatography (ISCO®; 40 g SepaFlash® Silica Flash Column, Eluent of 0~30% Ethyl acetate/Petroleum ether gradient @ 40 mL/min) to give 5(2) (0.94 g, 2.82 mmol, 20.54%) as a colorless oil.

To a solution of 5(2) (3.39 g, 10.16 mmol) in MeOH (30 mL) was added HCl/dioxane (4 M, 17.84 mL, 20 eq.) at 15° C. The mixture was stirred at 15° C. for 1 h. The mixture was concentrated under reduced pressure to give crude 5(3) (1.4 g, HCl salt) as a brown oil, which was used into the next step without further purification.

To a solution of crude 5(3) (450 mg, 2.97 mmol, 1.5 eq.) in THF (25 mL) was added DIPEA (1.28 g, 9.89 mmol, 1.72 mL, 5 eq.) at 10° C. The mixture was stirred at 10° C. for 1 h. Sulfonyl chloride (533.54 mg, 1.98 mmol, 1 eq.) was added to the mixture, which was then stirred at 10° C. for 15 h. The mixture was concentrated under reduced pressure to give a residue, which was purified by flash silica gel chromatography (ISCO®; 12 g SepaFlash® Silica Flash Column, Eluent of 0~45% Ethyl acetate/Petroleum ether gradient @ 20 mL/min) to give 5(4) (150 mg, 430.55 µmol, 21.76%) as a brown oil.

To a solution of 5(4) (150 mg, 430.55 µmol, 1 eq.) in DMF (3 mL) was added dropwise LiHMDS (1 M, 1.5 mL, 3.48 eq.) at 10° C. The mixture was stirred at 80° C. for 5 h. The reaction was quenched by the addition of sat. aq. NH$_4$Cl (15 mL) at 10° C. The mixture was then diluted with H$_2$O (15 mL) and extracted with EtOAc (3×15 mL). The combined organic layers were washed with brine (30 mL), dried over anhydrous Na$_2$SO$_4$, filtered and concentrated under reduced pressure to give a residue. The residue was purified by flash silica gel chromatography (ISCO®; 4 g SepaFlash® Silica Flash Column, Eluent of 0~25% Ethyl acetate/Petroleum ether gradient @ 20 mL/min) to give 5(5) (130 mg, 307.36 µmol, 71.39% yield, 77.64% purity) as a yellow oil. The enantiomers were separated by chiral HPLC.

To a solution of 5(5) (130 mg, 395.88 µmol, 1 eq.) and 5-amino-2-fluorobenzonitrile (75.45 mg, 554.23 µmol, 1.4 eq.) in THF (8 mL) was added LiHMDS (1 M, 1.58 mL, 4 eq.) at 10° C. After the addition, the mixture was stirred at 10° C. for 2 h. TLC (Petroleum ether:Ethyl acetate (2:1)) indicated the starting material was consumed completely. The reaction was quenched with sat. aq. NH$_4$Cl (15 mL) and H$_2$O (10 mL), and then extracted with EtOAc (3×20 mL). The combined organic layers were washed with brine (40 mL), dried over anhydrous Na$_2$SO$_4$, filtered and concentrated to give a residue. The residue was purified by flash silica gel chromatography (ISCO®; 4 g SepaFlash® Silica Flash Column, Eluent of 0~35% Ethyl acetate/Petroleum ether gradient @ 20 mL/min) to give 5(6) (100 mg, 223.57 µmol, 56.47% yield, 93.55% purity) as a brown solid. The enantiomers, Compound 5A and Compound 5B, were separated by chiral HPLC. The stereochemistry shown for each of Compounds 5A and 5B is relative and not absolute.

Example 7

Compound 6A

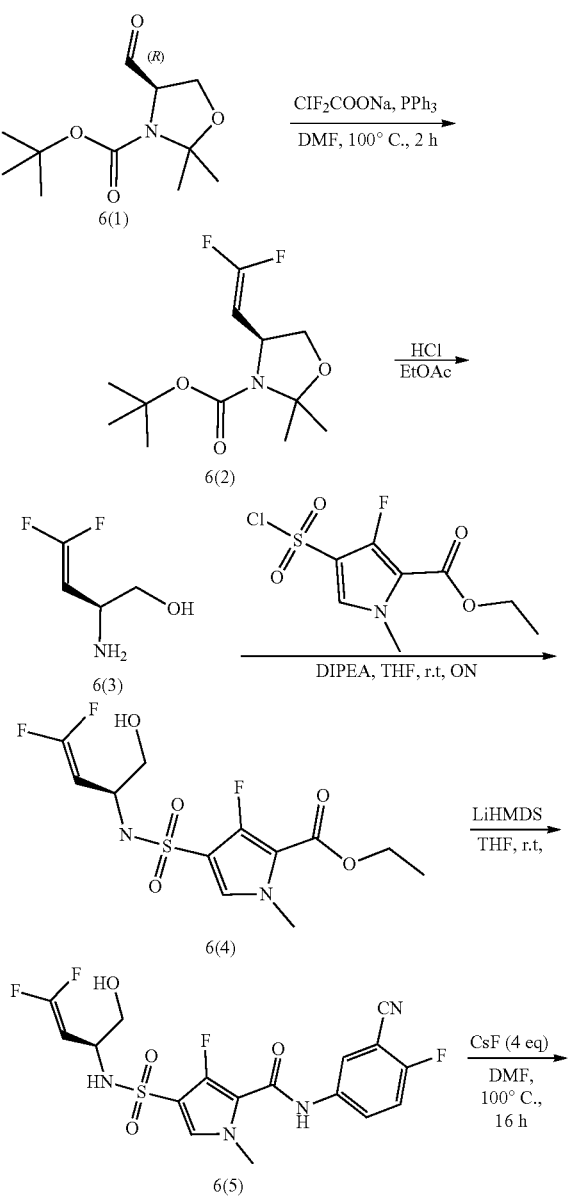

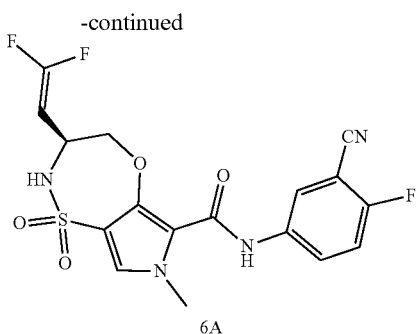

6A

To a solution of 6(1) (0.50 g, 2.18 mmol, 1 eq.) and PPh₃ (1.72 g, 6.54 mmol, 3 eq.) in DMF (5 mL) was added sodium 2-chloro-2,2-difluoro-acetate (997.46 mg, 6.54 mmol, 3.0 eq.) at 100° C. under N₂. The mixture was stirred at 100° C. for 2 h. The mixture was diluted with H₂O (20 mL) and extracted with EtOAc (3×25 mL). The combined organic layers were washed with brine (25 mL), dried over anhydrous Na₂SO₄, filtered and concentrated under reduced pressure to give a residue, which was purified by flash silica gel chromatography (ISCO®; 20 g SepaFlash® Silica Flash Column, Eluent of 0~3% Ethyl acetate/Petroleum ether gradient) to give 5(2) (0.53 g, 2.01 mmol, 92.31% yield) as a colorless oil.

A solution of 6(2) (0.530 g, 2.01 mmol, 1 eq.) in HCl/EtOAc (4 M, 1.8 mL, 3.58 eq.) was stirred at 15° C. for 0.5 h. The mixture was concentrated to dryness to give crude 6(3) (0.32 g, 2.01 mmol, 99.62% yield, HCl salt) as a light yellow solid, which was used directly for next step without purification.

A mixture of 6(3) (0.250 g, 2.03 mmol, 1.22 eq.) and DIPEA (1.08 g, 8.34 mmol, 1.45 mL, 5 eq.) in THF (20 mL) was stirred at 15° C. for 1 h. Then sulfonyl chloride (0.450 g, 1.67 mmol, 1 eq.) was added. The mixture was stirred at 15° C. for 15 h. The mixture was concentrated to give a residue, which was purified by flash silica gel chromatography (ISCO®; 20 g SepaFlash® Silica Flash Column, Eluent of 0~90% Ethyl acetate/Petroleum ether gradient) to give 6(4) (0.48 g, 80.73%) as a yellow solid.

To a solution of 6(4) (0.25 g, 701.62 µmol, 1 eq.), 5-amino-2-fluorobenzonitrile (143.26 mg, 1.05 mmol, 1.5 eq.) in THF (5 mL) was added LiHMDS (1 M in THF, 3.5 mL, 3.5 mmol, 4.99 eq.) dropwise at 15° C. The mixture was stirred at 15° C. for 3 h. The reaction was quenched with sat. aq. NH₄Cl (10 mL) and H₂O (5 mL). The mixture was extracted with EtOAc (3×20 mL). The combined organic layers were washed with brine (20 mL), dried over anhydrous Na₂SO₄, filtered and concentrated to give a residue. The residue was purified by flash silica gel chromatography (ISCO®; 4 g SepaFlash® Silica Flash Column, Eluent of 30~65% Ethyl acetate/Petroleum ether gradient) to give the crude product (310 mg) as a purple solid. The crude product (190 mg) was re-purified by flash silica gel chromatography (ISCO®; 4 g SepaFlash® Silica Flash Column, Eluent of 10~50% Ethyl acetate/Petroleum ether gradient) to give 6(5) (180 mg) as a purple solid.

To a solution of 6(5) (0.11 g, 246.43 µmol, 1 eq.) in DMF (2 mL) was added CsF (149.73 mg, 985.72 µmol, 4 eq.). The mixture was stirred at 100° C. for 16 h. The mixture was diluted with H₂O (15 mL) and extracted with EtOAc (3×15 mL). The combined organic layers were washed with brine (2×15 mL), dried over anhydrous Na₂SO₄, filtered and concentrated to give a residue. The residue was purified by flash silica gel chromatography (ISCO®; 12 g SepaFlash® Silica Flash Column, Eluent of 0~100% Ethyl acetate/Petroleum ether gradient @ 25 mL/min) to give the crude product (35 mg) as a red gum, which was re-purified by prep-HPLC (Instrument: BK; Column: Xtimate C18 150*25 mm*5 um; Condition: water(0.05% HCl)-ACN; Begin B: 35; End B: 65; Gradient Time (min): 11.5; 100% B Hold Time (min): 2; FlowRate (ml/min): 25) to give compound 6A (1.4 mg) as a white solid.

Example 8

Compounds 7A and 7B

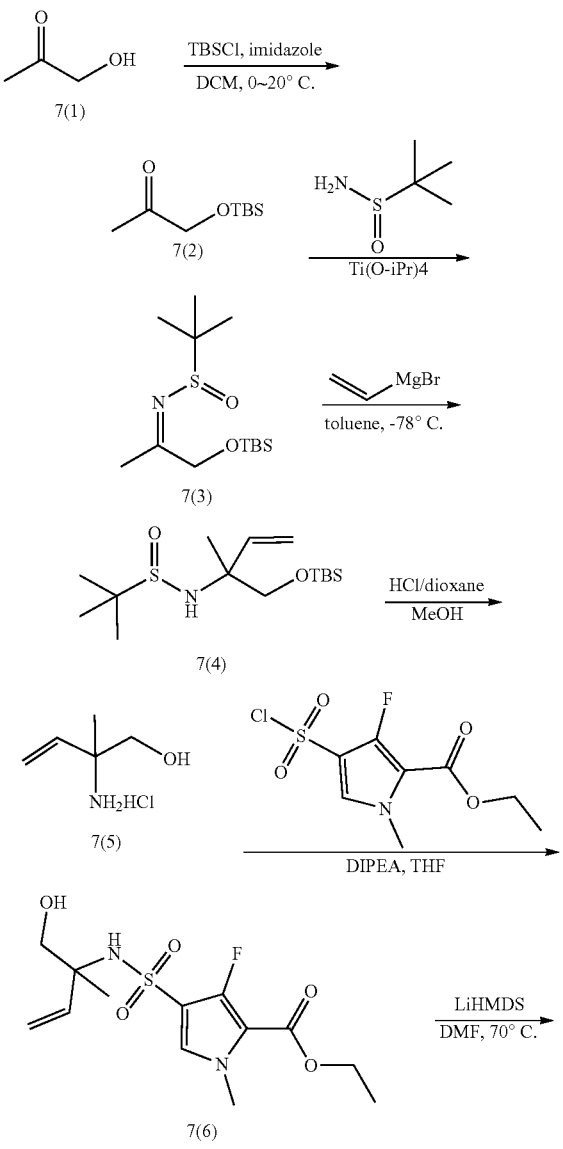

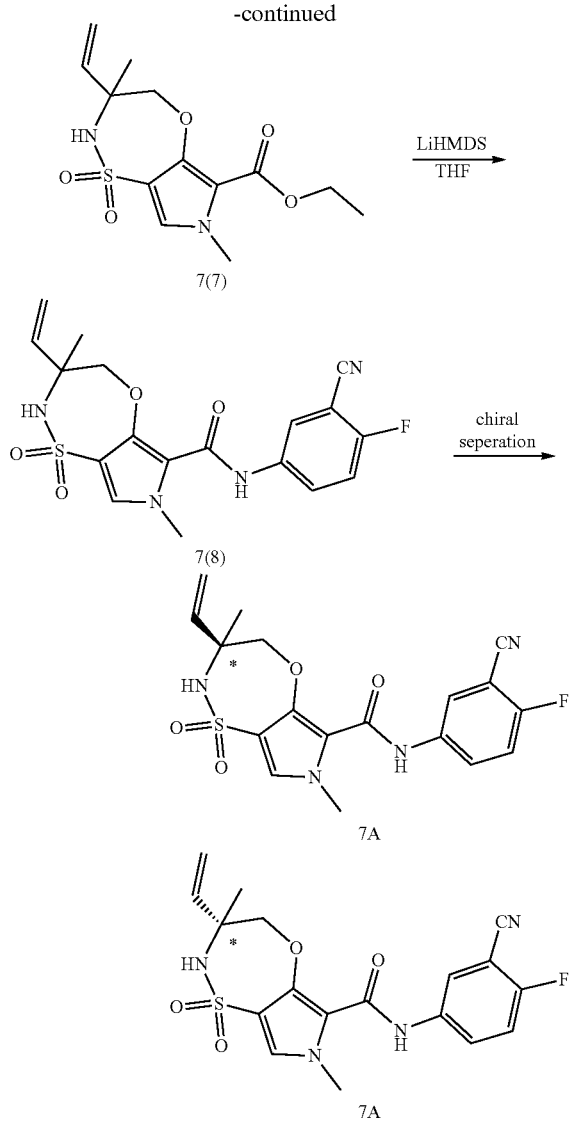

To a solution of 1-hydroxypropan-2-one (20 g, 269.98 mmol, 18.52 mL, 1 eq.) and imidazole (25.73 g, 377.98 mmol, 1.4 eq.) in DCM (200 mL) was added TBSCl (44.76 g, 296.98 mmol, 36.39 mL, 1.1 eq.) at 0° C. The mixture was stirred at 20° C. for 12 h. The mixture was concentrated under reduced pressure to give a residue. The residue was diluted with H₂O (200 mL), extracted with EtOAc (3×150 mL). The combined organic layers were washed with brine (200 mL), dried over anhydrous Na₂SO₄, filtered and concentrated under reduced pressure to give the crude 7(2) (47 g, 249.55 mmol, 92.43% yield) as a yellow oil, which was used into the next step without further purification.

To a mixture of crude (2) (37 g, 196.45 mmol, 1 eq.) in THF (370 mL) was added tetraisopropoxytitanium (139.59 g, 491.14 mmol, 144.95 mL, 2 eq.) and 2-methylpropane-2-sulfinamide (23.81 g, 196.45 mmol, 1 eq.) at 15° C. The mixture was stirred at 70° C. for 14 h. After cooling to 15° C., the mixture was poured into brine (400 mL) with stirring. The resulting suspension was filtered by diatomite and washed with EtOAc (6×50 mL). The filtrate was concentrated to give a residue. To the residue was added H₂O (200 mL). The mixture was extracted with EtOAc (3×150 mL). The combined organic layers were washed with brine (200 mL), dried over anhydrous Na₂SO₄, filtered and concentrated under reduced pressure to give the crude product, which was purified by flash silica gel chromatography (ISCO®; 220 g SepaFlash® Silica Flash Column, Eluent of 0~15% Ethyl acetate/Petroleum ether gradient @ 100 mL/min) to give 7(3) (9 g, 30.87 mmol, 15.71% yield) as a yellow oil.

To a solution of (3) (5 g, 17.15 mmol, 1 eq.) in toluene (50 mL) was added bromo(vinyl)magnesium (1.6 M in 2-MeTHF, 32.16 mL, 3 eq.) at −78° C. under N₂. The mixture was stirred at −78° C. for 2 h. The reaction was quenched with sat. NH₄Cl(100 mL) at −78° C. The mixture was allowed to warm to 15° C. slowly. The mixture was then filtered and extracted with EtOAc (3×50 mL). The combined organic layers were washed with brine (100 mL), dried over anhydrous Na₂SO₄, filtered and concentrated under reduced pressure to give a residue. The residue was purified by flash silica gel chromatography (ISCO®; 40 g SepaFlash® Silica Flash Column, Eluent of 0~20% Ethyl acetate/Petroleum ether gradient @ 40 mL/min) to give 7(4) (1.5 g, 4.69 mmol, 27.37% yield) as a yellow oil.

To a solution of 7(4) (1.5 g, 4.69 mmol, 1 eq.) in MeOH (15 mL) was added HCl/dioxane (4 M, 11.73 mL, 10 eq.) at 15° C. The mixture was stirred at 15° C. for 1 h. The mixture was concentrated under reduced pressure to give a residue. The residue was diluted with MTBE (30 mL) and extracted with H₂O (3×60 mL). The combined aqueous layers were concentrated under reduced pressure to give 7(5) (620 mg, 4.51 mmol, 95.99% yield, HCl salt) as a brown oil, which was used into the next step without further purification To a solution of 7(5) (400 mg, 2.91 mmol, 1.5 eq.) in THF (25 mL) was added DIPEA (1.25 g, 9.69 mmol, 1.69 mL, 5 eq.) at 10° C. The mixture was stirred at 10° C. for 1 h. Then to the mixture was added sulfonyl chloride (522.60 mg, 1.94 mmol, 1 eq.). The mixture was stirred at 10° C. for 19 h. The mixture was concentrated under reduced pressure to give a residue. The residue was purified by flash silica gel chromatography (ISCO®; 12 g SepaFlash® Silica Flash Column, Eluent of 0~50% Ethyl acetate/Petroleum ether gradient @ 30 mL/min) to give 7(6) (170 mg, 508.43 μmol, 26.24% yield) as a brown oil.

To a solution of 7(6) (170 mg, 508.43 μmol, 1 eq.) in DMF (4 mL) was added LiHMDS (1 M, 1.77 mL, 3.48 eq.) at 10° C. The mixture was stirred at 80° C. for 6 h. TLC (Petroleum ether:Ethyl acetate (1:1)) indicated the starting material was consumed completely. The reaction was quenched with sat. aq. NH₄Cl(15 mL) at 10° C. The mixture was then diluted with H₂O (15 mL) and extracted with EtOAc (3×15 mL). The combined organic layers were washed with brine (30 mL), dried over anhydrous Na₂SO₄, filtered and concentrated under reduced pressure to give a residue. The residue was purified by flash silica gel chromatography (ISCO®; 4 g SepaFlash® Silica Flash Column, Eluent of 0~25% Ethyl acetate/Petroleum ether; gradient @ 20 mL/min) to give 7(7) (130 mg, 370.37 mol, 72.85% yield, 89.56% purity) as a yellow oil.

To a solution of 7(7) (130 mg, 413.54 μmol, 1 eq.) and 5-amino-2-fluorobenzonitrile (78.81 mg, 578.96 μmol, 1.4 eq.) in THF (8 mL) was added LiHMDS (1 M, 1.65 mL, 4 eq.) at 10° C. The mixture was stirred at 10° C. for 2 h. TLC (Petroleum ether:Ethyl acetate (2:1)) indicated the starting material was consumed completely. The reaction was quenched with sat. aq. NH$_4$Cl(15 mL) and H$_2$O (10 mL). The mixture was then extracted with EtOAc (3×20 mL). The combined organic layers were washed with brine (40 mL), dried over anhydrous Na$_2$SO$_4$, filtered and concentrated to give a residue, which was purified by flash silica gel chromatography (ISCO®; 4 g SepaFlash® Silica Flash Column, Eluent of 0~35% Ethyl acetate/Petroleum ether; gradient @ 20 mL/min) to give 7(8) (100 mg, 58.62% yield, 98.03% purity) as a brown solid. The enantiomers, compound 7A and compound 7B, were further separated by chiral HPLC. The stereochemistry shown for each of Compounds 7A and 7B is relative and not absolute.

Example 9

Additional Compounds

The foregoing syntheses are exemplary and can be used as a starting point to prepare a large number of additional compounds, including those provided in Table 1. Examples of compounds of Formulae (I) and (II) that can be prepared in various ways, including those synthetic schemes shown and described herein, are provided below. Those skilled in the art will be able to recognize modifications of the disclosed syntheses and to devise routes based on the disclosures herein; all such modifications and alternate routes are within the scope of the claims.

TABLE 1

| Compound No. | Structure | MS [M + 1]$^+$ | $^1$H NMR |
|---|---|---|---|
| 8 | 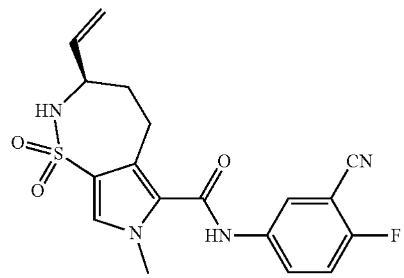 [SMILES: C=C[C@H]1CCc2c(cn(C)c2C(=O)Nc2ccc(F)c(C#N)c2)S(=O)(=O)N1] | 389.4 | (400 MHz, CDCl$_3$) δ: 8.13-7.98 (m, 2H), 7.80 (ddd, J = 2.8, 4.5, 9.1 Hz, 1H), 7.24 (t, J = 8.7 Hz, 1H), 7.14 (s, 1H), 5.86 (ddd, J = 4.9, 10.6, 17.3 Hz, 1H), 5.38-5.15 (m, 2H), 4.37 (br s, 1H), 4.12 (br d, J = 8.4 Hz, 1H), 3.78 (s, 3H), 3.27-3.05 (m, 2H), 2.17 (br dd, J = 6.5, 14.6 Hz, 1H), 1.55 (br d, J = 3.4 Hz, 1H) |
| 9A | 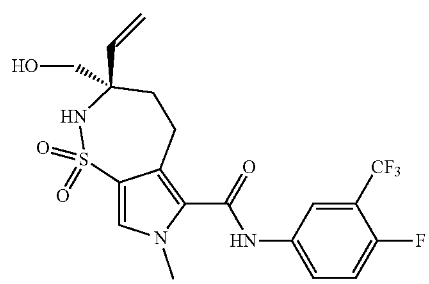 [SMILES: C=C[C@@]1(CO)CCc2c(cn(C)c2C(=O)Nc2ccc(F)c(C(F)(F)F)c2)S(=O)(=O)N1] | 462.3 | (400 MHz, CDOD$_3$) δ: 8.07 (dd, J = 2.7, 6.3 Hz, 1H), 7.93-7.82 (m, 1H), 7.38-7.27 (m, 2H), 6.02 (dd, J = 11.1, 17.8 Hz, 1H), 5.33-5.22 (m, 2H), 3.77 (s, 3H), 3.63-3.55 (m, 1H), 3.54-3.43 (m, 1H), 3.20-3.00 (m, 2H), 2.30-2.12 (m, 2H) |
| 9B | 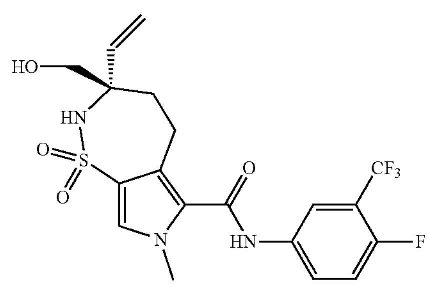 [SMILES: C=C[C@]1(CO)CCc2c(cn(C)c2C(=O)Nc2ccc(F)c(C(F)(F)F)c2)S(=O)(=O)N1] | 462.3 | (400 MHz, CDOD$_3$) δ: 8.09 (dd, J = 2.6, 6.3 Hz, 1H), 7.89 (td, J = 3.8, 8.7 Hz, 1H), 7.41-7.28 (m, 2H), 6.04 (dd, J = 11.2, 17.7 Hz, 1H), 5.35-5.21 (m, 2H), 3.79 (s, 3H), 3.64-3.58 (m, 1H), 3.56-3.48 (m, 1H), 3.20-3.00 (m, 2H), 2.33-2.14 (m, 2H) |
| 10A | 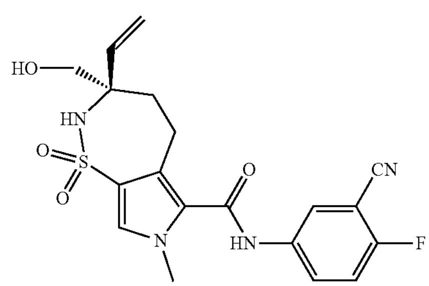 [SMILES: C=C[C@@]1(CO)CCc2c(cn(C)c2C(=O)Nc2ccc(F)c(C#N)c2)S(=O)(=O)N1] | 419.1 | (400 MHz, CDOD$_3$) δ: 8.11 (dd, J = 2.7, 5.7 Hz, 1H), 7.91 (ddd, J = 2.8, 4.7, 9.2 Hz, 1H), 7.36 (t, J = 9.0 Hz, 1H), 7.30 (s, 1H), 6.02 (dd, J = 11.2, 17.7 Hz, 1H), 5.34-5.20 (m, 2H), 3.77 (s, 3H), 3.62-3.46 (m, 2H), 3.22-2.99 (m, 2H), 2.32-2.13 (m, 2H) |

TABLE 1-continued

| Compound No. | Structure | MS [M + 1]+ | 1H NMR |
|---|---|---|---|
| 10B | 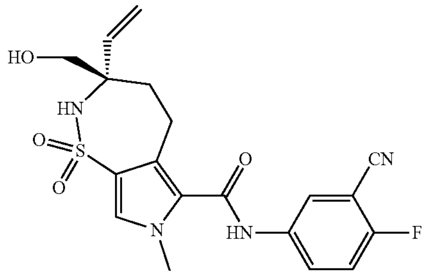 | 419.1 | (400 MHz, CDCl3) δ: 8.07-7.96 (m, 1H), 7.85 (br s, 1H), 7.27-7.14 (m, 2H), 5.94 (br dd, J = 11.7, 17.1 Hz, 1H), 5.40-5.20 (m, 2H), 5.08 (br s, 1H), 3.81 (s, 3H), 3.70-3.50 (m, 2H), 3.11 (br d, J = 5.6 Hz, 2H), 2.32 (br s, 2H), 2.17-2.05 (m, 1H) |
| 11A | 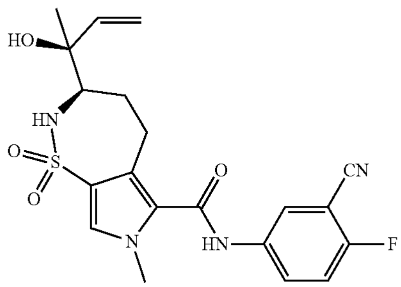 [SMILES: C=C[C@](C)(O)[C@H]1CCc2c(cn(C)c2C(=O)Nc2ccc(F)c(C#N)c2)S(=O)(=O)N1] | 433.4 | (400 MHz, DMSO-d6) δ: 10.60 (s, 1H), 8.18 (dd, J = 2.4, 5.6 Hz, 1H), 8.02-7.87 (m, 1H), 7.54 (t, J = 9.1 Hz, 1H), 7.46 (s, 1H), 6.92 (d, J = 10.8 Hz, 1H), 5.92 (dd, J = 10.7, 17.1 Hz, 1H), 5.20 (dd, J = 1.9, 17.3 Hz, 1H), 5.06-4.95 (m, 1H), 4.76 (s, 1H), 3.68 (s, 3H), 3.03 (br dd, J = 6.8, 15.1 Hz, 1H), 2.73 (br d, J = 13.5 Hz, 1H), 2.13-2.04 (m, 1H), 1.26-1.09 (m, 5H) |
| 11B | 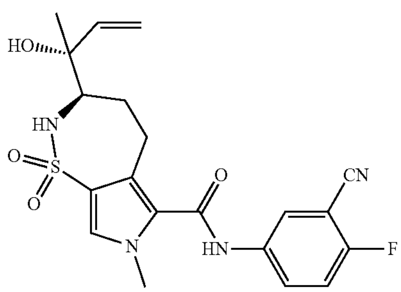 [SMILES: C=C[C@@](C)(O)[C@H]1CCc2c(cn(C)c2C(=O)Nc2ccc(F)c(C#N)c2)S(=O)(=O)N1] | 433.4 | (400 MHz, DMSO-d6) δ: 10.59 (s, 1H), 8.18 (dd, J = 2.6, 5.8 Hz, 1H), 7.95 (ddd, J = 2.7, 4.9, 9.2 Hz, 1H), 7.53 (t, J = 9.1 Hz, 1H), 7.45 (s, 1H), 6.81 (d, J = 10.6 Hz, 1H), 6.00 (dd, J = 10.7, 17.3 Hz, 1H), 5.22 (dd, J = 1.9, 17.3 Hz, 1H), 5.02 (dd, J = 2.0, 10.6 Hz, 1H), 4.62 (s, 1H), 3.69 (s, 3H), 3.03 (br dd, J = 6.6, 14.6 Hz, 1H), 2.79-2.65 (m, 1H), 2.07 (s, 1H), 1.47-1.32 (m, 1H), 1.15 (s, 3H) |
| 12A | 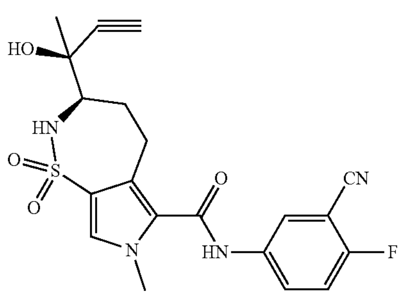 [SMILES: C#C[C@](C)(O)[C@H]1CCc2c(cn(C)c2C(=O)Nc2ccc(F)c(C#N)c2)S(=O)(=O)N1] | 431.1 | (400 MHz, DMSO-d6) δ: 10.61 (s, 1H), 8.19 (dd, J = 2.7, 5.8 Hz, 1H), 7.96 (ddd, J = 2.7, 4.8, 9.1 Hz, 1H), 7.54 (t, J = 9.1 Hz, 1H), 7.46 (s, 1H), 6.90 (d, J = 10.8 Hz, 1H), 5.53 (s, 1H), 3.69 (s, 3H), 3.40-3.36 (m, 1H), 3.28 (s, 1H), 3.09 (br dd, J = 6.9, 13.8 Hz, 1H), 2.80-2.70 (m, 1H), 2.25 (br dd, J = 6.9, 13.8 Hz, 1H), 1.49 (q, J = 12.0 Hz, 1H), 1.41 (s, 3H) |
| 12B | 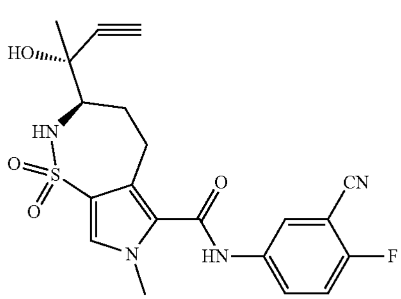 [SMILES: C#C[C@@](C)(O)[C@H]1CCc2c(cn(C)c2C(=O)Nc2ccc(F)c(C#N)c2)S(=O)(=O)N1] | 431.1 | (400 MHz, DMSO-d6) δ: 10.61 (br s, 1H), 8.19 (dd, J = 2.6, 5.8 Hz, 1H), 8.00-7.92 (m, 1H), 7.54 (t, J = 9.1 Hz, 1H), 7.45 (s, 1H), 6.93 (br s, 1H), 5.52 (br s, 1H), 3.69 (s, 3H), 3.51-3.41 (m, 1H), 3.34 (br s, 1H), 3.10 (br dd, J = 6.6, 14.8 Hz, 1H), 2.82-2.65 (m, 2H), 2.25 (br dd, J = 6.6, 13.9 Hz, 1H), 1.48 (q, J = 11.6 Hz, 1H), 1.35 (s, 3H) |

TABLE 1-continued

| Compound No. | Structure | MS [M + 1]+ | 1H NMR |
|---|---|---|---|
| 13 | 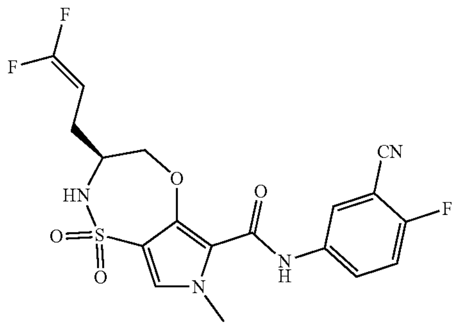 [SMILES: Cn1cc2c(c1C(=O)Nc1ccc(F)c(C#N)c1)OC[C@H](CC=C(F)F)NS2(=O)=O] | 441.0 | (400 MHz, CDCl3) δ: 8.78 (s, 1H), 7.96 (dd, J = 2.7, 5.3 Hz, 1H), 7.72 (ddd, J = 2.9, 4.4, 8.9 Hz, 1H), 7.20 (t, J = 8.6 Hz, 1H), 7.09 (s, 1H), 4.77-4.64 (m, 2H), 4.43-4.18 (m, 2H), 3.96 (s, 4H), 2.40 (br t, J = 7.5 Hz, 2H) |
| 14A | 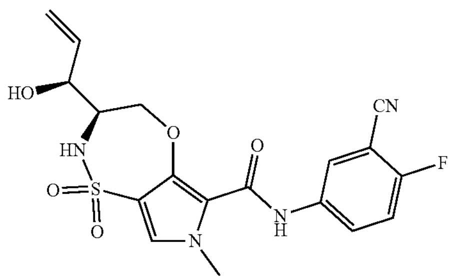 [SMILES: C=C[C@H](O)[C@H]1COc2c(cn(C)c2C(=O)Nc2ccc(F)c(C#N)c2)S(=O)(=O)N1] | 421.2 | (400 MHz, CD3OD) δ: 8.17 (dd, J = 2.7, 5.6 Hz, 1H), 7.91 (ddd, J = 2.8, 4.7, 8.8 Hz, 1H), 7.36 (t, J = 8.9 Hz, 1H), 7.30 (s, 1H), 6.14-6.00 (m, 1H), 5.42 (d, J = 17.1 Hz, 1H), 5.30 (d, J = 10.5 Hz, 1H), 4.95 (d, J = 2.0 Hz, 1H), 4.26 (t, J = 6.0 Hz, 1H), 4.18 (dd, J = 8.7, 12.8 Hz, 1H), 3.94 (s, 3H), 3.83-3.75 (m, 1H) |
| 14B | 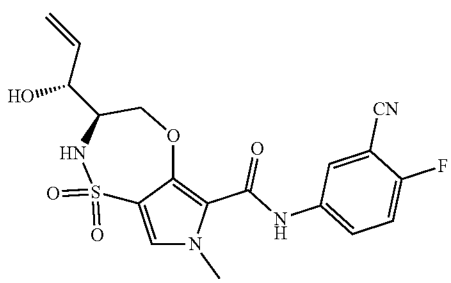 [SMILES: C=C[C@@H](O)[C@H]1COc2c(cn(C)c2C(=O)Nc2ccc(F)c(C#N)c2)S(=O)(=O)N1] | 421.1 | (400 MHz, DMSO-d6) δ: 9.54 (s, 1H), 8.20 (dd, J = 2.6, 5.6 Hz, 1H), 8.05 (ddd, J = 2.8, 4.8, 9.0 Hz, 1H), 7.68-7.36 (m, 3H), 6.03-5.85 (m, 1H), 5.57-5.07 (m, 3H), 4.72 (br d, J = 12.3 Hz, 1H), 4.25 (br s, 1H), 3.97-3.70 (m, 5H) |
| 15A | 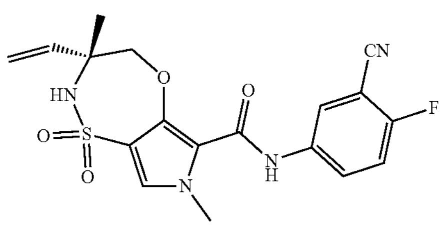 [SMILES: C=C[C@]1(C)COc2c(cn(C)c2C(=O)Nc2ccc(F)c(C#N)c2)S(=O)(=O)N1] | 405.0 | (400 MHz, CDCl3) δ: 8.73 (s, 1H), 7.90 (dd, J = 2.7, 5.4 Hz, 1H), 7.76 (ddd, J = 2.8, 4.5, 9.0 Hz, 1H), 7.20 (t, J = 8.7 Hz, 1H), 7.06 (s, 1H), 6.10 (dd, J = 10.8, 17.4 Hz, 1H), 5.48 (d, J = 17.4 Hz, 1H), 5.40 (d, J = 10.8 Hz, 1H), 4.87 (s, 1H), 4.78-4.72 (m, 1H), 4.68-4.61 (m, 1H), 3.96 (s, 3H), 2.02 (s, 1H), 1.59 (s, 3H) |
| 15B | 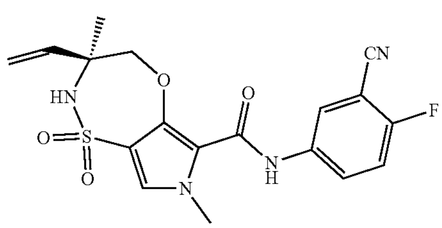 [SMILES: C=C[C@@]1(C)COc2c(cn(C)c2C(=O)Nc2ccc(F)c(C#N)c2)S(=O)(=O)N1] | 405.0 | (400 MHz, CDCl3) δ: 8.73 (s, 1H), 7.90 (dd, J = 2.8, 5.4 Hz, 1H), 7.80-7.73 (m, 1H), 7.20 (t, J = 8.7 Hz, 1H), 7.06 (s, 1H), 6.10 (dd, J = 10.8, 17.4 Hz, 1H), 5.48 (d, J = 17.3 Hz, 1H), 5.40 (d, J = 10.8 Hz, 1H), 4.88 (s, 1H), 4.78-4.72 (m, 1H), 4.67-4.61 (m, 1H), 3.96 (s, 3H), 2.02 (s, 1H), 1.59 (s, 3H) |

TABLE 1-continued

| Compound No. | Structure | MS [M + 1]+ | 1H NMR |
|---|---|---|---|
| 16A | 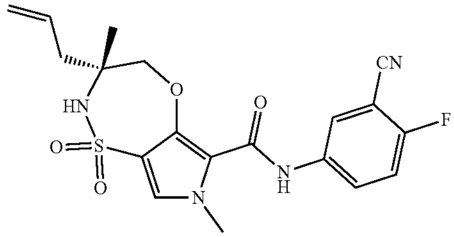 [SMILES: C=CC[C@]1(C)COc2c(cn(C)c2C(=O)Nc2ccc(F)c(C#N)c2)S(=O)(=O)N1] | 419.0 | (400 MHz, CDCl3) δ: 8.76 (s, 1H), 7.91 (dd, J = 2.8, 5.4 Hz, 1H), 7.75 (ddd, J = 2.8, 4.6, 9.0 Hz, 1H), 7.20 (t, J = 8.6 Hz, 1H), 7.05 (s, 1H), 5.99-5.85 (m, 1H), 5.35-5.23 (m, 2H), 4.75 (s, 1H), 4.70-4.58 (m, 2H), 3.96 (s, 3H), 2.67 (dd, J = 7.4, 13.8 Hz, 1H), 2.41 (dd, J = 7.5, 13.8 Hz, 1H), 1.45 (s, 3H) |
| 16B | 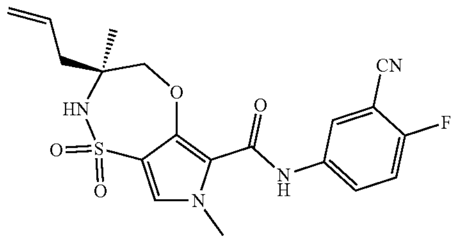 [SMILES: C=CC[C@@]1(C)COc2c(cn(C)c2C(=O)Nc2ccc(F)c(C#N)c2)S(=O)(=O)N1] | 419.0 | (400 MHz, CDCl3) δ: 8.77 (s, 1H), 7.91 (dd, J = 2.8, 5.4 Hz, 1H), 7.75 (ddd, J = 2.9, 4.5, 9.1 Hz, 1H), 7.20 (t, J = 8.6 Hz, 1H), 7.05 (s, 1H), 5.98-5.84 (m, 1H), 5.35-5.24 (m, 2H), 4.75 (s, 1H), 4.70-4.58 (m, 2H), 3.96 (s, 3H), 2.67 (dd, J = 7.3, 13.4 Hz, 1H), 2.41 (dd, J = 7.8, 13.6 Hz, 1H), 2.02 (s, 1H), 1.45 (s, 3H) |
| 17A | 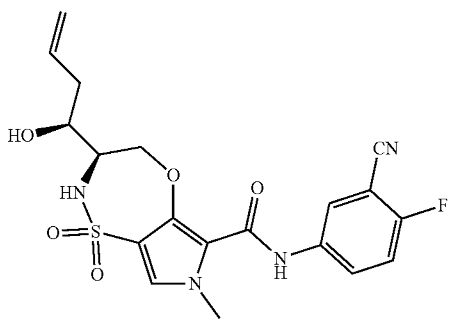 [SMILES: C=CC[C@H](O)[C@H]1COc2c(cn(C)c2C(=O)Nc2ccc(F)c(C#N)c2)S(=O)(=O)N1] | 435.5 | (400 MHz, CDCl3) δ: 8.87 (s, 1H), 7.96 (dd, J = 2.6, 5.4 Hz, 1H), 7.74 (ddd, J = 2.9, 4.4, 9.0 Hz, 1H), 7.20 (t, J = 8.6 Hz, 1H), 7.09 (s, 1H), 5.85 (br d, J = 8.0 Hz, 1H), 5.35-5.19 (m, 2H), 5.05 (d, J = 9.6 Hz, 1H), 4.89 (dd, J = 2.2, 12.9 Hz, 1H), 4.35 (dd, J = 9.1, 12.9 Hz, 1H), 4.02-3.83 (m, 5H), 2.59 (br s, 1H), 2.45-2.27 (m, 1H), 2.09 (d, J = 3.6 Hz, 1H) |
| 17B | 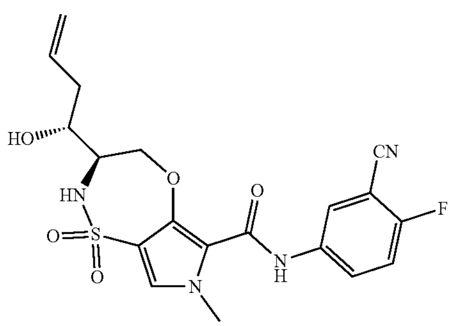 [SMILES: C=CC[C@@H](O)[C@H]1COc2c(cn(C)c2C(=O)Nc2ccc(F)c(C#N)c2)S(=O)(=O)N1] | 435.5 | (400 MHz, CDCl3) δ: 8.91 (s, 1H), 7.95 (dd, J = 2.7, 5.4 Hz, 1H), 7.75 (ddd, J = 2.8, 4.6, 9.1 Hz, 1H), 7.21 (t, J = 8.7 Hz, 1H), 7.12 (s, 1H), 5.95-5.71 (m, 1H), 5.39-5.21 (m, 2H), 5.01 (d, J = 10.4 Hz, 1H), 4.72 (dd, J = 1.6, 12.8 Hz, 1H), 4.29 (dd, J = 9.2, 12.8 Hz, 1H), 4.08-3.88 (m, 5H), 2.63-2.44 (m, 2H), 2.09-1.94 (m, 1H) |
| 18 | 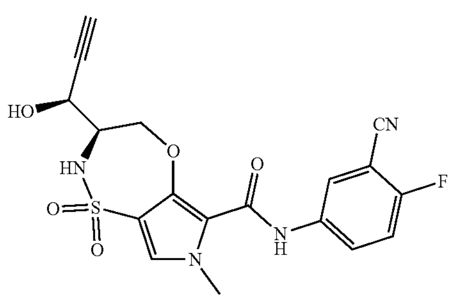 [SMILES: C#C[C@H](O)[C@H]1COc2c(cn(C)c2C(=O)Nc2ccc(F)c(C#N)c2)S(=O)(=O)N1] | 419.2 | (400 MHz, CD3OD) δ: 8.17 (dd, J = 2.8, 5.6 Hz, 1H), 7.92 (ddd, J = 2.7, 4.7, 9.1 Hz, 1H), 7.36 (t, J = 8.9 Hz, 1H), 7.30 (s, 1H), 5.04 (dd, J = 2.0, 12.8 Hz, 1H), 4.57 (dd, J = 2.1, 5.7 Hz, 1H), 4.26 (dd, J = 8.8, 12.8 Hz, 1H), 3.98-3.90 (m, 4H), 3.05 (d, J = 2.1 Hz, 1H) |

TABLE 1-continued

| Compound No. | Structure | MS [M + 1]+ | 1H NMR |
|---|---|---|---|
| 19A | 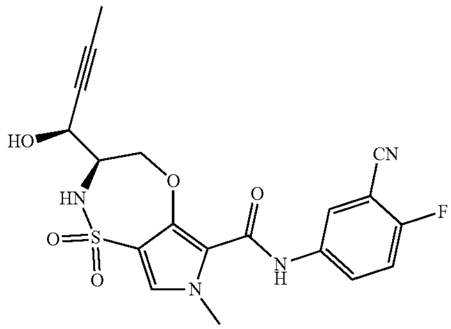 [SMILES: CC#C[C@H](O)[C@H]1COc2c(cn(C)c2C(=O)Nc2ccc(F)c(C#N)c2)S(=O)(=O)N1] | 433.0 | (400 MHz, DMSO-d6) δ: 9.54 (s, 1H), 8.21 (dd, J = 2.8, 5.8 Hz, 1H), 8.05 (ddd, J = 2.8, 5.0, 9.3 Hz, 1H), 7.79 (br d, J = 4.3 Hz, 1H), 7.56-7.48 (m, 2H), 5.88 (d, J = 6.0 Hz, 1H), 4.89 (dd, J = 1.9, 12.7 Hz, 1H), 4.34-4.24 (m, 1H), 4.02 (dd, J = 9.3, 12.8 Hz, 1H), 3.83 (s, 3H), 3.70-3.61 (m, 1H), 1.86 (d, J = 2.0 Hz, 3H) |
| 19B | 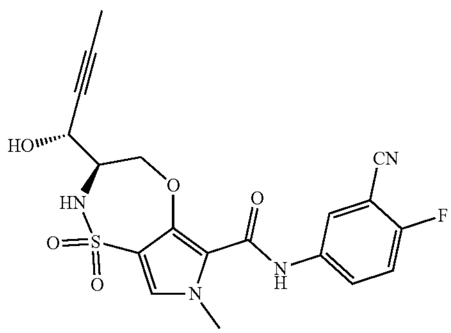 [SMILES: CC#C[C@@H](O)[C@H]1COc2c(cn(C)c2C(=O)Nc2ccc(F)c(C#N)c2)S(=O)(=O)N1] | 433.3 | (400 MHz, CDCl3) δ: 8.87 (s, 1H), 7.98 (dd, J = 2.8, 5.4 Hz, 1H), 7.72 (ddd, J = 2.7, 4.5, 9.0 Hz, 1H), 7.20 (t, J = 8.7 Hz, 1H), 7.11 (s, 1H), 4.95 (dd, J = 2.1, 12.9 Hz, 2H), 4.78-4.65 (m, 2H), 4.30 (dd, J = 8.6, 12.8 Hz, 1H), 4.11 (ddd, J = 2.3, 5.6, 8.2 Hz, 1H), 3.97 (s, 3H), 2.35 (br s, 1H), 1.89 (d, J = 2.1 Hz, 3H) |
| 20 | 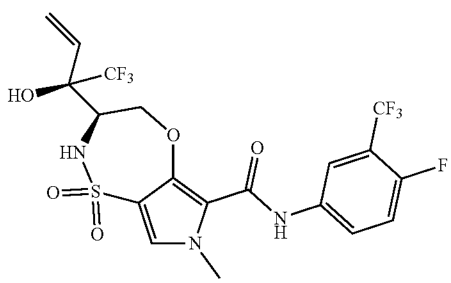 [SMILES: C=C[C@@](O)([C@H]1COc2c(cn(C)c2C(=O)Nc2ccc(F)c(C(F)(F)F)c2)S(=O)(=O)N1)C(F)(F)F] | 532.1 | (400 MHz, CDCl3) δ: 8.69 (s, 1H), 7.86 (dd, J = 2.6, 6.1 Hz, 1H), 7.75-7.68 (m, 1H), 7.21 (t, J = 9.2 Hz, 1H), 7.10 (s, 1H), 6.09 (dd, J = 10.9, 17.1 Hz, 1H), 5.81 (d, J = 17.1 Hz, 1H), 5.70 (d, J = 10.9 Hz, 1H), 4.98-4.89 (m, 2H), 4.39 (dd, J = 9.1, 12.9 Hz, 1H), 4.29 (br d, J = 7.5 Hz, 1H), 3.98 (s, 3H), 3.40 (s, 1H) |
| 21 | 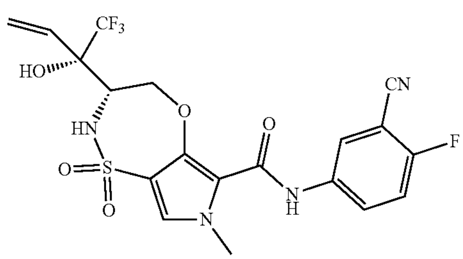 [SMILES: C=C[C@](O)([C@@H]1COc2c(cn(C)c2C(=O)Nc2ccc(F)c(C#N)c2)S(=O)(=O)N1)C(F)(F)F] | 489.2 | 1H NMR (400 MHz, DMSO-d6) δ: 9.52 (s, 1H), 8.18 (dd, J = 2.8, 5.8 Hz, 1H), 8.02 (ddd, J = 2.8, 4.9, 9.1 Hz, 2H), 7.57-7.44 (m, 2H), 6.96 (s, 1H), 6.10 (dd, J = 10.9, 17.0 Hz, 1H), 5.67 (dd, J = 1.3, 17.0 Hz, 1H), 5.49 (d, J = 11.9 Hz, 1H), 4.72 (d, J = 11.8 Hz, 1H), 4.11 (br s, 1H), 3.82 (s, 3H), 3.74 (dd, J = 8.9, 12.7 Hz, 1H) |
| 22A | 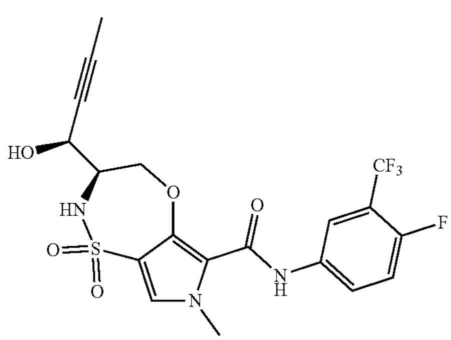 [SMILES: CC#C[C@H](O)[C@H]1COc2c(cn(C)c2C(=O)Nc2ccc(F)c(C(F)(F)F)c2)S(=O)(=O)N1] | 476.1 | (400 MHz, CDCl3) δ: 8.84 (s, 1H), 7.84 (dd, J = 2.6, 6.1 Hz, 1H), 7.73 (td, J = 3.5, 8.8 Hz, 1H), 5.04 (br s, 1H), 4.95 (dd, J = 1.4, 12.5 Hz, 1H), 4.71 (br s, 1H), 4.27-4.16 (m, 1H), 4.16-4.08 (m, 1H), 3.98 (s, 3H), 2.33 (br s, 1H), 1.91 (d, J = 2.1 Hz, 3H) |

TABLE 1-continued

| Compound No. | Structure | MS [M + 1]+ | 1H NMR |
|---|---|---|---|
| 22B | 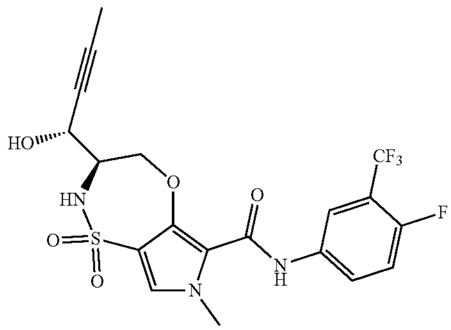 | 476.3 | (400 MHz, CDCl3) δ: 8.85 (s, 1H), 7.91-7.79 (m, 1H), 7.78-7.69 (m, 1H), 7.19 (t, J = 9.3 Hz, 1H), 7.10 (s, 1H), 5.05-4.83 (m, 2H), 4.78-4.63 (m, 2H), 4.30 (dd, J = 8.7, 12.8 Hz, 1H), 4.11 (br s, 1H), 3.98 (s, 3H), 1.89 (d, J = 2.0 Hz, 3H) |
| 23A | 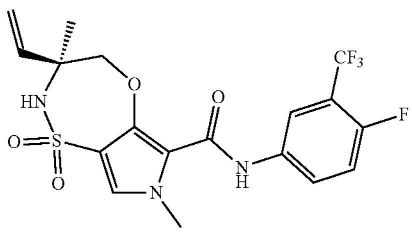 [SMILES: C=C[C@@]1(C)COc2c(cn(C)c2C(=O)Nc2ccc(F)c(C(F)(F)F)c2)S(=O)(=O)N1] | 448.2 | (400 MHz, CDCl3) δ: 8.69 (s, 1H), 7.81-7.69 (m, 2H), 7.18 (t, J = 9.3 Hz, 1H), 7.04 (s, 1H), 6.09 (dd, J = 10.8, 17.3 Hz, 1H), 5.52-5.34 (m, 2H), 4.85 (s, 1H), 4.78-4.70 (m, 1H), 4.68-4.58 (m, 1H), 3.95 (s, 3H), 1.58 (s, 3H) |
| 23B | 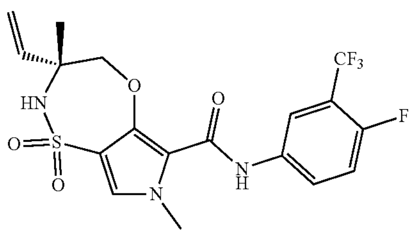 [SMILES: C=C[C@]1(C)COc2c(cn(C)c2C(=O)Nc2ccc(F)c(C(F)(F)F)c2)S(=O)(=O)N1] | 448.2 | (400 MHz, CDCl3) δ: 8.69 (s, 1H), 7.82-7.68 (m, 2H), 7.18 (t, J = 9.4 Hz, 1H), 7.04 (s, 1H), 6.09 (dd, J = 10.8, 17.4 Hz, 1H), 5.54-5.33 (m, 2H), 4.86 (s, 1H), 4.79-4.58 (m, 2H), 3.95 (s, 3H), 1.58 (s, 3H) |
| 24 | 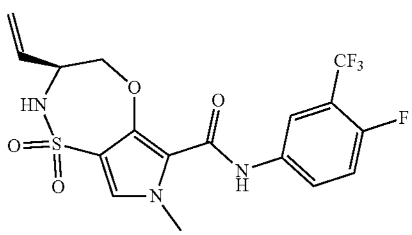 [SMILES: C=C[C@H]1COc2c(cn(C)c2C(=O)Nc2ccc(F)c(C(F)(F)F)c2)S(=O)(=O)N1] | 434.2 | (400 MHz, CDCl3) δ: 8.81 (s, 1H), 7.83 (dd, J = 2.6, 6.1 Hz, 1H), 7.79-7.71 (m, 1H), 7.28 (s, 2H), 7.21 (t, J = 9.4 Hz, 1H), 7.10 (s, 1H), 6.01-5.86 (m, 1H), 5.58-5.36 (m, 2H), 4.83-4.69 (m, 2H), 4.61 (br d, J = 8.3 Hz, 1H), 4.21 (dd, J = 8.5, 12.9 Hz, 1H), 3.99 (s, 3H) |
| 25A | 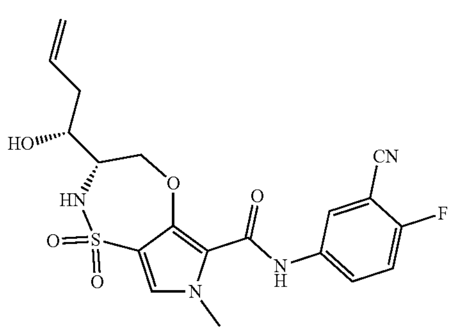 [SMILES: C=CC[C@@H](O)[C@@H]1COc2c(cn(C)c2C(=O)Nc2ccc(F)c(C#N)c2)S(=O)(=O)N1] | 435.4 | (400 MHz, CDCl3) δ: 8.88 (br s, 1H), 7.98 (br d, J = 2.0 Hz, 1H), 7.76 (br d, J = 3.8 Hz, 1H), 7.25-7.18 (m, 1H), 7.11 (br s, 1H), 5.99-5.73 (m, 1H), 5.47-5.21 (m, 2H), 5.16-4.81 (m, 2H), 4.37 (br dd, J = 9.4, 12.6 Hz, 1H), 4.15-3.79 (m, 5H), 2.63 (td, J = 2.9, 5.6 Hz, 1H), 2.47-2.27 (m, 1H), 2.21-1.99 (m, 1H) |

TABLE 1-continued

| Compound No. | Structure | MS [M + 1]+ | 1H NMR |
|---|---|---|---|
| 25B | 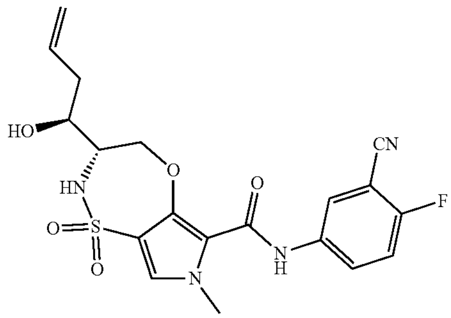 [SMILES: C=CC[C@H](O)[C@@H]1COc2c(cn(C)c2C(=O)Nc2ccc(F)c(C#N)c2)S(=O)(=O)N1] | 435.4 | (400 MHz, CDCl3) δ: 8.90 (br s, 1H), 7.95 (br d, J = 2.6 Hz, 1H), 7.81-7.67 (m, 1H), 7.21 (br t, J = 8.7 Hz, 1H), 7.12 (s, 1H), 5.92-5.75 (m, 1H), 5.38-5.21 (m, 2H), 4.99 (br d, J = 10.3 Hz, 1H), 4.72 (br d, J = 13.0 Hz, 1H), 4.29 (br dd, J = 9.5, 12.3 Hz, 1H), 4.08-3.85 (m, 5H), 2.63-2.43 (m, 2H), 2.00 (br s, 1H) |
| 26 | 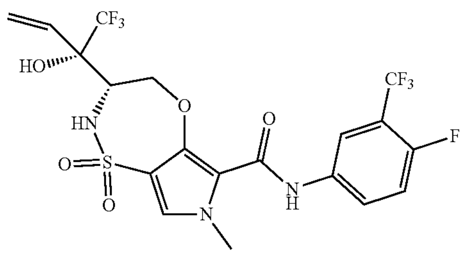 [SMILES: C=C[C@](O)([C@@H]1COc2c(cn(C)c2C(=O)Nc2ccc(F)c(C(F)(F)F)c2)S(=O)(=O)N1)C(F)(F)F] | 532.2 | (400 MHz, CDCl3) δ: 8.70 (s, 1H), 7.86 (dd, J = 2.6, 6.1 Hz, 1H), 7.71 (td, J = 3.5, 8.7 Hz, 1H), 7.20 (t, J = 9.3 Hz, 1H), 7.10 (s, 1H), 6.08 (dd, J = 10.9, 17.0 Hz, 1H), 5.81 (d, J = 17.1 Hz, 1H), 5.70 (d, J = 10.8 Hz, 1H), 4.94 (dd, J = 2.4, 13.1 Hz, 2H), 4.46-4.35 (m, 1H), 4.27 (br d, J = 7.8 Hz, 1H), 3.97 (s, 3H), 3.45 (br d, J = 1.8 Hz, 1H) |
| 27A | 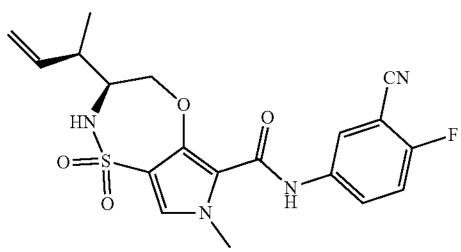 [SMILES: C=C[C@@H](C)[C@H]1COc2c(cn(C)c2C(=O)Nc2ccc(F)c(C#N)c2)S(=O)(=O)N1] | 419.1 | (400 MHz, DMSO-d6) δ: 9.52 (s, 1H), 8.19 (dd, J = 2.7, 5.7 Hz, 1H), 8.03 (ddd, J = 2.8, 4.8, 9.2 Hz, 1H), 7.67 (br s, 1H), 7.56-7.48 (m, 2H), 5.90-5.76 (m, 1H), 5.18-5.04 (m, 2H), 4.70-4.59 (m, 1H), 3.92 (dd, J = 9.4, 12.8 Hz, 1H), 3.83 (s, 3H), 3.59-3.50 (m, 1H), 1.08 (d, J = 6.8 Hz, 3H) |
| 27B | 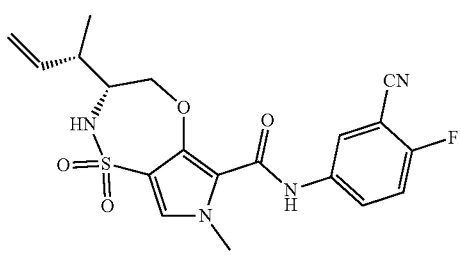 [SMILES: C=C[C@H](C)[C@@H]1COc2c(cn(C)c2C(=O)Nc2ccc(F)c(C#N)c2)S(=O)(=O)N1] | 419.1 | (400 MHz, DMSO-d6) δ: 9.54 (s, 1H), 8.19 (dd, J = 2.4, 5.7 Hz, 1H), 8.05 (ddd, J = 2.8, 5.0, 9.2 Hz, 1H), 7.63-7.57 (m, 1H), 7.56-7.50 (m, 2H), 5.92-5.79 (m, 1H), 5.15-5.00 (m, 2H), 4.65 (br d, J = 12.1 Hz, 1H), 3.90-3.85 (m, 1H), 3.83 (s, 3H), 3.71-3.59 (m, 1H), 1.10-1.04 (m, 3H) |
| 27C | 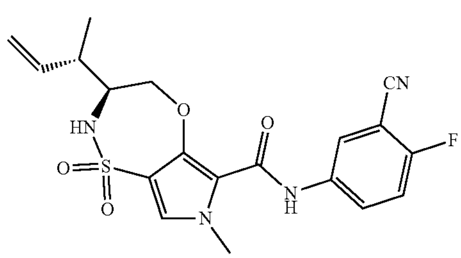 [SMILES: C=C[C@H](C)[C@H]1COc2c(cn(C)c2C(=O)Nc2ccc(F)c(C#N)c2)S(=O)(=O)N1] | 419.1 | (400 MHz, DMSO-d6) δ: 9.54 (s, 1H), 8.19 (dd, J = 2.6, 5.6 Hz, 1H), 8.05 (ddd, J = 2.9, 4.9, 9.0 Hz, 1H), 7.66-7.42 (m, 3H), 5.93-5.77 (m, 1H), 5.18-5.00 (m, 2H), 4.65 (d, J = 12.3 Hz, 1H), 3.90-3.85 (m, 1H), 3.83 (s, 3H), 3.70-3.62 (m, 1H), 1.07 (d, J = 7.0 Hz, 3H) |

TABLE 1-continued

| Compound No. | Structure | MS [M + 1]+ | 1H NMR |
|---|---|---|---|
| 27D | 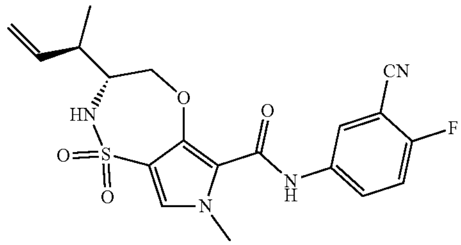 [SMILES: C=C[C@@H](C)[C@@H]1COc2c(cn(C)c2C(=O)Nc2ccc(F)c(C#N)c2)S(=O)(=O)N1] | 419.1 | (400 MHz, DMSO-d6) δ: 9.52 (s, 1H), 8.19 (dd, J = 2.7, 5.7 Hz, 1H), 8.03 (ddd, J = 2.6, 4.9, 9.2 Hz, 1H), 7.67 (d, J = 9.5 Hz, 1H), 7.57-7.48 (m, 2H), 5.90-5.74 (m, 1H), 5.16-5.03 (m, 2H), 4.65 (dd, J = 1.4, 12.8 Hz, 1H), 3.92 (dd, J = 9.4, 12.6 Hz, 1H), 3.83 (s, 3H), 3.59-3.49 (m, 1H), 1.08 (d, J = 6.8 Hz, 3H) |
| 28A | 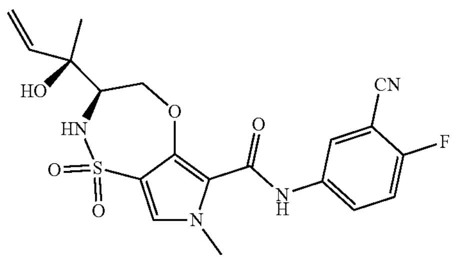 [SMILES: C=C[C@@](C)(O)[C@H]1COc2c(cn(C)c2C(=O)Nc2ccc(F)c(C#N)c2)S(=O)(=O)N1] | 435.2 | (400 MHz, DMSO-d6) δ: 9.49 (s, 1H), 8.19 (dd, J = 2.7, 5.7 Hz, 1H), 8.04 (ddd, J = 2.7, 4.8, 9.1 Hz, 1H), 7.59 (br s, 1H), 7.50 (s, 2H), 5.94 (dd, J = 10.8, 17.0 Hz, 1H), 5.30 (d, J = 2.0 Hz, 1H), 5.33-5.22 (m, 1H), 5.04 (dd, J = 2.0, 10.6 Hz, 1H), 4.84 (d, J = 12.0 Hz, 1H), 3.82 (s, 3H), 3.72 (dd, J = 9.1, 12.4 Hz, 1H), 3.64 (br s, 1H), 1.31 (s, 3H) |
| 28B | 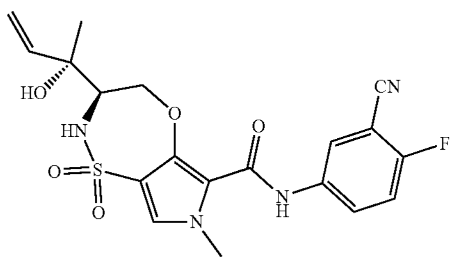 [SMILES: C=C[C@](C)(O)[C@H]1COc2c(cn(C)c2C(=O)Nc2ccc(F)c(C#N)c2)S(=O)(=O)N1] | 435.3 | (400 MHz, DMSO-d6) δ: 9.51 (s, 1H), 8.19 (dd, J = 2.6, 5.8 Hz, 1H), 8.02 (br s, 1H), 7.58-7.41 (m, 3H), 6.07 (dd, J = 10.6, 17.3 Hz, 1H), 5.30 (dd, J = 1.5, 17.3 Hz, 1H), 5.13 (dd, J = 1.6, 10.7 Hz, 1H), 5.05 (s, 1H), 4.84 (d, J = 12.0 Hz, 1H), 3.91 (br d, J = 12.6 Hz, 1H), 3.82 (s, 3H), 3.65-3.55 (m, 1H), 3.31 (s, 3H), 1.20 (s, 3H) |
| 29A | 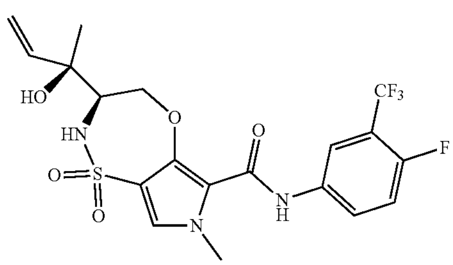 [SMILES: C=C[C@@](C)(O)[C@H]1COc2c(cn(C)c2C(=O)Nc2ccc(F)c(C(F)(F)F)c2)S(=O)(=O)N1] | 478.2 | (400 MHz, DMSO-d6) δ: 9.55 (s, 1H), 8.19 (dd, J = 2.6, 6.3 Hz, 1H), 7.99-7.89 (m, 1H), 7.55-7.44 (m, 3H), 6.08 (dd, J = 10.7, 17.2 Hz, 1H), 5.30 (dd, J = 1.5, 17.3 Hz, 1H), 5.17-5.08 (m, 1H), 5.04 (s, 1H), 4.82 (d, J = 12.4 Hz, 1H), 3.92 (dd, J = 8.9, 12.4 Hz, 1H), 3.82 (s, 3H), 3.60 (br t, J = 9.5 Hz, 1H), 1.20 (s, 3H) |
| 29B | 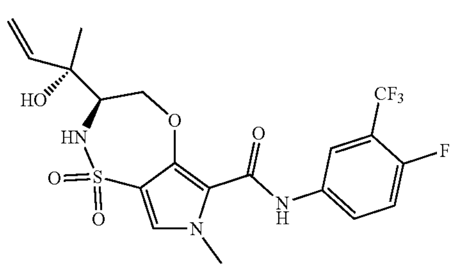 [SMILES: C=C[C@](C)(O)[C@H]1COc2c(cn(C)c2C(=O)Nc2ccc(F)c(C(F)(F)F)c2)S(=O)(=O)N1] | 478.2 | (400 MHz, DMSO-d6) δ: 9.54 (s, 1H), 8.19 (dd, J = 2.5, 6.5 Hz, 1H), 7.98-7.89 (m, 1H), 7.59 (br d, J = 9.3 Hz, 1H), 7.53-7.42 (m, 2H), 5.94 (dd, J = 10.6, 17.0 Hz, 1H), 5.35-5.21 (m, 2H), 5.04 (dd, J = 2.1, 10.7 Hz, 1H), 4.81 (d, J = 12.3 Hz, 1H), 3.82 (s, 3H), 3.72 (dd, J = 9.1, 12.3 Hz, 1H), 3.67-3.59 (m, 1H), 2.07 (s, 3H), 1.31 (s, 3H) |

TABLE 1-continued

| Compound No. | Structure | MS [M + 1]+ | 1H NMR |
|---|---|---|---|
| 30A | 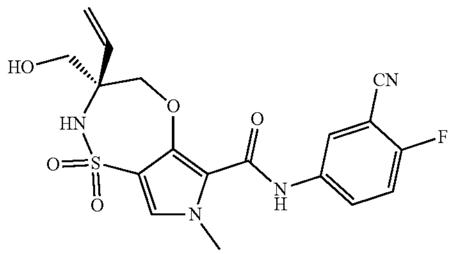 [SMILES: C=C[C@@]1(CO)COc2c(cn(C)c2C(=O)Nc2ccc(F)c(C#N)c2)S(=O)(=O)N1] | 421.2 | (400 MHz, DMSO-$d_6$) δ: 9.41 (s, 1H), 8.17 (dd, J = 2.7, 5.7 Hz, 1H), 8.02 (ddd, J = 2.7, 4.8, 9.2 Hz, 1H), 7.83 (br s, 1H), 7.54 (t, J = 9.1 Hz, 1H), 7.47 (s, 1H), 5.89 (dd, J = 11.0, 17.5 Hz, 1H), 5.47 (d, J = 1.1 Hz, 1H), 5.42 (d, J = 1.3 Hz, 1H), 5.27 (dd, J = 1.1, 11.0 Hz, 1H), 5.16 (t, J = 5.9 Hz, 1H), 4.76-4.65 (m, 2H), 3.81 (s, 3H), 3.76 (dd, J = 5.9, 10.8 Hz, 1H), 3.40-3.37 (m, 1H), 3.33 (s, 1H), 3.31 (s, 16H) |
| 30B | 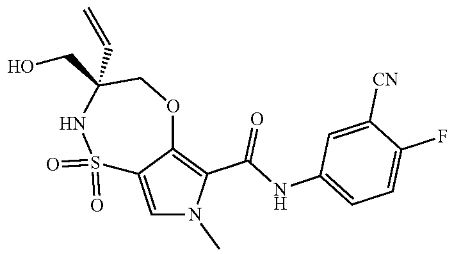 [SMILES: C=C[C@]1(CO)COc2c(cn(C)c2C(=O)Nc2ccc(F)c(C#N)c2)S(=O)(=O)N1] | 421.2 | (400 MHz, DMSO-$d_6$) δ: 9.42 (s, 1H), 8.17 (dd, J = 2.7, 5.7 Hz, 1H), 8.02 (ddd, J = 2.7, 4.9, 9.2 Hz, 1H), 7.84 (br s, 1H), 7.54 (t, J = 9.1 Hz, 1H), 7.47 (s, 1H), 5.89 (dd, J = 11.0, 17.5 Hz, 1H), 5.45 (dd, J = 1.1, 17.5 Hz, 1H), 5.27 (dd, J = 1.2, 10.9 Hz, 1H), 5.17 (t, J = 6.0 Hz, 1H), 4.78-4.62 (m, 2H), 3.81 (s, 3H), 3.76 (dd, J = 6.0, 10.8 Hz, 1H), 3.39 (br d, J = 6.3 Hz, 1H) |
| 31A | 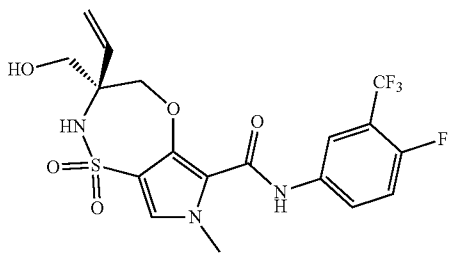 | 464.3 | (400 MHz, DMSO-$d_6$) δ: 9.46 (s, 1H), 8.18 (dd, J = 2.5, 6.4 Hz, 1H), 7.95-7.90 (m, 1H), 7.85 (br s, 1H), 7.52 (t, J = 9.8 Hz, 1H), 7.47 (s, 1H), 5.90 (dd, J = 10.9, 17.5 Hz, 1H), 5.45 (dd, J = 0.9, 17.5 Hz, 1H), 5.28 (dd, J = 0.9, 10.9 Hz, 1H), 5.17 (br t, J = 5.9 Hz, 1H), 4.77-4.64 (m, 2H), 3.82 (s, 3H), 3.77 (br dd, J = 5.9, 10.8 Hz, 1H), 3.39 (dd, J = 5.5, 10.6 Hz, 1H) |
| 31B | 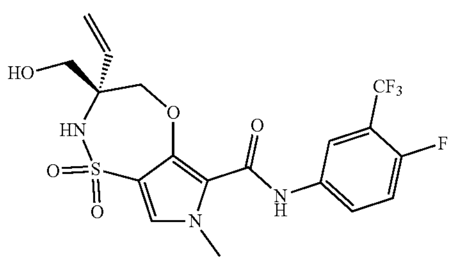 | 464.3 | (400 MHz, DMSO-$d_6$) δ: 9.45 (s, 1H), 8.17 (dd, J = 2.4, 6.4 Hz, 1H), 7.95-7.89 (m, 1H), 7.85 (s, 1H), 7.52 (t, J = 9.8 Hz, 1H), 7.46 (s, 1H), 5.89 (dd, J = 11.0, 17.5 Hz, 1H), 5.44 (d, J = 17.5 Hz, 1H), 5.27 (d, J = 10.9 Hz, 1H), 5.16 (t, J = 5.9 Hz, 1H), 4.75-4.64 (m, 2H), 3.81 (s, 3H), 3.76 (dd, J = 6.1, 10.7 Hz, 1H), 3.38 (dd, J = 5.9, 10.7 Hz, 1H) |
| 32 | 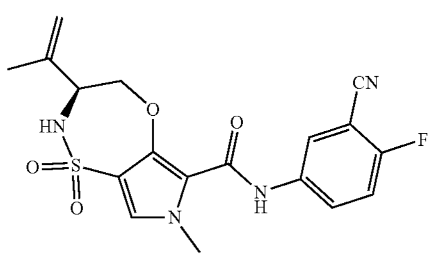 [SMILES: C=C(C)[C@H]1COc2c(cn(C)c2C(=O)Nc2ccc(F)c(C#N)c2)S(=O)(=O)N1] | 405.1 | (400 MHz, CDCl$_3$) δ: 8.84 (s, 1H), 7.95 (dd, J = 2.8, 5.4 Hz, 1H), 7.73 (ddd, J = 2.8, 4.5, 9.1 Hz, 1H), 7.20 (t, J = 8.6 Hz, 1H), 7.10 (s, 1H), 5.12 (d, J = 1.4 Hz, 1H), 5.04-4.93 (m, 1H), 4.80 (dd, J = 2.3, 12.8 Hz, 1H), 4.66 (d, J = 9.0 Hz, 1H), 4.44 (br t, J = 8.1 Hz, 1H), 4.21 (dd, J = 8.4, 12.8 Hz, 1H), 3.97 (s, 3H), 1.99-1.86 (m, 1H), 1.95 (s, 3H) |

TABLE 1-continued

| Compound No. | Structure | MS [M + 1]+ | 1H NMR |
|---|---|---|---|
| 33 | 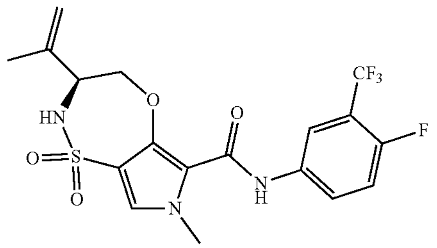 | 448.2 | (400 MHz, CDCl3) δ: 8.82 (s, 1H), 7.84 (dd, J = 2.6, 6.0 Hz, 1H), 7.74 (td, J = 3.6, 8.7 Hz, 1H), 7.21 (t, J = 9.3 Hz, 1H), 7.10 (s, 1H), 5.13 (d, J = 1.4 Hz, 1H), 5.03 (s, 1H), 4.81 (dd, J = 2.3, 12.8 Hz, 1H), 4.66 (br d, J = 3.9 Hz, 1H), 4.46 (br s, 1H), 4.21 (dd, J = 8.4, 12.8 Hz, 1H), 3.99 (s, 3H), 1.96 (s, 3H) |
| 34 | 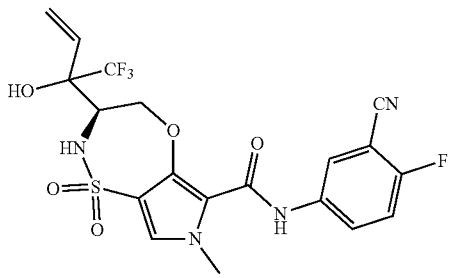 [SMILES: C=CC(O)([C@H]1COc2c(cn(C)c2C(=O)Nc2ccc(F)c(C#N)c2)S(=O)(=O)N1)C(F)(F)F] | 489.1 | (400 MHz, DMSO-d6) δ: 9.52 (s, 1H), 8.18 (dd, J = 2.8, 5.8 Hz, 1H), 8.08-7.97 (m, 2H), 7.60-7.45 (m, 2H), 6.97 (s, 1H), 6.10 (dd, J = 10.9, 17.0 Hz, 1H), 5.67 (dd, J = 1.2, 17.1 Hz, 1H), 5.49 (d, J = 11.8 Hz, 1H), 4.72 (d, J = 11.6 Hz, 1H), 4.11 (br t, J = 9.6 Hz, 1H), 3.83 (s, 3H), 3.75 (dd, J = 9.0, 12.6 Hz, 1H) |
| 35A | 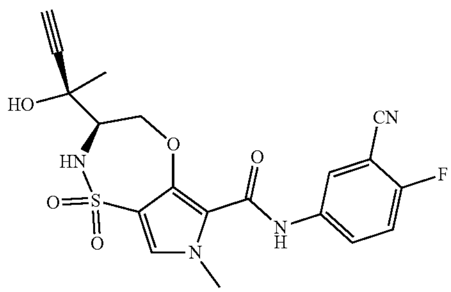 [SMILES: C#C[C@](C)(O)[C@H]1COc2c(cn(C)c2C(=O)Nc2ccc(F)c(C#N)c2)S(=O)(=O)N1] | 433.2 | (400 MHz, DMSO-d6) δ: 9.55 (s, 1H), 8.20 (dd, J = 2.6, 5.6 Hz, 1H), 8.10-7.95 (m, 1H), 7.64 (br s, 1H), 7.57-7.41 (m, 2H), 5.94 (s, 1H), 5.02 (d, J = 12.1 Hz, 1H), 3.98 (dd, J = 8.8, 12.7 Hz, 1H), 3.82 (s, 3H), 3.70 (br d, J = 8.5 Hz, 1H), 3.53 (s, 1H), 1.41 (s, 3H) |
| 35B | 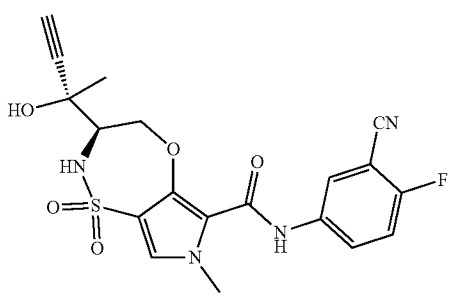 [SMILES: C#C[C@@](C)(O)[C@H]1COc2c(cn(C)c2C(=O)Nc2ccc(F)c(C#N)c2)S(=O)(=O)N1] | 433.2 | (400 MHz, DMSO-d6) δ: 9.53 (s, 1H), 8.20 (dd, J = 2.7, 5.8 Hz, 1H), 8.06 (ddd, J = 2.8, 4.9, 9.3 Hz, 1H), 7.62 (br s, 1H), 7.57-7.46 (m, 2H), 5.98 (s, 1H), 5.02 (d, J = 11.5 Hz, 1H), 4.08-3.94 (m, 1H), 3.83 (s, 3H), 3.63 (br s, 1H), 1.48 (s, 3H) |
| 36A | 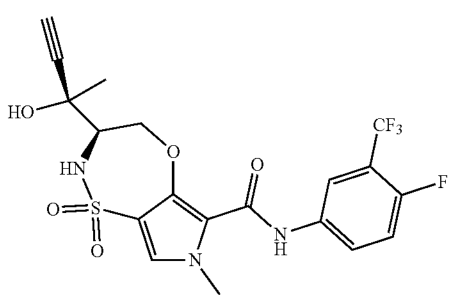 [SMILES: C#C[C@](C)(O)[C@H]1COc2c(cn(C)c2C(=O)Nc2ccc(F)c(C(F)(F)F)c2)S(=O)(=O)N1] | 476.3 | (400 MHz, DMSO-d6) δ: 9.59 (s, 1H), 8.20 (dd, J = 2.6, 6.6 Hz, 1H), 7.99-7.92 (m, 1H), 7.72-7.56 (m, 1H), 7.53-7.45 (m, 2H), 5.93 (s, 1H), 5.00 (d, J = 12.0 Hz, 1H), 3.99 (dd, J = 8.8, 12.6 Hz, 1H), 3.82 (s, 3H), 3.70 (br d, J = 8.9 Hz, 1H), 3.52 (s, 1H), 1.41 (s, 3H) |

TABLE 1-continued

| Compound No. | Structure | MS [M + 1]+ | 1H NMR |
|---|---|---|---|
| 36B | 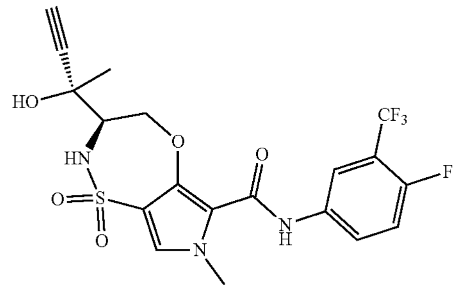 | 476.3 | (400 MHz, DMSO-d6) δ: 9.57 (s, 1H), 8.20 (dd, J = 2.6, 6.4 Hz, 1H), 7.97 (br dd, J = 3.6, 8.8 Hz, 1H), 7.60 (br s, 1H), 7.53-7.42 (m, 2H), 5.98 (s, 1H), 4.99 (d, J = 11.6 Hz, 1H), 4.00 (dd, J = 8.9, 12.5 Hz, 1H), 3.83 (s, 3H), 3.70-3.57 (m, 1H), 1.48 (s, 3H) |
| 37 | 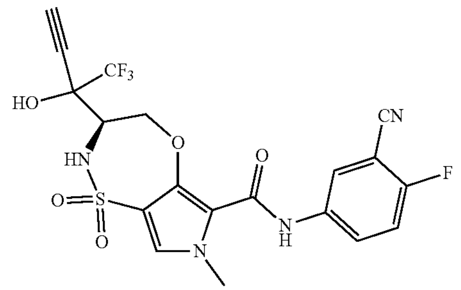 [SMILES: C#CC(O)([C@H]1COc2c(cn(C)c2C(=O)Nc2ccc(F)c(C#N)c2)S(=O)(=O)N1)C(F)(F)F] | 487.1 | (400 MHz, CDCl3) δ: 8.70 (s, 1H), 8.00 (dd, J = 2.7, 5.6 Hz, 1H), 7.66-7.59 (m, 1H), 7.19 (t, J = 8.6 Hz, 1H), 7.13 (s, 1H), 6.84 (d, J = 4.4 Hz, 1H), 5.29 (d, J = 4.3 Hz, 1H), 5.22 (dd, J = 2.5, 13.9 Hz, 1H), 5.01 (br d, J = 13.6 Hz, 1H), 4.59 (s, 1H), 3.98 (s, 3H), 2.85 (s, 1H) |
| 38A | 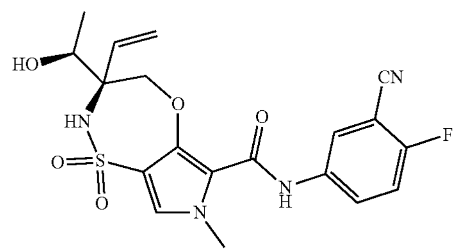 [SMILES: C=C[C@@]1([C@H](C)O)COc2c(cn(C)c2C(=O)Nc2ccc(F)c(C#N)c2)S(=O)(=O)N1] | 435.1 | (400 MHz, DMSO-d6) δ: 9.36 (s, 1H), 8.17 (dd, J = 2.6, 5.6 Hz, 1H), 8.07-7.98 (m, 1H), 7.70 (s, 1H), 7.53 (t, J = 9.1 Hz, 1H), 7.48 (s, 1H), 5.79 (dd, J = 11.1, 17.6 Hz, 1H), 5.44 (d, J = 17.8 Hz, 1H), 5.34 (d, J = 11.6 Hz, 1H), 5.20 (d, J = 5.9 Hz, 1H), 4.89-4.82 (m, 1H), 4.06 (quin, J = 6.1 Hz, 1H), 3.82 (s, 3H), 1.05 (d, J = 6.3 Hz, 3H) |
| 38B | 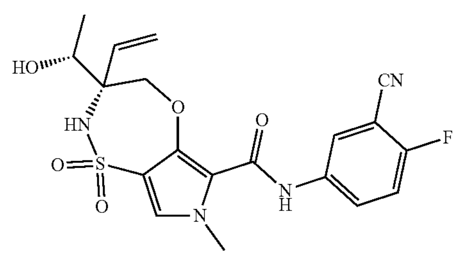 [SMILES: C=C[C@]1([C@@H](C)O)COc2c(cn(C)c2C(=O)Nc2ccc(F)c(C#N)c2)S(=O)(=O)N1] | 435.3 | (400 MHz, DMSO-d6) δ: 9.36 (s, 1H), 8.17 (dd, J = 2.7, 5.7 Hz, 1H), 8.02 (ddd, J = 2.8, 4.9, 9.1 Hz, 1H), 7.70 (br s, 1H), 7.53 (t, J = 9.1 Hz, 1H), 7.47 (s, 1H), 5.79 (dd, J = 11.1, 17.6 Hz, 1H), 5.44 (dd, J = 1.1, 17.6 Hz, 1H), 5.34 (d, J = 11.3 Hz, 1H), 5.21 (br d, J = 5.6 Hz, 1H), 4.88-4.72 (m, 2H), 4.10-4.01 (m, 1H), 3.82 (s, 3H), 1.05 (d, J = 6.1 Hz, 3H) |
| 38C | 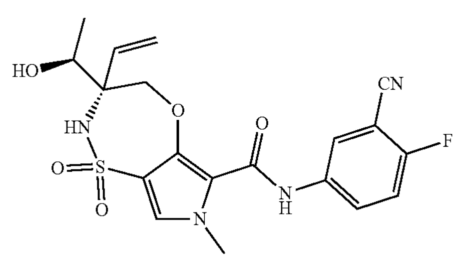 [SMILES: C=C[C@]1([C@H](C)O)COc2c(cn(C)c2C(=O)Nc2ccc(F)c(C#N)c2)S(=O)(=O)N1] | 435.3 | (400 MHz, DMSO-d6) δ: 9.37 (s, 1H), 8.17 (dd, J = 2.7, 5.7 Hz, 1H), 8.02 (ddd, J = 2.8, 4.8, 9.2 Hz, 1H), 7.57-7.43 (m, 3H), 5.87 (dd, J = 11.1, 17.8 Hz, 1H), 5.42-5.25 (m, 2H), 4.93-4.82 (m, 2H), 4.73 (d, J = 13.6 Hz, 1H), 3.89 (quin, J = 6.2 Hz, 1H), 3.81 (s, 3H), 1.13 (d, J = 6.4 Hz, 3H) |

TABLE 1-continued

| Compound No. | Structure | MS [M + 1]+ | 1H NMR |
|---|---|---|---|
| 38D | 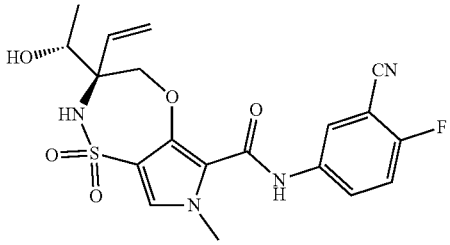 [SMILES: C=C[C@@]1([C@@H](C)O)COc2c(cn(C)c2C(=O)Nc2ccc(F)c(C#N)c2)S(=O)(=O)N1] | 435.1 | (400 MHz, DMSO-d6) δ: 9.37 (s, 1H), 8.17 (dd, J = 2.7, 5.7 Hz, 1H), 8.02 (ddd, J = 2.6, 4.9, 9.2 Hz, 1H), 7.56-7.45 (m, 3H), 5.37 (d, J = 17.3 Hz, 1H), 5.28 (d, J = 11.4 Hz, 1H), 4.89-4.83 (m, 2H), 4.73 (d, J = 13.6 Hz, 1H), 3.89 (quin, J = 6.3 Hz, 1H), 3.81 (s, 3H), 1.13 (d, J = 6.4 Hz, 3H) |
| 39A | 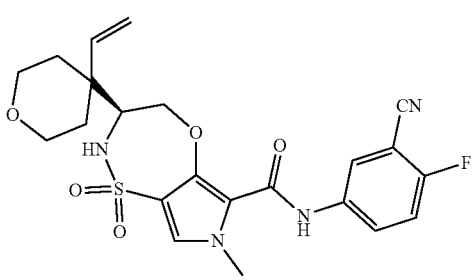 [SMILES: C=CC1([C@H]2COc3c(cn(C)c3C(=O)Nc3ccc(F)c(C#N)c3)S(=O)(=O)N2)CCOCC1] | 475.2 | (400 MHz, DMSO-d6) δ: 9.56 (s, 1H), 8.19 (dd, J = 2.8, 5.8 Hz, 1H), 8.08-8.01 (m, 1H), 7.62-7.49 (m, 3H), 5.71 (dd, J = 11.1, 17.8 Hz, 1H), 5.35 (d, J = 11.4 Hz, 1H), 5.17 (d, J = 17.5 Hz, 1H), 4.71 (br d, J = 12.3 Hz, 1H), 3.82 (s, 3H), 3.76 (br dd, J = 9.1, 12.8 Hz, 1H), 3.73-3.65 (m, 2H), 3.59 (br s, 1H), 3.49-3.38 (m, 2H), 1.89-1.74 (m, 2H), 1.72-1.57 (m, 2H) |
| 39B | 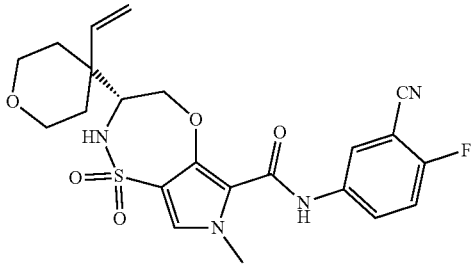 [SMILES: C=CC1([C@@H]2COc3c(cn(C)c3C(=O)Nc3ccc(F)c(C#N)c3)S(=O)(=O)N2)CCOCC1] | 475.2 | (400 MHz, DMSO-d6) δ: 9.55 (s, 1H), 8.18 (dd, J = 2.6, 5.6 Hz, 1H), 8.07-8.01 (m, 1H), 7.60-7.49 (m, 3H), 5.70 (dd, J = 11.1, 17.8 Hz, 1H), 5.34 (d, J = 11.0 Hz, 1H), 5.17 (br d, J = 17.8 Hz, 1H), 4.71 (br d, J = 12.6 Hz, 1H), 3.82 (s, 3H), 3.76 (br dd, J = 9.0, 12.6 Hz, 1H), 3.72-3.64 (m, 2H), 3.62-3.54 (m, 1H), 3.48-3.38 (m, 2H), 1.89-1.55 (m, 4H) |
| 40A | 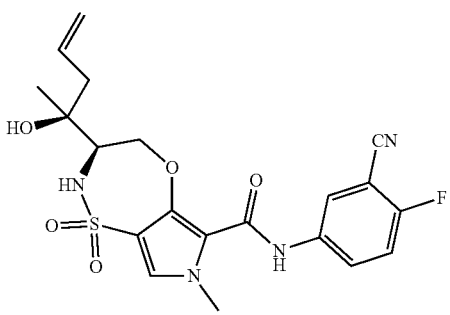 [SMILES: C=CC[C@](C)(O)[C@H]1COc2c(cn(C)c2C(=O)Nc2ccc(F)c(C#N)c2)S(=O)(=O)N1] | 449.1 | (400 MHz, DMSO-d6) δ: 9.51 (s, 1H), 8.20 (dd, J = 2.8, 5.8 Hz, 1H), 8.06 (ddd, J = 2.8, 4.9, 9.2 Hz, 1H), 7.57-7.43 (m, 3H), 5.93-5.78 (m, 1H), 5.13-5.03 (m, 2H), 4.98 (d, J = 12.1 Hz, 1H), 4.81 (s, 1H), 3.96 (dd, J = 8.8, 12.7 Hz, 1H), 3.83 (s, 3H), 3.58 (br t, J = 9.1 Hz, 1H), 2.37-2.28 (m, 1H), 2.10 (br dd, J = 7.1, 13.9 Hz, 1H), 1.19 (s, 3H) |
| 40B | 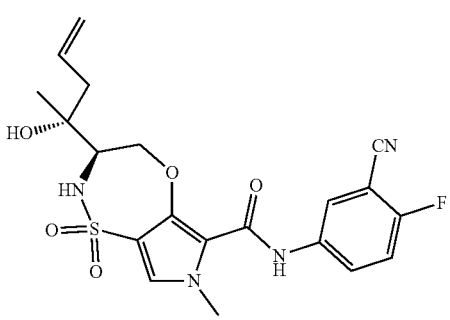 [SMILES: C=CC[C@@](C)(O)[C@H]1COc2c(cn(C)c2C(=O)Nc2ccc(F)c(C#N)c2)S(=O)(=O)N1] | 449.3 | (400 MHz, DMSO-d6) δ: 9.52 (s, 1H), 8.20 (dd, J = 2.8, 5.8 Hz, 1H), 8.04 (ddd, J = 2.7, 4.8, 9.2 Hz, 1H), 7.57-7.44 (m, 3H), 5.89 (dt, J = 2.2, 9.2 Hz, 1H), 5.16-5.05 (m, 2H), 4.99 (d, J = 11.9 Hz, 1H), 4.87 (s, 1H), 3.94 (dd, J = 8.9, 12.5 Hz, 1H), 3.83 (s, 3H), 3.62 (br t, J = 9.6 Hz, 1H), 2.39-2.22 (m, 2H), 1.01 (s, 3H) |

TABLE 1-continued

| Compound No. | Structure | MS [M + 1]+ | 1H NMR |
|---|---|---|---|
| 41A | 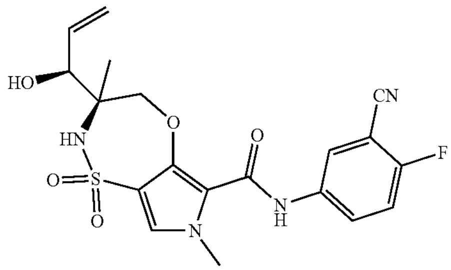 [SMILES: C=C[C@H](O)[C@]1(C)COc2c(cn(C)c2C(=O)Nc2ccc(F)c(C#N)c2)S(=O)(=O)N1] | 435.1 | (400 MHz, CDCl$_3$) δ: 8.79 (s, 1H), 7.93 (dd, J = 2.8, 5.4 Hz, 1H), 7.74 (ddd, J = 2.8, 4.5, 9.1 Hz, 1H), 7.20 (t, J = 8.7 Hz, 1H), 7.06 (s, 1H), 6.08 (ddd, J = 6.4, 10.6, 17.2 Hz, 1H), 5.56-5.41 (m, 2H), 5.04 (s, 1H), 4.92 (d, J = 13.4 Hz, 1H), 4.75 (d, J = 13.3 Hz, 1H), 4.50 (d, J = 6.4 Hz, 1H), 3.96 (s, 3H), 2.14 (br s, 1H), 1.43 (s, 4H) |
| 41B | 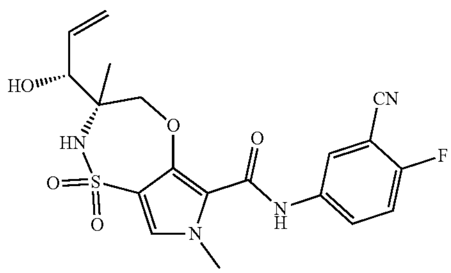 [SMILES: C=C[C@@H](O)[C@@]1(C)COc2c(cn(C)c2C(=O)Nc2ccc(F)c(C#N)c2)S(=O)(=O)N1] | 435.0 | (400 MHz, CDCl$_3$) δ: 8.79 (s, 1H), 7.93 (dd, J = 2.8, 5.5 Hz, 1H), 7.74 (ddd, J = 2.9, 4.5, 9.1 Hz, 1H), 7.20 (t, J = 8.6 Hz, 1H), 7.06 (s, 1H), 6.08 (ddd, J = 6.3, 10.6, 17.1 Hz, 1H), 5.57-5.35 (m, 2H), 5.06 (s, 1H), 4.91 (d, J = 13.3 Hz, 1H), 4.75 (d, J = 13.4 Hz, 1H), 4.50 (br d, J = 6.3 Hz, 1H), 3.95 (s, 3H), 2.18 (br d, J = 2.6 Hz, 1H), 1.43 (s, 3H) |
| 41C | 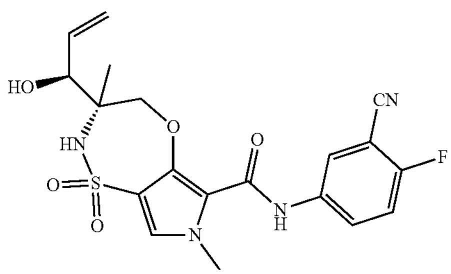 [SMILES: C=C[C@H](O)[C@@]1(C)COc2c(cn(C)c2C(=O)Nc2ccc(F)c(C#N)c2)S(=O)(=O)N1] | 435.1 | (400 MHz, CDCl$_3$) δ: 8.76 (s, 1H), 7.91 (dd, J = 2.8, 5.4 Hz, 1H), 7.75 (ddd, J = 2.8, 4.5, 9.1 Hz, 1H), 7.22 (t, J = 8.7 Hz, 1H), 7.09 (s, 1H), 5.99 (ddd, J = 7.4, 10.2, 17.3 Hz, 1H), 5.53-5.42 (m, 2H), 5.28 (s, 1H), 4.83 (d, J = 13.5 Hz, 1H), 4.64 (d, J = 13.5 Hz, 1H), 4.38 (dd, J = 4.9, 7.3 Hz, 1H), 3.98 (s, 3H), 2.56 (d, J = 4.9 Hz, 1H), 1.45 (s, 3H) |
| 41D | 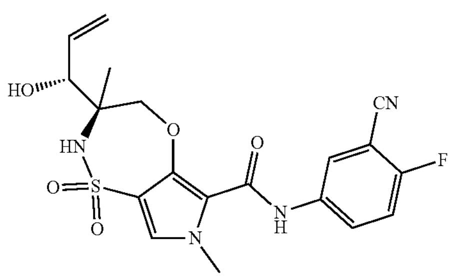 [SMILES: C=C[C@@H](O)[C@]1(C)COc2c(cn(C)c2C(=O)Nc2ccc(F)c(C#N)c2)S(=O)(=O)N1] | 435.1 | (400 MHz, CDCl$_3$) δ: 8.75 (s, 1H), 7.90 (dd, J = 2.8, 5.4 Hz, 1H), 7.74 (ddd, J = 2.8, 4.5, 9.1 Hz, 1H), 7.20 (t, J = 8.7 Hz, 1H), 7.07 (s, 1H), 6.09-5.84 (m, 1H), 5.97 (ddd, J = 7.4, 10.2, 17.3 Hz, 1H), 5.52-5.40 (m, 2H), 5.30 (br s, 1H), 4.81 (d, J = 13.5 Hz, 1H), 4.62 (d, J = 13.5 Hz, 1H), 4.36 (br d, J = 7.4 Hz, 1H), 3.96 (s, 3H), 2.61 (br s, 1H), 2.02 (s, 1H), 1.49-1.36 (m, 1H), 1.43 (s, 2H) |
| 42A | 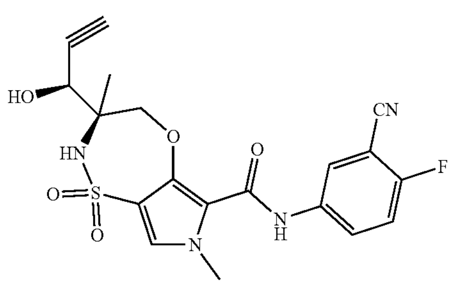 [SMILES: C#C[C@H](O)[C@]1(C)COc2c(cn(C)c2C(=O)Nc2ccc(F)c(C#N)c2)S(=O)(=O)N1] | 433.1 | (400 MHz, DMSO-d$_6$) δ: 9.40 (br s, 1H), 8.18 (dd, J = 2.6, 5.6 Hz, 1H), 8.10-7.87 (m, 1H), 7.58-7.36 (m, 2H), 6.04 (br s, 1H), 4.77-4.45 (m, 3H), 3.81 (s, 3H), 3.33 (br s, 1H), 1.43-1.29 (m, 3H) |

TABLE 1-continued

| Compound No. | Structure | MS [M + 1]+ | 1H NMR |
|---|---|---|---|
| 42B | 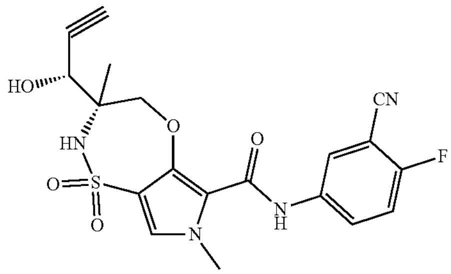 [SMILES: C#C[C@@H](O)[C@@]1(C)COc2c(cn(C)c2C(=O)Nc2ccc(F)c(C#N)c2)S(=O)(=O)N1] | 433.1 | (400 MHz, DMSO-d6) δ: 9.41 (br s, 1H), 8.18 (dd, J = 2.6, 5.8 Hz, 1H), 8.10-7.84 (m, 2H), 7.58-7.40 (m, 2H), 6.02 (br s, 1H), 4.78-4.48 (m, 3H), 3.81 (s, 3H), 3.22 (br s, 1H), 1.36 (s, 3H) |
| 42C | 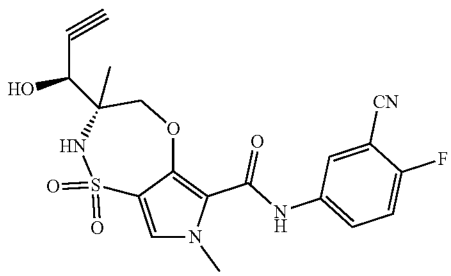 [SMILES: C#C[C@H](O)[C@@]1(C)COc2c(cn(C)c2C(=O)Nc2ccc(F)c(C#N)c2)S(=O)(=O)N1] | 433.1 | (400 MHz, DMSO-d6) δ: 9.45 (s, 1H), 8.17 (dd, J = 2.6, 5.8 Hz, 1H), 8.00 (ddd, J = 2.7, 4.8, 9.1 Hz, 1H), 7.82 (br d, J = 3.0 Hz, 1H), 7.52 (t, J = 9.1 Hz, 1H), 7.44 (s, 1H), 5.90-5.75 (m, 1H), 4.66-4.54 (m, 3H), 3.80 (s, 3H), 3.51 (d, J = 2.1 Hz, 1H), 1.33 (s, 3H) |
| 42D | 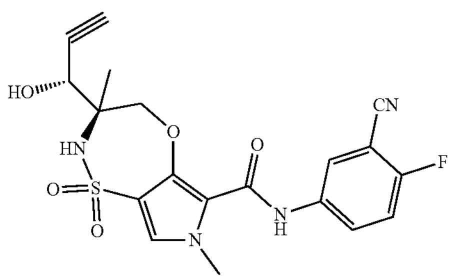 [SMILES: C#C[C@@H](O)[C@]1(C)COc2c(cn(C)c2C(=O)Nc2ccc(F)c(C#N)c2)S(=O)(=O)N1] | 433.1 | (400 MHz, DMSO-d6) δ: 9.45 (s, 1H), 8.17 (dd, J = 2.7, 5.7 Hz, 1H), 8.00 (ddd, J = 2.7, 4.9, 9.2 Hz, 1H), 7.83 (br s, 1H), 7.52 (t, J = 9.1 Hz, 1H), 7.44 (s, 1H), 5.83 (d, J = 6.3 Hz, 1H), 4.68-4.54 (m, 3H), 3.80 (s, 3H), 3.51 (d, J = 2.1 Hz, 1H), 1.33 (s, 3H) |
| 43A | 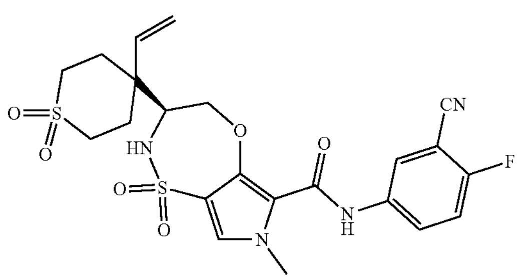 [SMILES: C=CC1([C@H]2COc3c(cn(C)c3C(=O)Nc3ccc(F)c(C#N)c3)S(=O)(=O)N2)CCS(=O)(=O)CC1] | 523.1 | (400 MHz, CD3CN) δ: 9.06-8.95 (m, 1H), 8.03 (dd, J = 2.8, 5.6 Hz, 1H), 7.95 (ddd, J = 2.8, 4.8, 9.1 Hz, 1H), 7.31 (t, J = 9.1 Hz, 1H), 7.19 (s, 1H), 5.71 (dd, J = 11.0, 17.8 Hz, 2H), 5.51 (d, J = 11.0 Hz, 1H), 5.34 (d, J = 17.8 Hz, 1H), 4.82 (dd, J = 1.6, 12.8 Hz, 1H), 3.99-3.87 (m, 4H), 3.76 (d, J = 7.9 Hz, 1H), 3.04-2.90 (m, 4H), 2.46-2.33 (m, 1H), 2.30-2.18 (m, 3H) |
| 43B | 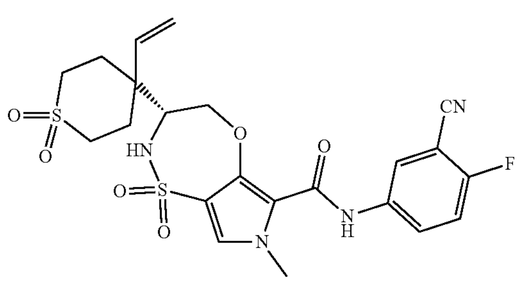 [SMILES: C=CC1([C@@H]2COc3c(cn(C)c3C(=O)Nc3ccc(F)c(C#N)c3)S(=O)(=O)N2)CCS(=O)(=O)CC1] | 523.1 | (400 MHz, CD3CN) δ: 9.01 (s, 1H), 8.02 (dd, J = 2.7, 5.6 Hz, 1H), 7.98-7.90 (m, 1H), 7.31 (t, J = 9.1 Hz, 1H), 7.19 (s, 1H), 5.71 (br dd, J = 11.0, 17.6 Hz, 2H), 5.51 (d, J = 11.0 Hz, 1H), 5.34 (d, J = 17.8 Hz, 1H), 4.82 (dd, J = 1.4, 12.6 Hz, 1H), 3.99-3.88 (m, 4H), 3.81-3.70 (m, 1H), 3.05-2.91 (m, 4H), 2.47-2.33 (m, 1H), 2.31-2.18 (m, 4H) |

TABLE 1-continued

| Compound No. | Structure | MS [M + 1]+ | 1H NMR |
|---|---|---|---|
| 44A | 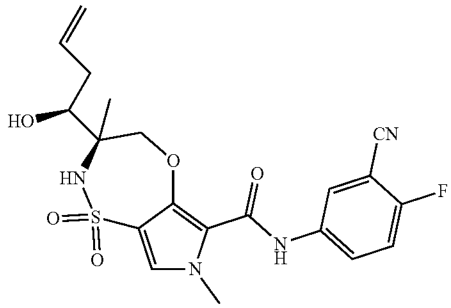 [SMILES: C=CC[C@H](O)[C@]1(C)COc2c(cn(C)c2C(=O)Nc2ccc(F)c(C#N)c2)S(=O)(=O)N1] | 449.1 | (400 MHz, CDCl$_3$) δ: 8.82 (s, 1H), 7.96 (dd, J = 2.7, 5.4 Hz, 1H), 7.74 (ddd, J = 2.7, 4.6, 9.1 Hz, 1H), 7.22 (t, J = 8.7 Hz, 1H), 7.07 (s, 1H), 6.00-5.80 (m, 1H), 5.35-5.21 (m, 2H), 5.07-4.84 (m, 2H), 4.73 (d, J = 13.3 Hz, 1H), 4.06 (td, J = 2.4, 10.4 Hz, 1H), 3.97 (s, 3H), 2.79 (br dd, J = 3.6, 13.8 Hz, 1H), 2.18-2.00 (m, 2H), 1.47 (s, 3H) |
| 44B | 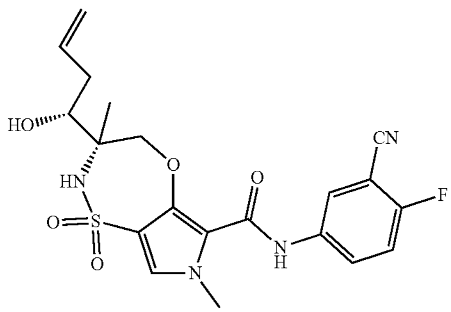 [SMILES: C=CC[C@@H](O)[C@@]1(C)COc2c(cn(C)c2C(=O)Nc2ccc(F)c(C#N)c2)S(=O)(=O)N1] | 449.1 | (400 MHz, CDCl$_3$) δ: 8.82 (s, 1H), 7.96 (dd, J = 2.8, 5.5 Hz, 1H), 7.74 (ddd, J = 2.8, 4.5, 9.1 Hz, 1H), 7.22 (t, J = 8.7 Hz, 1H), 7.07 (s, 1H), 6.00-5.74 (m, 1H), 5.34-5.20 (m, 2H), 5.01 (d, J = 13.4 Hz, 1H), 4.91 (s, 1H), 4.73 (d, J = 13.4 Hz, 1H), 4.06 (br d, J = 10.6 Hz, 1H), 3.97 (s, 3H), 2.79 (br dd, J = 3.6, 13.8 Hz, 1H), 2.20-2.00 (m, 2H), 1.47 (s, 3H) |
| 44C | 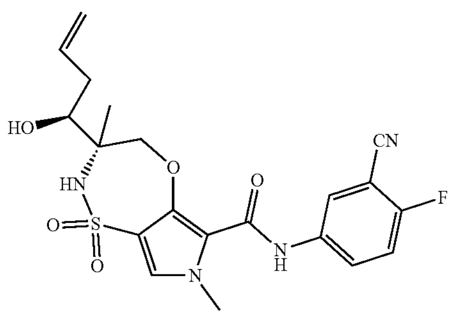 [SMILES: C=CC[C@H](O)[C@@]1(C)COc2c(cn(C)c2C(=O)Nc2ccc(F)c(C#N)c2)S(=O)(=O)N1] | 449.1 | (400 MHz, CDCl$_3$) δ: 8.77 (s, 1H), 7.91 (dd, J = 2.7, 5.4 Hz, 1H), 7.76 (ddd, J = 2.8, 4.6, 9.1 Hz, 1H), 7.20 (t, J = 8.7 Hz, 1H), 7.08 (s, 1H), 5.87 (dddd, J = 5.9, 8.3, 10.6, 16.4 Hz, 1H), 5.38-5.11 (m, 3H), 4.78 (d, J = 13.3 Hz, 1H), 4.57 (d, J = 13.3 Hz, 1H), 3.96 (s, 3H), 3.74 (br d, J = 9.4 Hz, 1H), 2.58-2.42 (m, 2H), 2.35 (td, J = 9.3, 14.0 Hz, 1H), 1.50 (s, 3H) |
| 44D | 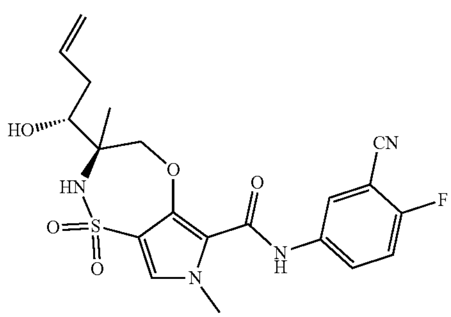 [SMILES: C=CC[C@@H](O)[C@]1(C)COc2c(cn(C)c2C(=O)Nc2ccc(F)c(C#N)c2)S(=O)(=O)N1] | 449.1 | (400 MHz, CDCl$_3$) δ: 8.77 (s, 1H), 7.91 (dd, J = 2.7, 5.4 Hz, 1H), 7.76 (ddd, J = 2.8, 4.5, 9.1 Hz, 1H), 7.20 (t, J = 8.7 Hz, 1H), 7.08 (s, 1H), 5.97-5.78 (m, 1H), 5.44-5.08 (m, 3H), 4.78 (d, J = 13.3 Hz, 1H), 4.57 (d, J = 13.3 Hz, 1H), 3.96 (s, 3H), 3.80-3.69 (m, 1H), 2.58-2.42 (m, 2H), 2.35 (td, J = 9.3, 14.1 Hz, 1H), 1.50 (s, 3H) |
| 45A | 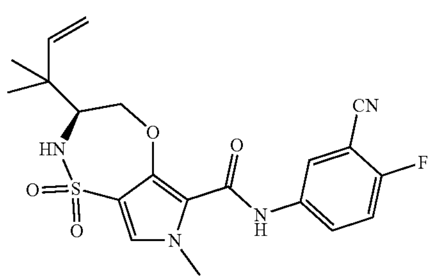 [SMILES: C=CC(C)(C)[C@H]1COc2c(cn(C)c2C(=O)Nc2ccc(F)c(C#N)c2)S(=O)(=O)N1] | 433.1 | (400 MHz, CDCl$_3$) δ: 8.83 (s, 1H), 7.94 (dd, J = 2.7, 5.4 Hz, 1H), 7.74 (ddd, J = 2.8, 4.5, 9.1 Hz, 1H), 7.21 (t, J = 8.7 Hz, 1H), 7.09 (s, 1H), 5.81 (dd, J = 10.8, 17.4 Hz, 1H), 5.27-5.16 (m, 2H), 4.80 (dd, J = 1.9, 12.6 Hz, 1H), 4.52-4.46 (m, 1H), 4.00-3.92 (m, 4H), 3.79 (br t, J = 7.4 Hz, 1H), 1.27 (s, 3H), 1.20 (s, 3H) |

TABLE 1-continued
| Compound No. | Structure | MS [M + 1]+ | 1H NMR |
|---|---|---|---|
| 45B | 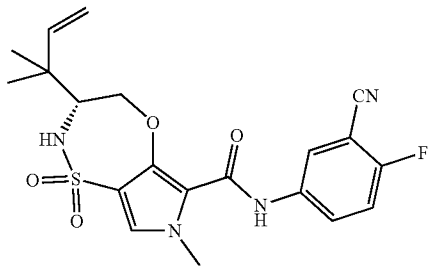 [SMILES: C=CC(C)(C)[C@@H]1COc2c(cn(C)c2C(=O)Nc2ccc(F)c(C#N)c2)S(=O)(=O)N1] | 433.2 | (400 MHz, CDCl3) δ: 8.83 (s, 1H), 7.94 (dd, J = 2.8, 5.4 Hz, 1H), 7.74 (ddd, J = 2.8, 4.5, 9.1 Hz, 1H), 7.20 (t, J = 8.7 Hz, 1H), 7.09 (s, 1H), 5.81 (dd, J = 10.7, 17.4 Hz, 1H), 5.29-5.13 (m, 2H), 4.80 (dd, J = 1.8, 12.6 Hz, 1H), 4.51 (d, J = 10.5 Hz, 1H), 4.01-3.92 (m, 4H), 3.84-3.76 (m, 1H), 1.27 (s, 3H), 1.20 (s, 3H) |
| 46 | 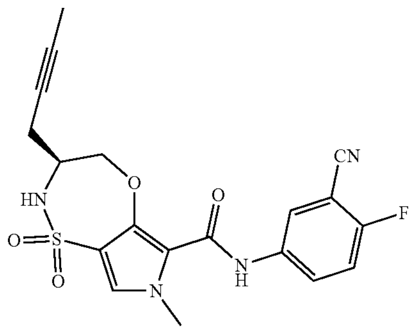 [SMILES: CC#CC[C@H]1COc2c(cn(C)c2C(=O)Nc2ccc(F)c(C#N)c2)S(=O)(=O)N1] | 416.8 | (400 MHz, DMSO-d6) δ: 9.55 (s, 1H), 8.18 (m, 1H), 8.02 (m, 1H), 7.80 (m, 1H), 7.50-7.54 (m, 2H), 4.70 (m, 1H), 3.92-3.97 (m, 1H), 3.81 (s, 3H), 3.73 (m, 1H), 2.33-2.42 (m, 2H), 1.78 (s, 3H) |
| 47 | 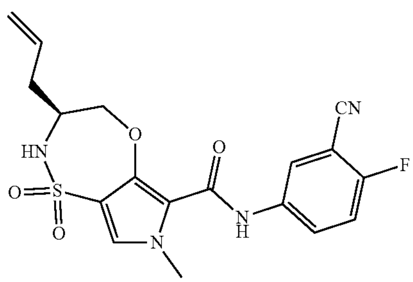 [SMILES: C=CC[C@H]1COc2c(cn(C)c2C(=O)Nc2ccc(F)c(C#N)c2)S(=O)(=O)N1] | 405.0 | (400 MHz, DMSO-d6) δ: 8.83 (s, 1H), 7.95 (dd, J = 2.8, 5.3 Hz, 1H), 7.73 (ddd, J = 2.8, 4.6, 9.2 Hz, 1H), 7.20 (t, J = 8.7 Hz, 1H), 7.08 (s, 1H), 5.89-5.75 (m, 1H), 5.29 (s, 1H), 5.27-5.22 (m, 1H), 4.74 (dd, J = 2.3, 12.8 Hz, 1H), 4.69-4.59 (m, 1H), 4.15 (dd, J = 7.8, 12.8 Hz, 1H), 4.09-3.99 (m, 1H), 3.96 (s, 3H), 2.60-2.35 (m, 2H) |
The stereochemistry shown for each of compounds in Table 1 is relative and not absolute.
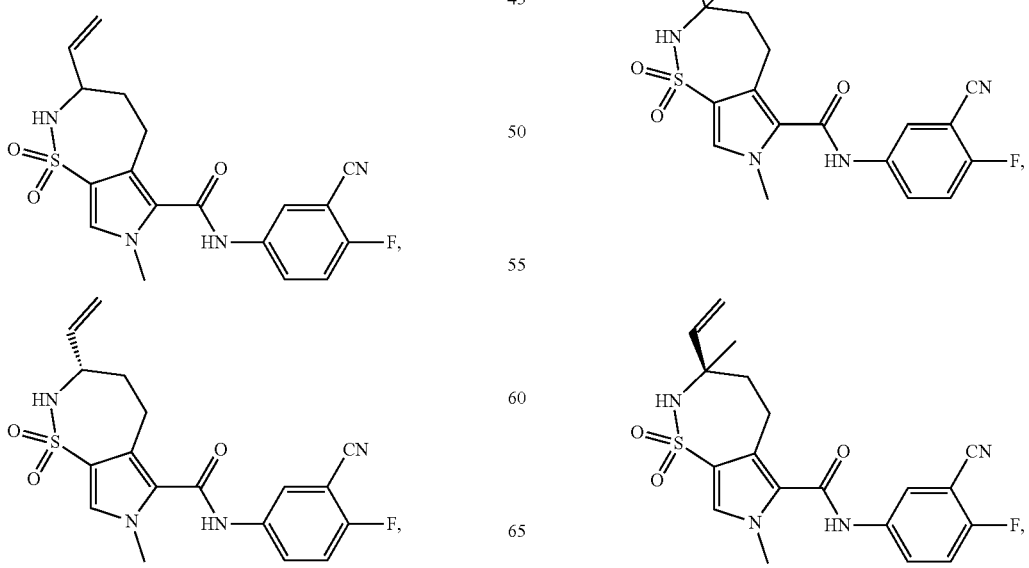

135
-continued
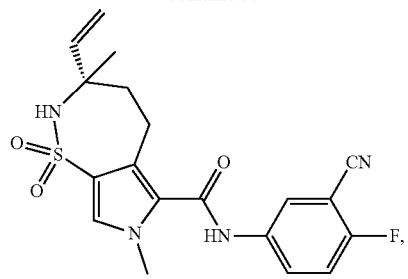
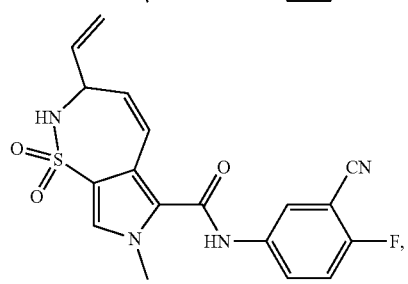
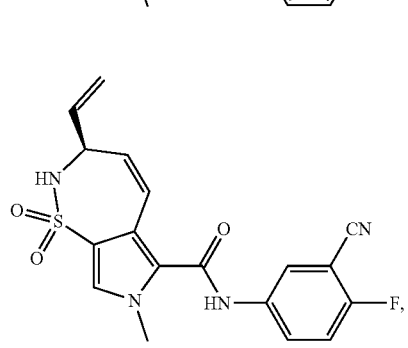
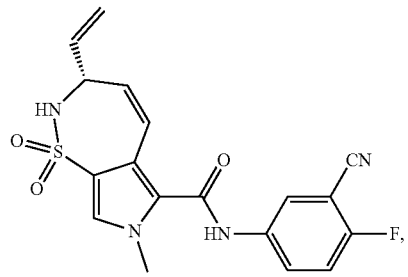
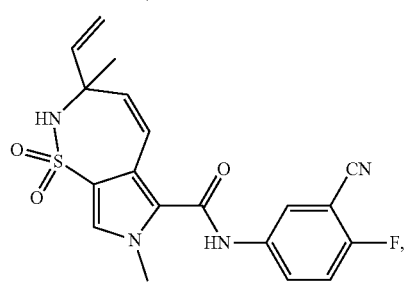
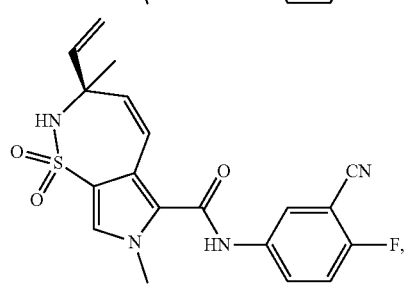
136
-continued
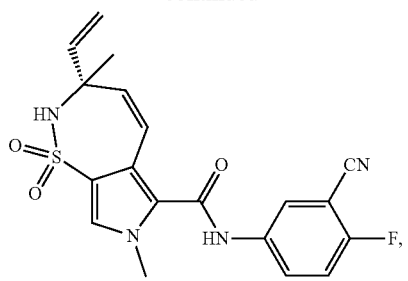
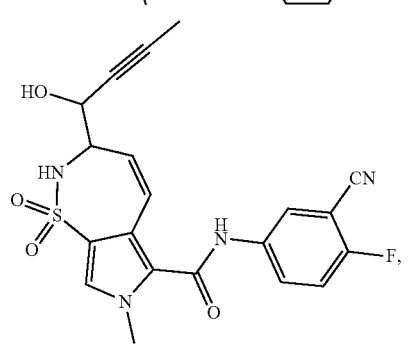
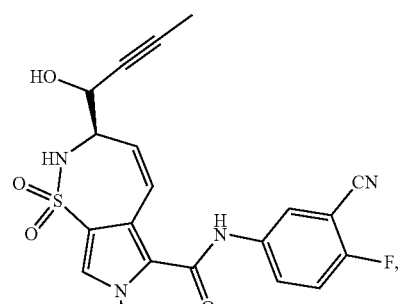
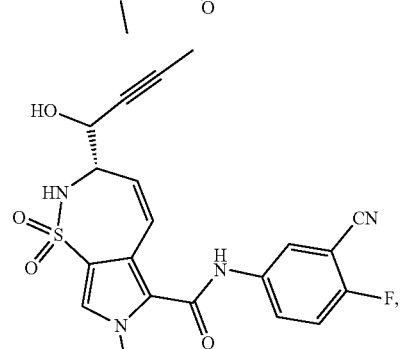
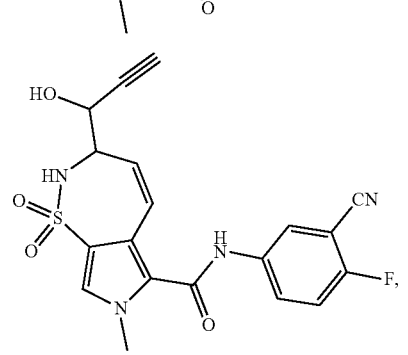

137
-continued
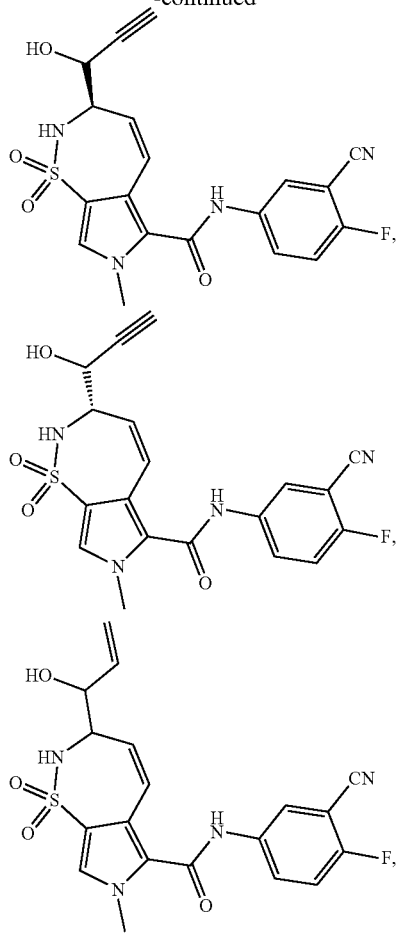
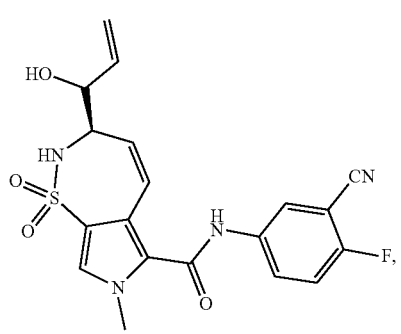
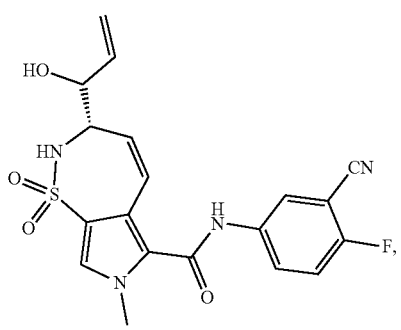
138
-continued
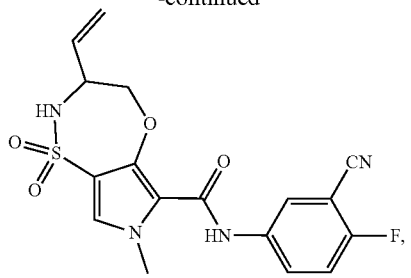
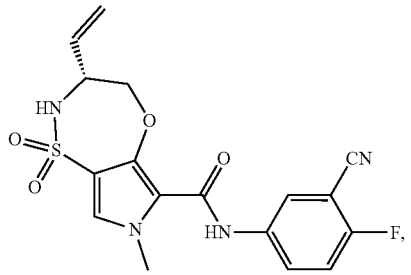
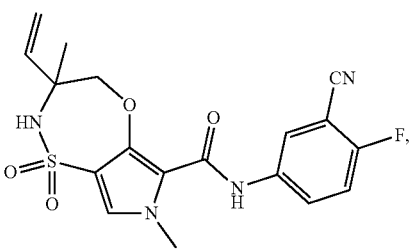
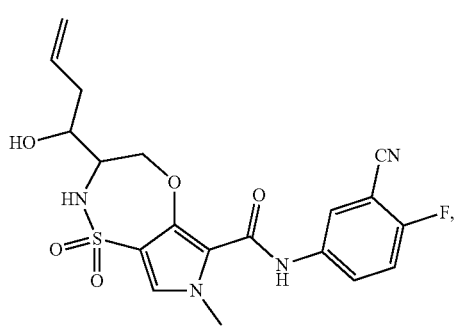
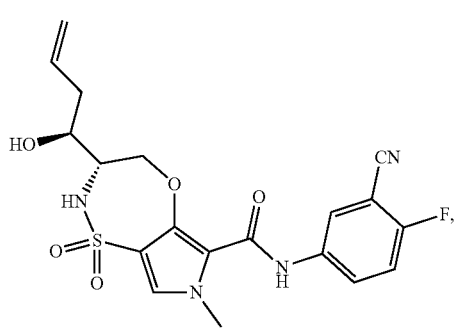

139
-continued
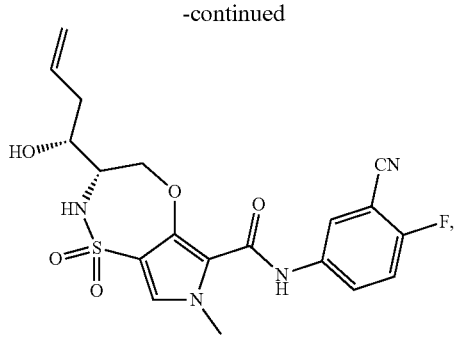
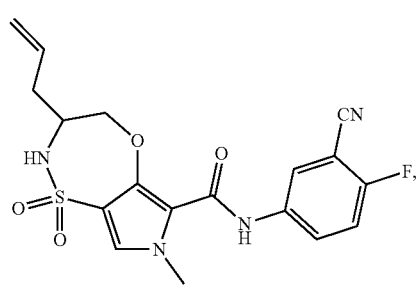
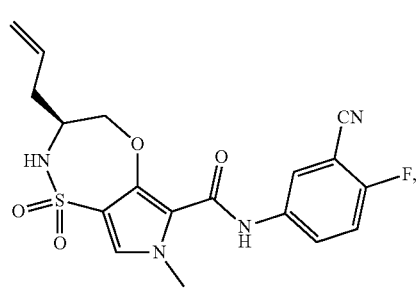
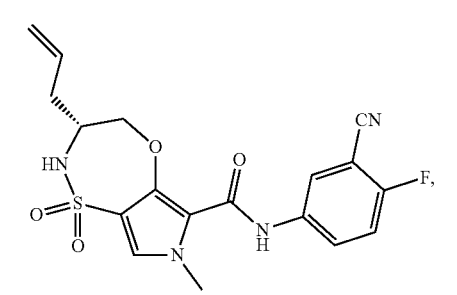
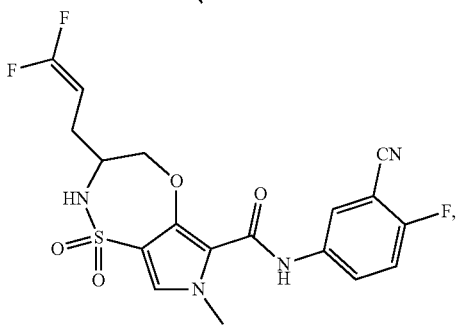
140
-continued
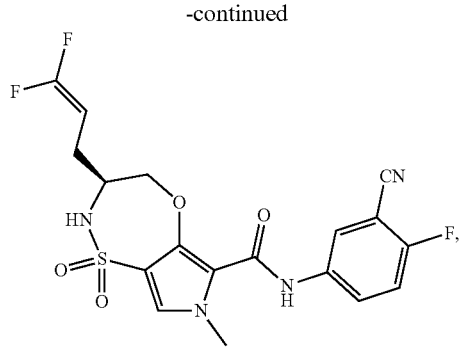
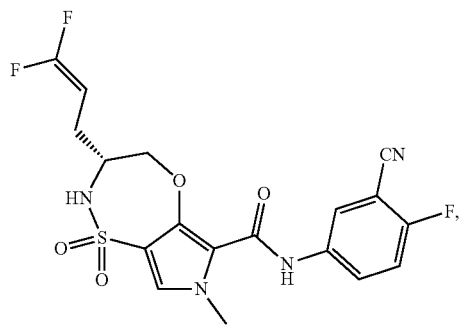
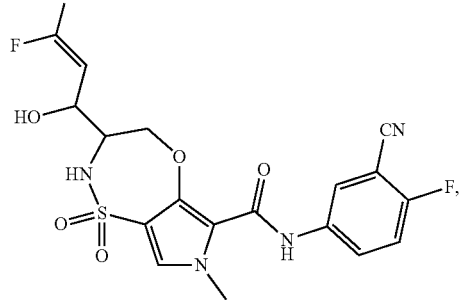
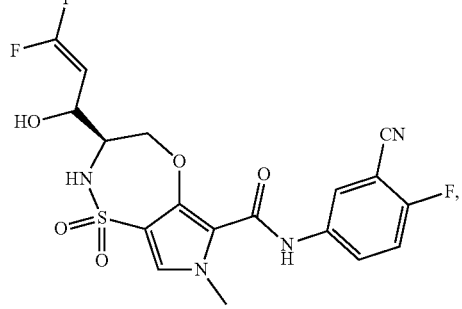
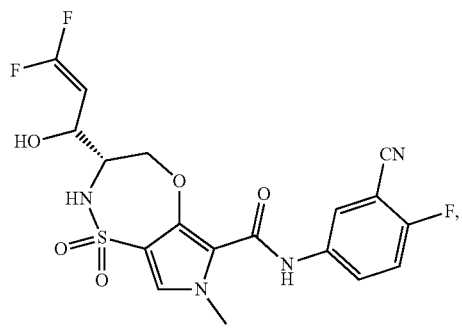

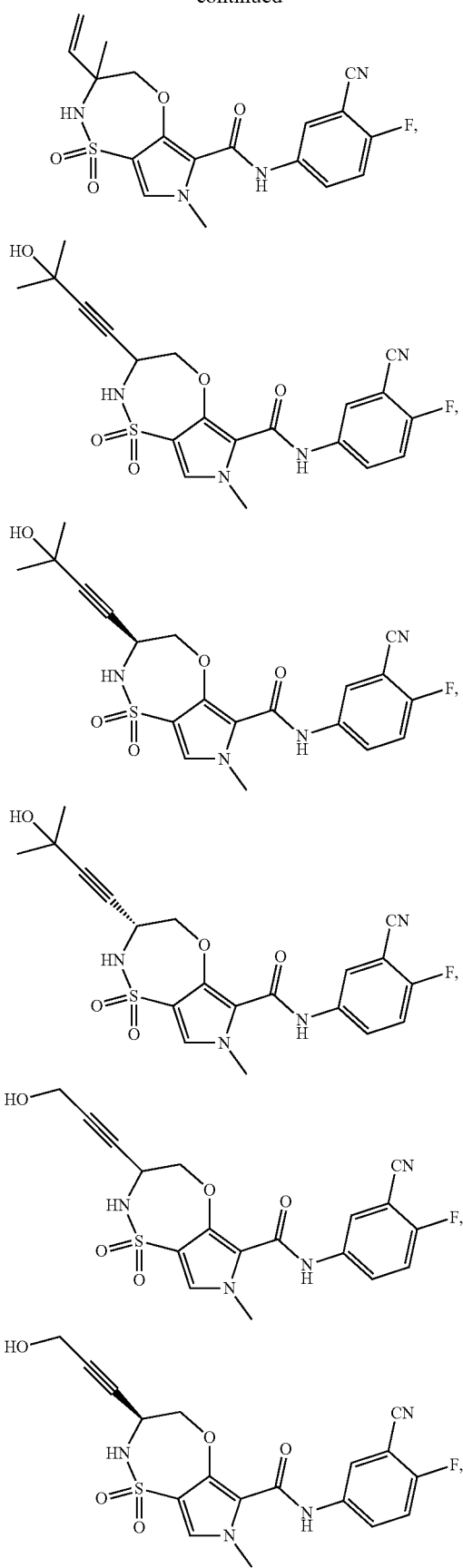
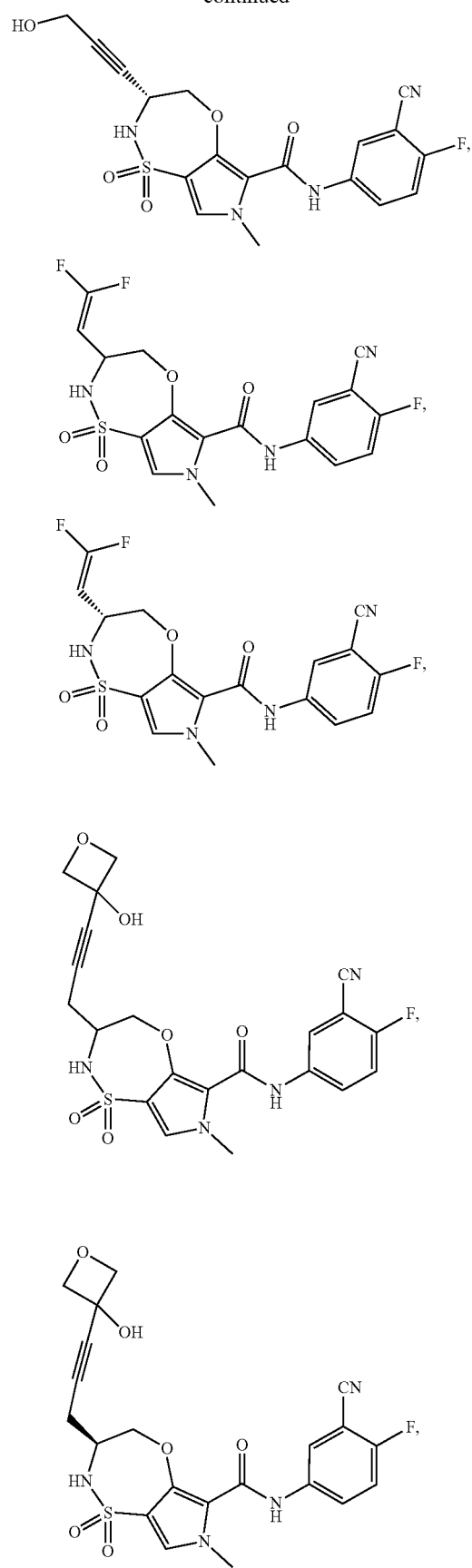

143
-continued
144
-continued
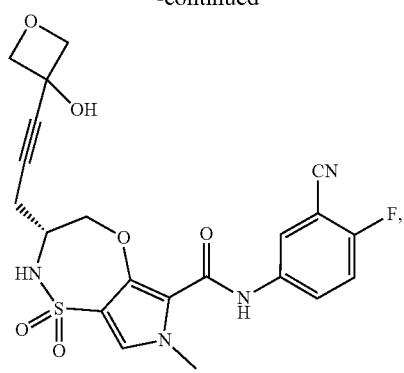
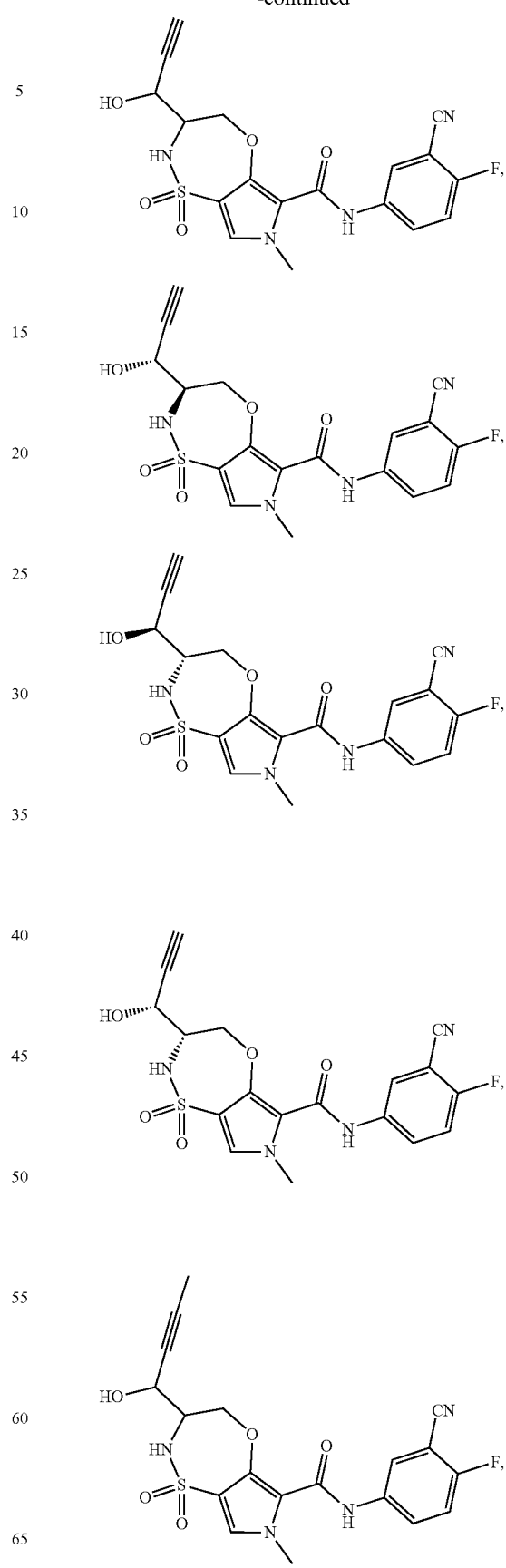

145
-continued
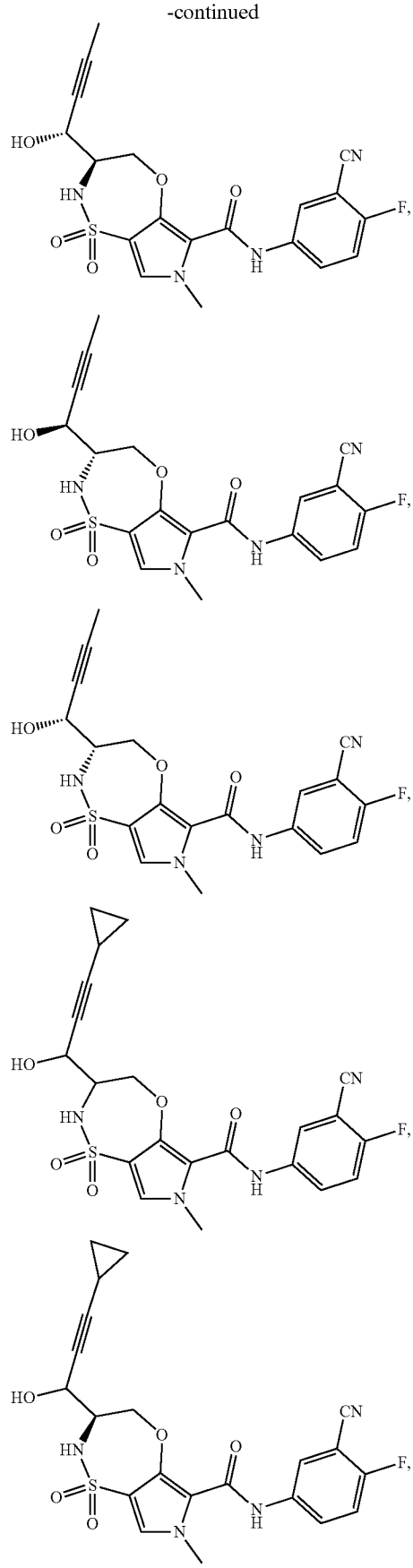
146
-continued
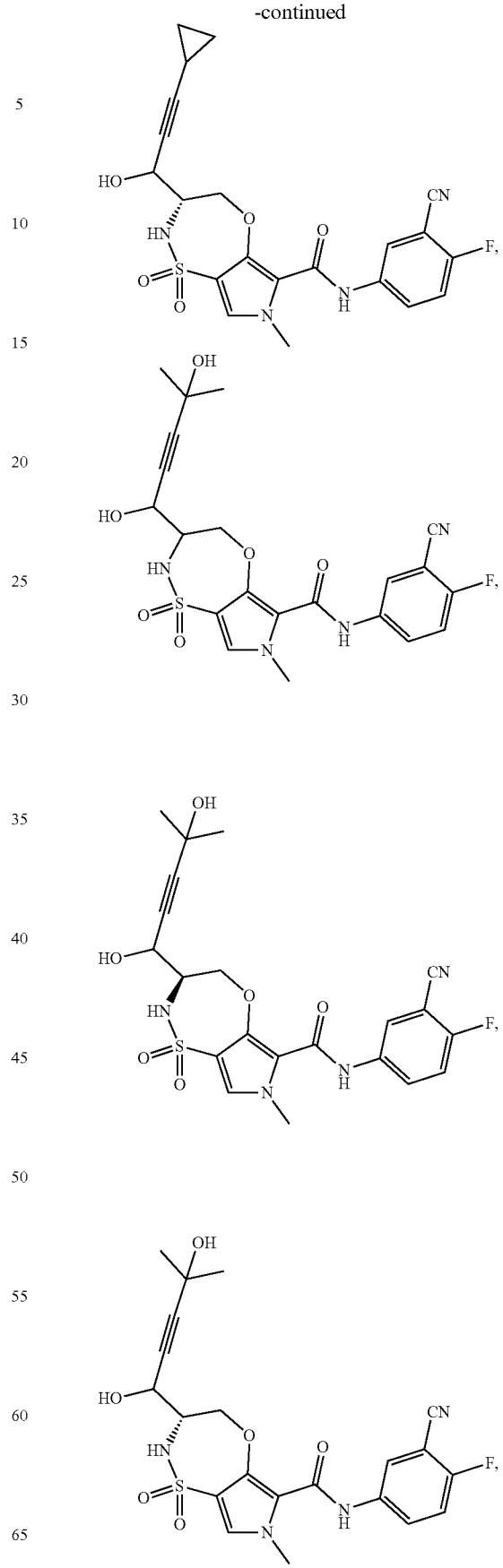

147
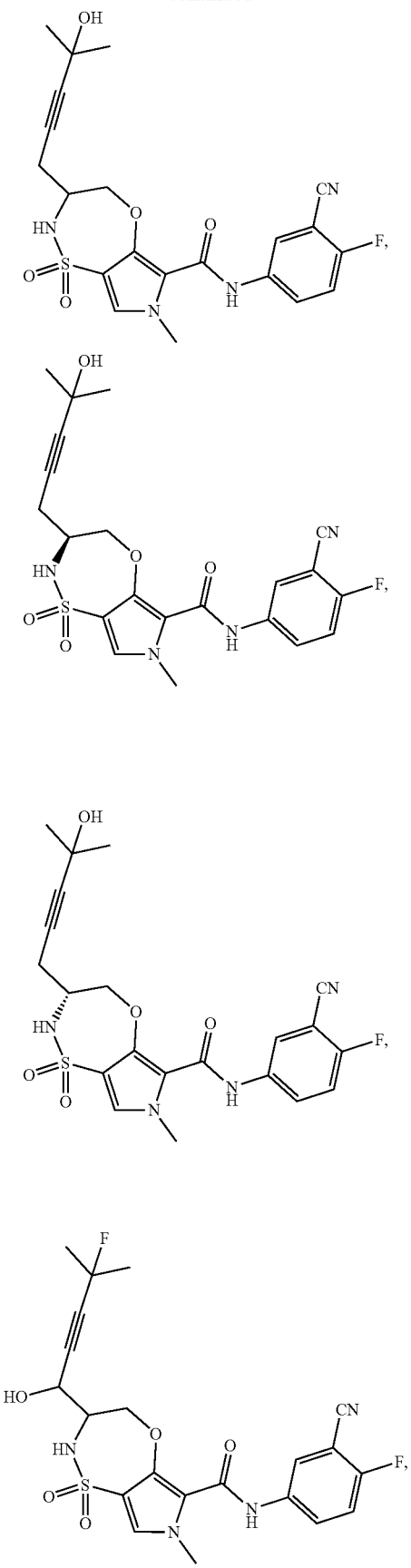
148
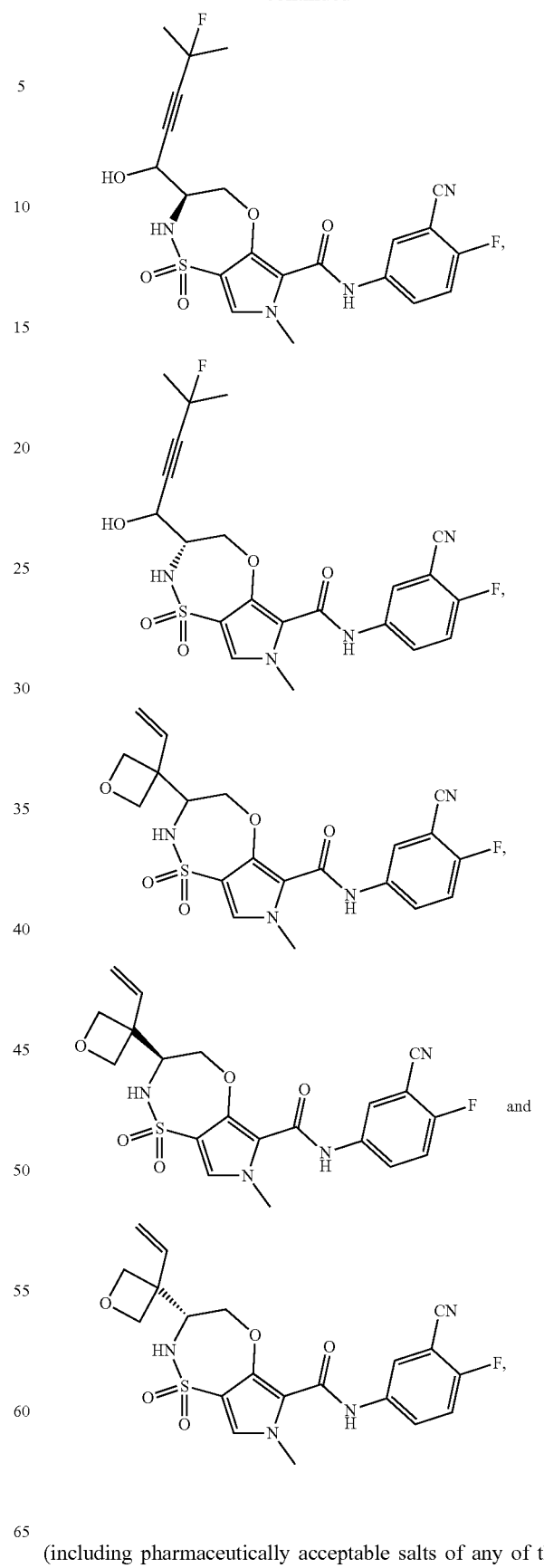
(including pharmaceutically acceptable salts of any of the foregoing).

Example A

HBV-DNA Antiviral Assay Using HepG2.2.15 Cells

The following assay procedure describes the HBV antiviral assay. This assay uses HepG2.2.15 cells, which have been transfected with HBV genome, and extracellular HBV DNA quantification as endpoint. Cell viability is assessed in parallel by measuring the intracellular ATP content using the CellTiter-Glo® reagent from Promega.

On day 0, HepG2.2.15 cells were seeded in 96-well plates at a density of $6.0 \times 10^4$ cells/well(0.1 ml/well). The cells were incubated at 37° C. and 5% $CO_2$.

On day 1, the test articles were diluted and added to cell culture wells (8 concentrations, 4-fold dilution, in duplicate). GLS4, Tenofovir and Sorafenib were used as reference compounds. 100 µl of culture medium containing the compounds was added to the plate, and the final total volume per well was 200 µl. The final concentration of DMSO in the culture medium was 0.5%. The plate map of compound treatment is shown below. The cells were cultured at 37° C. and 5% $CO_2$ for 3 days. The plate map of compound treatment is shown in FIG. 1.

On day 4, the plates were refreshed with culture media with compounds.

On day 7, cell viability was assessed using the CellTiter-Glo®, and the cell culture supernatants were collected for determination of HBV DNA by qPCR.

HBV DNA Quantification by qPCR

Extracellular DNA was isolated with QIAamp 96 DNA Blood Kit per the manufacturer's manual. HBV DNA was then quantified by qPCR with HBV specific primers and probes as specified in Table 2 using the FastStart Universal MasterMix from Roche on an ABI-7900HT. The PCR cycle program consisted of 95° C. for 10 min, followed by 40 cycles at 95° C. for 15 sec and 60° C. for 1 min.

TABLE 2

HBV DNA Primers and Probe

| Items | Name | Sequence (5'→3') |
|---|---|---|
| HBV Primer | HBV-forward | GTGTCTGCGGCGTTTTATCA (SEQ ID NO: 1) |
| | HBV-reverse | GACAAACGGGCAACATACCTT (SEQ ID NO: 2) |
| HBV Probe | HBV probe | FAM-CCTCTKCATCCTGCTGCTATGCCTCATC-TAMRA (SEQ ID NO: 3) |

A DNA standard was prepared by dilution of the pAAV2 HBV1.3 plasmid with concentrations ranging from 10 to $1 \times 10^7$ copies/L and used to generate a standard curve by plotting Ct value vs. the concentration of the HBV plasmid DNA standard. The quantity of HBV DNA in each sample was determined by interpolating from the standard curve.

Cell Viability

After harvest of the supernatants, the cell viability was detected by CellTiter-Glo© according to the manufacturer's manual. In brief, 50 µL of fresh cell culture medium was added to the culture plates, followed by addition of 50 µL CellTiter-Glo into each well. The plates were incubated at room temperature for 10 mins. The luminescence signal was collected on a BioTek Synergy 2 plate reader.

Data Analysis

Cell viability was calculated as follows: % Cell viability=(luminescence value of test sample−average luminescence value of blank)/(average luminescence value of 0.5% DMSO control−average luminescence of blank)×100%. HBV DNA inhibition was calculated as follows: 100−(HBV DNA copy number of test sample−HBV DNA copy number of ETV)/HBV DNA copy number of 0.5% DMSO control−HBV DNA copy number of ETV)×100%. The $CC_{50}$, $EC_{50}$ and $EC_{90}$ values were determined by dose-response curves fitted by GraphPad Prism using "log (agonist) vs. response—Variable slope".

Compounds of Formula (I) and Formula (II) are active against HBV as shown in Table 3, where 'A' indicates an $EC_{50} < 1$ µM, 'B' indicates an $EC_{50}$ of $>1$ µM and $<10$ µM and 'C' indicates an $EC_{50} > 10$ µM and $<50$ µM.

TABLE 3

Activity of compounds

| No. | $EC_{50}$ |
|---|---|
| 1 | A |
| 2A, | A* |
| 2B, | |
| 2C | |
| 2D | |
| 3A, | A* |
| 3B, | |
| 3C | |
| 3D | |
| 4A, | A* |
| 4B, | |
| 4C | |
| 4D | |
| 6A | A |

*Indicate that at least 2 of the diastereomers have the indicated activity

Example B

HBV-DNA Antiviral Assay Using HepG2.117 Cells

The following assay procedure describes the HBV antiviral assay, using HepG2.117 cells, which carry a stably integrated genotype D HBV genome under the control of a Tet-off promoter, and intracellular HBV DNA quantification as endpoint. Cell viability is assessed in parallel by measuring the intracellular ATP content using ATPlite (Perkin Elmer).

On day 0, HepG2.117 cells (which are maintained in routine cell culture with doxycycline present in the medium at a final concentration of 1 µg/mL) were seeded in 96-well plates (white with clear bottom) at a density of $2.0 \times 10^4$ cells/well (0.1 mL/well) in medium without doxycycline to induce pgRNA transcription and subsequent formation of HBV particles. The cells were incubated at 37° C. and 5% $CO_2$.

On day 1, medium was removed from each well, the test articles were diluted in culture medium without doxycyline and 100 µL was added to cell culture wells (9 concentrations, 4-fold dilution). For each plate, 6 untreated (merely DMSO) wells were included. The final concentration of DMSO in the culture medium was 2%. Each plate was prepared in duplicate (one for HBV DNA extraction, one for ATPlite measurement). The cells were incubated at 37° C. and 5% $CO_2$ for 3 days.

On day 4, cell viability was assessed using ATPlite and cell lysates were prepared for HBV DNA extraction and subsequent quantification by qPCR.

HBV DNA Quantification by qPCR

Medium was removed from each well and 100 μL of 0.33% NP-40 in H$_2$O was added to each well. Plates were sealed, incubated at 4° C. for 5 mins, vortexed extensively and centrifuged briefly. Next, 35 μL of lysate was added to 65 μL QuickExtract DNA Extraction Solution (Epicentre) in a PCR plate for each well. PCR plate was incubated at 65° C. for 6 mins, 98° C. for 2 mins and finally cooled to 4° C. HBV DNA was then quantified by qPCR with HBV-specific primers and probes as specified in Table 4 using the Bio-Rad SSOAdvanced Universal Probes Supermix on a CFX96 machine (Bio-Rad). The PCR cycle program consisted of 95° C. for 3 mins, followed by 40 cycles at 95° C. for 10 sec and 60° C. for 30 sec.

TABLE 4

HBV DNA Primers and Probe for HepG2.117 assay

| Items | Name | Sequence (5'→3') |
|---|---|---|
| HBV Primer | HBV-forward | GTGTCTGCGGCGTTTTATCA (SEQ ID NO: 1) |
| | HBV-reverse | GACAAACGGGCAACATACCTT (SEQ ID NO: 2) |
| HBV Probe | HBV probe | FAM/CCTCTKCAT/ZEN/CCTGCTGCTATGCCTC ATC/3IABkFQ/ (SEQ ID NO: 4) |

A DNA standard was prepared by dilution of an IDT gBlock corresponding to the amplicon with concentrations ranging from 10^2 to 10^8 copies/input (i.e. per 4 μL) and used to generate a standard curve by plotting Cq values vs. HBV DNA standard concentration. The quantity of HBV DNA in each sample was determined by interpolating from the standard curve.

Cell Viability

Using the other plates, the cell viability was quantified by ATPlite according to the manufacturer's manual. In brief, 50 μL of cell lysis solution was added to the culture plates and shaken for 5', followed by addition of 50 μL substrate into each well and further shaking. The plates were incubated at room temperature for 10 mins and luminescence signal was subsequently measured on a VarioSkan Lux (ThermoFisher) plate reader.

Data Analysis

Cell viability was calculated as follows: % Cell viability= (luminescence value of test sample)/(average luminescence value of 2% DMSO control)×100%. HBV DNA inhibition was calculated as follows: 100−(HBV DNA copy number of test sample)/(average HBV DNA copy number of 2% DMSO control)×100%. No normalization to entecavir was required due to the excellent dynamic window of this assay. The CC$_{50}$, EC$_{50}$ and EC$_{90}$ values were determined by dose-response curves fitted by GraphPad Prism using "log (agonist) vs. response—Variable slope".

Compounds of Formulae (I) and (II) are active against HBV as shown in Table 5, where 'A' indicates an EC$_{50}$<1 nM, 'B' indicates an EC$_{50}$ of >1 nM and <10 nM, 'C' indicates an EC$_{50}$>10 nM and <100 nM, and 'D' indicates an EC$_{50}$>100 nM and <1000 nM.

TABLE 5

| Compound | EC$_{50}$ HepG2.117 (nM) |
|---|---|
| 1 | B |
| 8 | B |
| 9A | C |
| 9B | C |
| 10A | C |
| 10B | C |
| 11A | B |
| 11B | B |
| 12A | C |
| 12B | C |
| 13 | B |
| 14A | B |
| 14B | B |
| 15A | B |
| 15B | B |
| 16A | B |
| 16B | B |
| 17A | B |
| 17B | B |
| 18 | B |
| 19A | B |
| 19B | B |
| 20 | B |
| 21 | C |
| 22A | C |
| 22B | B |
| 23A | B |
| 23B | B |
| 24 | B |
| 25A | C |
| 25B | C |
| 26 | C |
| 27A | C |
| 27B | B |
| 27C | C |
| 27D | A |
| 28A | B |
| 28B | B |
| 29A | C |
| 29B | B |
| 30A | B |
| 30B | C |
| 31A | B |
| 31B | B |
| 32 | B |
| 33 | B |
| 34 | A |
| 35A | B |
| 35B | B |
| 36A | C |
| 36B | B |
| 37 | C |
| 38A | C |
| 38B | C |
| 38C | B |
| 38D | D |
| 39A | C |
| 39B | C |
| 40A | B |
| 40B | B |
| 41A | B |
| 41B | B |
| 41C | C |
| 41D | C |
| 42A | B |
| 42B | B |
| 42C | B |
| 42D | C |
| 43A | C |
| 43B | C |
| 44A | C |
| 44B | B |
| 44C | B |
| 44C | C |
| 45A | B |
| 45B | B |
| 46 | B |
| 47 | B |

Although the foregoing has been described in some detail by way of illustrations and examples for purposes of clarity and understanding, it will be understood by those of skill in the art that numerous and various modifications can be made without departing from the spirit of the present disclosure. Therefore, it should be clearly understood that the forms disclosed herein are illustrative only and are not intended to limit the scope of the present disclosure, but rather to also cover all modification and alternatives coming with the true scope and spirit of the invention.

What is claimed is:

1. A compound of Formula (I), or a pharmaceutically acceptable salt thereof, having the structure:

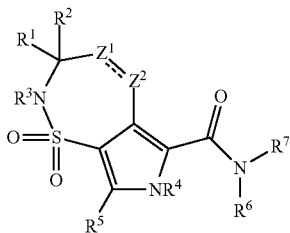

wherein:
- - - - - is a single or a double bond,
  wherein when - - - - - is a single bond, then $Z^1$ is $CR^{8A}R^{9A}$ and $Z^2$ is $CR^{8B}R^{9B}$; and
  wherein when - - - - - is a double bond, then $Z^1$ and $Z^2$ are each independently $CR^{10}$;
$R^1$ is a substituted or an unsubstituted $C_{2-8}$ alkenyl or a substituted or an unsubstituted $C_{2-8}$ alkynyl, wherein the substituted $C_{2-8}$ alkenyl and the substituted $C_{2-8}$ alkynyl is substituted with one or more substituents independently selected from halogen, hydroxy, an optionally substituted monocyclic $C_{3-6}$ cycloalkyl, an optionally substituted bicyclic $C_{3-8}$ cycloalkyl, an optionally substituted monocyclic heterocyclyl and $R^{11A}$;
$R^2$ is hydrogen, deuterium or a substituted or an unsubstituted $C_{1-4}$ alkyl, wherein the substituted $C_{1-4}$ alkyl is substituted with one or more substituents selected from halogen, hydroxy and $R^{11B}$;
$R^3$ is hydrogen, deuterium or an unsubstituted $C_{1-4}$ alkyl;
$R^4$ is hydrogen, deuterium or an unsubstituted $C_{1-4}$ alkyl;
$R^5$ is hydrogen, deuterium, halogen, an unsubstituted $C_{1-4}$ alkyl, cyano, an unsubstituted $C_{1-4}$ haloalkyl or an unsubstituted $C_{3-8}$ monocyclic cycloalkyl;
$R^6$ is a substituted phenyl or a substituted pyridyl, wherein the substituted phenyl and the substituted pyridyl is substituted with one or more substituents independently selected from halogen, cyano, an unsubstituted $C_{1-4}$ haloalkyl and an unsubstituted $C_{1-4}$ alkyl; and
$R^7$ is hydrogen, deuterium or an unsubstituted $C_{1-4}$ alkyl;
$R^{8A}$, $R^{8B}$, $R^{9A}$ and $R^{9B}$ are independently hydrogen, deuterium, halogen, an unsubstituted $C_{1-4}$ alkyl or hydroxy;
each $R^{10}$ are independently hydrogen, deuterium, halogen or an unsubstituted $C_{1-4}$ alkyl; and
$R^{11A}$ and $R^{11B}$ are independently an optionally substituted —O-acyl, an unsubstituted O-linked α-amino acid, —O—P(=O)(OH)$_2$ or —CH$_2$—P(=O)(OH)$_2$.

2. The compound of claim 1, or a pharmaceutically acceptable salt thereof, wherein - - - - - is a single or a double bond; $Z^1$ is $CR^{8A}R^{9A}$; $Z^2$ is $CR^{8B}R^{9B}$; $R^{8A}$ is hydrogen; $R^{9A}$ is hydrogen; $R^{8B}$ is hydrogen; and $R^{9B}$ is hydrogen.

3. The compound of claim 1, or a pharmaceutically acceptable salt thereof, wherein is - - - - - a double bond, $Z^1$ and $Z^2$ are each independently $CR^{10}$; and $R^{10}$ is hydrogen.

4. The compound of claim 1, or a pharmaceutically acceptable salt thereof, wherein $R^1$ is an unsubstituted $C_{2-8}$ alkenyl or an unsubstituted $C_{2-8}$ alkynyl.

5. The compound of claim 1, or a pharmaceutically acceptable salt thereof, wherein $R^1$ is a substituted $C_{2-8}$ alkenyl, wherein the substituted $C_{2-8}$ alkenyl is substituted with one or more substituents independently selected from halogen, hydroxy, an optionally substituted monocyclic $C_{3-6}$ cycloalkyl, an optionally substituted bicyclic $C_{3-8}$ cycloalkyl, an optionally substituted monocyclic heterocyclyl and $R^{11A}$; or wherein $R^1$ is a substituted $C_{2-8}$ alkynyl, wherein the substituted $C_{2-8}$ alkynyl is substituted with one or more substituents independently selected from halogen, hydroxy, an optionally substituted monocyclic $C_{3-6}$ cycloalkyl, an optionally substituted bicyclic $C_{3-8}$ cycloalkyl, an optionally substituted monocyclic heterocyclyl and $R^{11A}$.

6. The compound of claim 5, or a pharmaceutically acceptable salt thereof, wherein $R^2$ is hydrogen.

7. The compound of claim 5, or a pharmaceutically acceptable salt thereof, wherein $R^2$ is an unsubstituted $C_{1-4}$ alkyl or a substituted $C_{1-4}$ alkyl.

8. The compound of claim 5, or a pharmaceutically acceptable salt thereof, wherein $R^3$ is hydrogen.

9. The compound of claim 5, or a pharmaceutically acceptable salt thereof, wherein $R^4$ is an unsubstituted $C_{1-4}$ alkyl.

10. The compound of claim 5, or a pharmaceutically acceptable salt thereof, wherein $R^5$ is hydrogen.

11. The compound of claim 5, or a pharmaceutically acceptable salt thereof, wherein $R^7$ is hydrogen.

12. A compound of Formula (II), or a pharmaceutically acceptable salt thereof, having the structure:

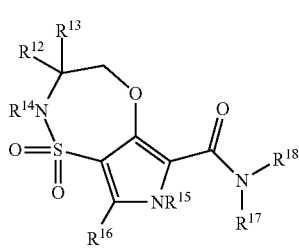

wherein:
$R^{12}$ is a substituted or an unsubstituted $C_{2-8}$ alkenyl or a substituted or an unsubstituted $C_{2-8}$ alkynyl, wherein the substituted $C_{2-8}$ alkenyl and the substituted $C_{2-8}$ alkynyl is substituted with one or more substituents independently selected from halogen, hydroxy, an optionally substituted monocyclic $C_{3-6}$ cycloalkyl, an optionally substituted bicyclic $C_{3-8}$ cycloalkyl, an optionally substituted monocyclic heterocyclyl and $R^{19A}$;
$R^{13}$ is hydrogen, deuterium or a substituted or an unsubstituted $C_{1-4}$ alkyl, wherein the substituted $C_{1-4}$ alkyl is substituted with one or more substituents selected from halogen, hydroxy and $R^{19B}$;
$R^{14}$ is hydrogen, deuterium or an unsubstituted $C_{1-4}$ alkyl;
$R^{15}$ is hydrogen, deuterium or an unsubstituted $C_{1-4}$ alkyl;
$R^{16}$ is hydrogen, deuterium, halogen, an unsubstituted $C_{1-4}$ alkyl, cyano, an unsubstituted $C_{1-4}$ haloalkyl or an unsubstituted $C_{3-8}$ monocyclic cycloalkyl;
$R^{17}$ is a substituted phenyl or a substituted pyridyl, wherein the substituted phenyl and the substituted pyridyl is substituted with one or more substituents independently selected from halogen, cyano, an unsubstituted $C_{1-4}$ haloalkyl and an unsubstituted $C_{1-4}$ alkyl;
$R^{18}$ is hydrogen, deuterium or an unsubstituted $C_{1-4}$ alkyl; and $R^{19A}$ and $R^{19B}$ are independently an optionally substituted —O-acyl, an unsubstituted O-linked α-amino acid, —O—P(=O)(OH)$_2$ or —CH$_2$—P(=O)(OH)$_2$; and provided that when $R^{12}$ is an unsubstituted 2-butynyl, $R^{13}$ is hydrogen, $R^{14}$ and $R^{18}$ are each hydrogen, $R^{15}$ is methyl and $R^{16}$ is hydrogen, then $R^{17}$ is not 3,4-difluorophenyl.

13. The compound of claim 12, or a pharmaceutically acceptable salt thereof, wherein $R^{12}$ is an unsubstituted $C_{2-8}$ alkenyl or an unsubstituted $C_{2-8}$ alkynyl.

14. The compound of claim 12, or a pharmaceutically acceptable salt thereof, wherein $R^{12}$ is a substituted $C_{2-8}$ alkenyl, wherein the substituted $C_{2-8}$ alkenyl is substituted with one or more substituents independently selected from halogen, hydroxy, an optionally substituted monocyclic $C_{3-6}$ cycloalkyl, an optionally substituted bicyclic $C_{3-8}$ cycloalkyl, an optionally substituted monocyclic heterocyclyl and $R^{19A}$; or wherein $R^{12}$ is a substituted $C_{2-8}$ alkynyl, wherein the substituted $C_{2-8}$ alkynyl is substituted with one or more substituents independently selected from halogen, hydroxy, an optionally substituted monocyclic $C_{3-6}$ cycloalkyl, an optionally substituted bicyclic $C_{3-8}$ cycloalkyl, an optionally substituted monocyclic heterocyclyl and $R^{19A}$.

15. The compound of claim 12, or a pharmaceutically acceptable salt thereof, wherein $R^{13}$ is hydrogen.

16. The compound of claim 12, or a pharmaceutically acceptable salt thereof, wherein $R^{13}$ is an unsubstituted $C_{1-4}$ alkyl or a substituted $C_{1-4}$ alkyl.

17. The compound of claim 12, or a pharmaceutically acceptable salt thereof, wherein $R^{14}$ is hydrogen.

18. The compound of claim 12, or a pharmaceutically acceptable salt thereof, wherein $R^{15}$ is an unsubstituted $C_{1-4}$ alkyl.

19. The compound of claim 12, or a pharmaceutically acceptable salt thereof, wherein $R^{18}$ is hydrogen.

20. The compound of claim 5, wherein the compound is selected from the group consisting of:

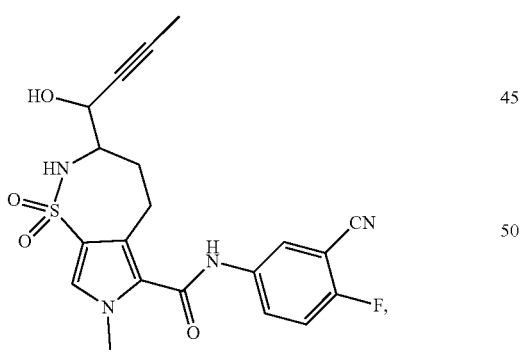

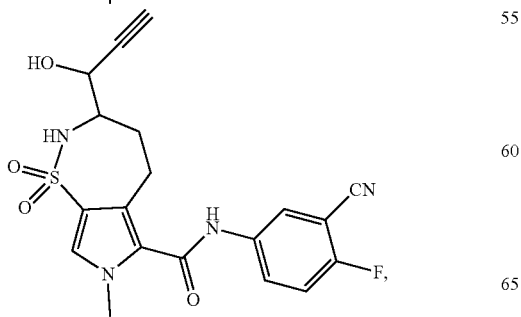

-continued

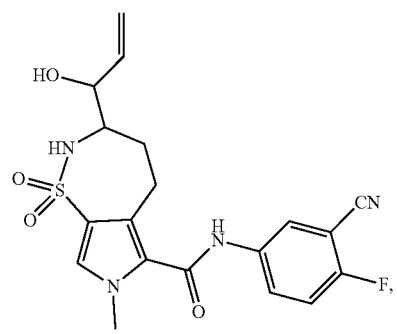

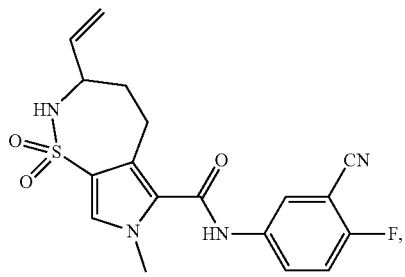

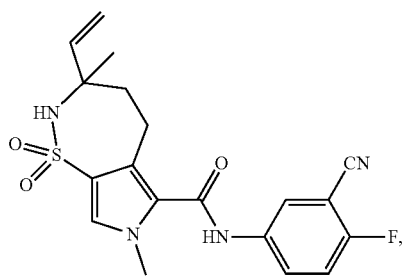

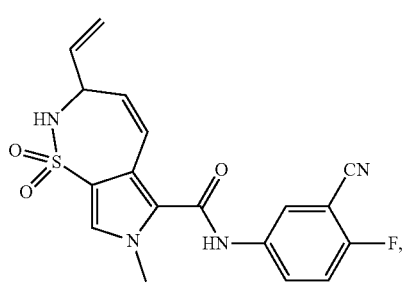

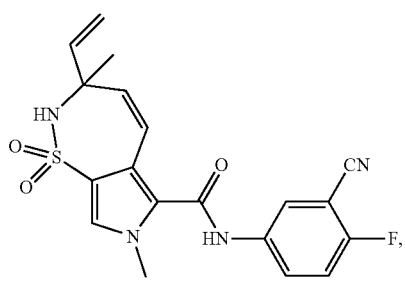

-continued
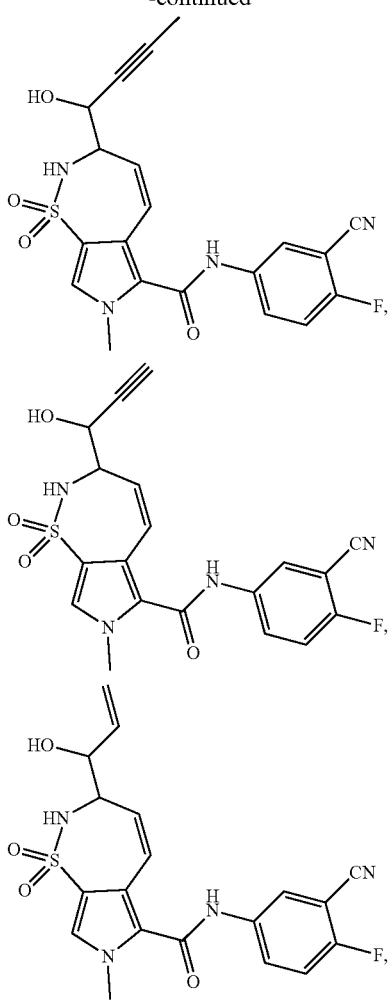
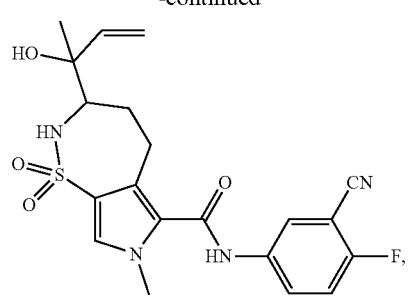
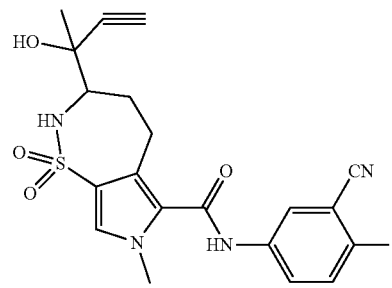
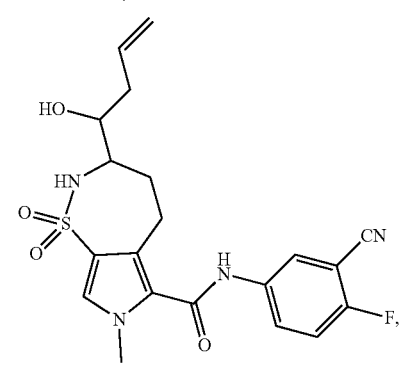
and
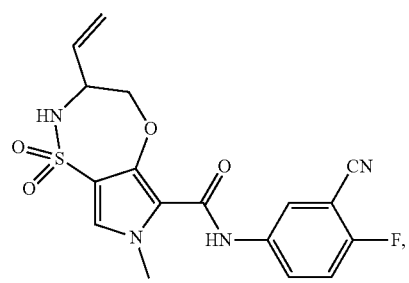
pharmaceutically acceptable salt of any of the foregoing.
21. The compound of claim 12, wherein the compound is selected from the group consisting of:
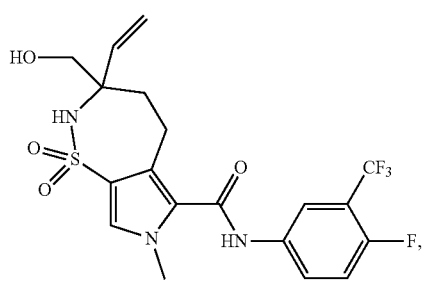
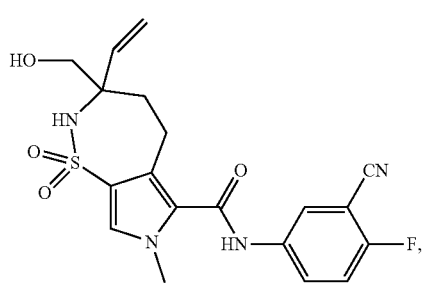

161
-continued
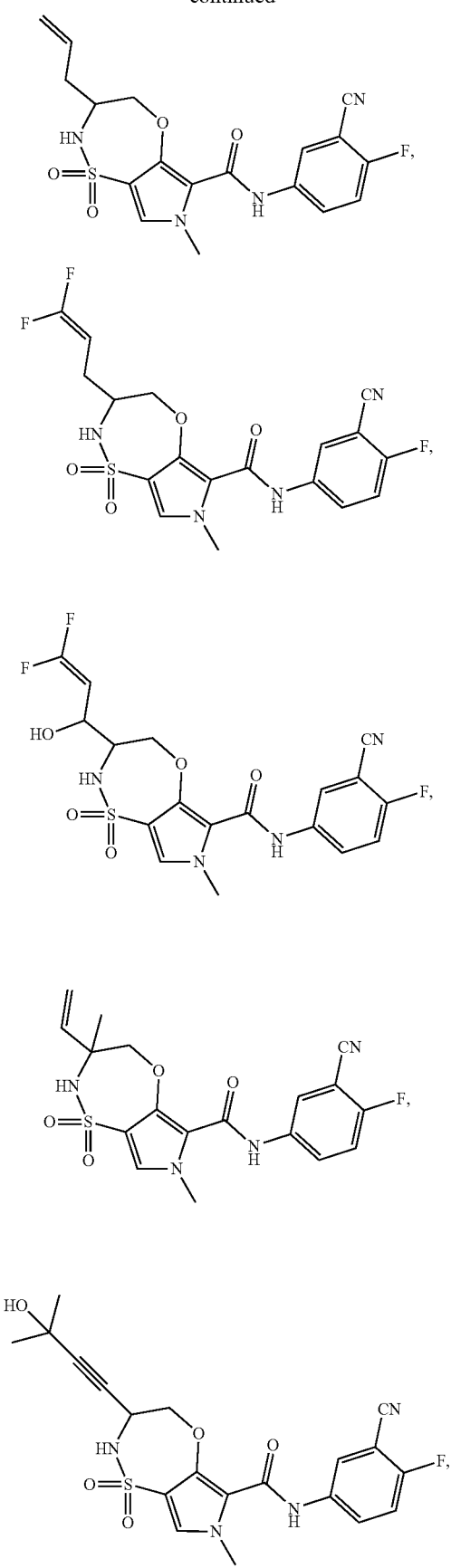
162
-continued
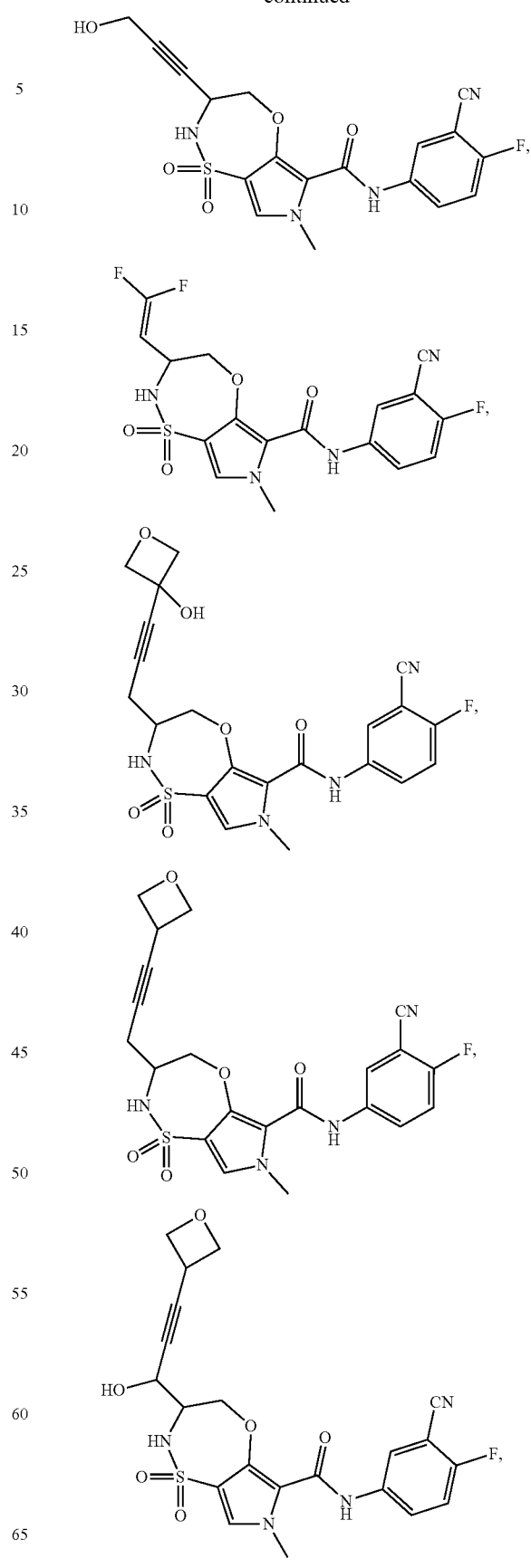

163
-continued
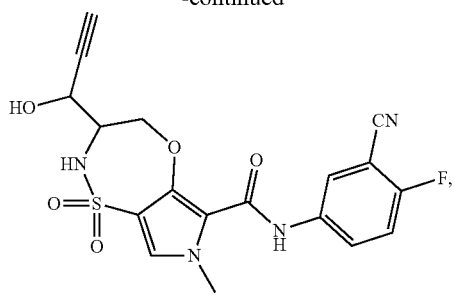
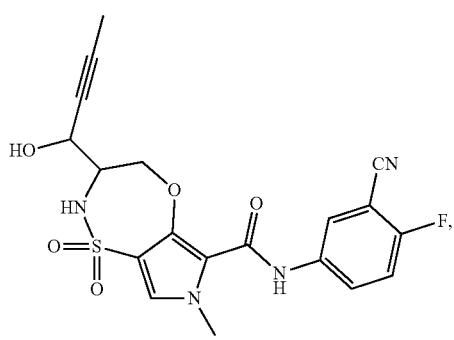
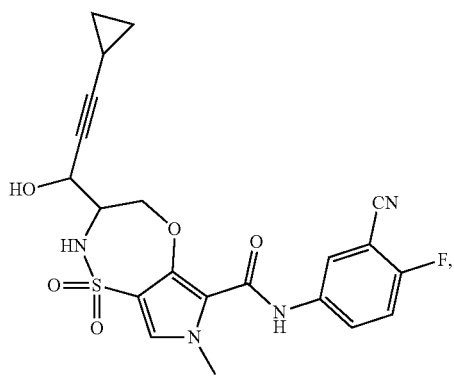
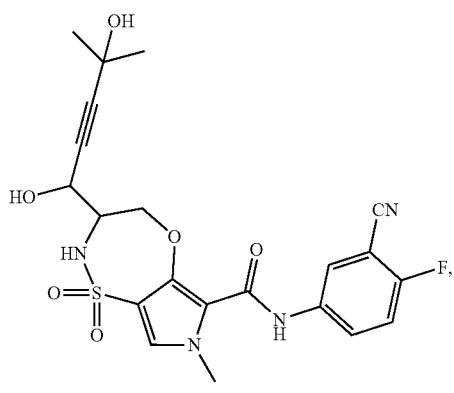
164
-continued
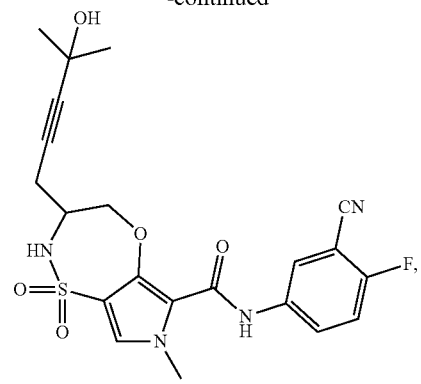
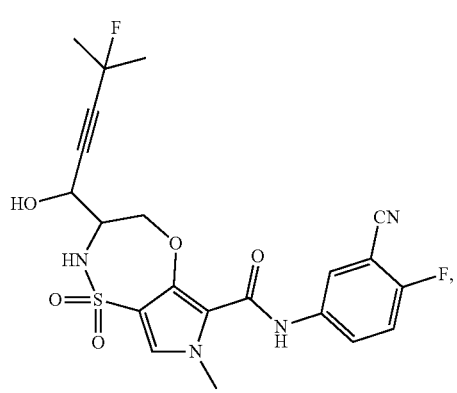
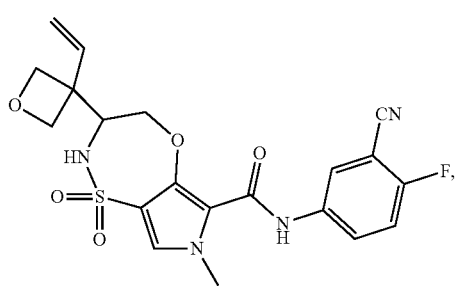
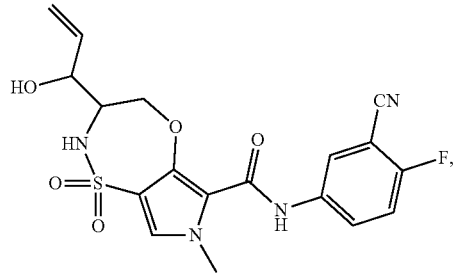
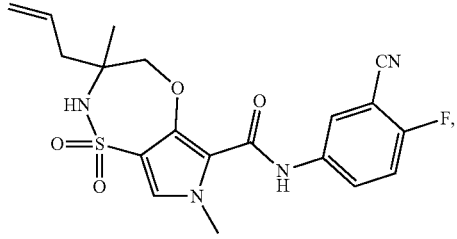

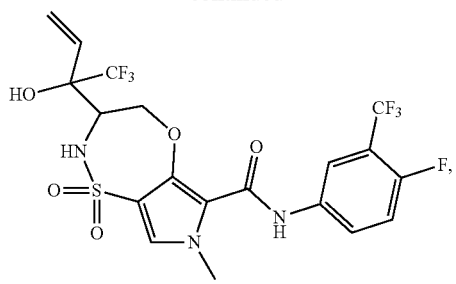
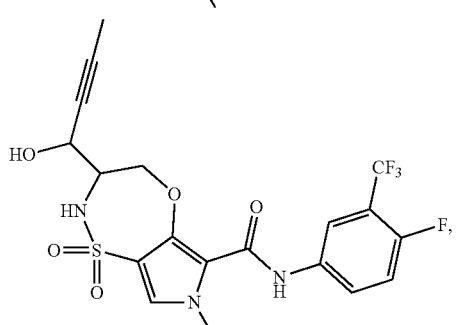
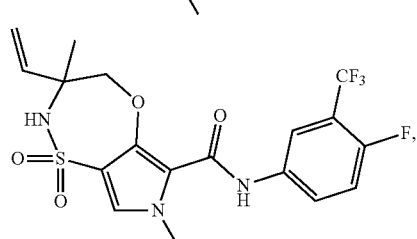
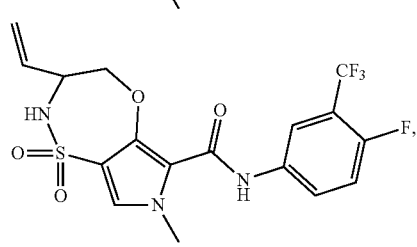
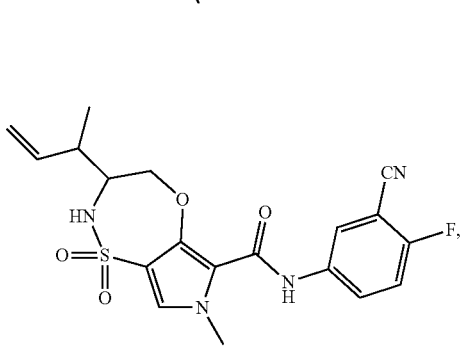
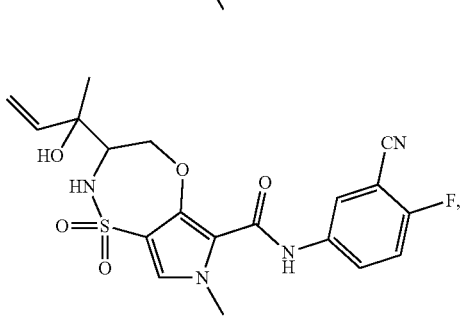
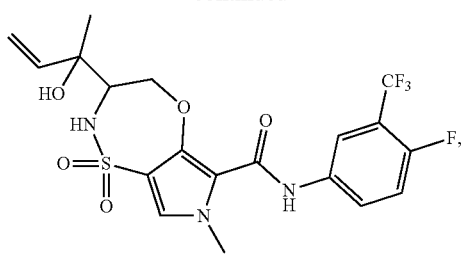
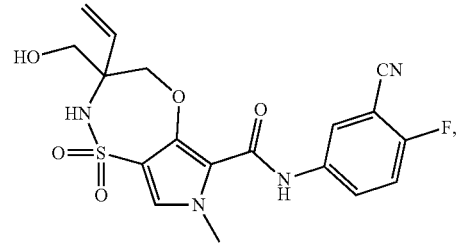
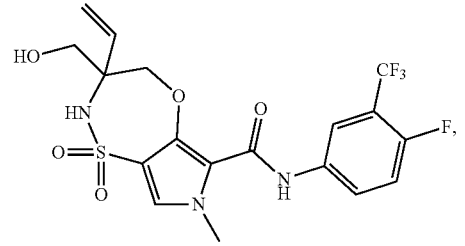
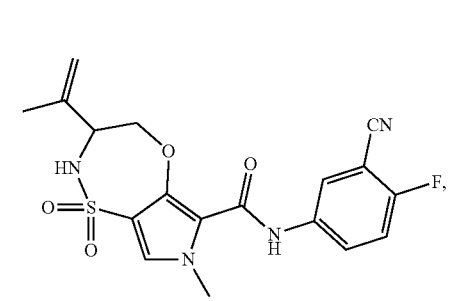
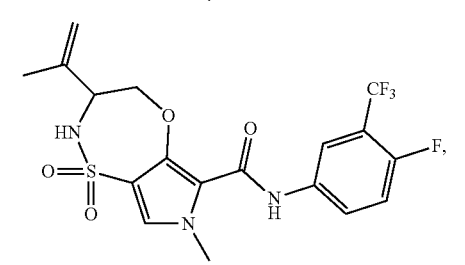
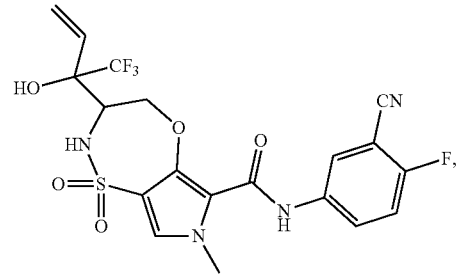

-continued
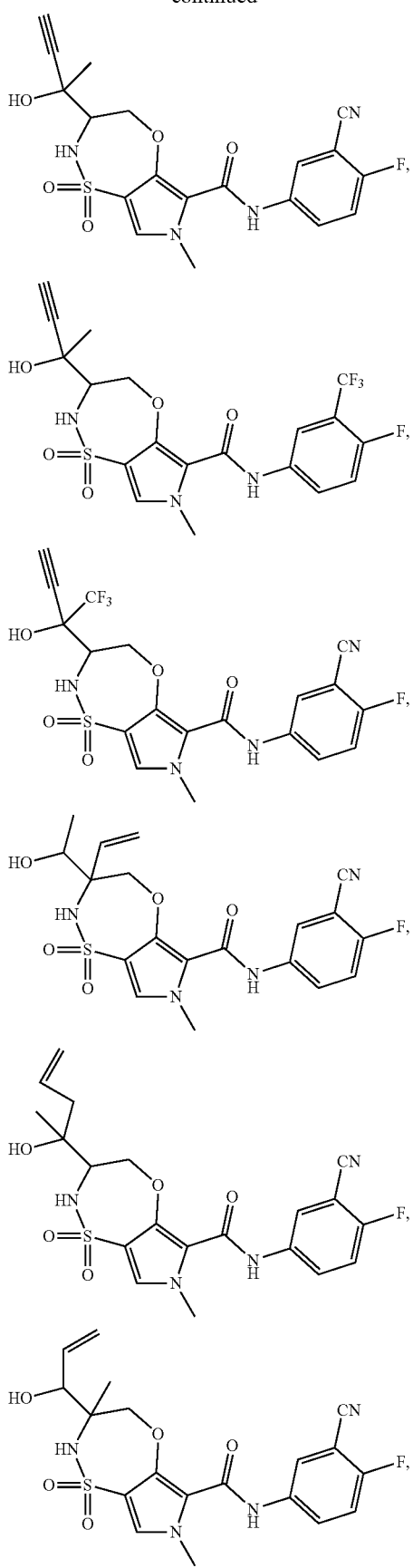
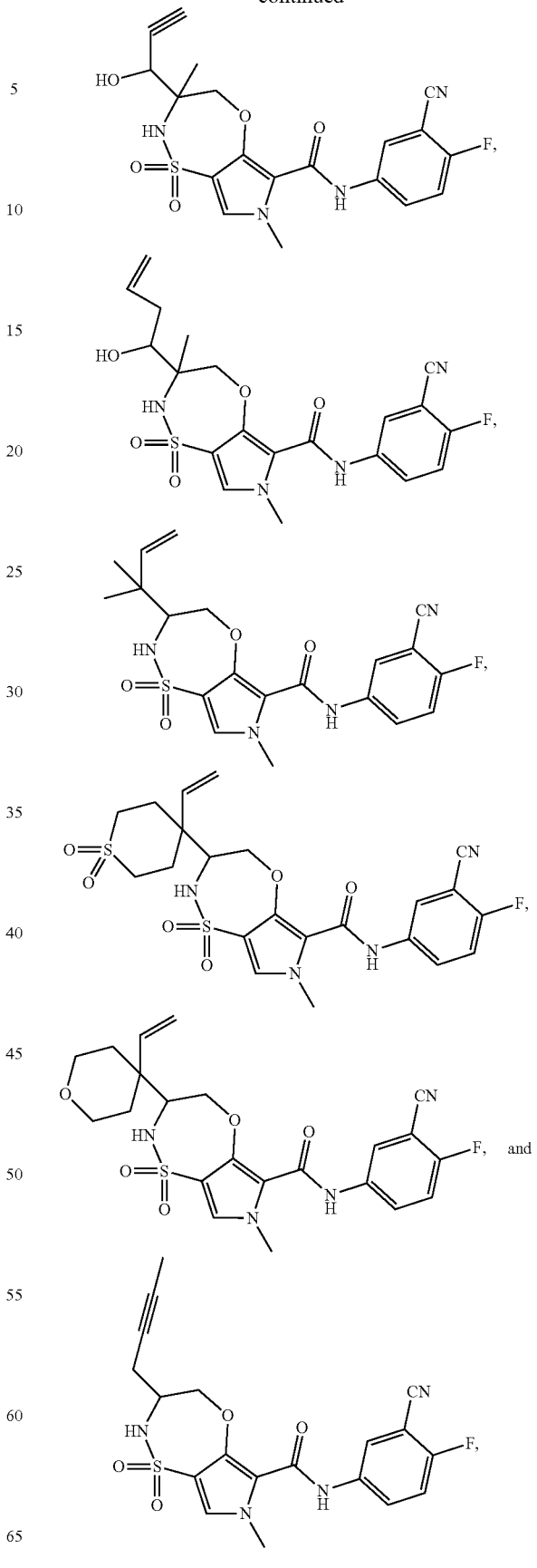
and or a pharmaceutically acceptable salt of any of the foregoing.

22. A pharmaceutical composition comprising an effective amount of a compound of claim 5, or a pharmaceutically acceptable salt thereof, and excipient.

23. A method for treating hepatitis B or hepatitis D in a subject comprising administering to the subject suffering from hepatitis B an effective amount of a compound of claim 5, or a pharmaceutically acceptable salt thereof.

24. The method of claim 23, further comprising administering an additional agent selected from the group consisting of recombinant interferon alpha 2b, IFN-α, PEG-IFN-α-2a, lamivudine, telbivudine, adefovir dipivoxil, clevudine, entecavir, tenofovir alafenamide, tenofovir disoproxil, JNJ-6379, GLS4, ABI-H0731, JNJ-440, NZ-4, RG7907, AB-423, AB-506, ABI-H2158 REP 2139 and REP 2165.

25. A pharmaceutical composition comprising an effective amount of a compound of claim 12, or a pharmaceutically acceptable salt thereof, and excipient.

26. A method for treating hepatitis B or hepatitis D in a subject comprising administering to the subject suffering from hepatitis B an effective amount of a compound of claim 12, or a pharmaceutically acceptable salt thereof.

27. The method of claim 26, further comprising administering an additional agent selected from the group consisting of recombinant interferon alpha 2b, IFN-α, PEG-IFN-α-2a, lamivudine, telbivudine, adefovir dipivoxil, clevudine, entecavir, tenofovir alafenamide, tenofovir disoproxil, JNJ-6379, GLS4, ABI-H0731, JNJ-440, NZ-4, RG7907, AB-423, AB-506, ABI-H2158 REP 2139 and REP 2165.

* * * * *

UNITED STATES PATENT AND TRADEMARK OFFICE
CERTIFICATE OF CORRECTION

PATENT NO. : 11,033,556 B2  
APPLICATION NO. : 16/789298  
DATED : June 15, 2021  
INVENTOR(S) : Leonid Beigelman et al.

Page 1 of 4

It is certified that error appears in the above-identified patent and that said Letters Patent is hereby corrected as shown below:

In the Specification

In Column 2, Line 34, delete "Heptaology" and insert -- Hepatology --.

In Column 4, Line 66, delete "benzoisoxazole," and insert -- benzisoxazole, --.

In Column 6, Lines 66-67, delete "$X_3CS(O)_2N(R)$—" and insert -- $X_3CS(O)_2N(R_A)$— --.

In Column 10, Line 65, delete "Z" and insert -- $Z^1$ --.

In Column 14, Line 7, delete "—O—C(=O)$R^{1B}$," and insert -- —O—C(=O)$R^{11B1}$, --.

In Column 14, Lines 9-10, delete "—O—C(=O)$R^{11B1}$" and insert -- —O—C(=O)$R^{11B1}$, --.

In Column 15, Line 19, delete "$C_1$" and insert -- Cl --.

In Column 18, Line 26, delete "$C_{3-8}$" and insert -- $C_{3-5}$ --.

In Column 19, Line 25, delete "$R^{9A}$" and insert -- $R^{19A}$ --.

In Column 19, Line 33, delete "$R^{9A}$" and insert -- $R^{19A}$ --.

In Column 19, Lines 66-67, delete "—O—C(=O)$R^{19B1}$" and insert -- —O—C(=O)$R^{19B1}$, --.

Signed and Sealed this  
First Day of March, 2022

Drew Hirshfeld  
*Performing the Functions and Duties of the*  
*Under Secretary of Commerce for Intellectual Property and*  
*Director of the United States Patent and Trademark Office*

CERTIFICATE OF CORRECTION (continued)
U.S. Pat. No. 11,033,556 B2

In Column 28, Lines 1-14, delete " 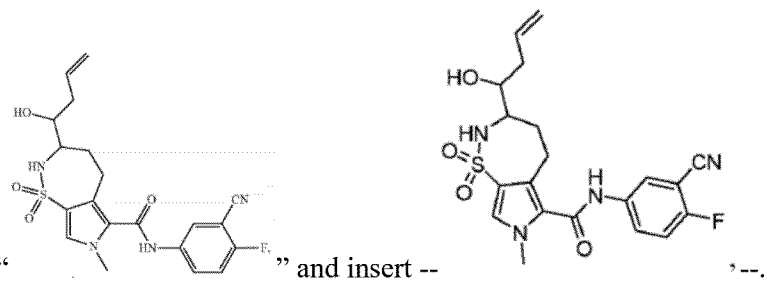 " and insert --  --.

In Column 48, Lines 57-66, delete " 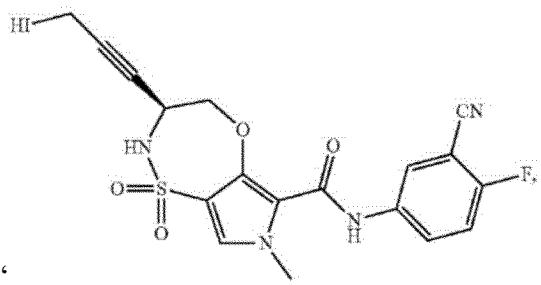 " and insert --  --.

In Column 49, Lines 1-11, delete " 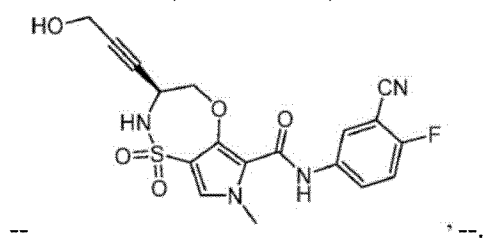 " and insert --  --.

In Column 73, Line 65, delete "R<sup>x</sup>" and insert -- $R^X$ --.

In Column 81, Lines 50-51, delete "alafenanide" and insert -- alafenamide --.

In Column 88, Line 63, delete "CH₂C₂/CH₃OH" and insert -- $CH_2Cl_2/CH_3OH$ --.

In Column 89, Line 3, delete "Sum;" and insert -- 5 um; --.

In Column 89, Line 17, delete "Sum;" and insert -- 5 um; --.

In Column 91, Lines 1-15, delete " 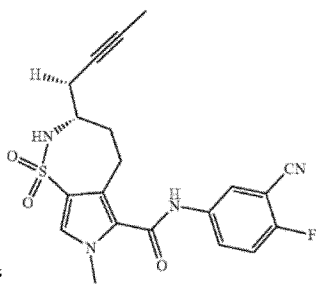 " and insert 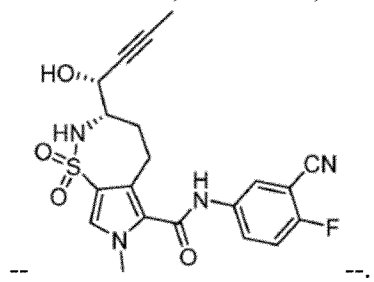 --.

In Column 91, Line 43, delete "Sum;" and insert -- 5 um; --.

In Column 91, Line 47, delete "Sum;" and insert -- 5 um; --.

In Column 101, Line 43 (approx.), delete "7A" and insert -- 7B --.

In Column 102, Line 37, after "purification" insert -- . --.

In Column 149, Line 56, delete "copies/L" and insert -- copies/µL --.

In Column 150, Line 57, delete "doxcycyline" and insert -- doxycycline --.

In the Claims

In Column 155, Lines 56-57, Claim 2, after "single" delete "or a double".

In Column 156, Line 12, Claim 6, delete "5," and insert -- 1, --.

In Column 156, Line 14, Claim 7, delete "5," and insert -- 1, --.

In Column 156, Line 17, Claim 8, delete "5," and insert -- 1, --.

In Column 156, Line 19, Claim 9, delete "5," and insert -- 1, --.

In Column 156, Line 22, Claim 10, delete "5," and insert -- 1, --.

In Column 156, Line 24, Claim 11, delete "5," and insert -- 1, --.

CERTIFICATE OF CORRECTION (continued)
U.S. Pat. No. 11,033,556 B2

In Column 157, Line 38, Claim 20, delete "5," and insert -- 1, --.

In Column 169, Line 4, Claim 22, delete "5," and insert -- 1, --.

In Column 169, Line 9, Claim 23, delete "5," and insert -- 1, --.

In Column 169, Line 16, Claim 24, delete "ABI-H2158 REP 2139" and insert -- ABI-H2158, REP 2139 --.

In Column 169, Line 30, Claim 27, delete "ABI-H2158 REP 2139" and insert -- ABI-H2158, REP 2139 --.

```
                              SEQUENCE LISTING

<160> NUMBER OF SEQ ID NOS: 4

<210> SEQ ID NO 1
<211> LENGTH: 20
<212> TYPE: DNA
<213> ORGANISM: Artificial Sequence
<220> FEATURE:
<223> OTHER INFORMATION: Synthetic HBV-forward primer

<400> SEQUENCE: 1
gtgtctgcgg cgttttatca                                                   20

<210> SEQ ID NO 2
<211> LENGTH: 21
<212> TYPE: DNA
<213> ORGANISM: Artificial Sequence
<220> FEATURE:
<223> OTHER INFORMATION: Synthetic HBV-reverse primer

<400> SEQUENCE: 2
gacaaacggg caacatacct t                                                 21

<210> SEQ ID NO 3
<211> LENGTH: 28
<212> TYPE: DNA
<213> ORGANISM: Artificial Sequence
<220> FEATURE:
<223> OTHER INFORMATION: Synthetic HBV probe
<220> FEATURE:
<221> NAME/KEY: modified_base
<222> LOCATION: 1
<223> OTHER INFORMATION: N=FAM-C
<220> FEATURE:
<221> NAME/KEY: modified_base
<222> LOCATION: 28
<223> OTHER INFORMATION: N=C-TAMRA

<400> SEQUENCE: 3
nctctkcatc ctgctgctat gcctcatn                                          28

<210> SEQ ID NO 4
<211> LENGTH: 28
<212> TYPE: DNA
<213> ORGANISM: Artificial Sequence
<220> FEATURE:
<223> OTHER INFORMATION: Synthetic HBV probe
<220> FEATURE:
<221> NAME/KEY: modified_base
<222> LOCATION: 1
<223> OTHER INFORMATION: N=FAM-C
<220> FEATURE:
<221> NAME/KEY: modified_base
<222> LOCATION: 9
<223> OTHER INFORMATION: N=T-ZEN
<220> FEATURE:
<221> NAME/KEY: modified_base
<222> LOCATION: 28
<223> OTHER INFORMATION: N=C-3IABkFQ

<400> SEQUENCE: 4
nctctkcanc ctgctgctat gcctcatn                                          28
```